US010745688B2

(12) United States Patent
Scharenberg et al.

(10) Patent No.: US 10,745,688 B2
(45) Date of Patent: *Aug. 18, 2020

(54) COUPLING ENDONUCLEASES WITH END-PROCESSING ENZYMES DRIVES HIGH EFFICIENCY GENE DISRUPTION

(71) Applicant: Seattle Children's Hospital, Seattle, WA (US)

(72) Inventors: Andrew M. Scharenberg, Seattle, WA (US); Michael T. Certo, Seattle, WA (US); Kamila Sabina Gwiazda, Seattle, WA (US)

(73) Assignee: SEATTLE CHILDREN'S RESEARCH INSTITUTE, Seattle, WA (US)

( * ) Notice: Subject to any disclaimer, the term of this patent is extended or adjusted under 35 U.S.C. 154(b) by 398 days.

This patent is subject to a terminal disclaimer.

(21) Appl. No.: 15/215,428

(22) Filed: Jul. 20, 2016

(65) Prior Publication Data

US 2017/0152504 A1 Jun. 1, 2017

Related U.S. Application Data

(60) Continuation of application No. 14/949,744, filed on Nov. 23, 2015, which is a division of application No. 14/173,705, filed on Feb. 5, 2014, which is a division of application No. 13/405,183, filed on Feb. 24, 2012, now Pat. No. 8,673,557.

(60) Provisional application No. 61/447,672, filed on Feb. 28, 2011.

(51) Int. Cl.

| | |
|---|---|
| ***A61K 38/46*** | (2006.01) |
| ***C12Q 1/68*** | (2018.01) |
| ***C12Q 1/37*** | (2006.01) |
| ***C12N 9/12*** | (2006.01) |
| ***C12N 15/10*** | (2006.01) |
| ***A61K 38/45*** | (2006.01) |
| ***A61K 38/52*** | (2006.01) |
| ***C12N 9/90*** | (2006.01) |
| ***C12N 15/62*** | (2006.01) |
| ***C12N 9/22*** | (2006.01) |
| ***A61K 9/00*** | (2006.01) |
| ***A61K 35/28*** | (2015.01) |
| *A61K 35/12* | (2015.01) |

(52) U.S. Cl.

CPC .......... *C12N 15/102* (2013.01); *A61K 9/0019* (2013.01); *A61K 35/28* (2013.01); *A61K 38/45* (2013.01); *A61K 38/465* (2013.01); *A61K 38/52* (2013.01); *C12N 9/1252* (2013.01); *C12N 9/22* (2013.01); *C12N 9/90* (2013.01); *C12N 15/62* (2013.01); *A61K 2035/124* (2013.01); *C07K 2319/60* (2013.01); *C12N 2800/80* (2013.01); *C12N 2840/203* (2013.01)

(58) Field of Classification Search

CPC .................................... C12Q 1/68; C12Q 1/37

See application file for complete search history.

(56) References Cited

U.S. PATENT DOCUMENTS

| | | | |
|---|---|---|---|
| 2004/0180352 | A1 | 9/2004 | Padgett et al. |
| 2006/0206949 | A1 | 9/2006 | Arnould et al. |
| 2008/0271166 | A1 | 10/2008 | Epinat et al. |
| 2012/0244131 | A1 | 9/2012 | Delacote et al. |
| 2013/0337454 | A1 | 12/2013 | Duchateau et al. |
| 2017/0152505 | A1 | 6/2017 | Scharenberg et al. |
| 2018/0320165 | A1 | 11/2018 | Scharenberg et al. |

FOREIGN PATENT DOCUMENTS

| | | | |
|---|---|---|---|
| CA | 2815512 | A1 | 10/2011 |
| EP | 2 412 806 | A1 | 2/2012 |
| WO | WO 2012/058458 | A2 | 5/2012 |
| WO | WO 2013/009525 | A1 | 1/2013 |

OTHER PUBLICATIONS

Ahn, Byungchan et al., "Regulation of WRN Helicase Activity in Human Base Excision Repair" The Journal of Biological Chemistry, Dec. 17, 2004, pp. 53465-53474, vol. 279, No. 51.

Ashworth, Justin et al., "Computational redesign of endonuclease DNA binding and cleavage specificity" Nature, Jun. 1, 2006, pp. 656-659, vol. 441.

Balasubramanian, Nandakumar et al., "Physical Interaction between the Herpes Simplex Virus Type 1 Exonuclease, UL12, and the DNA Double-Strand Break-Sensing MRN Complex" Journal of Virology, Dec. 2010, pp. 12504-12514, vol. 84, No. 24.

Bennardo, N., and J.M. Stark, "ATM Limits Incorrect End Utilization During Non-Homologous End Joining of Multiple Chromosome Breaks," *PLoS Genetics* 6(11):1-11, Nov. 2010.

Bennardo, N., et al., "Limiting the Persistence of a Chromosome Break Diminishes Its Mutagenic Potential," *PLoS Genetics* 5(10):1-14, Oct. 2009.

Boch, Jens et al., "Breaking the Code of DNA Binding Specificity of TAL-Type III Effectors" Science, Dec. 11, 2009, pp. 1509-1512, vol. 326.

Chevalier, Brett S. et al., "Design, Activity, and Structure of a Highly Specific Artificial Endonuclease" Molecular Cell, Oct. 2002, pp. 895-905, vol. 10.

(Continued)

*Primary Examiner* — Maryam Monshipouri

(74) *Attorney, Agent, or Firm* — Rothwell, Figg, Ernst & Manbeck, P.C.

(57) ABSTRACT

The present disclosure relates to the co-expression of an endonuclease with an end-processing enzyme for the purpose of enhanced processing of the polynucleotide ends generated by endonuclease cleavage.

21 Claims, 39 Drawing Sheets

Specification includes a Sequence Listing.

(56) References Cited

OTHER PUBLICATIONS

Coates, Brad S., et al., "A Helitron-Like Transposon Superfamily from Lepidoptera Disrupts $(GAAA)_n$ Microsatellites and is Responsible for Flanking Sequence Similarity within a Microsatellite Family," J. Mol. Evol. 70:275-288, 2010.
Dahlroth, Sue-Li et al., "Crystal structure of the shutoff and exonuclease protein from the oncogenic Kaposi's sarcoma-associated herpesvirus" FEBS Journal, 2009, pp. 6636-6645, vol. 276.
EP communication received in application No. 12751744.9, dated Mar. 18, 2015.
Epinat, Jean-Charles et al., "A novel engineered meganuclease induces homologous recombination in yeast and mammalian cells" Nucleic Acids Research, 2003, pp. 2952-2962, vol. 31, No. 11.
Farjardo-Sanchez, E., "Computer Design of Obligate Heterodimer Meganucleases Allows Efficient Cutting of Custom DNA Sequences," *Nucleic Acids Res*. 36(7):2164-2173, 2008.
File History of U.S. Appl. No. 13/405,183, filed Feb. 24, 2012.
File History of U.S. Appl. No. 14/173,705, filed Feb. 5, 2014.
File History of U.S. Appl. No. 14/949,744, filed Nov. 23, 2015.
File History of U.S. Appl. No. 15/215,405, filed Jul. 20, 2016.
File History of U.S. Appl. No. 15/215,461, filed Jul. 20, 2016.
File History of U.S. Appl. No. 15/215,396, filed Jul. 20, 2016.
Gammon, Don B. et al., "The 3'-to-5' Exonuclease Activity of Vaccinia Virus DNA Polymerase Is Essential and Plays a Role in Promoting Virus Genetic Recombination" Journal of Virology, May 2009, pp. 4236-4250, vol. 83, No. 9.
Garcia, Valerie et al., "Bidirectional resection of DNA double-strand breaks by Mre11 and Exo1" Nature, Nov. 10, 2011, pp. 241-244, vol. 479.
Glaunsinger, Britt et al., "The Exonuclease and Host Shutoff Functions of the SOX Protein of Kaposi's Sarcoma-Associated Herpesvirus Are Genetically Separable" Journal of Virology, Jun. 2005, pp. 7396-7401, vol. 79, No. 12.
Gunn, A., et al., Correct End Use During End Joining of Multiple Chromosomal Double Strand Breaks Is Influenced by Repair Protein RAD50, DNA-Dependent Protein Kinase DNA-PKcs, and Transcription Context, *J. Biol. Chem*. 286(49):42470-42482, Dec. 9, 2011.
International Search Report and Written Opinion dated Jun. 7, 2012, received in connection with PCT/US 12/26653.
Ishchenko, Alexander A., et al., "The 3'→5' Exonuclease of Apn1 Provides an Alternative Pathway to Repair 7,8-Dihydro-8-Oxodeoxyguanosine in *Saccharomyces cerevisiae*," Molecular and Cellular Biology, pp. 6380-6390, Aug. 2005.
Jagannathan, Indu et al., "Activity of FEN1 Endonuclease on Nucleosome Substrates Is Dependent upon DNA Sequence but Not Flap Orientation" The Journal of Biological Chemistry, May 20, 2011, pp. 17521-17529, vol. 286, No. 20.
Kratz, Katja, et al., "Deficiency of FANCD2-Associated Nuclease KIAA1018/FAN1 Sensitizes Cells to Interstrand Crosslinking Agents," Cell 142, 77-99, Jul. 9, 2010.
Kurosawa, Aya et al., "Functions and Regulation of Artemis: A Goddess in the Maintenance of Genome Integrity" J. Radiat. Res., 2010, pp. 503-509, vol. 51.
Lee, Byung-In et al., "The RAD2 Domain of Human Exonuclease 1 Exhibits 5' to 3' Exonuclease and Flap Structure-specific Endonuclease Activities" The Journal of Biological Chemistry, Dec. 31, 1999, pp. 37763-37769, vol. 274, No. 53.
Lenain, Christelle et al., "The Apollo 5' Exonuclease Functions Together with TRF2 to Protect Telomeres from DNA Repair" Current Biology, Jul. 11, 2006, pp. 1303-1310, vol. 16.
Mahajan, Kiran N. et al., "Association of terminal deoxynucleotidyl transferase with Ku" PNAS, Nov. 23, 1999, pp. 13926-13931, vol. 96, No. 24.
Marcaida, Maria J. et al. (2010) Homing endonucleases: from basics to therapeutic applications, Cell. Mol. Life Sci., 67:727-748.
Mashimo, Tomoji et al., "Efficient gene targeting by TAL effector nucleases coinjected with exonucleases in zygotes" Scientific Reports, Feb. 13, 2013 vol. 3, Article No. 1253.
Mazur, Dan J. et al., "Excision of 3' Termini by the Trex1 and TREX2 3'→5' Exonucleases—Characterization of the Recombinant Proteins" The Journal of Biological Chemistry, May 18, 2001, pp. 17022-17029, vol. 276, No. 20.
Monteilhet, Claude et al. (1990) Purification and characterization of the in vitro activity of I-Sce I, a novel and highly specific endonuclease encoded by a group I intron, Nucleic Acids Research, 18(6):1407-1413.
Moscou, Matthew J. et al., "A Simple Cipher Governs DNA Recognition by TAL Effectors" Science, Dec. 11, 2009, p. 1501, vol. 326.
Nicolette, M.L., et al., "Mre11-Rad50-Xrs2 and Sae2 Promote 5' Strand Resection of DNA Double-Strand Breaks," *Nat. Struct. Mol. Biol*. 17(12):1478-1485, Dec. 2010.
Nimonkar, Amitabh V. et al., "BLM-DNA2-RPA-MRN and EXO1-BLM-RPA-MRN constitute two DNA end resection machineries for human DNA break repair" Genes & Development, 2011, pp. 350-362, vol. 25.
Orans, Jillian et al., "Structures of Human Exonuclease 1 DNA Complexes Suggest a Unified Mechanism for Nuclease Family" Cell, Apr. 15, 2011, pp. 212-223, vol. 145.
Paques, Frédéric et al., "Meganucleases and DNA Double-Strand Break-Induced Recombination: Perspectives for Gene Therapy" Current Gene Therapy, 2007, pp. 49-66, vol. 7.
Porteus, M.H. and Baltimore D., "Chimeric Nucleases Stimulate Gene Targeting in Human Cells," *Science* 300(5620):763, May 2003.
Reuven, Nina Bacher et al., "The Herpes Simplex Virus Type 1 Alkaline Nuclease and Single-Stranded DNA Binding Protein Mediate Strand Exchange in Vitro" Journal of Virology, Jul. 2003, pp. 7245-7433, vol. 77, No. 13.
Smith, J., et al., "A Combinatorial Approach to Create Artificial Homing Endonucleases Cleaving Chosen Sequences," *Nucleic Acids Res*. 34(22):1-12, 2006.
Tsutakawa, Susan E. et al., "Human Flap Endonuclease Structures, DNA Double-Base Flipping, and a Unified Understanding of the FEN1 Superfamily" Cell, Apr. 15, 2011, pp. 198-211, vol. 145.
Vallur, et al., Complementary Roles for Exonuclease 1 and Flap Endonuclease 1 in Maintenance of Triplet Repeats, The Journal of Biological Chemistry 285(37):28514-28519, Sep. 10, 2010.
Yoon, Jung-Hoon et al., "Characterization of the 3' → 5' Exonuclease Activity Found in Human Nucleoside Diphosphate Kinase 1 (NDK1) and Several of Its Homologues" Biochemistry, 2005, pp. 15774-15786, vol. 44.
Zhang, Jinjin et al., "Crystal Structure of *E. coli* RecE Protein Reveals a Toroidal Tetramer for Processing Double-Stranded DNA Breaks" Structure, May 13, 2009, pp. 690-702, vol. 17.
Zhang, Jinjin et al., "Crystal structures of λ exonuclease in complex with DNA suggest an electrostatic ratchet mechanism for processivity" PNAS, Jul. 19, 2011, pp. 11872-11877, vol. 108, No. 29.
Office Action in corresponding Canadian application No. 2828303, dated Dec. 14, 2017.
Andrec et al., "A large data set comparison of protein structures determined by crystallography and NMR: Statistical test for structural differences and the effect of crystal packing," Proteins (2007) p. 449-465.
Berkner et al., "Polynucleotide Kinase Exchange Reaction," J. Biol. Chem. (May 25, 1977) 252(10):3176-3184.
Cannon et al., "Structure-Function Studies of the Human Immunodeficiency Virus Type 1 Matrix Protein, p17," J. Virol., 71(5):3474-3483 (1997).
Certo et al., "Tracking genome engineering outcome at individual DNA breakpoints," Nature Methods (2011) 8(8):671-667; and Supplementary Material.
Chen et al., "Biochemical and cellular characteristics of the 3'_5'exonuclease TREX2," Nucl. Acids Res. (2007) 35(8):2682-2694.
Christian et al., "Targeting DNA Double-Strand Breaks with TAL Effector Nucleases," Genetics Soc. America (Oct. 2010) 186:757-761.

(56) References Cited

OTHER PUBLICATIONS

Cuatrecasas et al., "Catalytic Properties and Specificity of the Extracellular Nuclease of *Staphylococcus aureus*," J. Biol. Chem. (1967) vol. 242, No. 7, pp. 1541-1547.
Das et al., "Processing of abasic DNA clusters in hApelsilenced primary fibroblasts exposed to low doses of X-irradiation," J. Biosci. (2911) vol. 36(1), pp. 105-116.
De Silva et al., "DNA binding induces active site conformational change in the human TREX2 3'-exonuclease," Nucleic Acids Research (2009) vol. 37, No. 7, pp. 2411-2417.
Fitzgerald et al., "Development of an Acid-Soluble Assay for Measuring Retrovirus Integrase 3'-OH Terminal Nuclease Activity," Analytical Biochemistry (1991) vol. 196, pp. 19-23.
Garbuzynskiy et al., "Comparison of X-ray and NMR Structures: Is There a Systematic Difference in Residue Contacts between X-ray and NMR Resolved Protein Structures?" Proteins: Structures, Function, and Bioinformatics (2005) 60:139-147.
Grizot et al., "Efficient targeting of a SCID gene by an engineered single-chain homing endonuclease," Nucleic Acids Research (2009) 37:5405-5419.
Ilyinskii et al., "The proteosomal degradation of fusion proteins cannot be predicted from the proteosome susceptibility of their individual components," Protein Science (2008) 17:1077-1085.
Kawamura et al., "Unusually Infrequent Cleavage with Several Endonucleases and Physical Map Construction of Bacillus subtilis Bacteriophage ϕ1 DNA," Journal of Virology (1981) vol. 37, No. 3, pp. 1099-1102.
Kim et al., "Hybrid restriction enzymes: Zinc finger fusions to Fok I cleavage domain," PNAS (Feb. 1996) 93:1156-1160.
Meiss et al., "Biochemical Characterization of *Anabaena* sp. Strain PCC 7120 Non-Specific Nuclease NucA and Its Inhibitor NuiA," Eur. J. Biochem. (1998) vol. 251, pp. 924-934.
Orlando et al., "Zinc-finger nuclease-driven targeted integration into mammalian genomes using donors with limited chromosomal homology," Nucleic Acids Research (2010) 38(15):e152.
Perrino et al., "The Human TREX2 3' a□ 5'-Exonuclease Structure Suggests a Mechanism for Efficient Nonprocessive DNA Catalysis," The Journal of Biological Chemistry (2005) vol. 280, No. 15, pp. 15212-15218.
Santiago et al., "Targeted gene knockout in mammalian cells by using engineered zinc-finger nucleases," PNAS (Apr. 15, 2008) vol. 105, No. 15, pp. 5809-5814.
Sheflin et al., "Altered DNA conformations detected by mung bean nuclease occur in promoter and terminator regions of supercoiled pBR322 DNA," Nucleic Acids Research (1985) vol. 13, No. 7, pp. 6137-6154.
Snapp, Erik, "Design and Use of Fluorescent Fusion Proteins in Cell Biology," Curr Protoc Cell Biol. (2005) Chapter: Unit-21.4.
Thompson et al., "Cleavage and recognition pattern of a double-strand-specific endonuclease (I-Crel) encoded by the chloroplast 23s rRNA intron of Chlamydomonas reinhardtii," Gene (1992) 119:247-251.
Thusberg et al., "Bioinformatic Analysis of Protein Structure-Function Relationships; Case Study of Leukocyte Elastase (ELA2) Missense Mutations," Human Mutation (2006) 27(12):1230-1243.
Tsien, Roger Y., "The green fluorescent protein," Annu. Rev. Biochem. (1998) 67:509-544.
Urnov et al., "Highly efficient endogenous human gene correction using designed zinc-finger nucleases," Nature (Jun. 2005) vol. 435, pp. 646-651.
Weinfeld et al., "Selective hydrolysis by exo- and endonucleases of phosphodiester bonds adjacent to an apurinic site," Nucleic Acid Research (1989) vol. 17, No. 10, pp. 3735-3745.
Wiegand et al., "Specificity of the S1 Nuclease from Aspergillus oryzae," The Journal of Biological Chemistry, (1975) vol. 250, No. 22, pp. 8848-8855.
Wu et al., "Identification of Regions in the Moloney Murine Leukemia Virus SU Protein That Tolerate the Insertion of an Integrin-Binding Peptide," Virology (2000) vol. 269, pp. 7-17.
Wu et al., "Cloning and Characterization of a Periplasmic Nuclease of Vibrio vulnificus and Its Role in Preventing Uptake of Foreign DNA," Applied and Environmental Microbiology (2001) vol. 67, No. 1, pp. 82-88.
Christian, M., et al., "Targeting DNA Double-Strand Breaks with TAL Effector Nucleases," Genetics 186, pp. 757-761 (Oct. 2010).
Decision on Motions 37 CFR 41.125(a), *Seattle Children's Research Institute* v. *Cellectis*, Interference No. 106,052, filed Apr. 27, 2017, 55 pages.
Decision on Priority 37 CFR 41.125(a), *Cellectis* v. *Seattle Children's Research Institute*, Interference No. 106,052, filed Aug. 30, 2018, 44 pages.
Communication pursuant to Rule 69 EPC issued for European patent application No. 19183306.0 dated Feb. 10, 2020, 9 pages.
Communication dated Apr. 10, 2017 in the European Patent Application No. 12751744.9 filed Sep. 26, 2013.

Sce

| SEQ ID NO | |
|---|---|
| 10 | TAGGTCAGGGTTCACACTAGTTAGGGATAACAGGGTAATACCTGCAGGTTGCCGGTGGTGCA |
| 11 | TAGGTCAGGGTTCACACTAGTTAGG---------GTAATACCTGCAGGTTGCCGGTGGTGCA |
| 12 | TAGGTCAGGGTTCACACTAGTTAGGGATAACAGGGTAATACCTGCAGGTTGCCGGTGGTGCA |
| 13 | TAGGTCAGGGTTCACACTAGTTAGGGATAACAGGGTAATACCTGCAGGTTGCCGGTGGTGCA |
| 14 | TAGGTCAGGGTTCACACTAGTTAGGGATAACAGGGTAATACCTGCAGGTTGCCGGTGGTGCA |
| 15 | TAGGTCAGGGTTCACACTAGTTAGGGATAACAGGGTAATACCTGCAGGTTGCCGGTGGTGCA |
| 16 | TAGGTCAGGGTTCACACTAGTTAGGGATAACAGGGTAATACCTGCAGGTTGCCGGTGGTGCA |
| 17 | TAGGTCAGGGTTCACACTAG------ATAACAGGGTAATACCTGCAGGTTGCCGGTGGTGCA |
| 18 | TAGGTCAGGGTTCACACTAGTTAGGGATA-CAGGGTAATACCTGCAGGTTGCCGGTGGTGCA |
| 19 | TAGGTCAGGGTTCACACTAGTTAGGGATAACAGGGTAATACCTGCAGGTTGCCGGTGGTGCA |
| 20 | TAGGTCAGGGTTCACACTAGTTAGG---------GTAATACCTGCAAGTTGCCGGTGGTGCA |
| 21 | TAGGTCAGGGTTCACACTAGTTAGGGA---------------TGCAGGTTGCCGGTGGTGCA |
| 22 | TAGGTCAGGGTTCACACTAGTTAGGGATAACAGGGTAATACCTGCAGGTTGCCGGTGGTGCA |
| 23 | TAGGTCAGGGTTCACACTA-------------------TACCTGCAGGTTGCCGGTGGTGCA |
| 24 | TAGGTCAGGGTTCACACTAGTTAGGGATAACAGGGTAATACCTGCAGGTTGCCGGTGGTGCA |
| 25 | TAGGTCAGGGTTCACACTAGTTAGGGATAACAGGGTAATACCTGCAGGTTGCCGGTGGTGCA |
| 26 | TAGGTCAGGGTTCACACTAGTTAGGGATAACAGGGTAATACCTGCAGGTTGCCGGTGGTGCA |
| 27 | TAGGTCAGGGTTCACACTAGGTAGGTA-----GGGCAA--CCTGCAGGTTGCCGGTGGTGCA |
| 28 | TAGGTCAGGGTTCACACTAGTTAGGGATAACAGGGTAATACCTGCAGGTTGCCGGTGGTGCA |
| 29 | TAGGTCAGGGTTCACACTAGTTAGGGATAACAGGGTAATACCTGCAGGTTGCCGGTGGTGCA |
| 30 | TAGGTCAGGGTTCACACTAGTTAGGGATAACAGGGTAATACCTGCAGGTTGCCGGTGGTGCA |
| 31 | TAGGTCAGGGTTCACACTAGTTAGGGATAACAGGGTAATACCTGCAGGTTGCCGGTGGTGCA |
| 32 | TAGGTCAGGGTTCACACTAGTTAGGGATAACAGGGTAATACCTGCAGGTTGCCGGTGGTGCA |
| 33 | TAGGTCAGGGTTCACACTAGTTAGG---------GTAATACCTGCAGGTTGCCGGTGGTGCA |
| 34 | TAGGTCAGGGTTCACACTAGTTAGGGATAACAGGGTAATACCTGCAGGTTGCCGGTGGTGCA |
| 35 | TAGGTCAGGGTTCACACTAGTTAGGGATAACAGGGTAATACCTGCAGGTTGCCGGTGGTGCA |
| 36 | TAGGTCAGGGTTCACACTAGTTAGGGATAACAGGGTAATACCTGCAGGTTGCCGGTGGTGCA |
| 37 | TAGGTCAGGGTTCACACTAGTTAGGGATAACAGGGTAATACCTGCAGGTTGCCGGTGGTGCA |
| 38 | TAGGTCAGGGTTCACACTAGTTAGGGATAAC-------TACCTGCAGGTTGCCGGTGGTGCA |
| 39 | TAGGTCAGGGTTCACACTAGTTAGGGATAACAGGGTAATACCTGCAGGTTGCCGGTGGTGCA |
| 40 | TAGGTCAGGGTTCACACTA-------ATAACAGGGTAATACCTGCAGGTTGCCGGTGGTGCA |
| 41 | TAGGTCAGGGTTCACACTAGTTAGGGATAACAGGGTAATACCTGCTGGTTGCCGGTGGTGCA |
| 42 | TAGGTCAGGGTTCACACTAGTTAGGGATAACAGGGTAATACCTGCAGGTTGCCGGTGGTGCA |
| 43 | TAGGTCAGGGTTCACACTAGTTAGGGATAACAGGGTAATACCTGCAGGTTGCCGGTGGTGCA |
| 44 | TAGGTCAGGGTTCACACTAGTTAGG---------GTAATACCTGCAAGTTGCCGGTGGTGCC |
| 45 | TAGGTCAGGGTTCACACTAGTTAGGGATAACAGGGTAATACCTGCAGGTTGCCGGTGGTGCA |
| 46 | TAGGTCAGGGTTCACACTAGTTAGG-ATAACAGGGTAATACCTGCAGGTTGCCGGTGGTGCA |
| 47 | TAGGTCAGGGTTCACACTAGTTAGG-ATAACAGGGTAATACCTGCAGGTTGCCGGTGGTGCA |
| 48 | TAGGTCAGGGTTCACACTAGTTAGGGATAACAGGGTAATACCTGCAGGTTGCCGGTGGTGCA |
| 49 | TAGGTCAGGGTTCACACTAGTTAGGGATAACAGGGTAATACCTGCAGGTTGCCGGTGGTGCA |
| 50 | TAGGTCAGGGTTCACACTAGTTAGGGATAACAGGGTAATACCTGCAGGTTGCCGGTGGTGCA |
| 51 | TAGGTCAGGGTTCACACTAGTTAGG-ATAACAGGGTAATACCTGCAGGTTGCCGGTGGTGCA |
| 52 | TAGGTCAGGGTTCACACTAG------ATAACAGGGTAATACCTGCAGGTTGCCGGTGGTGCA |
| 53 | TAGGTCAGGGTTCACACTAGTTAGGGATAACAGGGTAATACCTGCAGGTTACCGGTGGTGCA |
| 54 | TAGGTCAGGGTTCACACTAGTTAGGGATAACAGGGTAATACCTGCAGGTTGCCGGTGGTGCA |
| 55 | TAGGTCAGGGTTCACACTAGTTAGGGATAACAGGGTAATACATGCAGGTTGCCGGTGGTGCA |
| 56 | TAGGTCAGGGTTCACACTAGTTAGGGATAACAGGGTAATACCTGCAGGTTGCCGGTGGTGCA |
| 57 | TAGGTCAGGGTTCACACTAGTTAGGGATAACAGGGTAATACCTGCAGGTTGCCGGTGGTGCA |

FIG. 6A

Sce + Trex2

| SEQ ID NO | |
|---|---|
| 58 | CCGTAGGTCAGGGTTCACACTAGTTAGGGATAACAGGGTAATACCTGCAGGTTGCCG |
| 59 | CCGTAGGTCAGGGTTCACACTAGTTAGGGA--ACAGGGTAATACCTGCAGGTTGCCG |
| 60 | CCGTAGGTCAGGGTTCACACTAGTTAGGG----CAGGGTAATACCTGCAGGTTGCCG |
| 61 | CCGTAGGTCAGGGTTCACACTAGTTAGGGA--ACAGGGTAATACCTGCAGGTTGCCG |
| 62 | CCGTAGGTCAGGGTTCACACTAGTCAGGG---------TAATACCTGCAGGTTGCCG |
| 63 | CCGTAGGTCAGGGTTCACACTAGTTAGGG----CAGGGTAATACCTGCAGGTTGCCG |
| 64 | CCGTAGGTCAGGGTTCACACTAGTTAGGGA--ACAGGGTAATACCTGCAGGTTGCCG |
| 65 | CCGTAGGTCAGGGTTCACACTAGTTAGGGA--ACAGGGTAATACCTGCAGGTTGCCG |
| 66 | CCGTAGGTCAGGGTTCACACTAGTTAGGG---------TAATACCTGCAGGTTGCCG |
| 67 | CCGTAGGTCAGGGTTCACACTAGTTAGGG--------GTAATACCTGCAGGTTGCCG |
| 68 | CCGTAGGTCAGGGTTCACACTAGTTAGGGA--ACAGGGTAATACCTGCAGGTTGCCG |
| 69 | CCGTAGGTCAGGGTTCACACTAGTTAGGGA--ACAGGGTAATACCTGCAGGTTGCCG |
| 70 | CCGTAGGTCAGGGTTCACACTAGTTAGGG----CAGGGTAATACCTGCAGGTTGCCG |
| 71 | CCGTAGGTCAGGGTTCACACTAGTTAGGG----CAGGGTAATACCTGCAGGTTGCCG |
| 72 | CCGTAGGTCAGGGTTCACACTAGTTAGGGA--ACAGGGTAATACCTGCAGGTTGCCG |
| 73 | CCGTAGGTCAGGGTTCACACTAGTTAGGG----CAGGGTAATACCTGCAGGTTGCCG |
| 74 | CCGTAGGTCAGGGTTCACACTAGTTAGGGA--ACAGGGTAATACCTGCAGGTTGCCG |
| 75 | CCGTAGGTCAGGGTTCACACTAGTTAGGGA---CAGGGTAATACCTGCAGGTTGCCG |
| 76 | CCGTAGGTCAGGGTTCACACTAGTTAGGG----CAGGGTAATACCTGCAGGTTGCCG |
| 77 | CCGTAGGTCAGGGTTCACACTAGTTAGGGA--ACAGGGTAATACCTGCAGGTTGCCG |
| 78 | CCGTAGGTCAGGGTTCACACTAGTTAGGGA---CAGGGTAATACCTGCAGGTTGCCG |
| 79 | CCGTAGGTCAGGGTTCACACTAGTTAGGGA--ACAGGGTAATACCTGCAGGTTGCCG |
| 80 | CCGTAGGTCAGGGTTCACACTAGTTAGGGA---CAGGGTAATACCTGCAGGTTGCCG |
| 81 | CCGTAGGTCAGGGTTCACACTAGTTAGGGA--ACAGGGTAATACCTGCAGGTTGCCG |
| 82 | CCGTAGGTCAGGGTTCACACTAGTTAGGG--------GTAATACCTGCAGGTTGCCG |
| 83 | CCGTAGGTCAGGGTTCACACTAGTTAGGGA--ACAGGGTAATACCTGCAGGTTGCCG |
| 84 | CCGTAGGTCAGGGTTCACACTAGTTAGGG-------GGTAATACCTGCAGGTTGCCG |
| 85 | CCGTAGGTCAGGGTTCACACTAGTTAGGG--------GTAATACCTGCAGGTTGCCG |
| 86 | CAATAGGTCAGGGTTCACACTAGTTAGGGA--ACAGGGTAATACCTGCAGGTTGCCG |
| 87 | CCGTAGGTCAGGGTTCACACTAGTTAGGGA--ACAGGGTAATACCTGCAGGTTGCCG |
| 88 | CCGTAGGTCAGGGTTCACACTAGTTAGGG-------GGTAATACCTGCAGGTTGCCG |
| 89 | CCGTAGGTCAGGGTTCACACTAGTTAGGG----CAGGGTAATACCTGCAGGTTGCCG |
| 90 | CCGTAGGTCAGGGTTCACACTAGTTAGGG----CAGGGTAATACCTGCAGGTTGCCG |
| 91 | CCGTAGGTCAGGGTTCACACTAGTTAGGG----CAGGGTAATACCTGCAGGTTGCCG |
| 92 | CCGTGGGTCAGGGTTCACACTAGTTAGGG----CAGGGTAATACCTGCAGGTTGCCG |
| 93 | CCGTAGGTCAGGGTTCACACTAGTTAGGGA---CAGGGTAATACCTGCAGGTTGCCG |
| 94 | CCGTAGGTCAGGGTTCACACTAGTTAGGGA---CAGGGTAATACCTGCAGGTTGCCG |
| 95 | CCGTAGGTCAGGGTTCACACTAGTTAGGG----CAGGGTAATACCTGCAGGTTGCCG |
| 96 | CCGTAGGTCAGGGTTCACACTAGTTAGGGA--ACAGGGTAATACCTGCAGGTTGCCG |
| 97 | CCGTAGGTCAGGGTTCACACTAGTTAGGG----CAGGGTAATACCTGCAGGTTGCCG |
| 98 | CCGTAGGTCAGGGTTCACACTAGTTAGGG--------GTAATACCTGCAGGTTGCCG |
| 99 | CCGTAAGTCAGGGTTCACACTAGTTAGGG----CAGGGTAATACCTGCAGGTTGCCG |
| 100 | CCGTAGGTCAGGGTTCACACTAGTTAGGG-----AGGGTAATACCTGCAGGTTGCCG |
| 101 | CCGTAGGTCAGGGTTCACACTAGTTAGGG----CAGGGTAATACCTGCAGGTTGCCG |
| 102 | CCGTAGGTCAGGGTTCACACTAGTTAGGGA--ACAGGGTAATACCTGCAGGTTGCCG |
| 103 | CCGTAGGTCAGGGTTCACACTAGTTAGG-----CAGGGTAATACCTGCAGGTTGCCG |
| 104 | CCGTAGGTCAGGGTTCACACTAGTTAGGG---------TAATACCTGCAGGTTGCCG |
| 105 | CCGTAGGTCAGGGTTCACACTAGTTAGGG---------TAATACCTGCAGGTTGCCG |

FIG. 6B

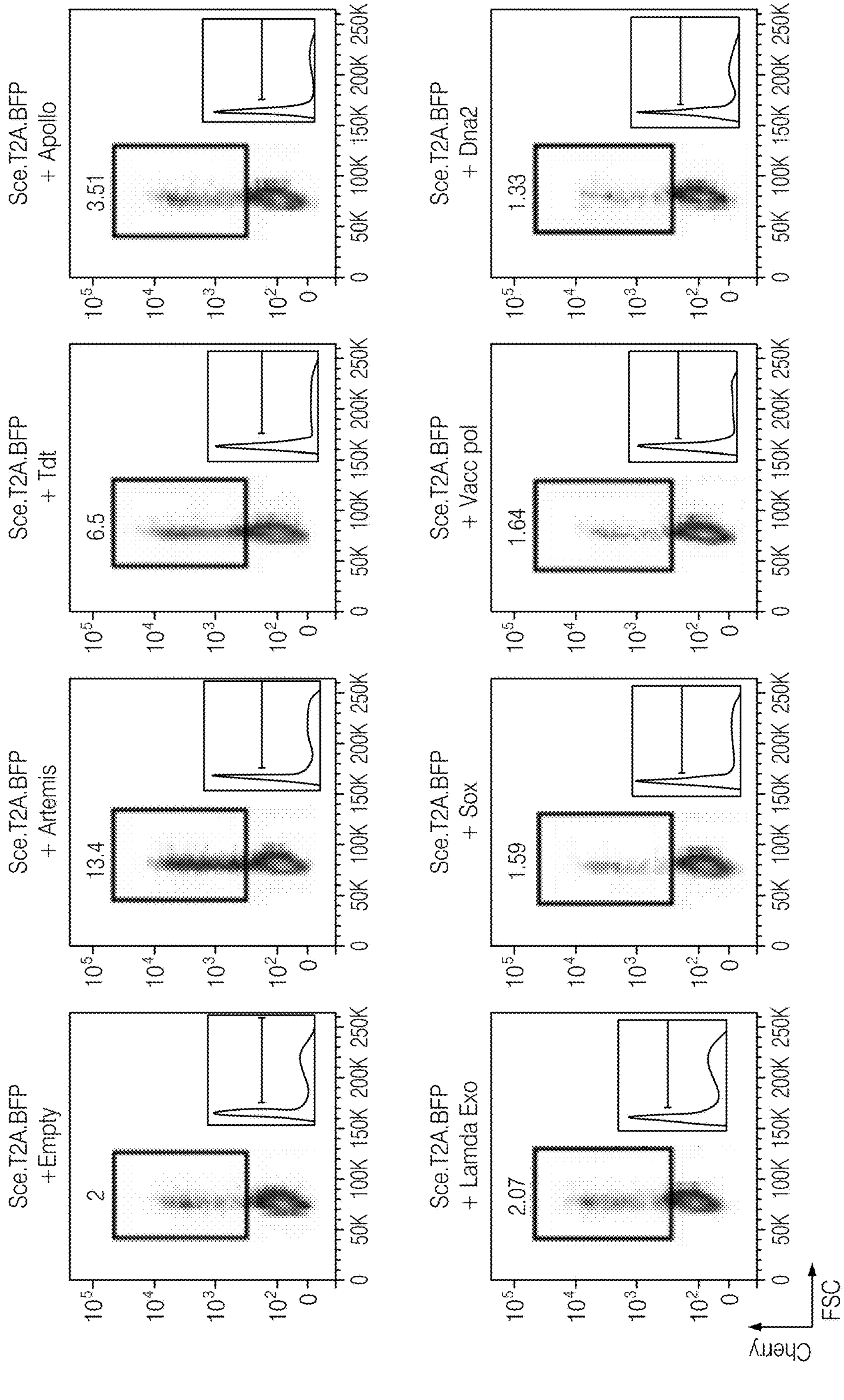
FIG. $17A_1$

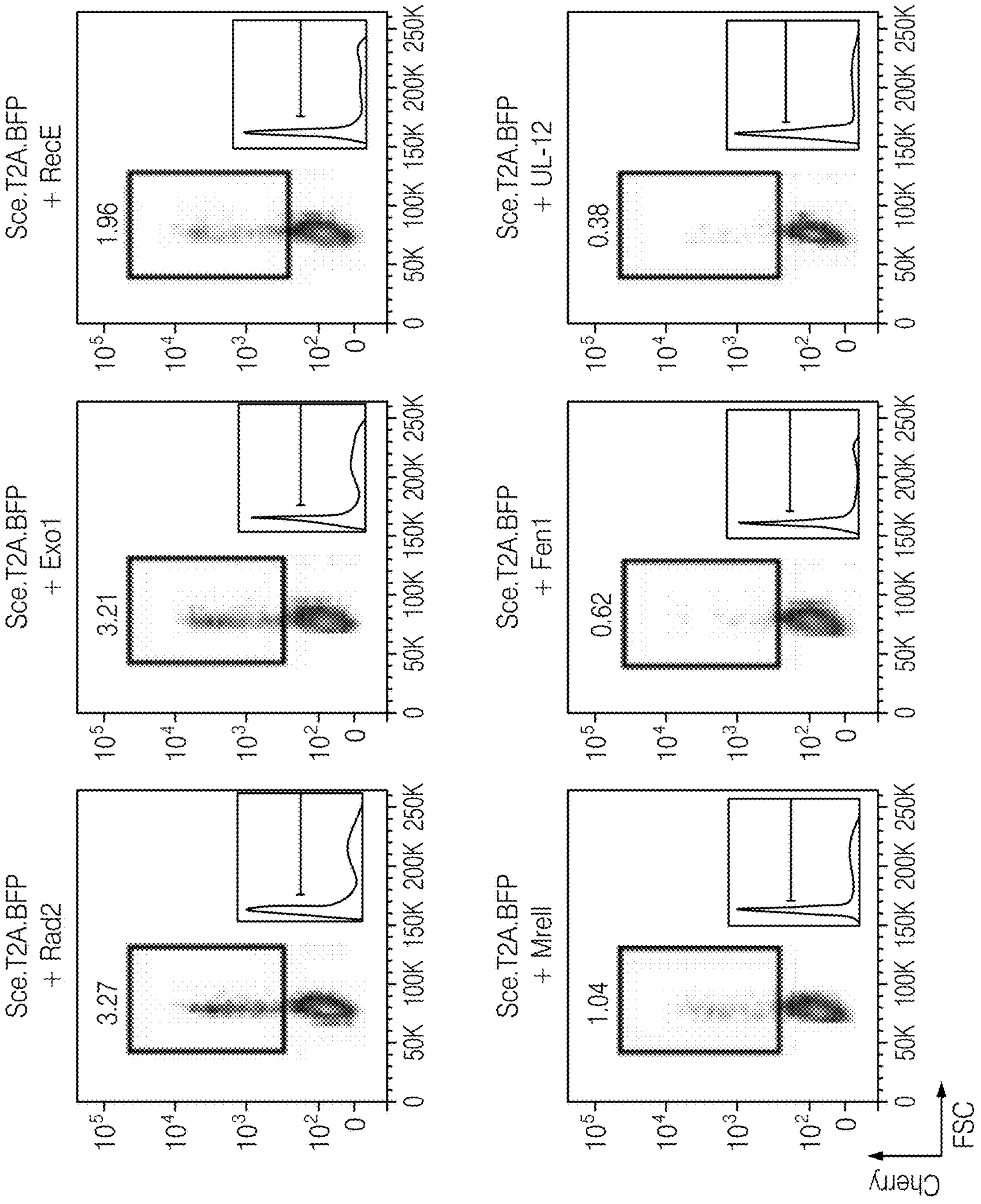
FIG. $17A_2$

SEQUENCE LISTING

```
<160> NUMBER OF SEQ ID NOS: 147

<210> SEQ ID NO 1
<211> LENGTH: 18
<212> TYPE: DNA
<213> ORGANISM: Artificial Sequence
<220> FEATURE:
<223> OTHER INFORMATION: Sequence of the I-SceI target site

<400> SEQUENCE: 1

tagggataac agggtaat                                                    18


<210> SEQ ID NO 2
<211> LENGTH: 22
<212> TYPE: DNA
<213> ORGANISM: Artificial Sequence
<220> FEATURE:
<223> OTHER INFORMATION: Sequence of the I-LtrI target site

<400> SEQUENCE: 2

aatgctccta tacgacgttt ag                                               22


<210> SEQ ID NO 3
<211> LENGTH: 22
<212> TYPE: DNA
<213> ORGANISM: Artificial Sequence
<220> FEATURE:
<223> OTHER INFORMATION: Sequence of the I-GpiI target site

<400> SEQUENCE: 3

ttttcctgta tatgacttaa at                                               22


<210> SEQ ID NO 4
<211> LENGTH: 22
<212> TYPE: DNA
<213> ORGANISM: Artificial Sequence
<220> FEATURE:
<223> OTHER INFORMATION: Sequence of the I-GzeI target site

<400> SEQUENCE: 4

gcccctcata acccgtatca ag                                               22


<210> SEQ ID NO 5
<211> LENGTH: 21
<212> TYPE: DNA
<213> ORGANISM: Artificial Sequence
<220> FEATURE:
<223> OTHER INFORMATION: Sequence of the I-xMpeMI target site

<400> SEQUENCE: 5

tagataacca taagtgctaa t                                                21
```

-continued

<210> SEQ ID NO 6
<211> LENGTH: 22
<212> TYPE: DNA
<213> ORGANISM: Artificial Sequence
<220> FEATURE:
<223> OTHER INFORMATION: Sequence of the I-PanMI target site

<400> SEQUENCE: 6
gctcctcata atccttatca ag 22

<210> SEQ ID NO 7
<211> LENGTH: 24
<212> TYPE: DNA
<213> ORGANISM: Artificial Sequence
<220> FEATURE:
<223> OTHER INFORMATION: Sequence of the I-CreI target site

<400> SEQUENCE: 7
tcaaaacgtc gtgagacagt ttgg 24

<210> SEQ ID NO 8
<211> LENGTH: 22
<212> TYPE: DNA
<213> ORGANISM: Artificial Sequence
<220> FEATURE:
<223> OTHER INFORMATION: Sequence of the I-OnuI target site

<400> SEQUENCE: 8
tttccactta ttcaaccttt ta 22

<210> SEQ ID NO 9
<211> LENGTH: 22
<212> TYPE: DNA
<213> ORGANISM: Artificial Sequence
<220> FEATURE:
<223> OTHER INFORMATION: Sequence of the I-HjeMI target site

<400> SEQUENCE: 9
ttgaggaggt ttctctgtta at 22

<210> SEQ ID NO 10
<211> LENGTH: 20
<212> TYPE: DNA
<213> ORGANISM: Artificial Sequence
<220> FEATURE:
<223> OTHER INFORMATION: Sequence of the I-AniI target site

<400> SEQUENCE: 10
tgaggaggtt tctctgtaaa 20

<210> SEQ ID NO 11
<211> LENGTH: 53
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 11
taggtcaggg ttcacactag ttagggtaat acctgcaggt tgccggtggt gca 53

<210> SEQ ID NO 12
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 12
taggtcaggg ttcacactag ttagggataa cagggtaata cctgcaggtt gccggtggtg 60
ca 62

<210> SEQ ID NO 13
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 13
taggtcaggg ttcacactag ttagggataa cagggtaata cctgcaggtt gccggtggtg 60
ca 62

<210> SEQ ID NO 14
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 14
taggtcaggg ttcacactag ttagggataa cagggtaata cctgcaggtt gccggtggtg 60
ca 62

<210> SEQ ID NO 15
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 15
taggtcaggg ttcacactag ttagggataa cagggtaata cctgcaggtt gccggtggtg 60
ca 62

<210> SEQ ID NO 16
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 16
taggtcaggg ttcacactag ttagggataa cagggtaata cctgcaggtt gccggtggtg 60
ca 62

<210> SEQ ID NO 17
<211> LENGTH: 56
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 17

-continued taggtcaggg ttcacactag ataacagggt aatacctgca ggttgccggt ggtgca 56

<210> SEQ ID NO 18
<211> LENGTH: 61
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 18
taggtcaggg ttcacactag ttagggatac agggtaatac ctgcaggttg ccggtggtgc 60
a 61

<210> SEQ ID NO 19
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 19
taggtcaggg ttcacactag ttagggataa cagggtaata cctgcaggtt gccggtggtg 60
ca 62

<210> SEQ ID NO 20
<211> LENGTH: 53
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 20
taggtcaggg ttcacactag ttagggtaat acctgcaggt tgccggtggt gca 53

<210> SEQ ID NO 21
<211> LENGTH: 47
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 21
taggtcaggg ttcacactag ttagggatgc aggttgccgg tggtgca 47

<210> SEQ ID NO 22
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 22
taggtcaggg ttcacactag ttagggataa cagggtaata cctgcaggtt gccggtggtg 60
ca 62

<210> SEQ ID NO 23
<211> LENGTH: 43
<212> TYPE: DNA
<213> ORGANISM: Artificial Sequence
<220> FEATURE:

-continued

<223> OTHER INFORMATION: Sequence of amplicon surrounding the I-SceI target site treated with I-SceI.

<400> SEQUENCE: 23
taggtcaggg ttcacactat acctgcaggt tgccggtggt gca 43

<210> SEQ ID NO 24
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 24
taggtcaggg ttcacactag ttagggataa cagggtaata cctgcaggtt gccggtggtg 60
ca 62

<210> SEQ ID NO 25
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 25
taggtcaggg ttcacactag ttagggataa cagggtaata cctgcaggtt gccggtggtg 60
ca 62

<210> SEQ ID NO 26
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 26
taggtcaggg ttcacactag ttagggataa cagggtaata cctgcaggtt gccggtggtg 60
ca 62

<210> SEQ ID NO 27
<211> LENGTH: 55
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 27
taggtcaggg ttcacactag ttaggtaggg caacctgcag gttgccggtg gtgca 55

<210> SEQ ID NO 28
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 28
taggtcaggg ttcacactag ttagggataa cagggtaata cctgcaggtt gccggtggtg 60
ca 62

<210> SEQ ID NO 29
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 29
taggtcaggg ttcacactag ttagggataa cagggtaata cctgcaggtt gccggtggtg 60
ca 62

<210> SEQ ID NO 30
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 30
taggtcaggg ttcacactag ttagggataa cagggtaata cctgcaggtt gccggtggtg 60
ca 62

<210> SEQ ID NO 31
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 31
taggtcaggg ttcacactag ttagggataa cagggtaata cctgcaggtt gccggtggtg 60
ca 62

<210> SEQ ID NO 32
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 32
taggtcaggg ttcacactag ttagggataa cagggtaata cctgcaggtt gccggtggtg 60
ca 62

<210> SEQ ID NO 33
<211> LENGTH: 53
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 33
taggtcaggg ttcacactag ttagggtaat acctgcaggt tgccggtggt gca 53

<210> SEQ ID NO 34
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 34
taggtcaggg ttcacactag ttagggataa cagggtaata cctgcaggtt gccggtggtg 60
ca 62

<210> SEQ ID NO 35
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 35
taggtcaggg ttcacactag ttagggataa cagggtaata cctgcaggtt gccggtggtg 60
ca 62

<210> SEQ ID NO 36
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 36
taggtcaggg ttcacactag ttagggataa cagggtaata cctgcaggtt gccggtggtg 60
ca 62

<210> SEQ ID NO 37
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 37
taggtcaggg ttcacactag ttagggataa cagggtaata cctgcaggtt gccggtggtg 60
ca 62

<210> SEQ ID NO 38
<211> LENGTH: 55
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 38
taggtcaggg ttcacactag ttagggataa ctacctgcag gttgccggtg gtgca 55

<210> SEQ ID NO 39
<211> LENGTH: 62
<212> TYPE: DNA
<213> ORGANISM: Artificial Sequence
<220> FEATURE:
<223> OTHER INFORMATION: Sequence of amplicon surrounding the I-SceI target site treated with I-SceI.

<400> SEQUENCE: 39

-continued taggtcaggg ttcacactag ttagggataa cagggtaata cctgcaggtt gccggtggtg 60
ca 62

<210> SEQ ID NO 40
<211> LENGTH: 55
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 40
taggtcaggg ttcacactaa taacagggta atacctgcag gttgccggtg gtgca 55

<210> SEQ ID NO 41
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 41
taggtcaggg ttcacactag ttagggataa cagggtaata cctgctggtt gccggtggtg 60
ca 62

<210> SEQ ID NO 42
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 42
taggtcaggg ttcacactag ttagggataa cagggtaata cctgcaggtt gccggtggtg 60
ca 62

<210> SEQ ID NO 43
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 43
taggtcaggg ttcacactag ttagggataa cagggtaata cctgcaggtt gccggtggtg 60
ca 62

<210> SEQ ID NO 44
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 44
taggtcaggg ttcacactag ttagggtaat acctgcaagt tgccggtggt gcc 53

<210> SEQ ID NO 45
<211> LENGTH: 62
<212> TYPE: DNA

-continued

<213> ORGANISM: Artificial Sequence
<220> FEATURE:
<223> OTHER INFORMATION: Sequence of amplicon surrounding the I-SceI
target site treated with I-SceI.

<400> SEQUENCE: 45
taggtcaggg ttcacactag ttagggataa cagggtaata cctgcaggtt gccggtggtg 60
ca 62

<210> SEQ ID NO 46
<211> LENGTH: 61
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 46
taggtcaggg ttcacactag ttaggataac agggtaatac ctgcaggttg ccggtggtgc 60
a 61

<210> SEQ ID NO 47
<211> LENGTH: 61
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 47
taggtcaggg ttcacactag ttaggataac agggtaatac ctgcaggttg ccggtggtgc 60
a 61

<210> SEQ ID NO 48
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 48
taggtcaggg ttcacactag ttagggataa cagggtaata cctgcaggtt gccggtggtg 60
ca 62

<210> SEQ ID NO 49
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 49
taggtcaggg ttcacactag ttagggataa cagggtaata cctgcaggtt gccggtggtg 60
ca 62

<210> SEQ ID NO 50
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 50
taggtcaggg ttcacactag ttagggataa cagggtaata cctgcaggtt gccggtggtg 60
ca 62

<210> SEQ ID NO 51
<211> LENGTH: 61
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 51
taggtcaggg ttcacactag ttaggataac agggtaatac ctgcaggttg ccggtggtgc 60
a 61

<210> SEQ ID NO 52
<211> LENGTH: 56
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 52
taggtcaggg ttcacactag ataacagggt aatacctgca ggttgccggt ggtgca 56

<210> SEQ ID NO 53
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 53
taggtcaggg ttcacactag ttagggataa cagggtaata cctgcaggtt accggtggtg 60
ca 62

<210> SEQ ID NO 54
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 54
taggtcaggg ttcacactag ttagggataa cagggtaata cctgcaggtt gccggtggtg 60
ca 62

<210> SEQ ID NO 55
<211> LENGTH: 62
<212> TYPE: DNA
<213> ORGANISM: Artificial Sequence
<220> FEATURE:
<223> OTHER INFORMATION: Sequence of amplicon surrounding the I-SceI
target site treated with I-SceI.

<400> SEQUENCE: 55
taggtcaggg ttcacactag ttagggataa cagggtaata catgcaggtt gccggtggtg 60
ca 62

<210> SEQ ID NO 56
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 56
taggtcaggg ttcacactag ttagggataa cagggtaata cctgcaggtt gccggtggtg     60
ca                                                                    62

<210> SEQ ID NO 57
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 57
taggtcaggg ttcacactag ttagggataa cagggtaata cctgcaggtt gccggtggtg     60
ca                                                                    62

<210> SEQ ID NO 58
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 58
ccgtaggtca gggttcacac tagttaggga taacagggta atacctgcag gttgccggtg     60
gt                                                                    62

<210> SEQ ID NO 59
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 59
ccgtaggtca gggttcacac tagttaggga acagggtaat acctgcaggt tgccggtggt     60

<210> SEQ ID NO 60
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 60
ccgtaggtca gggttcacac tagttagggc agggtaatac ctgcaggttg ccggtggt       58

<210> SEQ ID NO 61
<211> LENGTH: 60
<212> TYPE: DNA
<213> ORGANISM: Artificial Sequence
<220> FEATURE:
<223> OTHER INFORMATION: Sequence of amplicon surrounding the I-SceI -continued target site treated with I-SceI and Trex2.

<400> SEQUENCE: 61
ccgtaggtca gggttcacac tagttaggga acagggtaat acctgcaggt tgccggtggt 60

<210> SEQ ID NO 62
<211> LENGTH: 53
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 62
ccgtaggtca gggttcacac tagtcagggt aatacctgca ggttgccggt ggt 53

<210> SEQ ID NO 63
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 63
ccgtaggtca gggttcacac tagttagggc agggtaatac ctgcaggttg ccggtggt 58

<210> SEQ ID NO 64
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 64
ccgtaggtca gggttcacac tagttaggga acagggtaat acctgcaggt tgccggtggt 60

<210> SEQ ID NO 65
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 65
ccgtaggtca gggttcacac tagttaggga acagggtaat acctgcaggt tgccggtggt 60

<210> SEQ ID NO 66
<211> LENGTH: 53
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 66
ccgtaggtca gggttcacac tagttagggt aatacctgca ggttgccggt ggt 53

<210> SEQ ID NO 67
<211> LENGTH: 54
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 67
ccgtaggtca gggttcacac tagttagggg taatacctgc aggttgccgg tggt 54

<210> SEQ ID NO 68
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 68
ccgtaggtca gggttcacac tagttaggga acagggtaat acctgcaggt tgccggtggt 60

<210> SEQ ID NO 69
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 69
ccgtaggtca gggttcacac tagttaggga acagggtaat acctgcaggt tgccggtggt 60

<210> SEQ ID NO 70
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 70
ccgtaggtca gggttcacac tagttagggc agggtaatac ctgcaggttg ccggtggt 58

<210> SEQ ID NO 71
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 71
ccgtaggtca gggttcacac tagttagggc agggtaatac ctgcaggttg ccggtggt 58

<210> SEQ ID NO 72
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 72
ccgtaggtca gggttcacac tagttaggga acagggtaat acctgcaggt tgccggtggt 60

<210> SEQ ID NO 73
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 73
ccgtaggtca gggttcacac tagttagggc agggtaatac ctgcaggttg ccggtggt 58

<210> SEQ ID NO 74
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 74
ccgtaggtca gggttcacac tagttaggga acagggtaat acctgcaggt tgccggtggt 60

<210> SEQ ID NO 75
<211> LENGTH: 59
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 75
ccgtaggtca gggttcacac tagttaggga cagggtaata cctgcaggtt gccggtggt 59

<210> SEQ ID NO 76
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 76
ccgtaggtca gggttcacac tagttagggc aggtaatacc tgcaggtttg ccggtggt 58

<210> SEQ ID NO 77
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 77
ccgtaggtca gggttcacac tagttaggga acagggtaat acctgcaggt tgccggtggt 60

<210> SEQ ID NO 78
<211> LENGTH: 59
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 78
ccgtaggtca gggttcacac tagttaggga cagggtaata cctgcaggtt gccggtggt 59

<210> SEQ ID NO 79
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 79
ccgtaggtca gggttcacac tagttaggga acagggtaat acctgcaggt tgccggtggt 60

<210> SEQ ID NO 80
<211> LENGTH: 59
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 80
ccgtaggtca gggttcacac tagttaggga cagggtaata cctgcaggtt gccggtggt 59

<210> SEQ ID NO 81
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 81
ccgtaggtca gggttcacac tagttaggga acagggtaat acctgcaggt tgccggtggt 60

<210> SEQ ID NO 82
<211> LENGTH: 54
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 82
ccgtaggtca gggttcacac tagttagggg taatacctgc aggttgccgg tggt 54

<210> SEQ ID NO 83
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 83
ccgtaggtca gggttcacac tagttaggga acagggtaat acctgcaggt tgccggtggt 60

<210> SEQ ID NO 84
<211> LENGTH: 55
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 84
ccgtaggtca gggttcacac tagttagggg gtaatacctg caggttgccg gtggt 55

<210> SEQ ID NO 85
<211> LENGTH: 54
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 85

-continued ccgtaggtca gggttcacac tagttagggg taatacctgc aggttgccgg tggt 54

<210> SEQ ID NO 86
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 86
caataggtca gggttcacac tagttaggga acagggtaat acctgcaggt tgccggtggt 60

<210> SEQ ID NO 87
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 87
ccgtaggtca gggttcacac tagttaggga acagggtaat acctgcaggt tgccggtggt 60

<210> SEQ ID NO 88
<211> LENGTH: 55
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 88
ccgtaggtca gggttcacac tagttagggg gtaatacctg caggttgccg gtggt 55

<210> SEQ ID NO 89
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 89
ccgtaggtca gggttcacac tagttagggc agggtaatac ctgcaggttg ccggtggt 58

<210> SEQ ID NO 90
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 90
ccgtaggtca gggttcacac tagttagggc agggtaatac ctgcaggttg ccggtggt 58

<210> SEQ ID NO 91
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 91
ccgtaggtca gggttcacac tagttagggc agggtaatac ctgcaggttg ccggtggt 58

<210> SEQ ID NO 92
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 92
ccgtgggtca gggttcacac tagttagggc agggtaatac ctgcaggttg ccggtggt 58

<210> SEQ ID NO 93
<211> LENGTH: 59
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 93
ccgtaggtca gggttcacac tagttaggga cagggtaata cctgcaggtt gccggtggt 59

<210> SEQ ID NO 94
<211> LENGTH: 59
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 94
ccgtaggtca gggttcacac tagttaggga cagggtaata cctgcaggtt gccggtggt 59

<210> SEQ ID NO 95
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 95
ccgtaggtca gggttcacac tagttagggc agggtaatac ctgcaggttg ccggtggt 58

<210> SEQ ID NO 96
<211> LENGTH: 60
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 96
ccgtaggtca gggttcacac tagttaggga acagggtaat acctgcaggt tgccggtggt 60

<210> SEQ ID NO 97
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 97
cagggtaata cctgcaggtt gccggtggtc agggtaatac ctgcaggttg ccggtggt 58

<210> SEQ ID NO 98
<211> LENGTH: 54
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 98
cagggtaata cctgcaggtt gccggtggtg taatacctgc aggttgccgg tggt 54

<210> SEQ ID NO 99
<211> LENGTH: 58
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 99
cagggtaata cctgcaggtt gccggtggtc agggtaatac ctgcaggttg ccggtggt 58

<210> SEQ ID NO 100
<211> LENGTH: 57
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 100
ccgtaggtca gggttcacac tagttaggga gggtaatacc tgcaggttgc cggtggt 57

<210> SEQ ID NO 101
<211> LENGTH: 58
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 101
ccgtaggtca gggttcacac tagttagggc agggtaatac ctgcaggttg ccggtggt 58

<210> SEQ ID NO 102
<211> LENGTH: 60
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 102
ccgtaggtca gggttcacac tagttaggga acagggtaat acctgcaggt tgccggtggt 60

<210> SEQ ID NO 103
<211> LENGTH: 57
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 103
ccgtaggtca gggttcacac tagttaggca gggtaatacc tgcaggttgc cggtggt 57

<210> SEQ ID NO 104
<211> LENGTH: 53
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 104
ccgtaggtca gggttcacac tagttagggt aatacctgca ggttgccggt ggt 53

<210> SEQ ID NO 105
<211> LENGTH: 53
<212> TYPE: DNA
<213> ORGANISM: Artificial Sequence
<220> FEATURE:
<223> OTHER INFORMATION: Sequence of amplicon surrounding the I-SceI
target site treated with I-SceI and Trex2.

<400> SEQUENCE: 105
ccgtaggtca gggttcacac tagttagggt aatacctgca ggttgccggt ggt 53

<210> SEQ ID NO 106
<211> LENGTH: 18
<212> TYPE: DNA
<213> ORGANISM: Artificial Sequence
<220> FEATURE:
<223> OTHER INFORMATION: I-SceI target site 5'-3'

<400> SEQUENCE: 106
tagggataac agggtaat 18

<210> SEQ ID NO 107
<211> LENGTH: 18
<212> TYPE: DNA
<213> ORGANISM: Artificial Sequence
<220> FEATURE:
<223> OTHER INFORMATION: I-SceI target site 3'-5'

<400> SEQUENCE: 107
attaccctgt tatcccta 18

<210> SEQ ID NO 108
<211> LENGTH: 24
<212> TYPE: DNA
<213> ORGANISM: Artificial Sequence
<220> FEATURE:
<223> OTHER INFORMATION: VF2468 target site 5'-3'

<400> SEQUENCE: 108
gagcagcgtc ttcgagagtg agga 24

<210> SEQ ID NO 109
<211> LENGTH: 24
<212> TYPE: DNA
<213> ORGANISM: Artificial Sequence
<220> FEATURE:
<223> OTHER INFORMATION: VF2468 target site 3'-5'

<400> SEQUENCE: 109
tcctcactct cgaagacgct gctc 24

<210> SEQ ID NO 110
<211> LENGTH: 7611
<212> TYPE: DNA
<213> ORGANISM: Artificial Sequence
<220> FEATURE:

-continued

<223> OTHER INFORMATION: Plasmid pCVL.SFFV.HA.NLS.SceOpt.IRES.mTagBFP

<400> SEQUENCE: 110

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta gaaggagaga gatgggtgcg agagcgtcag tattaagcgg     600
gggagaatta gatcgcgatg ggaaaaaatt cggttaaggc cagggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga agagcaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctggggatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga aagaatagta    1860
gacataatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
```

-continued

```
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcaag aacatcaaga agaaccaggt   2460
catgaacctg ggccccaaca gcaagctgct gaaggagtac aagagccagc tgatcgagct   2520
gaacatcgag cagttcgagg ccggcatcgg cctgatcctg ggcgacgcct acatcaggag   2580
cagggacgag ggcaagacct actgcatgca gttcgagtgg aagaacaagg cctacatgga   2640
ccacgtgtgc ctgctgtacg accagtgggt gctgagcccc ccccacaaga aggagagggt   2700
gaaccacctg ggcaacctgg tcatcacctg gggcgcccag accttcaagc accaggcctt   2760
caacaagctg gccaacctgt tcatcgtgaa caacaagaag accatcccca acaacctggt   2820
ggagaactac ctgaccccca tgagcctggc ctactggttc atggacgacg gcggcaagtg   2880
ggactacaac aagaacagca ccaacaagag catcgtgctg aacacccaga gcttcacctt   2940
cgaggaggtg gagtacctgg tgaagggcct gaggaacaag ttccagctga actgctacgt   3000
gaagatcaac aagaacaagc ccatcatcta catcgacagc atgagctacc tgatcttcta   3060
caacctgatc aagccctacc tgatccccca gatgatgtac aagctgccca acaccatcag   3120
cagcgagacc ttcctgaagt gacctgcagg tcgagcatgc atctagggcg gccaattccg   3180
cccctctccc tcccccccc ctaacgttac tggccgaagc cgcttggaat aaggccggtg   3240
tgcgtttgtc tatatgtgat tttccaccat attgccgtct tttggcaatg tgagggcccg   3300
gaaacctggc cctgtcttct tgacgagcat tcctaggggt ctttcccctc tcgccaaagg   3360
aatgcaaggt ctgttgaatg tcgtgaagga agcagttcct ctggaagctt cttgaagaca   3420
aacaacgtct gtagcgaccc tttgcaggca gcggaacccc ccacctggcg acaggtgcct   3480
ctgcggccaa aagccacgtg tataagatac acctgcaaag gcggcacaac cccagtgcca   3540
cgttgtgagt tggatagttg tggaaagagt caaatggctc tcctcaagcg tattcaacaa   3600
ggggctgaag gatgcccaga aggtacccca ttgtatggga tctgatctgg ggcctcggtg   3660
cacatgcttt acatgtgttt agtcgaggtt aaaaaaacgt ctaggccccc cgaaccacgg   3720
ggacgtggtt ttcctttgaa aaacacgatg ataagcttgc cacaaccctt accggtcgcc   3780
accatgagcg agctgattaa ggagaacatg cacatgaagc tgtacatgga gggcaccgtg   3840
gacaaccatc acttcaagtg cacatccgag ggcgaaggca agccctacga gggcacccag   3900
accatgagaa tcaaggtggt cgagggcggc cctctcccct tcgccttcga catcctggct   3960
actagcttcc tctacggcag caagaccttc atcaaccaca cccagggcat ccccgacttc   4020
ttcaagcagt ccttccctga gggcttcaca tgggagagag tcaccacata cgaagacggg   4080
ggcgtgctga ccgctaccca ggacaccagc ctccaggacg gctgcctcat ctacaacgtc   4140
aagatcagag gggtgaactt cacatccaac ggccctgtga tgcagaagaa aacactcggc   4200
tgggaggcct tcaccgagac gctgtacccc gctgacggcg gcctggaagg cagaaacgac   4260
atggccctga agctcgtggg cgggagccat ctgatcgcaa acatcaagac cacatataga   4320
tccaagaaac ccgctaagaa cctcaagatg cctggcgtct actatgtgga ctacagactg   4380
gaaagaatca aggaggccaa caacgagacc tacgtcgagc agcacgaggt ggcagtggcc   4440
agatactgcg acctccctag caaactgggg cacaagctta attgattcta gagtcgaccg   4500
agcatcttac cgccatttat acccatattt gttctgtttt tcttgatttg ggtatacatt   4560
taaatgttaa tagaacaaaa tggtggggca atcatttaca tttttaggga tatgtaatta   4620
```

-continued ctagttcagg tgtattgcca caagacaaac atgttaagaa actttcccgt tatttacgct 4680
ctgttcctgt taatcaacct ctggattaca aaatttgtga aagattgact gatattctta 4740
actatgttgc tccttttacg ctgtgtggat atgctgcttt atagcctctg tatctagcta 4800
ttgcttcccg tacggctttc gttttctcct ccttgtataa atcctggttg ctgtctcttt 4860
tagaggagtt gtggcccgtt gtccgtcaac gtggcgtggt gtgctctgtg tttgctgacg 4920
caacccccac tggctggggc attgccacca cctgtcaact cctttctggg actttcgctt 4980
tccccctccc gatcgccacg gcagaactca tcgccgcctg ccttgcccgc tgctggacag 5040
gggctaggtt gctgggcact gataattccg tggtgttgtc atcggtacct ttttaaaaga 5100
aaagggggga ctggaagggc taattcactc ccaacgaaga caagatatca taacttcgta 5160
tagcatacat tatacgaagt tataatttat ttgtgaaatt tgtgatgcta ttgctttatt 5220
tgtaaccata tgtttatttg tgaaatttgt gatgctattg ctttatttgt aaccattgct 5280
ttttgcttgt actgggtctc tctggttaga ccagatctga gcctgggagc tctctggcta 5340
actagggaac ccactgctta agcctcaata aagcttgcct cgaccagcct cgactgtgcc 5400
ttctagttgc cagccatctg ttgtttgccc ctcccccgtg ccttccttga ccctggaagg 5460
tgccactccc actgtccttt cctaataaaa tgaggaaatt gcatcgcatt gtctgagtag 5520
gtgtcattct attctggggg gtggggtggg gcaggacagc aagggggagg attgggaaga 5580
caatagcagg catgctgggg atgcggtggg ctctatggcc tgcagctgca ttaatgaatc 5640
ggccaacgcg cggggagagg cggtttgcgt attgggcgct cttccgcttc ctcgctcact 5700
gactcgctgc gctcggtcgt tcggctgcgg cgagcggtat cagctcactc aaaggcggta 5760
atacggttat ccacagaatc aggggataac gcaggaaaga acatgtgagc aaaaggccag 5820
caaaaggcca ggaaccgtaa aaaggccgcg ttgctggcgt ttttccatag gctccgcccc 5880
cctgacgagc atcacaaaaa tcgacgctca agtcagaggt ggcgaaaccc gacaggacta 5940
taaagatacc aggcgtttcc ccctggaagc tccctcgtgc gctctcctgt tccgaccctg 6000
ccgcttaccg gatacctgtc cgcctttctc ccttcgggaa gcgtggcgct ttctcatagc 6060
tcacgctgta ggtatctcag ttcggtgtag gtcgttcgct ccaagctggg ctgtgtgcac 6120
gaaccccccg ttcagcccga ccgctgcgcc ttatccggta actatcgtct tgagtccaac 6180
ccggtaagac acgacttatc gccactggca gcagccactg gtaacaggat tagcagagcg 6240
aggtatgtag gcggtgctac agagttcttg aagtggtggc ctaactacgg ctacactaga 6300
aggacagtat ttggtatctg cgctctgctg aagccagtta ccttcggaaa aagagttggt 6360
agctcttgat ccggcaaaca aaccaccgct ggtagcggtg gtttttttgt ttgcaagcag 6420
cagattacgc gcagaaaaaa aggatctcaa gaagatcctt tgatcttttc tacggggtct 6480
gacgctcagt ggaacgaaaa ctcacgttaa gggattttgg tcatgagatt atcaaaaagg 6540
atcttcacct agatcctttt aaattaaaaa tgaagtttta aatcaatcta aagtatatat 6600
gagtaaactt ggtctgacag ttaccaatgc ttaatcagtg aggcacctat ctcagcgatc 6660
tgtctatttc gttcatccat agttgcctga ctccccgtcg tgtagataac tacgatacgg 6720
gagggcttac catctggccc cagtgctgca atgataccgc gagacccacg ctcaccggct 6780
ccagatttat cagcaataaa ccagccagcc ggaagggccg agcgcagaag tggtcctgca 6840
actttatccg cctccatcca gtctattaat tgttgccggg aagctagagt aagtagttcg 6900
ccagttaata gtttgcgcaa cgttgttgcc attgctacag gcatcgtggt gtcacgctcg 6960
tcgtttggta tggcttcatt cagctccggt tcccaacgat caaggcgagt tacatgatcc 7020

```
cccatgttgt gcaaaaaagc ggttagctcc ttcggtcctc cgatcgttgt cagaagtaag   7080

ttggccgcag tgttatcact catggttatg gcagcactgc ataattctct tactgtcatg   7140

ccatccgtaa gatgcttttc tgtgactggt gagtactcaa ccaagtcatt ctgagaatag   7200

tgtatgcggc gaccgagttg ctcttgcccg gcgtcaatac gggataatac cgcgccacat   7260

agcagaactt taaaagtgct catcattgga aaacgttctt cggggcgaaa actctcaagg   7320

atcttaccgc tgttgagatc cagttcgatg taacccactc gtgcacccaa ctgatcttca   7380

gcatctttta ctttcaccag cgtttctggg tgagcaaaaa caggaaggca aaatgccgca   7440

aaaaagggaa taagggcgac acggaaatgt tgaatactca tactcttcct ttttcaatat   7500

tattgaagca tttatcaggg ttattgtctc atgagcggat acatatttga atgtatttag   7560

aaaaataaac aaataggggt tccgcgcaca tttccccgaa aagtgccacc t            7611
```

<210> SEQ ID NO 111
<211> LENGTH: 7611
<212> TYPE: DNA
<213> ORGANISM: Artificial Sequence
<220> FEATURE:
<223> OTHER INFORMATION: Plasmid
pCVL.SFFV.HA.NLS.SceOptD44A.IRES.mTagBFP

<400> SEQUENCE: 111

```
gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc ctgatcttca gacctggagg aggagatatg    960

agggacaatt ggagaagtga attatataaa tataaagtag taaaaattga accattagga   1020

gtagcaccca ccaaggcaaa gagaagagtg gtgcagagag aaaaaagagc agtgggaata   1080

ggagctttgt tccttgggtt cttgggagca gcaggaagca ctatgggcgc agcgtcaatg   1140

acgctgacgg tacaggccag acaattattg tctggtatag tgcagcagca gaacaatttg   1200

ctgagggcta ttgaggcgca acagcatctg ttgcaactca cagtctgggg catcaagcag   1260

ctccaggcaa gaatcctggc tgtggaaaga tacctaaagg atcaacagct cctggggatt   1320

tggggttgct ctggaaaact catttgcacc actgctgtgc cttggaatgc tagttggagt   1380

aatgaatctc tggaacagat ttggaatcac acgacctgga tggagtggga cagagaaatt   1440
```

-continued

```
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcaag aacatcaaga agaaccaggt   2460
catgaacctg ggccccaaca gcaagctgct gaaggagtac aagagccagc tgatcgagct   2520
gaacatcgag cagttcgagg ccggcatcgg cctgatcctg ggcgctgcct acatcaggag   2580
cagggacgag ggcaagacct actgcatgca gttcgagtgg aagaacaagg cctacatgga   2640
ccacgtgtgc ctgctgtacg accagtgggt gctgagcccc ccccacaaga aggagagggt   2700
gaaccacctg ggcaacctgg tcatcacctg gggcgcccag accttcaagc accaggcctt   2760
caacaagctg gccaacctgt tcatcgtgaa caacaagaag accatcccca acaacctggt   2820
ggagaactac ctgaccccca tgagcctggc ctactggttc atggacgacg gcggcaagtg   2880
ggactacaac aagaacagca ccaacaagag catcgtgctg aacacccaga gcttcacctt   2940
cgaggaggtg gagtacctgg tgaagggcct gaggaacaag ttccagctga actgctacgt   3000
gaagatcaac aagaacaagc ccatcatcta catcgacagc atgagctacc tgatcttcta   3060
caacctgatc aagccctacc tgatccccca gatgatgtac aagctgccca acaccatcag   3120
cagcgagacc ttcctgaagt gacctgcagg tcgagcatgc atctagggcg gccaattccg   3180
cccctctccc tccccccccc ctaacgttac tggccgaagc cgcttggaat aaggccggtg   3240
tgcgtttgtc tatatgtgat tttccaccat attgccgtct tttggcaatg tgagggcccg   3300
gaaacctggc cctgtcttct tgacgagcat tcctaggggt ctttcccctc tcgccaaagg   3360
aatgcaaggt ctgttgaatg tcgtgaagga agcagttcct ctggaagctt cttgaagaca   3420
aacaacgtct gtagcgaccc tttgcaggca gcggaacccc ccacctggcg acaggtgcct   3480
ctgcggccaa aagccacgtg tataagatac acctgcaaag gcggcacaac cccagtgcca   3540
cgttgtgagt tggatagttg tggaaagagt caaatggctc tcctcaagcg tattcaacaa   3600
ggggctgaag gatgcccaga aggtacccca ttgtatggga tctgatctgg ggcctcggtg   3660
cacatgcttt acatgtgttt agtcgaggtt aaaaaaacgt ctaggccccc cgaaccacgg   3720
ggacgtggtt ttcctttgaa aaacacgatg ataagcttgc cacaaccctt accggtcgcc   3780
```

-continued

```
accatgagcg agctgattaa ggagaacatg cacatgaagc tgtacatgga gggcaccgtg   3840
gacaaccatc acttcaagtg cacatccgag ggcgaaggca agccctacga gggcacccag   3900
accatgagaa tcaaggtggt cgagggcggc cctctcccct tcgccttcga catcctggct   3960
actagcttcc tctacggcag caagaccttc atcaaccaca cccagggcat ccccgacttc   4020
ttcaagcagt ccttccctga gggcttcaca tgggagagag tcaccacata cgaagacggg   4080
ggcgtgctga ccgctaccca ggacaccagc ctccaggacg gctgcctcat ctacaacgtc   4140
aagatcagag gggtgaactt cacatccaac ggccctgtga tgcagaagaa aacactcggc   4200
tgggaggcct tcaccgagac gctgtacccc gctgacggcg gcctggaagg cagaaacgac   4260
atggccctga agctcgtggg cgggagccat ctgatcgcaa acatcaagac cacatataga   4320
tccaagaaac ccgctaagaa cctcaagatg cctggcgtct actatgtgga ctacagactg   4380
gaaagaatca aggaggccaa caacgagacc tacgtcgagc agcacgaggt ggcagtggcc   4440
agatactgcg acctccctag caaactgggg cacaagctta attgattcta gagtcgaccg   4500
agcatcttac cgccatttat acccatattt gttctgtttt tcttgatttg ggtatacatt   4560
taaatgttaa tagaacaaaa tggtggggca atcatttaca tttttaggga tatgtaatta   4620
ctagttcagg tgtattgcca caagacaaac atgttaagaa actttcccgt tatttacgct   4680
ctgttcctgt taatcaacct ctggattaca aaatttgtga aagattgact gatattctta   4740
actatgttgc tccttttacg ctgtgtggat atgctgcttt atagcctctg tatctagcta   4800
ttgcttcccg tacggctttc gttttctcct ccttgtataa atcctggttg ctgtctcttt   4860
tagaggagtt gtggcccgtt gtccgtcaac gtggcgtggt gtgctctgtg tttgctgacg   4920
caacccccac tggctggggc attgccacca cctgtcaact cctttctggg actttcgctt   4980
tccccctccc gatcgccacg gcagaactca tcgccgcctg ccttgcccgc tgctggacag   5040
gggctaggtt gctgggcact gataattccg tggtgttgtc atcggtacct ttttaaaaga   5100
aaagggggga ctggaagggc taattcactc ccaacgaaga caagatatca taacttcgta   5160
tagcatacat tatacgaagt tataatttat ttgtgaaatt tgtgatgcta ttgctttatt   5220
tgtaaccata tgtttatttg tgaaatttgt gatgctattg ctttatttgt aaccattgct   5280
ttttgcttgt actgggtctc tctggttaga ccagatctga gcctgggagc tctctggcta   5340
actagggaac ccactgctta agcctcaata aagcttgcct cgaccagcct cgactgtgcc   5400
ttctagttgc cagccatctg ttgtttgccc ctcccccgtg ccttccttga ccctggaagg   5460
tgccactccc actgtccttt cctaataaaa tgaggaaatt gcatcgcatt gtctgagtag   5520
gtgtcattct attctggggg gtggggtggg gcaggacagc aagggggagg attgggaaga   5580
caatagcagg catgctgggg atgcggtggg ctctatggcc tgcagctgca ttaatgaatc   5640
ggccaacgcg cggggagagg cggtttgcgt attgggcgct cttccgcttc ctcgctcact   5700
gactcgctgc gctcggtcgt tcggctgcgg cgagcggtat cagctcactc aaaggcggta   5760
atacggttat ccacagaatc aggggataac gcaggaaaga acatgtgagc aaaaggccag   5820
caaaaggcca ggaaccgtaa aaaggccgcg ttgctggcgt ttttccatag gctccgcccc   5880
cctgacgagc atcacaaaaa tcgacgctca agtcagaggt ggcgaaaccc gacaggacta   5940
taaagatacc aggcgtttcc ccctggaagc tccctcgtgc gctctcctgt tccgaccctg   6000
ccgcttaccg gatacctgtc cgcctttctc ccttcgggaa gcgtggcgct ttctcatagc   6060
tcacgctgta ggtatctcag ttcggtgtag gtcgttcgct ccaagctggg ctgtgtgcac   6120
gaaccccccg ttcagcccga ccgctgcgcc ttatccggta actatcgtct tgagtccaac   6180
```

ccggtaagac acgacttatc gccactggca gcagccactg gtaacaggat tagcagagcg 6240
aggtatgtag gcggtgctac agagttcttg aagtggtggc ctaactacgg ctacactaga 6300
aggacagtat ttggtatctg cgctctgctg aagccagtta ccttcggaaa aagagttggt 6360
agctcttgat ccggcaaaca aaccaccgct ggtagcggtg gtttttttgt ttgcaagcag 6420
cagattacgc gcagaaaaaa aggatctcaa gaagatcctt tgatcttttc tacggggtct 6480
gacgctcagt ggaacgaaaa ctcacgttaa gggattttgg tcatgagatt atcaaaaagg 6540
atcttcacct agatcctttt aaattaaaaa tgaagtttta aatcaatcta aagtatatat 6600
gagtaaactt ggtctgacag ttaccaatgc ttaatcagtg aggcacctat ctcagcgatc 6660
tgtctatttc gttcatccat agttgcctga ctccccgtcg tgtagataac tacgatacgg 6720
gagggcttac catctggccc cagtgctgca atgataccgc gagacccacg ctcaccggct 6780
ccagatttat cagcaataaa ccagccagcc ggaagggccg agcgcagaag tggtcctgca 6840
actttatccg cctccatcca gtctattaat tgttgccggg aagctagagt aagtagttcg 6900
ccagttaata gtttgcgcaa cgttgttgcc attgctacag gcatcgtggt gtcacgctcg 6960
tcgtttggta tggcttcatt cagctccggt tcccaacgat caaggcgagt tacatgatcc 7020
cccatgttgt gcaaaaaagc ggttagctcc ttcggtcctc cgatcgttgt cagaagtaag 7080
ttggccgcag tgttatcact catggttatg gcagcactgc ataattctct tactgtcatg 7140
ccatccgtaa gatgcttttc tgtgactggt gagtactcaa ccaagtcatt ctgagaatag 7200
tgtatgcggc gaccgagttg ctcttgcccg gcgtcaatac gggataatac cgcgccacat 7260
agcagaactt taaaagtgct catcattgga aaacgttctt cggggcgaaa actctcaagg 7320
atcttaccgc tgttgagatc cagttcgatg taacccactc gtgcacccaa ctgatcttca 7380
gcatctttta ctttcaccag cgtttctggg tgagcaaaaa caggaaggca aaatgccgca 7440
aaaaagggaa taagggcgac acggaaatgt tgaatactca tactcttcct ttttcaatat 7500
tattgaagca tttatcaggg ttattgtctc atgagcggat acatatttga atgtatttag 7560
aaaaataaac aaataggggt tccgcgcaca tttccccgaa aagtgccacc t 7611

<210> SEQ ID NO 112
<211> LENGTH: 8394
<212> TYPE: DNA
<213> ORGANISM: Artificial Sequence
<220> FEATURE:
<223> OTHER INFORMATION: Plasmid
pCVL.SFFV.HA.NLS.Sce(Opt).T2A.Trex2.IRES.mTagBFP

<400> SEQUENCE: 112
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600

-continued

```
gggagaatta gatcgcgatg ggaaaaaatt cggttaaggc caggggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcaag aacatcaaga agaaccaggt   2460
catgaacctg ggccccaaca gcaagctgct gaaggagtac aagagccagc tgatcgagct   2520
gaacatcgag cagttcgagg ccggcatcgg cctgatcctg ggcgacgcct acatcaggag   2580
cagggacgag ggcaagacct actgcatgca gttcgagtgg aagaacaagg cctacatgga   2640
ccacgtgtgc ctgctgtacg accagtgggt gctgagcccc ccccacaaga aggagagggt   2700
gaaccacctg ggcaacctgg tcatcacctg gggcgcccag accttcaagc accaggcctt   2760
caacaagctg gccaacctgt tcatcgtgaa caacaagaag accatcccca acaacctggt   2820
ggagaactac ctgaccccca tgagcctggc ctactggttc atggacgacg gcggcaagtg   2880
ggactacaac aagaacagca ccaacaagag catcgtgctg aacacccaga gcttcacctt   2940
```

-continued

```
cgaggaggtg gagtacctgg tgaagggcct gaggaacaag ttccagctga actgctacgt   3000
gaagatcaac aagaacaagc ccatcatcta catcgacagc atgagctacc tgatcttcta   3060
caacctgatc aagccctacc tgatccccca gatgatgtac aagctgccca acaccatcag   3120
cagcgagacc ttcctgaagg gcggcggcgg atccggtgag ggcagaggaa gtcttctaac   3180
atgcggtgac gtggaggaga atccgggccc ctccggatct gagccacctc gggctgagac   3240
ctttgtattc ctggacctag aagccactgg gctcccaaac atggaccctg agattgcaga   3300
gatatccctt tttgctgttc accgctcttc cctggagaac ccagaacggg atgattctgg   3360
ttccttggtg ctgccccgtg ttctggacaa gctcacactg tgcatgtgcc cggagcgccc   3420
ctttactgcc aaggccagtg agattactgg tttgagcagc gaaagcctga tgcactgcgg   3480
gaaggctggt ttcaatggcg ctgtggtaag gacactgcag ggcttcctaa gccgccagga   3540
gggccccatc tgccttgtgg cccacaatgg cttcgattat gacttcccac tgctgtgcac   3600
ggagctacaa cgtctgggtg cccatctgcc ccaagacact gtctgcctgg acacactgcc   3660
tgcattgcgg ggcctggacc gtgctcacag ccacggcacc agggctcaag gccgcaaaag   3720
ctacagcctg gccagtctct tccaccgcta cttccaggct gaacccagtg ctgcccattc   3780
agcagaaggt gatgtgcaca ccctgcttct gatcttcctg catcgtgctc ctgagctgct   3840
cgcctgggca gatgagcagg cccgcagctg ggctcatatt gagcccatgt acgtgccacc   3900
tgatggtcca agcctcgaag cctgacctgc aggtcgagca tgcatctagg gcggccaatt   3960
ccgcccctct ccctcccccc cccctaacgt tactggccga agccgcttgg aataaggccg   4020
gtgtgcgttt gtctatatgt gattttccac catattgccg tcttttggca atgtgagggc   4080
ccggaaacct ggccctgtct tcttgacgag cattcctagg ggtctttccc ctctcgccaa   4140
aggaatgcaa ggtctgttga atgtcgtgaa ggaagcagtt cctctggaag cttcttgaag   4200
acaaacaacg tctgtagcga ccctttgcag gcagcggaac cccccacctg gcgacaggtg   4260
cctctgcggc caaaagccac gtgtataaga tacacctgca aaggcggcac aaccccagtg   4320
ccacgttgtg agttggatag ttgtggaaag agtcaaatgg ctctcctcaa gcgtattcaa   4380
caaggggctg aaggatgccc agaaggtacc ccattgtatg ggatctgatc tggggcctcg   4440
gtgcacatgc tttacatgtg tttagtcgag gttaaaaaaa cgtctaggcc ccccgaacca   4500
cggggacgtg gttttccttt gaaaaacacg atgataagct tgccacaacc cttaccggtc   4560
gccaccatga gcgagctgat taaggagaac atgcacatga agctgtacat ggagggcacc   4620
gtggacaacc atcacttcaa gtgcacatcc gagggcgaag gcaagcccta cgagggcacc   4680
cagaccatga gaatcaaggt ggtcgagggc ggccctctcc ccttcgcctt cgacatcctg   4740
gctactagct tcctctacgg cagcaagacc ttcatcaacc acacccaggg catccccgac   4800
ttcttcaagc agtccttccc tgagggcttc acatgggaga gagtcaccac atacgaagac   4860
gggggcgtgc tgaccgctac ccaggacacc agcctccagg acggctgcct catctacaac   4920
gtcaagatca gaggggtgaa cttcacatcc aacggccctg tgatgcagaa gaaaacactc   4980
ggctgggagg ccttcaccga gacgctgtac cccgctgacg gcggcctgga aggcagaaac   5040
gacatggccc tgaagctcgt gggcgggagc catctgatcg caaacatcaa gaccacatat   5100
agatccaaga aacccgctaa gaacctcaag atgcctggcg tctactatgt ggactacaga   5160
ctggaaagaa tcaaggaggc caacaacgag acctacgtcg agcagcacga ggtggcagtg   5220
gccagatact gcgacctccc tagcaaactg ggcacaagc ttaattgatt ctagagtcga   5280
ccgagcatct taccgccatt tatacccata tttgttctgt tttcttgat ttgggtatac   5340
```

atttaaatgt taatagaaca aaatggtggg gcaatcattt acatttttag ggatatgtaa 5400
ttactagttc aggtgtattg ccacaagaca aacatgttaa gaaactttcc cgttatttac 5460
gctctgttcc tgttaatcaa cctctggatt acaaaatttg tgaaagattg actgatattc 5520
ttaactatgt tgctcctttt acgctgtgtg gatatgctgc tttatagcct ctgtatctag 5580
ctattgcttc ccgtacggct ttcgttttct cctccttgta taaatcctgg ttgctgtctc 5640
ttttagagga gttgtggccc gttgtccgtc aacgtggcgt ggtgtgctct gtgtttgctg 5700
acgcaacccc cactggctgg ggcattgcca ccacctgtca actcctttct gggactttcg 5760
ctttccccct cccgatcgcc acggcagaac tcatcgccgc ctgccttgcc cgctgctgga 5820
caggggctag gttgctgggc actgataatt ccgtggtgtt gtcatcggta ccttttttaaa 5880
agaaaagggg ggactggaag ggctaattca ctcccaacga agacaagata tcataacttc 5940
gtatagcata cattatacga agttataatt tatttgtgaa atttgtgatg ctattgcttt 6000
atttgtaacc atatgtttat ttgtgaaatt tgtgatgcta ttgctttatt tgtaaccatt 6060
gctttttgct tgtactgggt ctctctggtt agaccagatc tgagcctggg agctctctgg 6120
ctaactaggg aacccactgc ttaagcctca ataaagcttg cctcgaccag cctcgactgt 6180
gccttctagt tgccagccat ctgttgtttg cccctccccc gtgccttcct tgaccctgga 6240
aggtgccact cccactgtcc tttcctaata aaatgaggaa attgcatcgc attgtctgag 6300
taggtgtcat tctattctgg ggggtggggt ggggcaggac agcaaggggg aggattggga 6360
agacaatagc aggcatgctg gggatgcggt gggctctatg gcctgcagct gcattaatga 6420
atcggccaac gcgcggggag aggcggtttg cgtattgggc gctcttccgc ttcctcgctc 6480
actgactcgc tgcgctcggt cgttcggctg cggcgagcgg tatcagctca ctcaaaggcg 6540
gtaatacggt tatccacaga atcaggggat aacgcaggaa agaacatgtg agcaaaaggc 6600
cagcaaaagg ccaggaaccg taaaaaggcc gcgttgctgg cgtttttcca taggctccgc 6660
cccccctgacg agcatcacaa aaatcgacgc tcaagtcaga ggtggcgaaa cccgacagga 6720
ctataaagat accaggcgtt tccccctgga agctccctcg tgcgctctcc tgttccgacc 6780
ctgccgctta ccggatacct gtccgccttt ctcccttcgg gaagcgtggc gctttctcat 6840
agctcacgct gtaggtatct cagttcggtg taggtcgttc gctccaagct gggctgtgtg 6900
cacgaacccc ccgttcagcc cgaccgctgc gccttatccg gtaactatcg tcttgagtcc 6960
aacccggtaa gacacgactt atcgccactg gcagcagcca ctggtaacag gattagcaga 7020
gcgaggtatg taggcggtgc tacagagttc ttgaagtggt ggcctaacta cggctacact 7080
agaaggacag tatttggtat ctgcgctctg ctgaagccag ttaccttcgg aaaaagagtt 7140
ggtagctctt gatccggcaa acaaaccacc gctggtagcg gtggtttttt tgtttgcaag 7200
cagcagatta cgcgcagaaa aaaaggatct caagaagatc ctttgatctt ttctacgggg 7260
tctgacgctc agtggaacga aaactcacgt taagggattt tggtcatgag attatcaaaa 7320
aggatcttca cctagatcct tttaaattaa aaatgaagtt ttaaatcaat ctaaagtata 7380
tatgagtaaa cttggtctga cagttaccaa tgcttaatca gtgaggcacc tatctcagcg 7440
atctgtctat ttcgttcatc catagttgcc tgactccccg tcgtgtagat aactacgata 7500
cgggagggct taccatctgg ccccagtgct gcaatgatac cgcgagaccc acgctcaccg 7560
gctccagatt tatcagcaat aaaccagcca gccggaaggg ccgagcgcag aagtggtcct 7620
gcaactttat ccgcctccat ccagtctatt aattgttgcc gggaagctag agtaagtagt 7680

```
tcgccagtta atagtttgcg caacgttgtt gccattgcta caggcatcgt ggtgtcacgc   7740

tcgtcgtttg gtatggcttc attcagctcc ggttcccaac gatcaaggcg agttacatga   7800

tcccccatgt tgtgcaaaaa agcggttagc tccttcggtc ctccgatcgt tgtcagaagt   7860

aagttggccg cagtgttatc actcatggtt atggcagcac tgcataattc tcttactgtc   7920

atgccatccg taagatgctt ttctgtgact ggtgagtact caaccaagtc attctgagaa   7980

tagtgtatgc ggcgaccgag ttgctcttgc ccggcgtcaa tacgggataa taccgcgcca   8040

catagcagaa ctttaaaagt gctcatcatt ggaaaacgtt cttcggggcg aaaactctca   8100

aggatcttac cgctgttgag atccagttcg atgtaaccca ctcgtgcacc caactgatct   8160

tcagcatctt ttactttcac cagcgtttct gggtgagcaa aaacaggaag gcaaaatgcc   8220

gcaaaaaagg gaataagggc gacacggaaa tgttgaatac tcatactctt cctttttcaa   8280

tattattgaa gcatttatca gggttattgt ctcatgagcg gatacatatt tgaatgtatt   8340

tagaaaaata aacaaatagg ggttccgcgc acatttcccc gaaaagtgcc acct         8394
```

<210> SEQ ID NO 113
<211> LENGTH: 8394
<212> TYPE: DNA
<213> ORGANISM: Artificial Sequence
<220> FEATURE:
<223> OTHER INFORMATION: Plasmid
pCVL.SFFV.HA.NLS.SceOptD44A.T2A.Trex2.IRES.mTagBFP

<400> SEQUENCE: 113

```
gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc ctgatcttca gacctggagg aggagatatg    960

agggacaatt ggagaagtga attatataaa tataaagtag taaaaattga accattagga   1020

gtagcaccca ccaaggcaaa gagaagagtg gtgcagagag aaaaaagagc agtgggaata   1080

ggagctttgt tccttgggtt cttgggagca gcaggaagca ctatgggcgc agcgtcaatg   1140

acgctgacgg tacaggccag acaattattg tctggtatag tgcagcagca gaacaatttg   1200

ctgagggcta ttgaggcgca acagcatctg ttgcaactca cagtctgggg catcaagcag   1260

ctccaggcaa gaatcctggc tgtggaaaga tacctaaagg atcaacagct cctggggatt   1320
```

-continued

```
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcaag aacatcaaga agaaccaggt   2460
catgaacctg ggccccaaca gcaagctgct gaaggagtac aagagccagc tgatcgagct   2520
gaacatcgag cagttcgagg ccggcatcgg cctgatcctg ggcgctgcct acatcaggag   2580
cagggacgag ggcaagacct actgcatgca gttcgagtgg aagaacaagg cctacatgga   2640
ccacgtgtgc ctgctgtacg accagtgggt gctgagcccc ccccacaaga aggagagggt   2700
gaaccacctg ggcaacctgg tcatcacctg ggcgcccag accttcaagc accaggcctt   2760
caacaagctg gccaacctgt tcatcgtgaa caacaagaag accatcccca acaacctggt   2820
ggagaactac ctgaccccca tgagcctggc ctactggttc atggacgacg gcggcaagtg   2880
ggactacaac aagaacagca ccaacaagag catcgtgctg aacacccaga gcttcacctt   2940
cgaggaggtg gagtacctgg tgaagggcct gaggaacaag ttccagctga actgctacgt   3000
gaagatcaac aagaacaagc ccatcatcta catcgacagc atgagctacc tgatcttcta   3060
caacctgatc aagccctacc tgatccccca gatgatgtac aagctgccca acaccatcag   3120
cagcgagacc ttcctgaagg gcggcggcgg atccggtgag ggcagaggaa gtcttctaac   3180
atgcggtgac gtggaggaga atccgggccc ctccggatct gagccacctc gggctgagac   3240
ctttgtattc ctggacctag aagccactgg gctcccaaac atggaccctg agattgcaga   3300
gatatccctt tttgctgttc accgctcttc cctggagaac ccagaacggg atgattctgg   3360
ttccttggtg ctgccccgtg ttctggacaa gctcacactg tgcatgtgcc cggagcgccc   3420
ctttactgcc aaggccagtg agattactgg tttgagcagc gaaagcctga tgcactgcgg   3480
gaaggctggt ttcaatggcg ctgtggtaag gacactgcag ggcttcctaa gccgccagga   3540
gggccccatc tgccttgtgg cccacaatgg cttcgattat gacttcccac tgctgtgcac   3600
ggagctacaa cgtctgggtg cccatctgcc ccaagacact gtctgcctgg acacactgcc   3660
tgcattgcgg ggcctggacc gtgctcacag ccacggcacc agggctcaag gccgcaaaag   3720
```

-continued

```
ctacagcctg gccagtctct tccaccgcta cttccaggct gaacccagtg ctgcccattc   3780

agcagaaggt gatgtgcaca ccctgcttct gatcttcctg catcgtgctc ctgagctgct   3840

cgcctgggca gatgagcagg cccgcagctg ggctcatatt gagcccatgt acgtgccacc   3900

tgatggtcca agcctcgaag cctgacctgc aggtcgagca tgcatctagg gcggccaatt   3960

ccgcccctct ccctcccccc cccctaacgt tactggccga agccgcttgg aataaggccg   4020

gtgtgcgttt gtctatatgt gattttccac catattgccg tcttttggca atgtgagggc   4080

ccggaaacct ggccctgtct tcttgacgag cattcctagg ggtctttccc ctctcgccaa   4140

aggaatgcaa ggtctgttga atgtcgtgaa ggaagcagtt cctctggaag cttcttgaag   4200

acaaacaacg tctgtagcga ccctttgcag gcagcggaac cccccacctg gcgacaggtg   4260

cctctgcggc caaaagccac gtgtataaga tacacctgca aaggcggcac aaccccagtg   4320

ccacgttgtg agttggatag ttgtggaaag agtcaaatgg ctctcctcaa gcgtattcaa   4380

caaggggctg aaggatgccc agaaggtacc ccattgtatg ggatctgatc tggggcctcg   4440

gtgcacatgc tttacatgtg tttagtcgag gttaaaaaaa cgtctaggcc ccccgaacca   4500

cggggacgtg gttttccttt gaaaaacacg atgataagct tgccacaacc cttaccggtc   4560

gccaccatga gcgagctgat taaggagaac atgcacatga agctgtacat ggagggcacc   4620

gtggacaacc atcacttcaa gtgcacatcc gagggcgaag gcaagcccta cgagggcacc   4680

cagaccatga gaatcaaggt ggtcgagggc ggccctctcc ccttcgcctt cgacatcctg   4740

gctactagct tcctctacgg cagcaagacc ttcatcaacc acacccaggg catccccgac   4800

ttcttcaagc agtccttccc tgagggcttc acatgggaga gagtcaccac atacgaagac   4860

gggggcgtgc tgaccgctac ccaggacacc agcctccagg acggctgcct catctacaac   4920

gtcaagatca gaggggtgaa cttcacatcc aacggccctg tgatgcagaa gaaaacactc   4980

ggctgggagg ccttcaccga gacgctgtac cccgctgacg gcggcctgga aggcagaaac   5040

gacatggccc tgaagctcgt gggcgggagc catctgatcg caaacatcaa gaccacatat   5100

agatccaaga aacccgctaa gaacctcaag atgcctggcg tctactatgt ggactacaga   5160

ctggaaagaa tcaaggaggc caacaacgag acctacgtcg agcagcacga ggtggcagtg   5220

gccagatact gcgacctccc tagcaaactg ggcacaagc ttaattgatt ctagagtcga   5280

ccgagcatct taccgccatt tatacccata tttgttctgt ttttcttgat ttgggtatac   5340

atttaaatgt taatagaaca aaatggtggg gcaatcattt acatttttag ggatatgtaa   5400

ttactagttc aggtgtattg ccacaagaca aacatgttaa gaaactttcc cgttatttac   5460

gctctgttcc tgttaatcaa cctctggatt acaaaatttg tgaaagattg actgatattc   5520

ttaactatgt tgctcctttt acgctgtgtg gatatgctgc tttatagcct ctgtatctag   5580

ctattgcttc ccgtacggct ttcgttttct cctccttgta taaatcctgg ttgctgtctc   5640

ttttagagga gttgtggccc gttgtccgtc aacgtggcgt ggtgtgctct gtgtttgctg   5700

acgcaacccc cactggctgg ggcattgcca ccacctgtca actcctttct gggactttcg   5760

ctttcccct cccgatcgcc acggcagaac tcatcgccgc ctgccttgcc cgctgctgga   5820

caggggctag gttgctgggc actgataatt ccgtggtgtt gtcatcggta cctttttaaa   5880

agaaaagggg ggactggaag ggctaattca ctcccaacga agacaagata tcataacttc   5940

gtatagcata cattatacga agttataatt tatttgtgaa atttgtgatg ctattgcttt   6000

atttgtaacc atatgtttat ttgtgaaatt tgtgatgcta ttgctttatt tgtaaccatt   6060
```

-continued

```
gctttttgct tgtactgggt ctctctggtt agaccagatc tgagcctggg agctctctgg   6120
ctaactaggg aacccactgc ttaagcctca ataaagcttg cctcgaccag cctcgactgt   6180
gccttctagt tgccagccat ctgttgtttg cccctccccc gtgccttcct tgaccctgga   6240
aggtgccact cccactgtcc tttcctaata aaatgaggaa attgcatcgc attgtctgag   6300
taggtgtcat tctattctgg ggggtggggt ggggcaggac agcaaggggg aggattggga   6360
agacaatagc aggcatgctg gggatgcggt gggctctatg gcctgcagct gcattaatga   6420
atcggccaac gcgcggggag aggcggtttg cgtattgggc gctcttccgc ttcctcgctc   6480
actgactcgc tgcgctcggt cgttcggctg cggcgagcgg tatcagctca ctcaaaggcg   6540
gtaatacggt tatccacaga atcaggggat aacgcaggaa agaacatgtg agcaaaaggc   6600
cagcaaaagg ccaggaaccg taaaaaggcc gcgttgctgg cgtttttcca taggctccgc   6660
ccccctgacg agcatcacaa aaatcgacgc tcaagtcaga ggtggcgaaa cccgacagga   6720
ctataaagat accaggcgtt tccccctgga agctccctcg tgcgctctcc tgttccgacc   6780
ctgccgctta ccggatacct gtccgccttt ctcccttcgg gaagcgtggc gctttctcat   6840
agctcacgct gtaggtatct cagttcggtg taggtcgttc gctccaagct gggctgtgtg   6900
cacgaacccc ccgttcagcc cgaccgctgc gccttatccg gtaactatcg tcttgagtcc   6960
aacccggtaa gacacgactt atcgccactg gcagcagcca ctggtaacag gattagcaga   7020
gcgaggtatg taggcggtgc tacagagttc ttgaagtggt ggcctaacta cggctacact   7080
agaaggacag tatttggtat ctgcgctctg ctgaagccag ttaccttcgg aaaaagagtt   7140
ggtagctctt gatccggcaa acaaaccacc gctggtagcg gtggtttttt tgtttgcaag   7200
cagcagatta cgcgcagaaa aaaaggatct caagaagatc ctttgatctt ttctacgggg   7260
tctgacgctc agtggaacga aaactcacgt taagggattt tggtcatgag attatcaaaa   7320
aggatcttca cctagatcct tttaaattaa aaatgaagtt ttaaatcaat ctaaagtata   7380
tatgagtaaa cttggtctga cagttaccaa tgcttaatca gtgaggcacc tatctcagcg   7440
atctgtctat ttcgttcatc catagttgcc tgactccccg tcgtgtagat aactacgata   7500
cgggagggct taccatctgg ccccagtgct gcaatgatac cgcgagaccc acgctcaccg   7560
gctccagatt tatcagcaat aaaccagcca gccggaaggg ccgagcgcag aagtggtcct   7620
gcaactttat ccgcctccat ccagtctatt aattgttgcc gggaagctag agtaagtagt   7680
tcgccagtta atagtttgcg caacgttgtt gccattgcta caggcatcgt ggtgtcacgc   7740
tcgtcgtttg gtatggcttc attcagctcc ggttcccaac gatcaaggcg agttacatga   7800
tcccccatgt tgtgcaaaaa agcggttagc tccttcggtc ctccgatcgt tgtcagaagt   7860
aagttggccg cagtgttatc actcatggtt atggcagcac tgcataattc tcttactgtc   7920
atgccatccg taagatgctt ttctgtgact ggtgagtact caaccaagtc attctgagaa   7980
tagtgtatgc ggcgaccgag ttgctcttgc ccggcgtcaa tacgggataa taccgcgcca   8040
catagcagaa ctttaaaagt gctcatcatt ggaaaacgtt cttcggggcg aaaactctca   8100
aggatcttac cgctgttgag atccagttcg atgtaaccca ctcgtgcacc caactgatct   8160
tcagcatctt ttactttcac cagcgtttct gggtgagcaa aaacaggaag gcaaaatgcc   8220
gcaaaaaagg gaataagggc gacacggaaa tgttgaatac tcatactctt cctttttcaa   8280
tattattgaa gcatttatca gggttattgt ctcatgagcg gatacatatt tgaatgtatt   8340
tagaaaaata aacaaatagg ggttccgcgc acatttcccc gaaaagtgcc acct         8394
```

```
<210> SEQ ID NO 114
<211> LENGTH: 7671
<212> TYPE: DNA
<213> ORGANISM: Artificial Sequence
<220> FEATURE:
<223> OTHER INFORMATION: Plasmid pCVL.SFFV.HA.NLS.I-Ani I.IRES.mTagBFP

<400> SEQUENCE: 114

gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc ctgatcttca gacctggagg aggagatatg    960

agggacaatt ggagaagtga attatataaa tataaagtag taaaaattga accattagga   1020

gtagcaccca ccaaggcaaa gagaagagtg gtgcagagag aaaaaagagc agtgggaata   1080

ggagctttgt tccttgggtt cttgggagca gcaggaagca ctatgggcgc agcgtcaatg   1140

acgctgacgg tacaggccag acaattattg tctggtatag tgcagcagca gaacaatttg   1200

ctgagggcta ttgaggcgca acagcatctg ttgcaactca cagtctgggg catcaagcag   1260

ctccaggcaa gaatcctggc tgtggaaaga tacctaaagg atcaacagct cctggggatt   1320

tggggttgct ctggaaaact catttgcacc actgctgtgc cttggaatgc tagttggagt   1380

aatgaatctc tggaacagat ttggaatcac acgacctgga tggagtggga cagagaaatt   1440

aacaattaca caagcttaat acactcctta attgaagaat cgcaaaacca gcaagaaaag   1500

aatgaacaag aattattgga attagataaa tgggcaagtt tgtggaattg gtttaacata   1560

acaaattggc tgtggtatat aaaattattc ataatgatag taggaggctt ggtaggttta   1620

agaatagttt ttgctgtact ttctatagtg aatagagtta ggcagggata ttcaccatta   1680

tcgtttcaga cccacctccc aaccccgagg ggacccgaca ggcccgaagg aatagaagaa   1740

gaaggtggag agagagacag agacagatcc attcgattag tgaacggatc tcgacggtat   1800

cggttaactt ttaaaagaaa aggggggatt ggggggtaca gtgcagggga aagaatagta   1860

gacataatag caacagacat acaaactaaa gaattacaaa aacaaattac aaaaattcaa   1920

aattttatcg attacgcgtc acgtgctagc tgcagtaacg ccattttgca aggcatggaa   1980

aaataccaaa ccaagaatag agaagttcag atcaagggcg ggtacatgaa aatagctaac   2040

gttgggccaa acaggatatc tgcggtgagc agtttcggcc ccggcccggg gccaagaaca   2100
```

-continued gatggtcacc gcagtttcgg ccccggcccg aggccaagaa cagatggtcc ccagatatgg 2160
cccaaccctc agcagtttct taagacccat cagatgtttc caggctcccc caaggacctg 2220
aaatgaccct gcgccttatt tgaattaacc aatcagcctg cttctcgctt ctgttcgcgc 2280
gcttctgctt cccgagctct ataaaagagc tcacaacccc tcactcggcg cgccagtcct 2340
ccgacagact gagtcgcccg ctcgagccgc caccatggga tatccatacg atgtcccaga 2400
ttatgcgcca cctaagaaga aacgcaaagt cgaattcggc agcgatctga cctacgccta 2460
tctggtgggc ctgttcgagg gcgacggata tttttccatc actaaaaagg gcaagtacct 2520
gacctatgag ctgggaattg aactgtctat caaggatgtg cagctgatct acaagatcaa 2580
gaagatcctg ggatcggca ttgtgagctt caggaagaga aacgagattg aaatggtggc 2640
cctgaggatc agggataaga atcacctgaa atctaagatt ctgcccatct tcgagaagta 2700
tcctatgttt agtaacaaac agtacgacta tctgaggttt agaaatgctc tgctgagcgg 2760
catcatctcc ctggaggatc tgccagacta tacccggtcc gacgagcccc tgaacagcat 2820
cgaatccatc attaatacat cttacttcag tgcctggctg gtgggcttca tcgaggctga 2880
agggtgcttc tctgtgtaca aactgaacaa ggacgatgac tatctgattg ccagttttga 2940
tatcgctcag agggatggag acatcctgat tagcgccatc agaaagtacc tgtccttcac 3000
cacaaaggtg tatctggaca aaacaaattg tagcaaactg aaggtcacta gcgtgcgctc 3060
cgtggagaac atcattaagt tcctgcagaa tgctcctgtg aaactgctgg gcaacaaaaa 3120
gctgcagtac aaactgtggc tgaagcagct gcggaaaatc tctcgctaca gtgaaaaaat 3180
caagattcca tccaattatt aacctgcagg tcgagcatgc atctagggcg gccaattccg 3240
cccctctccc tcccccccc ctaacgttac tggccgaagc cgcttggaat aaggccggtg 3300
tgcgtttgtc tatatgtgat tttccaccat attgccgtct tttggcaatg tgagggcccg 3360
gaaacctggc cctgtcttct tgacgagcat tcctaggggt ctttcccctc tcgccaaagg 3420
aatgcaaggt ctgttgaatg tcgtgaagga agcagttcct ctggaagctt cttgaagaca 3480
aacaacgtct gtagcgaccc tttgcaggca gcggaacccc ccacctggcg acaggtgcct 3540
ctgcggccaa aagccacgtg tataagatac acctgcaaag gcggcacaac cccagtgcca 3600
cgttgtgagt tggatagttg tggaaagagt caaatggctc tcctcaagcg tattcaacaa 3660
ggggctgaag gatgcccaga aggtacccca ttgtatggga tctgatctgg ggcctcggtg 3720
cacatgcttt acatgtgttt agtcgaggtt aaaaaaacgt ctaggccccc cgaaccacgg 3780
ggacgtggtt ttcctttgaa aaacacgatg ataagcttgc cacaaccctt accggtcgcc 3840
accatgagcg agctgattaa ggagaacatg cacatgaagc tgtacatgga gggcaccgtg 3900
gacaaccatc acttcaagtg cacatccgag ggcgaaggca agccctacga gggcacccag 3960
accatgagaa tcaaggtggt cgagggcggc cctctcccct tcgccttcga catcctggct 4020
actagcttcc tctacggcag caagaccttc atcaaccaca cccagggcat ccccgacttc 4080
ttcaagcagt ccttccctga gggcttcaca tgggagagag tcaccacata cgaagacggg 4140
ggcgtgctga ccgctaccca ggacaccagc ctccaggacg gctgcctcat ctacaacgtc 4200
aagatcagag gggtgaactt cacatccaac ggccctgtga tgcagaagaa aacactcggc 4260
tgggaggcct tcaccgagac gctgtacccc gctgacggcg gcctggaagg cagaaacgac 4320
atggccctga agctcgtggg cgggagccat ctgatcgcaa acatcaagac cacatataga 4380
tccaagaaac ccgctaagaa cctcaagatg cctggcgtct actatgtgga ctacagactg 4440
gaaagaatca aggaggccaa caacgagacc tacgtcgagc agcacgaggt ggcagtggcc 4500

```
agatactgcg acctccctag caaactgggg cacaagctta attgattcta gagtcgaccg   4560
agcatcttac cgccatttat acccatattt gttctgtttt tcttgatttg ggtatacatt   4620
taaatgttaa tagaacaaaa tggtggggca atcatttaca tttttaggga tatgtaatta   4680
ctagttcagg tgtattgcca caagacaaac atgttaagaa actttcccgt tatttacgct   4740
ctgttcctgt taatcaacct ctggattaca aaatttgtga aagattgact gatattctta   4800
actatgttgc tccttttacg ctgtgtggat atgctgcttt atagcctctg tatctagcta   4860
ttgcttcccg tacggctttc gttttctcct ccttgtataa atcctggttg ctgtctcttt   4920
tagaggagtt gtggcccgtt gtccgtcaac gtggcgtggt gtgctctgtg tttgctgacg   4980
caacccccac tggctggggc attgccacca cctgtcaact cctttctggg actttcgctt   5040
tccccctccc gatcgccacg gcagaactca tcgccgcctg ccttgcccgc tgctggacag   5100
gggctaggtt gctgggcact gataattccg tggtgttgtc atcggtacct ttttaaaaga   5160
aaagggggga ctggaagggc taattcactc ccaacgaaga caagatatca taacttcgta   5220
tagcatacat tatacgaagt tataatttat ttgtgaaatt tgtgatgcta ttgctttatt   5280
tgtaaccata tgtttatttg tgaaatttgt gatgctattg ctttatttgt aaccattgct   5340
ttttgcttgt actgggtctc tctggttaga ccagatctga gcctgggagc tctctggcta   5400
actagggaac ccactgctta agcctcaata aagcttgcct cgaccagcct cgactgtgcc   5460
ttctagttgc cagccatctg ttgtttgccc ctcccccgtg ccttccttga ccctggaagg   5520
tgccactccc actgtccttt cctaataaaa tgaggaaatt gcatcgcatt gtctgagtag   5580
gtgtcattct attctggggg gtggggtggg gcaggacagc aagggggagg attgggaaga   5640
caatagcagg catgctgggg atgcggtggg ctctatggcc tgcagctgca ttaatgaatc   5700
ggccaacgcg cggggagagg cggtttgcgt attgggcgct cttccgcttc ctcgctcact   5760
gactcgctgc gctcggtcgt tcggctgcgg cgagcggtat cagctcactc aaaggcggta   5820
atacggttat ccacagaatc aggggataac gcaggaaaga acatgtgagc aaaaggccag   5880
caaaaggcca ggaaccgtaa aaaggccgcg ttgctggcgt ttttccatag gctccgcccc   5940
cctgacgagc atcacaaaaa tcgacgctca agtcagaggt ggcgaaaccc gacaggacta   6000
taaagatacc aggcgtttcc ccctggaagc tccctcgtgc gctctcctgt tccgaccctg   6060
ccgcttaccg gatacctgtc cgcctttctc ccttcgggaa gcgtggcgct ttctcatagc   6120
tcacgctgta ggtatctcag ttcggtgtag gtcgttcgct ccaagctggg ctgtgtgcac   6180
gaaccccccg ttcagcccga ccgctgcgcc ttatccggta actatcgtct tgagtccaac   6240
ccggtaagac acgacttatc gccactggca gcagccactg gtaacaggat tagcagagcg   6300
aggtatgtag gcggtgctac agagttcttg aagtggtggc ctaactacgg ctacactaga   6360
aggacagtat ttggtatctg cgctctgctg aagccagtta ccttcggaaa aagagttggt   6420
agctcttgat ccggcaaaca aaccaccgct ggtagcggtg gtttttttgt ttgcaagcag   6480
cagattacgc gcagaaaaaa aggatctcaa gaagatcctt tgatcttttc tacggggtct   6540
gacgctcagt ggaacgaaaa ctcacgttaa gggattttgg tcatgagatt atcaaaaagg   6600
atcttcacct agatcctttt aaattaaaaa tgaagtttta aatcaatcta aagtatatat   6660
gagtaaactt ggtctgacag ttaccaatgc ttaatcagtg aggcacctat ctcagcgatc   6720
tgtctatttc gttcatccat agttgcctga ctccccgtcg tgtagataac tacgatacgg   6780
gagggcttac catctggccc cagtgctgca atgataccgc gagacccacg ctcaccggct   6840
```

-continued

```
ccagatttat cagcaataaa ccagccagcc ggaagggccg agcgcagaag tggtcctgca   6900

actttatccg cctccatcca gtctattaat tgttgccggg aagctagagt aagtagttcg   6960

ccagttaata gtttgcgcaa cgttgttgcc attgctacag gcatcgtggt gtcacgctcg   7020

tcgtttggta tggcttcatt cagctccggt tcccaacgat caaggcgagt tacatgatcc   7080

cccatgttgt gcaaaaaagc ggttagctcc ttcggtcctc cgatcgttgt cagaagtaag   7140

ttggccgcag tgttatcact catggttatg gcagcactgc ataattctct tactgtcatg   7200

ccatccgtaa gatgcttttc tgtgactggt gagtactcaa ccaagtcatt ctgagaatag   7260

tgtatgcggc gaccgagttg ctcttgcccg gcgtcaatac gggataatac cgcgccacat   7320

agcagaactt taaaagtgct catcattgga aaacgttctt cggggcgaaa actctcaagg   7380

atcttaccgc tgttgagatc cagttcgatg taacccactc gtgcacccaa ctgatcttca   7440

gcatctttta ctttcaccag cgtttctggg tgagcaaaaa caggaaggca aaatgccgca   7500

aaaaagggaa taagggcgac acggaaatgt tgaatactca tactcttcct ttttcaatat   7560

tattgaagca tttatcaggg ttattgtctc atgagcggat acatatttga atgtatttag   7620

aaaaataaac aaataggggt tccgcgcaca tttccccgaa aagtgccacc t            7671
```

<210> SEQ ID NO 115
<211> LENGTH: 8445
<212> TYPE: DNA
<213> ORGANISM: Artificial Sequence
<220> FEATURE:
<223> OTHER INFORMATION: Plasmid
pCVL.SFFV.HA.NLS.IAni-I.T2A.Trex2.IRES.mTagBFP

<400> SEQUENCE: 115

```
gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc ctgatcttca gacctggagg aggagatatg    960

agggacaatt ggagaagtga attatataaa tataaagtag taaaaattga accattagga   1020

gtagcaccca ccaaggcaaa gagaagagtg gtgcagagag aaaaaagagc agtgggaata   1080

ggagctttgt tccttgggtt cttgggagca gcaggaagca ctatgggcgc agcgtcaatg   1140

acgctgacgg tacaggccag acaattattg tctggtatag tgcagcagca gaacaatttg   1200
```

-continued

```
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcggc agcgatctga cctacgccta   2460
tctggtgggc ctgttcgagg gcgacggata tttttccatc actaaaaagg gcaagtacct   2520
gacctatgag ctgggaattg aactgtctat caaggatgtg cagctgatct acaagatcaa   2580
gaagatcctg ggatcggca ttgtgagctt caggaagaga aacgagattg aaatggtggc   2640
cctgaggatc agggataaga atcacctgaa atctaagatt ctgcccatct tcgagaagta   2700
tcctatgttt agtaacaaac agtacgacta tctgaggttt agaaatgctc tgctgagcgg   2760
catcatctcc ctggaggatc tgccagacta tacccggtcc gacgagcccc tgaacagcat   2820
cgaatccatc attaatacat cttacttcag tgcctggctg gtgggcttca tcgaggctga   2880
agggtgcttc tctgtgtaca aactgaacaa ggacgatgac tatctgattg ccagttttga   2940
tatcgctcag agggatggag acatcctgat tagcgccatc agaaagtacc tgtccttcac   3000
cacaaaggtg tatctggaca aaacaaattg tagcaaactg aaggtcacta gcgtgcgctc   3060
cgtggagaac atcattaagt tcctgcagaa tgctcctgtg aaactgctgg gcaacaaaaa   3120
gctgcagtac aaactgtggc tgaagcagct gcggaaaatc tctcgctaca gtgaaaaaat   3180
caagattcca tccaattatg gatccggtga gggcagagga agtcttctaa catgcggtga   3240
cgtggaggag aatccgggcc cctccggatc tgagccacct cgggctgaga cctttgtatt   3300
cctggaccta gaagccactg ggctcccaaa catggaccct gagattgcag agatatccct   3360
ttttgctgtt caccgctctt ccctggagaa cccagaacgg gatgattctg gttccttggt   3420
gctgccccgt gttctggaca agctcacact gtgcatgtgc ccggagcgcc cctttactgc   3480
caaggccagt gagattactg gtttgagcag cgaaagcctg atgcactgcg ggaaggctgg   3540
tttcaatggc gctgtggtaa ggacactgca gggcttccta agccgccagg agggccccat   3600
```

-continued ctgccttgtg gcccacaatg gcttcgatta tgacttccca ctgctgtgca cggagctaca 3660
acgtctgggt gcccatctgc cccaagacac tgtctgcctg gacacactgc ctgcattgcg 3720
gggcctggac cgtgctcaca gccacggcac cagggctcaa ggccgcaaaa gctacagcct 3780
ggccagtctc ttccaccgct acttccaggc tgaacccagt gctgcccatt cagcagaagg 3840
tgatgtgcac accctgcttc tgatcttcct gcatcgtgct cctgagctgc tcgcctgggc 3900
agatgagcag gcccgcagct gggctcatat tgagcccatg tacgtgccac ctgatggtcc 3960
aagcctcgaa gcctgacctg caggtcgagc atgcatctag ggcggccaat tccgcccctc 4020
tccctccccc ccccctaacg ttactggccg aagccgcttg gaataaggcc ggtgtgcgtt 4080
tgtctatatg tgattttcca ccatattgcc gtcttttggc aatgtgaggg cccggaaacc 4140
tggccctgtc ttcttgacga gcattcctag gggtctttcc cctctcgcca aaggaatgca 4200
aggtctgttg aatgtcgtga aggaagcagt tcctctggaa gcttcttgaa gacaaacaac 4260
gtctgtagcg accctttgca ggcagcggaa ccccccacct ggcgacaggt gcctctgcgg 4320
ccaaaagcca cgtgtataag atacacctgc aaaggcggca caaccccagt gccacgttgt 4380
gagttggata gttgtggaaa gagtcaaatg gctctcctca agcgtattca acaaggggct 4440
gaaggatgcc cagaaggtac cccattgtat gggatctgat ctggggcctc ggtgcacatg 4500
ctttacatgt gtttagtcga ggttaaaaaa acgtctaggc cccccgaacc acggggacgt 4560
ggttttcctt tgaaaaacac gatgataagc ttgccacaac ccttaccggt cgccaccatg 4620
agcgagctga ttaaggagaa catgcacatg aagctgtaca tggagggcac cgtggacaac 4680
catcacttca agtgcacatc cgagggcgaa ggcaagccct acgagggcac ccagaccatg 4740
agaatcaagg tggtcgaggg cggccctctc cccttcgcct tcgacatcct ggctactagc 4800
ttcctctacg gcagcaagac cttcatcaac cacacccagg gcatccccga cttcttcaag 4860
cagtccttcc ctgagggctt cacatgggag agagtcacca catacgaaga cgggggcgtg 4920
ctgaccgcta cccaggacac cagcctccag gacggctgcc tcatctacaa cgtcaagatc 4980
agaggggtga acttcacatc caacggccct gtgatgcaga agaaaacact cggctgggag 5040
gccttcaccg agacgctgta ccccgctgac ggcggcctgg aaggcagaaa cgacatggcc 5100
ctgaagctcg tgggcgggag ccatctgatc gcaaacatca agaccacata tagatccaag 5160
aaacccgcta agaacctcaa gatgcctggc gtctactatg tggactacag actggaaaga 5220
atcaaggagg ccaacaacga gacctacgtc gagcagcacg aggtggcagt ggccagatac 5280
tgcgacctcc ctagcaaact ggggcacaag cttaattgat tctagagtcg accgagcatc 5340
ttaccgccat ttatacccat atttgttctg tttttcttga tttgggtata catttaaatg 5400
ttaatagaac aaaatggtgg ggcaatcatt tacattttta gggatatgta attactagtt 5460
caggtgtatt gccacaagac aaacatgtta agaaactttc ccgttattta cgctctgttc 5520
ctgttaatca acctctggat tacaaaattt gtgaaagatt gactgatatt cttaactatg 5580
ttgctccttt tacgctgtgt ggatatgctg ctttatagcc tctgtatcta gctattgctt 5640
cccgtacggc tttcgttttc tcctccttgt ataaatcctg gttgctgtct cttttagagg 5700
agttgtggcc cgttgtccgt caacgtggcg tggtgtgctc tgtgtttgct gacgcaaccc 5760
ccactggctg gggcattgcc accacctgtc aactcctttc tgggactttc gctttccccc 5820
tcccgatcgc cacggcagaa ctcatcgccg cctgccttgc ccgctgctgg acaggggcta 5880
ggttgctggg cactgataat tccgtggtgt tgtcatcggt accttttttaa aagaaaaggg 5940 gggactggaa gggctaattc actcccaacg aagacaagat atcataactt cgtatagcat 6000
acattatacg aagttataat ttatttgtga aatttgtgat gctattgctt tatttgtaac 6060
catatgttta tttgtgaaat ttgtgatgct attgctttat ttgtaaccat tgctttttgc 6120
ttgtactggg tctctctggt tagaccagat ctgagcctgg gagctctctg gctaactagg 6180
gaacccactg cttaagcctc aataaagctt gcctcgacca gcctcgactg tgccttctag 6240
ttgccagcca tctgttgttt gcccctcccc cgtgccttcc ttgaccctgg aaggtgccac 6300
tcccactgtc ctttcctaat aaaatgagga aattgcatcg cattgtctga gtaggtgtca 6360
ttctattctg gggggtgggg tggggcagga cagcaagggg gaggattggg aagacaatag 6420
caggcatgct ggggatgcgg tgggctctat ggcctgcagc tgcattaatg aatcggccaa 6480
cgcgcgggga gaggcggttt gcgtattggg cgctcttccg cttcctcgct cactgactcg 6540
ctgcgctcgg tcgttcggct gcggcgagcg gtatcagctc actcaaaggc ggtaatacgg 6600
ttatccacag aatcagggga taacgcagga aagaacatgt gagcaaaagg ccagcaaaag 6660
gccaggaacc gtaaaaaggc cgcgttgctg gcgtttttcc ataggctccg cccccctgac 6720
gagcatcaca aaaatcgacg ctcaagtcag aggtggcgaa acccgacagg actataaaga 6780
taccaggcgt ttccccctgg aagctccctc gtgcgctctc ctgttccgac cctgccgctt 6840
accggatacc tgtccgcctt tctcccttcg ggaagcgtgg cgctttctca tagctcacgc 6900
tgtaggtatc tcagttcggt gtaggtcgtt cgctccaagc tgggctgtgt gcacgaaccc 6960
cccgttcagc ccgaccgctg cgccttatcc ggtaactatc gtcttgagtc caacccggta 7020
agacacgact tatcgccact ggcagcagcc actggtaaca ggattagcag agcgaggtat 7080
gtaggcggtg ctacagagtt cttgaagtgg tggcctaact acggctacac tagaaggaca 7140
gtatttggta tctgcgctct gctgaagcca gttaccttcg gaaaaagagt tggtagctct 7200
tgatccggca aacaaaccac cgctggtagc ggtggttttt ttgtttgcaa gcagcagatt 7260
acgcgcagaa aaaaaggatc tcaagaagat cctttgatct tttctacggg gtctgacgct 7320
cagtggaacg aaaactcacg ttaagggatt ttggtcatga gattatcaaa aaggatcttc 7380
acctagatcc ttttaaatta aaaatgaagt tttaaatcaa tctaaagtat atatgagtaa 7440
acttggtctg acagttacca atgcttaatc agtgaggcac ctatctcagc gatctgtcta 7500
tttcgttcat ccatagttgc ctgactcccc gtcgtgtaga taactacgat acgggagggc 7560
ttaccatctg gccccagtgc tgcaatgata ccgcgagacc cacgctcacc ggctccagat 7620
ttatcagcaa taaaccagcc agccggaagg gccgagcgca gaagtggtcc tgcaacttta 7680
tccgcctcca tccagtctat taattgttgc cgggaagcta gagtaagtag ttcgccagtt 7740
aatagtttgc gcaacgttgt tgccattgct acaggcatcg tggtgtcacg ctcgtcgttt 7800
ggtatggctt cattcagctc cggttcccaa cgatcaaggc gagttacatg atcccccatg 7860
ttgtgcaaaa aagcggttag ctccttcggt cctccgatcg ttgtcagaag taagttggcc 7920
gcagtgttat cactcatggt tatggcagca ctgcataatt ctcttactgt catgccatcc 7980
gtaagatgct tttctgtgac tggtgagtac tcaaccaagt cattctgaga atagtgtatg 8040
cggcgaccga gttgctcttg cccggcgtca atacgggata ataccgcgcc acatagcaga 8100
actttaaaag tgctcatcat tggaaaacgt tcttcggggc gaaaactctc aaggatctta 8160
ccgctgttga gatccagttc gatgtaaccc actcgtgcac ccaactgatc ttcagcatct 8220
tttactttca ccagcgtttc tgggtgagca aaaacaggaa ggcaaaatgc cgcaaaaaag 8280
ggaataaggg cgacacggaa atgttgaata ctcatactct tcctttttca atattattga 8340
agcatttatc agggttattg tctcatgagc ggatacatat ttgaatgtat ttagaaaaat 8400
aaacaaatag gggttccgcg cacatttccc cgaaaagtgc cacct 8445

<210> SEQ ID NO 116
<211> LENGTH: 7011
<212> TYPE: DNA
<213> ORGANISM: Artificial Sequence
<220> FEATURE:
<223> OTHER INFORMATION: pCVL.MND.SceOPT.2A.TagBFP

<400> SEQUENCE: 116
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc caggggggaaa gaaaaaatat 660 aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560
acaaattggc tgtggtatat aaaattattc ataatgatag taggaggctt ggtaggttta 1620
agaatagttt ttgctgtact ttctatagtg aatagagtta ggcagggata ttcaccatta 1680
tcgtttcaga cccacctccc aaccccgagg ggacccgaca ggcccgaagg aatagaagaa 1740
gaaggtggag agagagacag agacagatcc attcgattag tgaacggatc tcgacggtat 1800
cggttaactt ttaaaagaaa aggggggatt ggggggtaca gtgcagggga aagaatagta 1860
gacataatag caacagacat acaaactaaa gaattacaaa aacaaattac aaaaattcaa 1920

-continued

```
aattttatcg attacgcgta ggaacagaga aacaggagaa tatgggccaa acaggatatc   1980
tgtggtaagc agttcctgcc ccggctcagg gccaagaaca gttggaacag cagaatatgg   2040
gccaaacagg atatctgtgg taagcagttc ctgccccggc tcagggccaa gaacagatgg   2100
tccccagatg cggtcccgcc ctcagcagtt tctagagaac catcagatgt ttccagggtg   2160
ccccaaggac ctgaaatgac cctgtgcctt atttgaacta accaatcagt tcgcttctcg   2220
cttctgttcg cgcgcttctg ctccccgagc tctatataag cagagctcgt ttagtgaacc   2280
gtcagatcgc ctggagacgc catccacgct gttttgactt ccatagaagg atctcgagcc   2340
accatgggcg tatacccccta cgacgtgccc gactacgccc ccgggccccc taagaaaaag   2400
aggaaggtga agaacatcaa gaagaaccag gtcatgaacc tgggccccaa cagcaagctg   2460
ctgaaggagt acaagagcca gctgatcgag ctgaacatcg agcagttcga ggccggcatc   2520
ggcctgatcc tgggcgacgc ctacatcagg agcagggacg agggcaagac ctactgcatg   2580
cagttcgagt ggaagaacaa ggcctacatg gaccacgtgt gcctgctgta cgaccagtgg   2640
gtgctgagcc ccccccacaa gaaggagagg gtgaaccacc tgggcaacct ggtcatcacc   2700
tggggcgccc agaccttcaa gcaccaggcc ttcaacaagc tggccaacct gttcatcgtg   2760
aacaacaaga agaccatccc caacaacctg gtggagaact acctgacccc catgagcctg   2820
gcctactggt tcatggacga cggcggcaag tgggactaca acaagaacag caccaacaag   2880
agcatcgtgc tgaacaccca gagcttcacc ttcgaggagg tggagtacct ggtgaagggc   2940
ctgaggaaca agttccagct gaactgctac gtgaagatca acaagaacaa gcccatcatc   3000
tacatcgaca gcatgagcta cctgatcttc tacaacctga tcaagcccta cctgatcccc   3060
cagatgatgt acaagctgcc caacaccatc agcagcgaga ccttcctgaa gggcggcggc   3120
ggatccggtg agggcagagg aagtcttcta acatgcggtg acgtggagga gaatccgggc   3180
cccatgagcg agctgattaa ggagaacatg cacatgaagc tgtacatgga gggcaccgtg   3240
gacaaccatc acttcaagtg cacatccgag ggcgaaggca agccctacga gggcacccag   3300
accatgagaa tcaaggtggt cgagggcggc cctctcccct tcgccttcga catcctggct   3360
actagcttcc tctacggcag caagaccttc atcaaccaca cccagggcat ccccgacttc   3420
ttcaagcagt ccttccctga gggcttcaca tgggagagag tcaccacata cgaagacggg   3480
ggcgtgctga ccgctaccca ggacaccagc ctccaggacg gctgcctcat ctacaacgtc   3540
aagatcagag gggtgaactt cacatccaac ggccctgtga tgcagaagaa aacactcggc   3600
tgggaggcct tcaccgagac gctgtacccc gctgacggcg gcctggaagg cagaaacgac   3660
atggccctga agctcgtggg cgggagccat ctgatcgcaa acatcaagac cacatataga   3720
tccaagaaac ccgctaagaa cctcaagatg cctggcgtct actatgtgga ctacagactg   3780
gaaagaatca aggaggccaa caacgagacc tacgtcgagc agcacgaggt ggcagtggcc   3840
agatactgcg acctccctag caaactgggg cacaagctta attgattcta gagtcgaccg   3900
agcatcttac cgccatttat acccatattt gttctgtttt tcttgatttg ggtatacatt   3960
taaatgttaa tagaacaaaa tggtggggca atcatttaca tttttaggga tatgtaatta   4020
ctagttcagg tgtattgcca caagacaaac atgttaagaa actttcccgt tatttacgct   4080
ctgttcctgt taatcaacct ctggattaca aaatttgtga aagattgact gatattctta   4140
actatgttgc tcctttttacg ctgtgtggat atgctgcttt atagcctctg tatctagcta   4200
ttgcttcccg tacggctttc gttttctcct ccttgtataa atcctggttg ctgtctcttt   4260
tagaggagtt gtggcccgtt gtccgtcaac gtggcgtggt gtgctctgtg tttgctgacg   4320
```

-continued

```
caaccccac tggctggggc attgccacca cctgtcaact cctttctggg actttcgctt   4380
tccccctccc gatcgccacg gcagaactca tcgccgcctg ccttgcccgc tgctggacag   4440
gggctaggtt gctgggcact gataattccg tggtgttgtc atcggtacct ttttaaaaga   4500
aaagggggga ctggaagggc taattcactc ccaacgaaga caagatatca taacttcgta   4560
tagcatacat tatacgaagt tataatttat ttgtgaaatt tgtgatgcta ttgctttatt   4620
tgtaaccata tgtttatttg tgaaatttgt gatgctattg ctttatttgt aaccattgct   4680
ttttgcttgt actgggtctc tctggttaga ccagatctga gcctgggagc tctctggcta   4740
actagggaac ccactgctta agcctcaata aagcttgcct cgaccagcct cgactgtgcc   4800
ttctagttgc cagccatctg ttgtttgccc ctcccccgtg ccttccttga ccctggaagg   4860
tgccactccc actgtccttt cctaataaaa tgaggaaatt gcatcgcatt gtctgagtag   4920
gtgtcattct attctggggg gtggggtggg gcaggacagc aagggggagg attgggaaga   4980
caatagcagg catgctgggg atgcggtggg ctctatggcc tgcagctgca ttaatgaatc   5040
ggccaacgcg cggggagagg cggtttgcgt attgggcgct cttccgcttc ctcgctcact   5100
gactcgctgc gctcggtcgt tcggctgcgg cgagcggtat cagctcactc aaaggcggta   5160
atacggttat ccacagaatc aggggataac gcaggaaaga acatgtgagc aaaaggccag   5220
caaaaggcca ggaaccgtaa aaaggccgcg ttgctggcgt ttttccatag gctccgcccc   5280
cctgacgagc atcacaaaaa tcgacgctca agtcagaggt ggcgaaaccc gacaggacta   5340
taaagatacc aggcgtttcc ccctggaagc tccctcgtgc gctctcctgt tccgaccctg   5400
ccgcttaccg gatacctgtc cgcctttctc ccttcgggaa gcgtggcgct ttctcatagc   5460
tcacgctgta ggtatctcag ttcggtgtag gtcgttcgct ccaagctggg ctgtgtgcac   5520
gaaccccccg ttcagcccga ccgctgcgcc ttatccggta actatcgtct tgagtccaac   5580
ccggtaagac acgacttatc gccactggca gcagccactg gtaacaggat tagcagagcg   5640
aggtatgtag gcggtgctac agagttcttg aagtggtggc ctaactacgg ctacactaga   5700
aggacagtat ttggtatctg cgctctgctg aagccagtta ccttcggaaa aagagttggt   5760
agctcttgat ccggcaaaca aaccaccgct ggtagcggtg gtttttttgt ttgcaagcag   5820
cagattacgc gcagaaaaaa aggatctcaa gaagatcctt tgatcttttc tacggggtct   5880
gacgctcagt ggaacgaaaa ctcacgttaa gggattttgg tcatgagatt atcaaaaagg   5940
atcttcacct agatcctttt aaattaaaaa tgaagtttta aatcaatcta aagtatatat   6000
gagtaaactt ggtctgacag ttaccaatgc ttaatcagtg aggcacctat ctcagcgatc   6060
tgtctatttc gttcatccat agttgcctga ctccccgtcg tgtagataac tacgatacgg   6120
gagggcttac catctggccc cagtgctgca atgataccgc gagacccacg ctcaccggct   6180
ccagatttat cagcaataaa ccagccagcc ggaagggccg agcgcagaag tggtcctgca   6240
actttatccg cctccatcca gtctattaat tgttgccggg aagctagagt aagtagttcg   6300
ccagttaata gtttgcgcaa cgttgttgcc attgctacag gcatcgtggt gtcacgctcg   6360
tcgtttggta tggcttcatt cagctccggt tcccaacgat caaggcgagt tacatgatcc   6420
cccatgttgt gcaaaaaagc ggttagctcc ttcggtcctc cgatcgttgt cagaagtaag   6480
ttggccgcag tgttatcact catggttatg gcagcactgc ataattctct tactgtcatg   6540
ccatccgtaa gatgcttttc tgtgactggt gagtactcaa ccaagtcatt ctgagaatag   6600
tgtatgcggc gaccgagttg ctcttgcccg gcgtcaatac gggataatac cgcgccacat   6660
```

agcagaactt taaaagtgct catcattgga aaacgttctt cggggcgaaa actctcaagg 6720
atcttaccgc tgttgagatc cagttcgatg taacccactc gtgcacccaa ctgatcttca 6780
gcatctttta ctttcaccag cgtttctggg tgagcaaaaa caggaaggca aaatgccgca 6840
aaaaagggaa taagggcgac acggaaatgt tgaatactca tactcttcct ttttcaatat 6900
tattgaagca tttatcaggg ttattgtctc atgagcggat acatatttga atgtatttag 6960
aaaaataaac aaataggggt tccgcgcaca tttccccgaa aagtgccacc t 7011

<210> SEQ ID NO 117
<211> LENGTH: 7968
<212> TYPE: DNA
<213> ORGANISM: Artificial Sequence
<220> FEATURE:
<223> OTHER INFORMATION: Plasmid pCVL.SFFV.HA.NLS.CLS4617..IRES.mTagBFP

<400> SEQUENCE: 117
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560
acaaattggc tgtggtatat aaaattattc ataatgatag taggaggctt ggtaggttta 1620
agaatagttt ttgctgtact ttctatagtg aatagagtta ggcagggata ttcaccatta 1680
tcgtttcaga cccacctccc aaccccgagg ggacccgaca ggcccgaagg aatagaagaa 1740

-continued

```
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgcc aataccaaat ataacgaaga   2460
gttcctgctg tacctggccg gctttgtgga cggtgacggt agcatcatcg ctcagattaa   2520
accacgtcag acctataagt ttaaacatca gctacgtttg acctttaaag tgggtcaaaa   2580
gacccagcgc cgttggtttc tggacaaact agtggatgaa attggcgttg gttacgtagc   2640
tgattctggt agcatgtccg aatacaactt aagcgaaatc aagccgctgc acaacttcct   2700
gactcaactg cagccgtttc tggaactgaa acagaaacag gcaaacctgg ttctgaaaat   2760
tatcgaacag ctgccgtctg caaaagaatc cccggacaaa ttcctggaag tttgtacctg   2820
ggtggatcag gttgcagctc tgaacgattc taagacgcgt aaaaccactt ctgaaaccgt   2880
tcgtgctgtg ctggacagcc tgagcgagaa gaagaaatcc tccccggcgg ccggtggatc   2940
tgataagtat aatcaggctc tgtctaaata caaccaagca ctgtccaagt acaatcaggc   3000
cctgtctggt ggaggcggtt ccaacaaaaa attcctgctg tatcttgctg gatttgtgga   3060
ttctgatggc tccatcattg ctcagataaa accaggtcaa cgttacaagt tcaaacacca   3120
gctccgtttg accttttacg tcactcagaa gacacaaaga aggtggttct tggacaaatt   3180
ggttgatcgt attggtgtgg gctatgtcta cgactctggc tctgcttcaa actaccagct   3240
gtctgaaatt aagcctcttc ataacctgct cacccaactg caacccttct tgaagctcaa   3300
acagaagcaa gcaaatctgg ttttgaaaat catcgagcaa ctgccatctg ccaaggagtc   3360
ccctgacaag tttcttgaag tgtgtacttg ggtggatcag gttgctgcct tgaatgactc   3420
caagaccaga aaaaccacct ctgagactgt gagggcagtt ctggatagcc agtctgagaa   3480
gaaaaagtac tctccttagc ctgcaggtcg agcatgcatc tagggcggcc aattccgccc   3540
ctctccctcc ccccccccta acgttactgg ccgaagccgc ttggaataag gccggtgtgc   3600
gtttgtctat atgtgatttt ccaccatatt gccgtctttt ggcaatgtga gggcccggaa   3660
acctggccct gtcttcttga cgagcattcc taggggtctt tcccctctcg ccaaaggaat   3720
gcaaggtctg ttgaatgtcg tgaaggaagc agttcctctg gaagcttctt gaagacaaac   3780
aacgtctgta gcgacccttt gcaggcagcg gaacccccca cctggcgaca ggtgcctctg   3840
cggccaaaag ccacgtgtat aagatacacc tgcaaaggcg gcacaacccc agtgccacgt   3900
tgtgagttgg atagttgtgg aaagagtcaa atggctctcc tcaagcgtat tcaacaaggg   3960
gctgaaggat gcccagaagg taccccattg tatgggatct gatctggggc ctcggtgcac   4020
atgctttaca tgtgtttagt cgaggttaaa aaaacgtcta ggccccccga accacgggga   4080
```

-continued

```
cgtggttttc ctttgaaaaa cacgatgata agcttgccac aacccttacc ggtcgccacc   4140
atgagcgagc tgattaagga gaacatgcac atgaagctgt acatggaggg caccgtggac   4200
aaccatcact tcaagtgcac atccgagggc gaaggcaagc cctacgaggg cacccagacc   4260
atgagaatca aggtggtcga gggcggccct ctccccttcg ccttcgacat cctggctact   4320
agcttcctct acggcagcaa gaccttcatc aaccacaccc agggcatccc cgacttcttc   4380
aagcagtcct tccctgaggg cttcacatgg gagagagtca ccacatacga agacgggggc   4440
gtgctgaccg ctacccagga caccagcctc caggacggct gcctcatcta caacgtcaag   4500
atcagagggg tgaacttcac atccaacggc cctgtgatgc agaagaaaac actcggctgg   4560
gaggccttca ccgagacgct gtaccccgct gacggcggcc tggaaggcag aaacgacatg   4620
gccctgaagc tcgtgggcgg gagccatctg atcgcaaaca tcaagaccac atatagatcc   4680
aagaaacccg ctaagaacct caagatgcct ggcgtctact atgtggacta cagactggaa   4740
agaatcaagg aggccaacaa cgagacctac gtcgagcagc acgaggtggc agtggccaga   4800
tactgcgacc tccctagcaa actggggcac aagcttaatt gattctagag tcgaccgagc   4860
atcttaccgc catttatacc catatttgtt ctgtttttct tgatttgggt atacatttaa   4920
atgttaatag aacaaaatgg tggggcaatc atttacattt ttagggatat gtaattacta   4980
gttcaggtgt attgccacaa gacaaacatg ttaagaaact ttcccgttat ttacgctctg   5040
ttcctgttaa tcaacctctg gattacaaaa tttgtgaaag attgactgat attcttaact   5100
atgttgctcc ttttacgctg tgtggatatg ctgctttata gcctctgtat ctagctattg   5160
cttcccgtac ggctttcgtt ttctcctcct tgtataaatc ctggttgctg tctcttttag   5220
aggagttgtg gcccgttgtc cgtcaacgtg gcgtggtgtg ctctgtgttt gctgacgcaa   5280
cccccactgg ctggggcatt gccaccacct gtcaactcct ttctgggact ttcgctttcc   5340
ccctcccgat cgccacggca gaactcatcg ccgcctgcct tgcccgctgc tggacagggg   5400
ctaggttgct gggcactgat aattccgtgg tgttgtcatc ggtacctttt taaaagaaaa   5460
ggggggactg gaagggctaa ttcactccca acgaagacaa gatatcataa cttcgtatag   5520
catacattat acgaagttat aatttatttg tgaaatttgt gatgctattg ctttatttgt   5580
aaccatatgt ttatttgtga aatttgtgat gctattgctt tatttgtaac cattgctttt   5640
tgcttgtact gggtctctct ggttagacca gatctgagcc tgggagctct ctggctaact   5700
agggaaccca ctgcttaagc ctcaataaag cttgcctcga ccagcctcga ctgtgccttc   5760
tagttgccag ccatctgttg tttgcccctc ccccgtgcct tccttgaccc tggaaggtgc   5820
cactcccact gtcctttcct aataaaatga ggaaattgca tcgcattgtc tgagtaggtg   5880
tcattctatt ctggggggtg gggtggggca ggacagcaag ggggaggatt gggaagacaa   5940
tagcaggcat gctggggatg cggtgggctc tatggcctgc agctgcatta atgaatcggc   6000
caacgcgcgg ggagaggcgg tttgcgtatt gggcgctctt ccgcttcctc gctcactgac   6060
tcgctgcgct cggtcgttcg gctgcggcga gcggtatcag ctcactcaaa ggcggtaata   6120
cggttatcca cagaatcagg ggataacgca ggaaagaaca tgtgagcaaa aggccagcaa   6180
aaggccagga accgtaaaaa ggccgcgttg ctggcgtttt tccataggct ccgcccccct   6240
gacgagcatc acaaaaatcg acgctcaagt cagaggtggc gaaacccgac aggactataa   6300
agataccagg cgtttccccc tggaagctcc ctcgtgcgct ctcctgttcc gaccctgccg   6360
cttaccggat acctgtccgc ctttctccct tcgggaagcg tggcgctttc tcatagctca   6420
cgctgtaggt atctcagttc ggtgtaggtc gttcgctcca agctgggctg tgtgcacgaa   6480
```

-continued

```
cccccgttc agcccgaccg ctgcgcctta tccggtaact atcgtcttga gtccaacccg   6540
gtaagacacg acttatcgcc actggcagca gccactggta acaggattag cagagcgagg   6600
tatgtaggcg gtgctacaga gttcttgaag tggtggccta actacggcta cactagaagg   6660
acagtatttg gtatctgcgc tctgctgaag ccagttacct tcggaaaaag agttggtagc   6720
tcttgatccg gcaaacaaac caccgctggt agcggtggtt tttttgtttg caagcagcag   6780
attacgcgca gaaaaaaagg atctcaagaa gatcctttga tcttttctac ggggtctgac   6840
gctcagtgga acgaaaactc acgttaaggg attttggtca tgagattatc aaaaaggatc   6900
ttcacctaga tccttttaaa ttaaaaatga agttttaaat caatctaaag tatatatgag   6960
taaacttggt ctgacagtta ccaatgctta atcagtgagg cacctatctc agcgatctgt   7020
ctatttcgtt catccatagt tgcctgactc cccgtcgtgt agataactac gatacgggag   7080
ggcttaccat ctggccccag tgctgcaatg ataccgcgag acccacgctc accggctcca   7140
gatttatcag caataaacca gccagccgga agggccgagc gcagaagtgg tcctgcaact   7200
ttatccgcct ccatccagtc tattaattgt tgccgggaag ctagagtaag tagttcgcca   7260
gttaatagtt tgcgcaacgt tgttgccatt gctacaggca tcgtggtgtc acgctcgtcg   7320
tttggtatgg cttcattcag ctccggttcc caacgatcaa ggcgagttac atgatccccc   7380
atgttgtgca aaaaagcggt tagctccttc ggtcctccga tcgttgtcag aagtaagttg   7440
gccgcagtgt tatcactcat ggttatggca gcactgcata attctcttac tgtcatgcca   7500
tccgtaagat gcttttctgt gactggtgag tactcaacca agtcattctg agaatagtgt   7560
atgcggcgac cgagttgctc ttgcccggcg tcaatacggg ataataccgc gccacatagc   7620
agaactttaa aagtgctcat cattggaaaa cgttcttcgg ggcgaaaact ctcaaggatc   7680
ttaccgctgt tgagatccag ttcgatgtaa cccactcgtg cacccaactg atcttcagca   7740
tcttttactt tcaccagcgt ttctgggtga gcaaaaacag gaaggcaaaa tgccgcaaaa   7800
aagggaataa gggcgacacg gaaatgttga atactcatac tcttcctttt tcaatattat   7860
tgaagcattt atcagggtta ttgtctcatg agcggataca tatttgaatg tatttagaaa   7920
aataaacaaa taggggttcc gcgcacattt ccccgaaaag tgccacct                7968
```

<210> SEQ ID NO 118
<211> LENGTH: 8742
<212> TYPE: DNA
<213> ORGANISM: Artificial Sequence
<220> FEATURE:
<223> OTHER INFORMATION: Plasmid
pCVL.SFFV.HA.NLS.CLS4617.T2A.Trex2.IRES.mTagBFP

<400> SEQUENCE: 118

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
```

-continued

```
attttgacta gcggaggcta gaaggagaga gatgggtgcg agagcgtcag tattaagcgg    600
gggagaatta gatcgcgatg ggaaaaaatt cggttaaggc caggggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgcc aataccaaat ataacgaaga   2460
gttcctgctg tacctggccg gctttgtgga cggtgacggt agcatcatcg ctcagattaa   2520
accacgtcag acctataagt ttaaacatca gctacgtttg acctttaaag tgggtcaaaa   2580
gacccagcgc cgttggtttc tggacaaact agtggatgaa attggcgttg gttacgtagc   2640
tgattctggt agcatgtccg aatacaactt aagcgaaatc aagccgctgc acaacttcct   2700
gactcaactg cagccgtttc tggaactgaa acagaaacag gcaaacctgg ttctgaaaat   2760
tatcgaacag ctgccgtctg caaaagaatc cccggacaaa ttcctggaag tttgtacctg   2820
ggtggatcag gttgcagctc tgaacgattc taagacgcgt aaaaccactt ctgaaaccgt   2880
```

-continued

```
tcgtgctgtg ctggacagcc tgagcgagaa gaagaaatcc tccccggcgg ccggtggatc   2940
tgataagtat aatcaggctc tgtctaaata caaccaagca ctgtccaagt acaatcaggc   3000
cctgtctggt ggaggcggtt ccaacaaaaa attcctgctg tatcttgctg gatttgtgga   3060
ttctgatggc tccatcattg ctcagataaa accaggtcaa cgttacaagt tcaaacacca   3120
gctccgtttg accttttacg tcactcagaa gacacaaaga aggtggttct tggacaaatt   3180
ggttgatcgt attggtgtgg gctatgtcta cgactctggc tctgcttcaa actaccagct   3240
gtctgaaatt aagcctcttc ataacctgct cacccaactg caacccttct tgaagctcaa   3300
acagaagcaa gcaaatctgg ttttgaaaat catcgagcaa ctgccatctg ccaaggagtc   3360
ccctgacaag tttcttgaag tgtgtacttg ggtggatcag gttgctgcct tgaatgactc   3420
caagaccaga aaaaccacct ctgagactgt gagggcagtt ctggatagcc agtctgagaa   3480
gaaaaagtac tctcctggat ccggtgaggg cagaggaagt cttctaacat gcggtgacgt   3540
ggaggagaat ccgggcccct ccggatctga gccacctcgg gctgagacct ttgtattcct   3600
ggacctagaa gccactgggc tcccaaacat ggaccctgag attgcagaga tatccctttt   3660
tgctgttcac cgctcttccc tggagaaccc agaacgggat gattctggtt ccttggtgct   3720
gccccgtgtt ctggacaagc tcacactgtg catgtgcccg gagcgcccct ttactgccaa   3780
ggccagtgag attactggtt tgagcagcga aagcctgatg cactgcggga aggctggttt   3840
caatggcgct gtggtaagga cactgcaggg cttcctaagc cgccaggagg gccccatctg   3900
ccttgtggcc cacaatggct tcgattatga cttcccactg ctgtgcacgg agctacaacg   3960
tctgggtgcc catctgcccc aagacactgt ctgcctggac acactgcctg cattgcgggg   4020
cctggaccgt gctcacagcc acggcaccag ggctcaaggc cgcaaaagct acagcctggc   4080
cagtctcttc caccgctact tccaggctga acccagtgct gcccattcag cagaaggtga   4140
tgtgcacacc ctgcttctga tcttcctgca tcgtgctcct gagctgctcg cctgggcaga   4200
tgagcaggcc cgcagctggg ctcatattga gcccatgtac gtgccacctg atggtccaag   4260
cctcgaagcc tgacctgcag gtcgagcatg catctagggc ggccaattcc gcccctctcc   4320
ctcccccccc cctaacgtta ctggccgaag ccgcttggaa taaggccggt gtgcgtttgt   4380
ctatatgtga ttttccacca tattgccgtc ttttggcaat gtgagggccc ggaaacctgg   4440
ccctgtcttc ttgacgagca ttcctagggg tctttcccct ctcgccaaag gaatgcaagg   4500
tctgttgaat gtcgtgaagg aagcagttcc tctggaagct tcttgaagac aaacaacgtc   4560
tgtagcgacc ctttgcaggc agcggaaccc cccacctggc gacaggtgcc tctgcggcca   4620
aaagccacgt gtataagata cacctgcaaa ggcggcacaa ccccagtgcc acgttgtgag   4680
ttggatagtt gtggaaagag tcaaatggct ctcctcaagc gtattcaaca aggggctgaa   4740
ggatgcccag aaggtacccc attgtatggg atctgatctg gggcctcggt gcacatgctt   4800
tacatgtgtt tagtcgaggt taaaaaaacg tctaggcccc ccgaaccacg gggacgtggt   4860
tttcctttga aaaacacgat gataagcttg ccacaaccct taccggtcgc caccatgagc   4920
gagctgatta aggagaacat gcacatgaag ctgtacatgg agggcaccgt ggacaaccat   4980
cacttcaagt gcacatccga gggcgaaggc aagccctacg agggcaccca gaccatgaga   5040
atcaaggtgg tcgagggcgg ccctctcccc ttcgccttcg acatcctggc tactagcttc   5100
ctctacggca gcaagacctt catcaaccac acccagggca tccccgactt cttcaagcag   5160
tccttccctg agggcttcac atgggagaga gtcaccacat acgaagacgg gggcgtgctg   5220
accgctaccc aggacaccag cctccaggac ggctgcctca tctacaacgt caagatcaga   5280
```

-continued

```
ggggtgaact tcacatccaa cggccctgtg atgcagaaga aaacactcgg ctgggaggcc   5340
ttcaccgaga cgctgtaccc cgctgacggc ggcctggaag gcagaaacga catggccctg   5400
aagctcgtgg gcgggagcca tctgatcgca aacatcaaga ccacatatag atccaagaaa   5460
cccgctaaga acctcaagat gcctggcgtc tactatgtgg actacagact ggaaagaatc   5520
aaggaggcca acaacgagac ctacgtcgag cagcacgagg tggcagtggc cagatactgc   5580
gacctcccta gcaaactggg gcacaagctt aattgattct agagtcgacc gagcatctta   5640
ccgccattta tacccatatt tgttctgttt ttcttgattt gggtatacat ttaaatgtta   5700
atagaacaaa atggtggggc aatcatttac atttttaggg atatgtaatt actagttcag   5760
gtgtattgcc acaagacaaa catgttaaga aactttcccg ttatttacgc tctgttcctg   5820
ttaatcaacc tctggattac aaaatttgtg aaagattgac tgatattctt aactatgttg   5880
ctccttttac gctgtgtgga tatgctgctt tatagcctct gtatctagct attgcttccc   5940
gtacggcttt cgttttctcc tccttgtata aatcctggtt gctgtctctt ttagaggagt   6000
tgtggcccgt tgtccgtcaa cgtggcgtgg tgtgctctgt gtttgctgac gcaaccccca   6060
ctggctgggg cattgccacc acctgtcaac tcctttctgg gactttcgct ttccccctcc   6120
cgatcgccac ggcagaactc atcgccgcct gccttgcccg ctgctggaca ggggctaggt   6180
tgctgggcac tgataattcc gtggtgttgt catcggtacc tttttaaaag aaaagggggg   6240
actggaaggg ctaattcact cccaacgaag acaagatatc ataacttcgt atagcataca   6300
ttatacgaag ttataattta tttgtgaaat ttgtgatgct attgctttat ttgtaaccat   6360
atgtttattt gtgaaatttg tgatgctatt gctttatttg taaccattgc tttttgcttg   6420
tactgggtct ctctggttag accagatctg agcctgggag ctctctggct aactagggaa   6480
cccactgctt aagcctcaat aaagcttgcc tcgaccagcc tcgactgtgc cttctagttg   6540
ccagccatct gttgtttgcc cctcccccgt gccttccttg accctggaag gtgccactcc   6600
cactgtcctt tcctaataaa atgaggaaat tgcatcgcat tgtctgagta ggtgtcattc   6660
tattctgggg ggtggggtgg ggcaggacag caagggggag gattgggaag acaatagcag   6720
gcatgctggg gatgcggtgg gctctatggc ctgcagctgc attaatgaat cggccaacgc   6780
gcggggagag gcggtttgcg tattgggcgc tcttccgctt cctcgctcac tgactcgctg   6840
cgctcggtcg ttcggctgcg gcgagcggta tcagctcact caaaggcggt aatacggtta   6900
tccacagaat caggggataa cgcaggaaag aacatgtgag caaaaggcca gcaaaaggcc   6960
aggaaccgta aaaaggccgc gttgctggcg tttttccata ggctccgccc ccctgacgag   7020
catcacaaaa atcgacgctc aagtcagagg tggcgaaacc cgacaggact ataaagatac   7080
caggcgtttc cccctggaag ctccctcgtg cgctctcctg ttccgaccct gccgcttacc   7140
ggatacctgt ccgcctttct cccttcggga agcgtggcgc tttctcatag ctcacgctgt   7200
aggtatctca gttcggtgta ggtcgttcgc tccaagctgg gctgtgtgca cgaacccccc   7260
gttcagcccg accgctgcgc cttatccggt aactatcgtc ttgagtccaa cccggtaaga   7320
cacgacttat cgccactggc agcagccact ggtaacagga ttagcagagc gaggtatgta   7380
ggcggtgcta cagagttctt gaagtggtgg cctaactacg gctacactag aaggacagta   7440
tttggtatct gcgctctgct gaagccagtt accttcggaa aaagagttgg tagctcttga   7500
tccggcaaac aaaccaccgc tggtagcggt ggtttttttg tttgcaagca gcagattacg   7560
cgcagaaaaa aaggatctca agaagatcct ttgatctttt ctacggggtc tgacgctcag   7620
```

```
tggaacgaaa actcacgtta agggattttg gtcatgagat tatcaaaaag gatcttcacc   7680
tagatccttt taaattaaaa atgaagtttt aaatcaatct aaagtatata tgagtaaact   7740
tggtctgaca gttaccaatg cttaatcagt gaggcaccta tctcagcgat ctgtctattt   7800
cgttcatcca tagttgcctg actccccgtc gtgtagataa ctacgatacg ggagggctta   7860
ccatctggcc ccagtgctgc aatgataccg cgagacccac gctcaccggc tccagattta   7920
tcagcaataa accagccagc cggaagggcc gagcgcagaa gtggtcctgc aactttatcc   7980
gcctccatcc agtctattaa ttgttgccgg gaagctagag taagtagttc gccagttaat   8040
agtttgcgca acgttgttgc cattgctaca ggcatcgtgg tgtcacgctc gtcgtttggt   8100
atggcttcat tcagctccgg ttcccaacga tcaaggcgag ttacatgatc ccccatgttg   8160
tgcaaaaaag cggttagctc cttcggtcct ccgatcgttg tcagaagtaa gttggccgca   8220
gtgttatcac tcatggttat ggcagcactg cataattctc ttactgtcat gccatccgta   8280
agatgctttt ctgtgactgg tgagtactca accaagtcat tctgagaata gtgtatgcgg   8340
cgaccgagtt gctcttgccc ggcgtcaata cgggataata ccgcgccaca tagcagaact   8400
ttaaaagtgc tcatcattgg aaaacgttct tcggggcgaa aactctcaag gatcttaccg   8460
ctgttgagat ccagttcgat gtaacccact cgtgcaccca actgatcttc agcatctttt   8520
actttcacca gcgtttctgg gtgagcaaaa acaggaaggc aaaatgccgc aaaaaaggga   8580
ataagggcga cacggaaatg ttgaatactc atactcttcc tttttcaata ttattgaagc   8640
atttatcagg gttattgtct catgagcgga tacatatttg aatgtattta gaaaaataaa   8700
caaatagggg ttccgcgcac atttccccga aaagtgccac ct                       8742
```

```
<210> SEQ ID NO 119
<211> LENGTH: 8757
<212> TYPE: DNA
<213> ORGANISM: Artificial Sequence
<220> FEATURE:
<223> OTHER INFORMATION: Plasmid pCVL.SFFV.HA.NLS.mCre
      I.T2A.Trex2.IRES.mTagBFP

<400> SEQUENCE: 119
```

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
```

-continued

```
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgac accaagtata acaaggagtt   2460
cctgctgtat ctggctggtt tcgtcgatgg cgatggcagc attattgcac agattaagcc   2520
aaaccagtcc tataagttta agcaccagtt gtctctcact tttcaggtga cccaaaaaac   2580
ccaacgccgc tggttcctcg acaagctggt agacgagatc ggtgtgggct acgttcgcga   2640
tcgcggctcc gtttccgact acatcctcag cgagattaaa ccgctgcaca attttctgac   2700
ccaactgcag ccgtttctga agctcaaaca gaagcaagcg aacctggtgc tgaaaatcat   2760
cgaacagctc ccgtccgcga aggaatctcc ggataagttt ctggaagtgt gcacctgggt   2820
ggaccagatt gctgcactga atgattccaa aacccgcaag accacttctg agaccgttcg   2880
cgccgttctg gactctctct ctgaaaaaaa aaaatcttcc ccgaccggta gcggctcagg   2940
atctaaatcc caggctgtgg ctcacccgac agacggccag agggatttcg gggccaaagg   3000
atctgggtcg ggaagcggta ccatgaatac taaatacaat aaagaatttc ttctctacct   3060
cgcgggcttt gtggacggtg acggttccat catcgctcaa atcaaaccta atcaaagcta   3120
caaattcaaa catcagctgt ccctgacctt ccaagttacg cagaaaacgc agcgtcgttg   3180
gtttctggat aaattggttg atgaaattgg cgtaggttat gtacgtgacc gtggttctgt   3240
gtctgattat attctgtccg aaatcaagcc tctccataac ttcctcacgc agctgcaacc   3300
```

-continued

```
attcctgaaa ctgaagcaga aacaggctaa tctcgttctg aaaattattg aacagctgcc   3360
atctgctaaa gagtcccctg acaaattcct cgaggtttgt acttgggttg atcaaatcgc   3420
ggcccttaac gacagcaaga ctcgtaaaac taccagcgaa actgtccgtg cagtactcga   3480
ttccctgtcg gagaagaaga agagctctcc aggatccggt gagggcagag gaagtcttct   3540
aacatgcggt gacgtggagg agaatccggg cccctccgga tctgagccac ctcgggctga   3600
gacctttgta ttcctggacc tagaagccac tgggctccca aacatggacc ctgagattgc   3660
agagatatcc ctttttgctg ttcaccgctc ttccctggag aacccagaac gggatgattc   3720
tggttccttg gtgctgcccc gtgttctgga caagctcaca ctgtgcatgt gcccggagcg   3780
ccccttact gccaaggcca gtgagattac tggtttgagc agcgaaagcc tgatgcactg    3840
cgggaaggct ggtttcaatg gcgctgtggt aaggacactg cagggcttcc taagccgcca   3900
ggagggcccc atctgccttg tggcccacaa tggcttcgat tatgacttcc cactgctgtg   3960
cacggagcta caacgtctgg gtgcccatct gccccaagac actgtctgcc tggacacact   4020
gcctgcattg cggggcctgg accgtgctca cagccacggc accagggctc aaggccgcaa   4080
aagctacagc ctggccagtc tcttccaccg ctacttccag gctgaaccca gtgctgccca   4140
ttcagcagaa ggtgatgtgc acaccctgct tctgatcttc ctgcatcgtg ctcctgagct   4200
gctcgcctgg gcagatgagc aggcccgcag ctgggctcat attgagccca tgtacgtgcc   4260
acctgatggt ccaagcctcg aagcctgacc tgcaggtcga gcatgcatct agggcggcca   4320
attccgcccc tctccctccc ccccccctaa cgttactggc cgaagccgct tggaataagg   4380
ccggtgtgcg tttgtctata tgtgattttc caccatattg ccgtcttttg gcaatgtgag   4440
ggcccggaaa cctggccctg tcttcttgac gagcattcct aggggtcttt cccctctcgc   4500
caaaggaatg caaggtctgt tgaatgtcgt gaaggaagca gttcctctgg aagcttcttg   4560
aagacaaaca acgtctgtag cgaccctttg caggcagcgg aaccccccac ctggcgacag   4620
gtgcctctgc ggccaaaagc cacgtgtata agatacacct gcaaaggcgg cacaacccca   4680
gtgccacgtt gtgagttgga tagttgtgga aagagtcaaa tggctctcct caagcgtatt   4740
caacaagggg ctgaaggatg cccagaaggt accccattgt atgggatctg atctggggcc   4800
tcggtgcaca tgctttacat gtgtttagtc gaggttaaaa aaacgtctag gccccccgaa   4860
ccacggggac gtggttttcc tttgaaaaac acgatgataa gcttgccaca acccttaccg   4920
gtcgccacca tgagcgagct gattaaggag aacatgcaca tgaagctgta catggagggc   4980
accgtggaca accatcactt caagtgcaca tccgagggcg aaggcaagcc ctacgagggc   5040
acccagacca tgagaatcaa ggtggtcgag ggcggccctc tccccttcgc cttcgacatc   5100
ctggctacta gcttcctcta cggcagcaag accttcatca accacaccca gggcatcccc   5160
gacttcttca agcagtcctt ccctgagggc ttcacatggg agagagtcac cacatacgaa   5220
gacgggggcg tgctgaccgc tacccaggac accagcctcc aggacggctg cctcatctac   5280
aacgtcaaga tcagaggggt gaacttcaca tccaacggcc ctgtgatgca gaagaaaaca   5340
ctcggctggg aggccttcac cgagacgctg taccccgctg acggcggcct ggaaggcaga   5400
aacgacatgg ccctgaagct cgtgggcggg agccatctga tcgcaaacat caagaccaca   5460
tatagatcca agaaacccgc taagaacctc aagatgcctg gcgtctacta tgtggactac   5520
agactggaaa gaatcaagga ggccaacaac gagacctacg tcgagcagca cgaggtggca   5580
gtggccagat actgcgacct ccctagcaaa ctggggcaca agcttaattg attctagagt   5640
```

```
cgaccgagca tcttaccgcc atttataccc atatttgttc tgtttttctt gatttgggta   5700
tacatttaaa tgttaataga acaaaatggt ggggcaatca tttacatttt tagggatatg   5760
taattactag ttcaggtgta ttgccacaag acaaacatgt taagaaactt tcccgttatt   5820
tacgctctgt tcctgttaat caacctctgg attacaaaat ttgtgaaaga ttgactgata   5880
ttcttaacta tgttgctcct tttacgctgt gtggatatgc tgctttatag cctctgtatc   5940
tagctattgc ttcccgtacg gctttcgttt tctcctcctt gtataaatcc tggttgctgt   6000
ctcttttaga ggagttgtgg cccgttgtcc gtcaacgtgg cgtggtgtgc tctgtgtttg   6060
ctgacgcaac ccccactggc tggggcattg ccaccacctg tcaactcctt tctgggactt   6120
tcgctttccc cctcccgatc gccacggcag aactcatcgc cgcctgcctt gcccgctgct   6180
ggacaggggc taggttgctg ggcactgata attccgtggt gttgtcatcg gtaccttttt   6240
aaaagaaaag gggggactgg aagggctaat tcactcccaa cgaagacaag atatcataac   6300
ttcgtatagc atacattata cgaagttata atttatttgt gaaatttgtg atgctattgc   6360
tttatttgta accatatgtt tatttgtgaa atttgtgatg ctattgcttt atttgtaacc   6420
attgcttttt gcttgtactg ggtctctctg gttagaccag atctgagcct gggagctctc   6480
tggctaacta gggaacccac tgcttaagcc tcaataaagc ttgcctcgac cagcctcgac   6540
tgtgccttct agttgccagc catctgttgt ttgcccctcc cccgtgcctt ccttgaccct   6600
ggaaggtgcc actcccactg tcctttccta ataaaatgag gaaattgcat cgcattgtct   6660
gagtaggtgt cattctattc tggggggtgg ggtggggcag gacagcaagg gggaggattg   6720
ggaagacaat agcaggcatg ctggggatgc ggtgggctct atggcctgca gctgcattaa   6780
tgaatcggcc aacgcgcggg gagaggcggt ttgcgtattg ggcgctcttc cgcttcctcg   6840
ctcactgact cgctgcgctc ggtcgttcgg ctgcggcgag cggtatcagc tcactcaaag   6900
gcggtaatac ggttatccac agaatcaggg gataacgcag gaaagaacat gtgagcaaaa   6960
ggccagcaaa aggccaggaa ccgtaaaaag gccgcgttgc tggcgttttt ccataggctc   7020
cgcccccctg acgagcatca caaaaatcga cgctcaagtc agaggtggcg aaacccgaca   7080
ggactataaa gataccaggc gtttccccct ggaagctccc tcgtgcgctc tcctgttccg   7140
accctgccgc ttaccggata cctgtccgcc tttctccctt cgggaagcgt ggcgctttct   7200
catagctcac gctgtaggta tctcagttcg gtgtaggtcg ttcgctccaa gctgggctgt   7260
gtgcacgaac cccccgttca gcccgaccgc tgcgccttat ccggtaacta tcgtcttgag   7320
tccaacccgg taagacacga cttatcgcca ctggcagcag ccactggtaa caggattagc   7380
agagcgaggt atgtaggcgg tgctacagag ttcttgaagt ggtggcctaa ctacggctac   7440
actagaagga cagtatttgg tatctgcgct ctgctgaagc cagttacctt cggaaaaaga   7500
gttggtagct cttgatccgg caaacaaacc accgctggta gcggtggttt ttttgtttgc   7560
aagcagcaga ttacgcgcag aaaaaaagga tctcaagaag atcctttgat cttttctacg   7620
gggtctgacg ctcagtggaa cgaaaactca cgttaaggga ttttggtcat gagattatca   7680
aaaaggatct tcacctagat ccttttaaat taaaaatgaa gttttaaatc aatctaaagt   7740
atatatgagt aaacttggtc tgacagttac caatgcttaa tcagtgaggc acctatctca   7800
gcgatctgtc tatttcgttc atccatagtt gcctgactcc ccgtcgtgta gataactacg   7860
atacgggagg gcttaccatc tggccccagt gctgcaatga taccgcgaga cccacgctca   7920
ccggctccag atttatcagc aataaaccag ccagccggaa gggccgagcg cagaagtggt   7980
cctgcaactt tatccgcctc catccagtct attaattgtt gccgggaagc tagagtaagt   8040
```

```
agttcgccag ttaatagttt gcgcaacgtt gttgccattg ctacaggcat cgtggtgtca   8100

cgctcgtcgt ttggtatggc ttcattcagc tccggttccc aacgatcaag gcgagttaca   8160

tgatccccca tgttgtgcaa aaaagcggtt agctccttcg gtcctccgat cgttgtcaga   8220

agtaagttgg ccgcagtgtt atcactcatg gttatggcag cactgcataa ttctcttact   8280

gtcatgccat ccgtaagatg cttttctgtg actggtgagt actcaaccaa gtcattctga   8340

gaatagtgta tgcggcgacc gagttgctct tgcccggcgt caatacggga taataccgcg   8400

ccacatagca gaactttaaa agtgctcatc attggaaaac gttcttcggg gcgaaaactc   8460

tcaaggatct taccgctgtt gagatccagt tcgatgtaac ccactcgtgc acccaactga   8520

tcttcagcat cttttacttt caccagcgtt tctgggtgag caaaaacagg aaggcaaaat   8580

gccgcaaaaa agggaataag ggcgacacgg aaatgttgaa tactcatact cttccttttt   8640

caatattatt gaagcattta tcagggttat tgtctcatga gcggatacat atttgaatgt   8700

atttagaaaa ataaacaaat aggggttccg cgcacatttc cccgaaaagt gccacct      8757


<210> SEQ ID NO 120
<211> LENGTH: 7986
<212> TYPE: DNA
<213> ORGANISM: Artificial Sequence
<220> FEATURE:
<223> OTHER INFORMATION: Plasmid pCVL.SFFV.HA.NLS.mCre.IRES.mTagBFP

<400> SEQUENCE: 120

gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc ctgatcttca gacctggagg aggagatatg    960

agggacaatt ggagaagtga attatataaa tataaagtag taaaaattga accattagga   1020

gtagcaccca ccaaggcaaa gagaagagtg gtgcagagag aaaaaagagc agtgggaata   1080

ggagctttgt tccttgggtt cttgggagca gcaggaagca ctatgggcgc agcgtcaatg   1140

acgctgacgg tacaggccag acaattattg tctggtatag tgcagcagca gaacaatttg   1200

ctgagggcta ttgaggcgca acagcatctg ttgcaactca cagtctgggg catcaagcag   1260

ctccaggcaa gaatcctggc tgtggaaaga tacctaaagg atcaacagct cctggggatt   1320
```

-continued

```
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgac accaagtata acaaggagtt   2460
cctgctgtat ctggctggtt tcgtcgatgg cgatggcagc attattgcac agattaagcc   2520
aaaccagtcc tataagttta agcaccagtt gtctctcact tttcaggtga cccaaaaaac   2580
ccaacgccgc tggttcctcg acaagctggt agacgagatc ggtgtgggct acgttcgcga   2640
tcgcggctcc gtttccgact acatcctcag cgagattaaa ccgctgcaca attttctgac   2700
ccaactgcag ccgtttctga agctcaaaca gaagcaagcg aacctggtgc tgaaaatcat   2760
cgaacagctc ccgtccgcga aggaatctcc ggataagttt ctggaagtgt gcacctgggt   2820
ggaccagatt gctgcactga atgattccaa aacccgcaag accacttctg agaccgttcg   2880
cgccgttctg gactctctct ctgaaaaaaa aaaatcttcc ccgaccggta gcggctcagg   2940
atctaaatcc caggctgtgg ctcacccgac agacggccag agggatttcg gggccaaagg   3000
atctgggtcg ggaagcggta ccatgaatac taaatacaat aaagaatttc ttctctacct   3060
cgcgggcttt gtggacggtg acggttccat catcgctcaa atcaaaccta atcaaagcta   3120
caaattcaaa catcagctgt ccctgacctt ccaagttacg cagaaaacgc agcgtcgttg   3180
gtttctggat aaattggttg atgaaattgg cgtaggttat gtacgtgacc gtggttctgt   3240
gtctgattat attctgtccg aaatcaagcc tctccataac ttcctcacgc agctgcaacc   3300
attcctgaaa ctgaagcaga aacaggctaa tctcgttctg aaaattattg aacagctgcc   3360
atctgctaaa gagtcccctg acaaattcct cgaggtttgt acttgggttg atcaaatcgc   3420
ggcccttaac gacagcaaga ctcgtaaaac taccagcgaa actgtccgtg cagtactcga   3480
ttccctgtcg gagaagaaga agagctctcc atagtaacct gcaggtcgag catgcatcta   3540
gggcggccaa ttccgcccct ctccctcccc ccccccctaac gttactggcc gaagccgctt   3600
ggaataaggc cggtgtgcgt ttgtctatat gtgattttcc accatattgc cgtcttttgg   3660
caatgtgagg gcccggaaac ctggccctgt cttcttgacg agcattccta ggggtctttc   3720
```

-continued

```
ccctctcgcc aaaggaatgc aaggtctgtt gaatgtcgtg aaggaagcag ttcctctgga   3780
agcttcttga agacaaacaa cgtctgtagc gaccctttgc aggcagcgga acccccacc   3840
tggcgacagg tgcctctgcg gccaaaagcc acgtgtataa gatacacctg caaaggcggc   3900
acaaccccag tgccacgttg tgagttggat agttgtggaa agagtcaaat ggctctcctc   3960
aagcgtattc aacaaggggc tgaaggatgc ccagaaggta ccccattgta tgggatctga   4020
tctggggcct cggtgcacat gctttacatg tgtttagtcg aggttaaaaa aacgtctagg   4080
ccccccgaac cacggggacg tggttttcct ttgaaaaaca cgatgataag cttgccacaa   4140
cccttaccgg tcgccaccat gagcgagctg attaaggaga acatgcacat gaagctgtac   4200
atggagggca ccgtggacaa ccatcacttc aagtgcacat ccgagggcga aggcaagccc   4260
tacgagggca cccagaccat gagaatcaag gtggtcgagg gcggccctct ccccttcgcc   4320
ttcgacatcc tggctactag cttcctctac ggcagcaaga ccttcatcaa ccacacccag   4380
ggcatccccg acttcttcaa gcagtccttc cctgagggct tcacatggga gagagtcacc   4440
acatacgaag acgggggcgt gctgaccgct acccaggaca ccagcctcca ggacggctgc   4500
ctcatctaca acgtcaagat cagaggggtg aacttcacat ccaacggccc tgtgatgcag   4560
aagaaaacac tcggctggga ggccttcacc gagacgctgt accccgctga cggcggcctg   4620
gaaggcagaa acgacatggc cctgaagctc gtgggcggga gccatctgat cgcaaacatc   4680
aagaccacat atagatccaa gaaacccgct aagaacctca agatgcctgg cgtctactat   4740
gtggactaca gactggaaag aatcaaggag gccaacaacg agacctacgt cgagcagcac   4800
gaggtggcag tggccagata ctgcgacctc cctagcaaac tggggcacaa gcttaattga   4860
ttctagagtc gaccgagcat cttaccgcca tttataccca tatttgttct gtttttcttg   4920
atttgggtat acatttaaat gttaatagaa caaaatggtg ggcaatcat ttacatttt    4980
agggatatgt aattactagt tcaggtgtat tgccacaaga caaacatgtt aagaaacttt   5040
cccgttattt acgctctgtt cctgttaatc aacctctgga ttacaaaatt tgtgaaagat   5100
tgactgatat tcttaactat gttgctcctt ttacgctgtg tggatatgct gctttatagc   5160
ctctgtatct agctattgct tcccgtacgg ctttcgtttt ctcctccttg tataaatcct   5220
ggttgctgtc tcttttagag gagttgtggc ccgttgtccg tcaacgtggc gtggtgtgct   5280
ctgtgtttgc tgacgcaacc cccactggct ggggcattgc caccacctgt caactccttt   5340
ctgggacttt cgctttcccc ctcccgatcg ccacggcaga actcatcgcc gcctgccttg   5400
cccgctgctg gacaggggct aggttgctgg gcactgataa ttccgtggtg ttgtcatcgg   5460
tacctttta aaagaaaagg ggggactgga agggctaatt cactcccaac gaagacaaga   5520
tatcataact tcgtatagca tacattatac gaagttataa tttatttgtg aaatttgtga   5580
tgctattgct ttatttgtaa ccatatgttt atttgtgaaa tttgtgatgc tattgcttta   5640
tttgtaacca ttgcttttg cttgtactgg gtctctctgg ttagaccaga tctgagcctg   5700
ggagctctct ggctaactag ggaacccact gcttaagcct caataaagct tgcctcgacc   5760
agcctcgact gtgccttcta gttgccagcc atctgttgtt tgcccctccc ccgtgccttc   5820
cttgaccctg gaaggtgcca ctcccactgt cctttcctaa taaaatgagg aaattgcatc   5880
gcattgtctg agtaggtgtc attctattct ggggggtggg gtggggcagg acagcaaggg   5940
ggaggattgg gaagacaata gcaggcatgc tggggatgcg gtgggctcta tggcctgcag   6000
ctgcattaat gaatcggcca acgcgcgggg agaggcggtt tgcgtattgg gcgctcttcc   6060
```

gcttcctcgc tcactgactc gctgcgctcg gtcgttcggc tgcggcgagc ggtatcagct 6120
cactcaaagg cggtaatacg gttatccaca gaatcagggg ataacgcagg aaagaacatg 6180
tgagcaaaag gccagcaaaa ggccaggaac cgtaaaaagg ccgcgttgct ggcgtttttc 6240
cataggctcc gcccccctga cgagcatcac aaaaatcgac gctcaagtca gaggtggcga 6300
aacccgacag gactataaag ataccaggcg tttccccctg gaagctccct cgtgcgctct 6360
cctgttccga ccctgccgct taccggatac ctgtccgcct ttctcccttc gggaagcgtg 6420
gcgctttctc atagctcacg ctgtaggtat ctcagttcgg tgtaggtcgt tcgctccaag 6480
ctgggctgtg tgcacgaacc ccccgttcag cccgaccgct gcgccttatc cggtaactat 6540
cgtcttgagt ccaacccggt aagacacgac ttatcgccac tggcagcagc cactggtaac 6600
aggattagca gagcgaggta tgtaggcggt gctacagagt tcttgaagtg gtggcctaac 6660
tacggctaca ctagaaggac agtatttggt atctgcgctc tgctgaagcc agttaccttc 6720
ggaaaaagag ttggtagctc ttgatccggc aaacaaacca ccgctggtag cggtggtttt 6780
tttgtttgca agcagcagat tacgcgcaga aaaaaaggat ctcaagaaga tcctttgatc 6840
ttttctacgg ggtctgacgc tcagtggaac gaaaactcac gttaagggat tttggtcatg 6900
agattatcaa aaaggatctt cacctagatc cttttaaatt aaaaatgaag ttttaaatca 6960
atctaaagta tatatgagta aacttggtct gacagttacc aatgcttaat cagtgaggca 7020
cctatctcag cgatctgtct atttcgttca tccatagttg cctgactccc cgtcgtgtag 7080
ataactacga tacgggaggg cttaccatct ggccccagtg ctgcaatgat accgcgagac 7140
ccacgctcac cggctccaga tttatcagca ataaaccagc cagccggaag ggccgagcgc 7200
agaagtggtc ctgcaacttt atccgcctcc atccagtcta ttaattgttg ccgggaagct 7260
agagtaagta gttcgccagt taatagtttg cgcaacgttg ttgccattgc tacaggcatc 7320
gtggtgtcac gctcgtcgtt tggtatggct tcattcagct ccggttccca acgatcaagg 7380
cgagttacat gatcccccat gttgtgcaaa aaagcggtta gctccttcgg tcctccgatc 7440
gttgtcagaa gtaagttggc cgcagtgtta tcactcatgg ttatggcagc actgcataat 7500
tctcttactg tcatgccatc cgtaagatgc ttttctgtga ctggtgagta ctcaaccaag 7560
tcattctgag aatagtgtat gcggcgaccg agttgctctt gcccggcgtc aatacgggat 7620
aataccgcgc cacatagcag aactttaaaa gtgctcatca ttggaaaacg ttcttcgggg 7680
cgaaaactct caaggatctt accgctgttg agatccagtt cgatgtaacc cactcgtgca 7740
cccaactgat cttcagcatc ttttactttc accagcgttt ctgggtgagc aaaaacagga 7800
aggcaaaatg ccgcaaaaaa gggaataagg gcgacacgga aatgttgaat actcatactc 7860
ttcctttttc aatattattg aagcatttat cagggttatt gtctcatgag cggatacata 7920
tttgaatgta tttagaaaaa taaacaaata ggggttccgc gcacatttcc ccgaaaagtg 7980
ccacct 7986

<210> SEQ ID NO 121
<211> LENGTH: 7665
<212> TYPE: DNA
<213> ORGANISM: Artificial Sequence
<220> FEATURE:
<223> OTHER INFORMATION: Plasmid pCVL.SFFV.HA.NLS.Hje.IRES.mTagBFP

<400> SEQUENCE: 121
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120

-continued gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc caggggggaaa gaaaaaatat 660 aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560
acaaattggc tgtggtatat aaaattattc ataatgatag taggaggctt ggtaggttta 1620
agaatagttt ttgctgtact ttctatagtg aatagagtta ggcagggata ttcaccatta 1680
tcgtttcaga cccacctccc aaccccgagg ggacccgaca ggcccgaagg aatagaagaa 1740
gaaggtggag agagagacag agacagatcc attcgattag tgaacggatc tcgacggtat 1800
cggttaactt ttaaaagaaa aggggggatt ggggggtaca gtgcagggga aagaatagta 1860
gacataatag caacagacat acaaactaaa gaattacaaa aacaaattac aaaaattcaa 1920
aattttatcg attacgcgtc acgtgctagc tgcagtaacg ccattttgca aggcatggaa 1980
aaataccaaa ccaagaatag agaagttcag atcaagggcg ggtacatgaa aatagctaac 2040
gttgggccaa acaggatatc tgcggtgagc agtttcggcc ccggcccggg gccaagaaca 2100
gatggtcacc gcagtttcgg ccccggcccg aggccaagaa cagatggtcc ccagatatgg 2160
cccaaccctc agcagtttct taagacccat cagatgtttc caggctcccc caaggacctg 2220
aaatgaccct gcgccttatt tgaattaacc aatcagcctg cttctcgctt ctgttcgcgc 2280
gcttctgctt ccccgagctct ataaaagagc tcacaacccc tcactcggcg cgccagtcct 2340
ccgacagact gagtcgcccg ctcgagccgc caccatggga tatccatacg atgtcccaga 2400
ttatgcgcca cctaagaaga aacgcaaagt cgaattcgat cttacgtacg cgtatttagt 2460

-continued

```
tggtctcttc gaaggggatg gatactttag tatcaccaag aaaggcaagt acttgactta   2520
tgaattaggt attgagctga gcatcaaaga cgtccaattg atttacaaga tcaaggacat   2580
cctaggtgtt ggcaaagtaa gcttcaggaa gagaaacgag attgaaatgg tttcattgag   2640
gatccgtgat aagaatcatc taaaaaactt catattgcct atatttgaca agtatccaat   2700
gttatccaac aaacagtacg actatttaag attcaaggat gcattgttat ctaacattat   2760
atactcagat gacttgcctg aatacgctag aagtaacgaa tcgattaatt ctgtagactc   2820
cattatcaac acatcatact tctccgcctg gctagttgga tttatagaag ctgagggctg   2880
tttcagtacg tacaagctga acaaagacga tgactacttg attgcttcat tcgacattgc   2940
ccaaaaagat ggtgatatct tgatttcagc aattcacaag tacttaagtt tcactactaa   3000
gatttaccta gacaagacta attgtagcag attgaaggtc accggtgtta gatccgtcaa   3060
gaacgtcgtt aagtttatcc agggtgctcc tgtcaaattg ttaggcaaca agaaactgca   3120
atacaagttg tggataaaac aactaaggaa gatttctagg tattccgaga agatccagct   3180
tccatcaaac tactagcctg caggtcgagc atgcatctag ggcggccaat tccgcccctc   3240
tccctccccc ccccctaacg ttactggccg aagccgcttg gaataaggcc ggtgtgcgtt   3300
tgtctatatg tgattttcca ccatattgcc gtcttttggc aatgtgaggg cccggaaacc   3360
tggccctgtc ttcttgacga gcattcctag gggtctttcc cctctcgcca aaggaatgca   3420
aggtctgttg aatgtcgtga aggaagcagt tcctctggaa gcttcttgaa gacaaacaac   3480
gtctgtagcg accctttgca ggcagcggaa ccccccacct ggcgacaggt gcctctgcgg   3540
ccaaaagcca cgtgtataag atacacctgc aaaggcggca caaccccagt gccacgttgt   3600
gagttggata gttgtggaaa gagtcaaatg gctctcctca agcgtattca acaaggggct   3660
gaaggatgcc cagaaggtac cccattgtat gggatctgat ctggggcctc ggtgcacatg   3720
ctttacatgt gtttagtcga ggttaaaaaa acgtctaggc cccccgaacc acggggacgt   3780
ggttttcctt tgaaaaacac gatgataagc ttgccacaac ccttaccggt cgccaccatg   3840
agcgagctga ttaaggagaa catgcacatg aagctgtaca tggagggcac cgtggacaac   3900
catcacttca agtgcacatc cgagggcgaa ggcaagccct acgagggcac ccagaccatg   3960
agaatcaagg tggtcgaggg cggccctctc cccttcgcct tcgacatcct ggctactagc   4020
ttcctctacg gcagcaagac cttcatcaac cacacccagg gcatccccga cttcttcaag   4080
cagtccttcc ctgagggctt cacatgggag agagtcacca catacgaaga cgggggcgtg   4140
ctgaccgcta cccaggacac cagcctccag gacggctgcc tcatctacaa cgtcaagatc   4200
agaggggtga acttcacatc caacggccct gtgatgcaga agaaaacact cggctgggag   4260
gccttcaccg agacgctgta ccccgctgac ggcggcctgg aaggcagaaa cgacatggcc   4320
ctgaagctcg tgggcgggag ccatctgatc gcaaacatca agaccacata tagatccaag   4380
aaacccgcta agaacctcaa gatgcctggc gtctactatg tggactacag actggaaaga   4440
atcaaggagg ccaacaacga gacctacgtc gagcagcacg aggtggcagt ggccagatac   4500
tgcgacctcc ctagcaaact ggggcacaag cttaattgat tctagagtcg accgagcatc   4560
ttaccgccat ttatacccat atttgttctg tttttcttga tttgggtata catttaaatg   4620
ttaatagaac aaaatggtgg ggcaatcatt tacattttta gggatatgta attactagtt   4680
caggtgtatt gccacaagac aaacatgtta agaaactttc ccgttattta cgctctgttc   4740
ctgttaatca acctctggat tacaaaattt gtgaaagatt gactgatatt cttaactatg   4800
ttgctccttt tacgctgtgt ggatatgctg ctttatagcc tctgtatcta gctattgctt   4860
```

-continued

```
cccgtacggc tttcgttttc tcctccttgt ataaatcctg gttgctgtct cttttagagg   4920
agttgtggcc cgttgtccgt caacgtggcg tggtgtgctc tgtgtttgct gacgcaaccc   4980
ccactggctg gggcattgcc accacctgtc aactcctttc tgggactttc gctttccccc   5040
tcccgatcgc cacggcagaa ctcatcgccg cctgccttgc ccgctgctgg acaggggcta   5100
ggttgctggg cactgataat tccgtggtgt tgtcatcggt acctttttaa aagaaaaggg   5160
gggactggaa gggctaattc actcccaacg aagacaagat atcataactt cgtatagcat   5220
acattatacg aagttataat ttatttgtga aatttgtgat gctattgctt tatttgtaac   5280
catatgttta tttgtgaaat ttgtgatgct attgctttat ttgtaaccat tgctttttgc   5340
ttgtactggg tctctctggt tagaccagat ctgagcctgg gagctctctg gctaactagg   5400
gaacccactg cttaagcctc aataaagctt gcctcgacca gcctcgactg tgccttctag   5460
ttgccagcca tctgttgttt gcccctcccc cgtgccttcc ttgaccctgg aaggtgccac   5520
tcccactgtc ctttcctaat aaaatgagga aattgcatcg cattgtctga gtaggtgtca   5580
ttctattctg gggggtgggg tggggcagga cagcaagggg gaggattggg aagacaatag   5640
caggcatgct ggggatgcgg tgggctctat ggcctgcagc tgcattaatg aatcggccaa   5700
cgcgcgggga gaggcggttt gcgtattggg cgctcttccg cttcctcgct cactgactcg   5760
ctgcgctcgg tcgttcggct gcggcgagcg gtatcagctc actcaaaggc ggtaatacgg   5820
ttatccacag aatcagggga taacgcagga aagaacatgt gagcaaaagg ccagcaaaag   5880
gccaggaacc gtaaaaaggc cgcgttgctg gcgtttttcc ataggctccg cccccctgac   5940
gagcatcaca aaaatcgacg ctcaagtcag aggtggcgaa acccgacagg actataaaga   6000
taccaggcgt ttccccctgg aagctccctc gtgcgctctc ctgttccgac cctgccgctt   6060
accggatacc tgtccgcctt tctcccttcg ggaagcgtgg cgctttctca tagctcacgc   6120
tgtaggtatc tcagttcggt gtaggtcgtt cgctccaagc tgggctgtgt gcacgaaccc   6180
cccgttcagc ccgaccgctg cgccttatcc ggtaactatc gtcttgagtc caacccggta   6240
agacacgact tatcgccact ggcagcagcc actggtaaca ggattagcag agcgaggtat   6300
gtaggcggtg ctacagagtt cttgaagtgg tggcctaact acggctacac tagaaggaca   6360
gtatttggta tctgcgctct gctgaagcca gttaccttcg gaaaaagagt tggtagctct   6420
tgatccggca aacaaaccac cgctggtagc ggtggttttt ttgtttgcaa gcagcagatt   6480
acgcgcagaa aaaaaggatc tcaagaagat cctttgatct tttctacggg gtctgacgct   6540
cagtggaacg aaaactcacg ttaagggatt ttggtcatga gattatcaaa aaggatcttc   6600
acctagatcc ttttaaatta aaaatgaagt tttaaatcaa tctaaagtat atatgagtaa   6660
acttggtctg acagttacca atgcttaatc agtgaggcac ctatctcagc gatctgtcta   6720
tttcgttcat ccatagttgc ctgactcccc gtcgtgtaga taactacgat acgggagggc   6780
ttaccatctg gccccagtgc tgcaatgata ccgcgagacc cacgctcacc ggctccagat   6840
ttatcagcaa taaaccagcc agccggaagg gccgagcgca gaagtggtcc tgcaacttta   6900
tccgcctcca tccagtctat taattgttgc cgggaagcta gagtaagtag ttcgccagtt   6960
aatagtttgc gcaacgttgt tgccattgct acaggcatcg tggtgtcacg ctcgtcgttt   7020
ggtatggctt cattcagctc cggttcccaa cgatcaaggc gagttacatg atcccccatg   7080
ttgtgcaaaa aagcggttag ctccttcggt cctccgatcg ttgtcagaag taagttggcc   7140
gcagtgttat cactcatggt tatggcagca ctgcataatt ctcttactgt catgccatcc   7200
```

-continued

```
gtaagatgct tttctgtgac tggtgagtac tcaaccaagt cattctgaga atagtgtatg   7260
cggcgaccga gttgctcttg cccggcgtca atacgggata ataccgcgcc acatagcaga   7320
actttaaaag tgctcatcat tggaaaacgt tcttcggggc gaaaactctc aaggatctta   7380
ccgctgttga gatccagttc gatgtaaccc actcgtgcac ccaactgatc ttcagcatct   7440
tttactttca ccagcgtttc tgggtgagca aaaacaggaa ggcaaaatgc cgcaaaaaag   7500
ggaataaggg cgacacggaa atgttgaata ctcatactct tcctttttca atattattga   7560
agcatttatc agggttattg tctcatgagc ggatacatat ttgaatgtat ttagaaaaat   7620
aaacaaatag gggttccgcg cacatttccc cgaaaagtgc cacct                   7665
```

<210> SEQ ID NO 122
<211> LENGTH: 8439
<212> TYPE: DNA
<213> ORGANISM: Artificial Sequence
<220> FEATURE:
<223> OTHER INFORMATION: Plasmid
pCVL.SFFV.HA.NLS.ReoHje.T2A.Trex2.IRES.mTagBFP

<400> SEQUENCE: 122

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc caggggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tggcaagttt tgtggaattg gtttaacata   1560
```

-continued

```
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgat cttacgtacg cgtatttagt   2460
tggtctcttc gaaggggatg gatactttag tatcaccaag aaaggcaagt acttgactta   2520
tgaattaggt attgagctga gcatcaaaga cgtccaattg atttacaaga tcaaggacat   2580
cctaggtgtt ggcaaagtaa gcttcaggaa gagaaacgag attgaaatgg tttcattgag   2640
gatccgtgat aagaatcatc taaaaaactt catattgcct atatttgaca agtatccaat   2700
gttatccaac aaacagtacg actatttaag attcaaggat gcattgttat ctaacattat   2760
atactcagat gacttgcctg aatacgctag aagtaacgaa tcgattaatt ctgtagactc   2820
cattatcaac acatcatact tctccgcctg gctagttgga tttatagaag ctgagggctg   2880
tttcagtacg tacaagctga acaaagacga tgactacttg attgcttcat tcgacattgc   2940
ccaaaaagat ggtgatatct tgatttcagc aattcacaag tacttaagtt tcactactaa   3000
gatttaccta gacaagacta attgtagcag attgaaggtc accggtgtta gatccgtcaa   3060
gaacgtcgtt aagtttatcc agggtgctcc tgtcaaattg ttaggcaaca agaaactgca   3120
atacaagttg tggataaaac aactaaggaa gatttctagg tattccgaga agatccagct   3180
tccatcaaac tacagatccg gtgagggcag aggaagtctt ctaacatgcg gtgacgtgga   3240
ggagaatccg ggcccctccg gatctgagcc acctcgggct gagacctttg tattcctgga   3300
cctagaagcc actgggctcc caaacatgga ccctgagatt gcagagatat cccttttgc   3360
tgttcaccgc tcttccctgg agaacccaga acgggatgat tctggttcct tggtgctgcc   3420
ccgtgttctg gacaagctca cactgtgcat gtgcccggag cgcccctta ctgccaaggc   3480
cagtgagatt actggtttga gcagcgaaag cctgatgcac tgcgggaagg ctggtttcaa   3540
tggcgctgtg gtaaggacac tgcagggctt cctaagccgc caggagggcc ccatctgcct   3600
tgtggcccac aatggcttcg attatgactt ccccactgctg tgcacggagc tacaacgtct   3660
gggtgcccat ctgccccaag acactgtctg cctggacaca ctgcctgcat tgcggggcct   3720
ggaccgtgct cacagccacg gcaccagggc tcaaggccgc aaaagctaca gcctggccag   3780
tctcttccac cgctacttcc aggctgaacc cagtgctgcc cattcagcag aaggtgatgt   3840
gcacaccctg cttctgatct tcctgcatcg tgctcctgag ctgctcgcct gggcagatga   3900
gcaggcccgc agctgggctc atattgagcc catgtacgtg ccacctgatg gtccaagcct   3960
```

cgaagcctga cctgcaggtc gagcatgcat ctagggcggc caattccgcc cctctccctc 4020
ccccccccct aacgttactg gccgaagccg cttggaataa ggccggtgtg cgtttgtcta 4080
tatgtgattt tccaccatat tgccgtcttt tggcaatgtg agggcccgga aacctggccc 4140
tgtcttcttg acgagcattc ctaggggtct ttcccctctc gccaaaggaa tgcaaggtct 4200
gttgaatgtc gtgaaggaag cagttcctct ggaagcttct tgaagacaaa caacgtctgt 4260
agcgaccctt tgcaggcagc ggaacccccc acctggcgac aggtgcctct gcggccaaaa 4320
gccacgtgta taagatacac ctgcaaaggc ggcacaaccc cagtgccacg ttgtgagttg 4380
gatagttgtg gaaagagtca aatggctctc ctcaagcgta ttcaacaagg ggctgaagga 4440
tgcccagaag gtaccccatt gtatgggatc tgatctgggg cctcggtgca catgctttac 4500
atgtgtttag tcgaggttaa aaaaacgtct aggccccccg aaccacgggg acgtggtttt 4560
cctttgaaaa acacgatgat aagcttgcca caacccttac cggtcgccac catgagcgag 4620
ctgattaagg agaacatgca catgaagctg tacatggagg gcaccgtgga caaccatcac 4680
ttcaagtgca catccgaggg cgaaggcaag ccctacgagg gcacccagac catgagaatc 4740
aaggtggtcg agggcggccc tctccccttc gccttcgaca tcctggctac tagcttcctc 4800
tacggcagca agaccttcat caaccacacc cagggcatcc ccgacttctt caagcagtcc 4860
ttccctgagg gcttcacatg ggagagagtc accacatacg aagacggggg cgtgctgacc 4920
gctacccagg acaccagcct ccaggacggc tgcctcatct acaacgtcaa gatcagaggg 4980
gtgaacttca catccaacgg ccctgtgatg cagaagaaaa cactcggctg ggaggccttc 5040
accgagacgc tgtaccccgc tgacggcggc ctggaaggca gaaacgacat ggccctgaag 5100
ctcgtgggcg ggagccatct gatcgcaaac atcaagacca catatagatc caagaaaccc 5160
gctaagaacc tcaagatgcc tggcgtctac tatgtggact acagactgga aagaatcaag 5220
gaggccaaca acgagaccta cgtcgagcag cacgaggtgg cagtggccag atactgcgac 5280
ctccctagca aactggggca caagcttaat tgattctaga gtcgaccgag catcttaccg 5340
ccatttatac ccatatttgt tctgtttttc ttgatttggg tatacattta aatgttaata 5400
gaacaaaatg gtggggcaat catttacatt tttagggata tgtaattact agttcaggtg 5460
tattgccaca agacaaacat gttaagaaac tttcccgtta tttacgctct gttcctgtta 5520
atcaacctct ggattacaaa atttgtgaaa gattgactga tattcttaac tatgttgctc 5580
cttttacgct gtgtggatat gctgctttat agcctctgta tctagctatt gcttcccgta 5640
cggctttcgt tttctcctcc ttgtataaat cctggttgct gtctctttta gaggagttgt 5700
ggcccgttgt ccgtcaacgt ggcgtggtgt gctctgtgtt tgctgacgca acccccactg 5760
gctggggcat tgccaccacc tgtcaactcc tttctgggac tttcgctttc cccctcccga 5820
tcgccacggc agaactcatc gccgcctgcc ttgcccgctg ctggacaggg gctaggttgc 5880
tgggcactga taattccgtg gtgttgtcat cggtaccttt ttaaaagaaa aggggggact 5940
ggaagggcta attcactccc aacgaagaca agatatcata acttcgtata gcatacatta 6000
tacgaagtta taatttattt gtgaaatttg tgatgctatt gctttatttg taaccatatg 6060
tttatttgtg aaatttgtga tgctattgct ttatttgtaa ccattgcttt ttgcttgtac 6120
tgggtctctc tggttagacc agatctgagc ctgggagctc tctggctaac tagggaaccc 6180
actgcttaag cctcaataaa gcttgcctcg accagcctcg actgtgcctt ctagttgcca 6240
gccatctgtt gtttgcccct cccccgtgcc ttccttgacc ctggaaggtg ccactcccac 6300

-continued

```
tgtcctttcc taataaaatg aggaaattgc atcgcattgt ctgagtaggt gtcattctat   6360
tctggggggt ggggtggggc aggacagcaa gggggaggat tgggaagaca atagcaggca   6420
tgctggggat gcggtgggct ctatggcctg cagctgcatt aatgaatcgg ccaacgcgcg   6480
gggagaggcg gtttgcgtat tgggcgctct tccgcttcct cgctcactga ctcgctgcgc   6540
tcggtcgttc ggctgcggcg agcggtatca gctcactcaa aggcggtaat acggttatcc   6600
acagaatcag gggataacgc aggaaagaac atgtgagcaa aaggccagca aaaggccagg   6660
aaccgtaaaa aggccgcgtt gctggcgttt ttccataggc tccgcccccc tgacgagcat   6720
cacaaaaatc gacgctcaag tcagaggtgg cgaaacccga caggactata aagataccag   6780
gcgtttcccc ctggaagctc cctcgtgcgc tctcctgttc cgaccctgcc gcttaccgga   6840
tacctgtccg cctttctccc ttcgggaagc gtggcgcttt ctcatagctc acgctgtagg   6900
tatctcagtt cggtgtaggt cgttcgctcc aagctgggct gtgtgcacga accccccgtt   6960
cagcccgacc gctgcgcctt atccggtaac tatcgtcttg agtccaaccc ggtaagacac   7020
gacttatcgc cactggcagc agccactggt aacaggatta gcagagcgag gtatgtaggc   7080
ggtgctacag agttcttgaa gtggtggcct aactacggct acactagaag gacagtattt   7140
ggtatctgcg ctctgctgaa gccagttacc ttcggaaaaa gagttggtag ctcttgatcc   7200
ggcaaacaaa ccaccgctgg tagcggtggt ttttttgttt gcaagcagca gattacgcgc   7260
agaaaaaaag gatctcaaga agatcctttg atcttttcta cggggtctga cgctcagtgg   7320
aacgaaaact cacgttaagg gattttggtc atgagattat caaaaaggat cttcacctag   7380
atccttttaa attaaaaatg aagttttaaa tcaatctaaa gtatatatga gtaaacttgg   7440
tctgacagtt accaatgctt aatcagtgag gcacctatct cagcgatctg tctatttcgt   7500
tcatccatag ttgcctgact ccccgtcgtg tagataacta cgatacggga gggcttacca   7560
tctggcccca gtgctgcaat gataccgcga gacccacgct caccggctcc agatttatca   7620
gcaataaacc agccagccgg aagggccgag cgcagaagtg gtcctgcaac tttatccgcc   7680
tccatccagt ctattaattg ttgccgggaa gctagagtaa gtagttcgcc agttaatagt   7740
ttgcgcaacg ttgttgccat tgctacaggc atcgtggtgt cacgctcgtc gtttggtatg   7800
gcttcattca gctccggttc ccaacgatca aggcgagtta catgatcccc catgttgtgc   7860
aaaaaagcgg ttagctcctt cggtcctccg atcgttgtca gaagtaagtt ggccgcagtg   7920
ttatcactca tggttatggc agcactgcat aattctctta ctgtcatgcc atccgtaaga   7980
tgcttttctg tgactggtga gtactcaacc aagtcattct gagaatagtg tatgcggcga   8040
ccgagttgct cttgcccggc gtcaatacgg gataataccg cgccacatag cagaacttta   8100
aaagtgctca tcattggaaa acgttcttcg gggcgaaaac tctcaaggat cttaccgctg   8160
ttgagatcca gttcgatgta acccactcgt gcacccaact gatcttcagc atcttttact   8220
ttcaccagcg tttctgggtg agcaaaaaca ggaaggcaaa atgccgcaaa aaagggaata   8280
agggcgacac ggaaatgttg aatactcata ctcttccttt ttcaatatta ttgaagcatt   8340
tatcagggtt attgtctcat gagcggatac atatttgaat gtatttagaa aaataaacaa   8400
ataggggttc cgcgcacatt tccccgaaaa gtgccacct                           8439
```

<210> SEQ ID NO 123
<211> LENGTH: 7803
<212> TYPE: DNA
<213> ORGANISM: Artificial Sequence
<220> FEATURE:
<223> OTHER INFORMATION: Plasmid pCVL.SFFV.HA.NLS.sPan2.IRES.mTagBFP

<400> SEQUENCE: 123

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
```

-continued

```
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattctct actttggaat ctaagttgaa   2460
cccatcttac atctctggtt tcgtcgacgg tgaaggttct ttcatgttga ctatcatcaa   2520
ggacaacaag tacaagttgg gttggagagt tgtttgtaga ttcgttatct ctttgcacaa   2580
gaaggacttg tctttgttga acaagatcaa ggaatttttc gacgtcggta acgttttctt   2640
gatgactaag gactctgctc aatacagagt tgaatctttg aagggtttgg acttgatcat   2700
caaccacttc gacaagtacc cattgatcac taagaagcaa gctgactaca agttgttcaa   2760
gatggctcac aacttaatta agaacaagtc tcacttgact aaggaaggtt tgttggaatt   2820
ggttgctatc aaggctgtta tcaacaacgg tttgaacaac gacttgtcta tcgctttccc   2880
aggtatcaac actatcttga ggcctgacac ttctttgcca caaatcttga acccattctg   2940
gttgtctggt ttcgttgacg ctgaaggttg tttctctgtt gttgttttca agtctaagac   3000
ttctaagttg ggtgaagctg ttaagttgtc tttcatcttg actcaatcta acagagacga   3060
atacttgatc aagtctttga tcgaatacct aggttgtggt aacacttctt tggacccaag   3120
aggtactatc gacttcaagg ttactaactt ctcttctatc aaggacatca tcgttccatt   3180
cttcatcaag tacccattga agggtaacaa gaacttggac ttcactgact tctgtgaagt   3240
tgttagattg atggaaaaca agtctcactt gactaaggaa ggtttggacc aaatcaagaa   3300
gatcagaaac agaatgaaca ctaacagaaa gtagcctgca ggtcgagcat gcatctaggg   3360
cggccaattc cgcccctctc cctccccccc ccctaacgtt actggccgaa gccgcttgga   3420
ataaggccgg tgtgcgtttg tctatatgtg attttccacc atattgccgt cttttggcaa   3480
tgtgagggcc cggaaacctg gccctgtctt cttgacgagc attcctaggg gtctttcccc   3540
tctcgccaaa ggaatgcaag gtctgttgaa tgtcgtgaag gaagcagttc ctctggaagc   3600
ttcttgaaga caaacaacgt ctgtagcgac cctttgcagg cagcggaacc ccccacctgg   3660
cgacaggtgc ctctgcggcc aaaagccacg tgtataagat acacctgcaa aggcggcaca   3720
accccagtgc cacgttgtga gttggatagt tgtggaaaga gtcaaatggc tctcctcaag   3780
cgtattcaac aaggggctga aggatgccca gaaggtaccc cattgtatgg gatctgatct   3840
ggggcctcgg tgcacatgct ttacatgtgt ttagtcgagg ttaaaaaaac gtctaggccc   3900
cccgaaccac ggggacgtgg ttttcctttg aaaaacacga tgataagctt gccacaaccc   3960
ttaccggtcg ccaccatgag cgagctgatt aaggagaaca tgcacatgaa gctgtacatg   4020
gagggcaccg tggacaacca tcacttcaag tgcacatccg agggcgaagg caagccctac   4080
gagggcaccc agaccatgag aatcaaggtg gtcgagggcg gccctctccc cttcgccttc   4140
gacatcctgg ctactagctt cctctacggc agcaagacct tcatcaacca cacccagggc   4200
atccccgact tcttcaagca gtccttccct gagggcttca catgggagag agtcaccaca   4260
tacgaagacg gggcgtgct gaccgctacc caggacacca gcctccagga cggctgcctc   4320
atctacaacg tcaagatcag aggggtgaac ttcacatcca acggccctgt gatgcagaag   4380
aaaacactcg gctgggaggc cttcaccgag acgctgtacc ccgctgacgg cggcctggaa   4440
ggcagaaacg acatggccct gaagctcgtg ggcgggagcc atctgatcgc aaacatcaag   4500
accacatata gatccaagaa acccgctaag aacctcaaga tgcctggcgt ctactatgtg   4560
gactacagac tggaaagaat caaggaggcc aacaacgaga cctacgtcga gcagcacgag   4620
gtggcagtgg ccagatactg cgacctccct agcaaactgg ggcacaagct taattgattc   4680
```

-continued

```
tagagtcgac cgagcatctt accgccattt atacccatat ttgttctgtt tttcttgatt   4740
tgggtataca tttaaatgtt aatagaacaa aatggtgggg caatcattta catttttagg   4800
gatatgtaat tactagttca ggtgtattgc cacaagacaa acatgttaag aaactttccc   4860
gttatttacg ctctgttcct gttaatcaac ctctggatta caaaatttgt gaaagattga   4920
ctgatattct taactatgtt gctcctttta cgctgtgtgg atatgctgct ttatagcctc   4980
tgtatctagc tattgcttcc cgtacggctt tcgttttctc ctccttgtat aaatcctggt   5040
tgctgtctct tttagaggag ttgtggcccg ttgtccgtca acgtggcgtg gtgtgctctg   5100
tgtttgctga cgcaaccccc actggctggg gcattgccac cacctgtcaa ctcctttctg   5160
ggactttcgc tttccccctc ccgatcgcca cggcagaact catcgccgcc tgccttgccc   5220
gctgctggac aggggctagg ttgctgggca ctgataattc cgtggtgttg tcatcggtac   5280
ctttttaaaa gaaaaggggg gactggaagg gctaattcac tcccaacgaa gacaagatat   5340
cataacttcg tatagcatac attatacgaa gttataattt atttgtgaaa tttgtgatgc   5400
tattgcttta tttgtaacca tatgtttatt tgtgaaattt gtgatgctat tgctttattt   5460
gtaaccattg ctttttgctt gtactgggtc tctctggtta gaccagatct gagcctggga   5520
gctctctggc taactaggga acccactgct taagcctcaa taaagcttgc ctcgaccagc   5580
ctcgactgtg ccttctagtt gccagccatc tgttgtttgc ccctcccccg tgccttcctt   5640
gaccctggaa ggtgccactc ccactgtcct ttcctaataa aatgaggaaa ttgcatcgca   5700
ttgtctgagt aggtgtcatt ctattctggg gggtggggtg gggcaggaca gcaaggggga   5760
ggattgggaa gacaatagca ggcatgctgg ggatgcggtg ggctctatgg cctgcagctg   5820
cattaatgaa tcggccaacg cgcggggaga ggcggtttgc gtattgggcg ctcttccgct   5880
tcctcgctca ctgactcgct gcgctcggtc gttcggctgc ggcgagcggt atcagctcac   5940
tcaaaggcgg taatacggtt atccacagaa tcaggggata acgcaggaaa gaacatgtga   6000
gcaaaaggcc agcaaaaggc caggaaccgt aaaaaggccg cgttgctggc gtttttccat   6060
aggctccgcc cccctgacga gcatcacaaa aatcgacgct caagtcagag gtggcgaaac   6120
ccgacaggac tataaagata ccaggcgttt ccccctggaa gctccctcgt gcgctctcct   6180
gttccgaccc tgccgcttac cggatacctg tccgcctttc tcccttcggg aagcgtggcg   6240
ctttctcata gctcacgctg taggtatctc agttcggtgt aggtcgttcg ctccaagctg   6300
ggctgtgtgc acgaaccccc cgttcagccc gaccgctgcg ccttatccgg taactatcgt   6360
cttgagtcca acccggtaag acacgactta tcgccactgg cagcagccac tggtaacagg   6420
attagcagag cgaggtatgt aggcggtgct acagagttct tgaagtggtg gcctaactac   6480
ggctacacta gaaggacagt atttggtatc tgcgctctgc tgaagccagt taccttcgga   6540
aaaagagttg gtagctcttg atccggcaaa caaaccaccg ctggtagcgg tggttttttt   6600
gtttgcaagc agcagattac gcgcagaaaa aaaggatctc aagaagatcc tttgatcttt   6660
tctacggggt ctgacgctca gtggaacgaa aactcacgtt aagggatttt ggtcatgaga   6720
ttatcaaaaa ggatcttcac ctagatcctt ttaaattaaa aatgaagttt taaatcaatc   6780
taaagtatat atgagtaaac ttggtctgac agttaccaat gcttaatcag tgaggcacct   6840
atctcagcga tctgtctatt tcgttcatcc atagttgcct gactccccgt cgtgtagata   6900
actacgatac gggagggctt accatctggc cccagtgctg caatgatacc gcgagaccca   6960
cgctcaccgg ctccagattt atcagcaata aaccagccag ccggaagggc cgagcgcaga   7020
```

-continued agtggtcctg caactttatc cgcctccatc cagtctatta attgttgccg ggaagctaga 7080
gtaagtagtt cgccagttaa tagtttgcgc aacgttgttg ccattgctac aggcatcgtg 7140
gtgtcacgct cgtcgtttgg tatggcttca ttcagctccg gttcccaacg atcaaggcga 7200
gttacatgat cccccatgtt gtgcaaaaaa gcggttagct ccttcggtcc tccgatcgtt 7260
gtcagaagta agttggccgc agtgttatca ctcatggtta tggcagcact gcataattct 7320
cttactgtca tgccatccgt aagatgcttt tctgtgactg gtgagtactc aaccaagtca 7380
ttctgagaat agtgtatgcg gcgaccgagt tgctcttgcc cggcgtcaat acgggataat 7440
accgcgccac atagcagaac tttaaaagtg ctcatcattg gaaaacgttc ttcggggcga 7500
aaactctcaa ggatcttacc gctgttgaga tccagttcga tgtaacccac tcgtgcaccc 7560
aactgatctt cagcatcttt tactttcacc agcgtttctg ggtgagcaaa aacaggaagg 7620
caaaatgccg caaaaaaggg aataagggcg acacggaaat gttgaatact catactcttc 7680
ctttttcaat attattgaag catttatcag ggttattgtc tcatgagcgg atacatattt 7740
gaatgtattt agaaaaataa acaaataggg gttccgcgca catttccccg aaaagtgcca 7800
cct 7803

<210> SEQ ID NO 124
<211> LENGTH: 8577
<212> TYPE: DNA
<213> ORGANISM: Artificial Sequence
<220> FEATURE:
<223> OTHER INFORMATION: Plasmid
pCVL.SFFV.HA.NLS.sPan2.T2A.Trex2.IRES.mTagBFP

<400> SEQUENCE: 124
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200

-continued

```
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattctct actttggaat ctaagttgaa   2460
cccatcttac atctctggtt tcgtcgacgg tgaaggttct ttcatgttga ctatcatcaa   2520
ggacaacaag tacaagttgg gttggagagt tgtttgtaga ttcgttatct ctttgcacaa   2580
gaaggacttg tctttgttga acaagatcaa ggaatttttc gacgtcggta acgttttctt   2640
gatgactaag gactctgctc aatacagagt tgaatctttg aagggtttgg acttgatcat   2700
caaccacttc gacaagtacc cattgatcac taagaagcaa gctgactaca agttgttcaa   2760
gatggctcac aacttaatta agaacaagtc tcacttgact aaggaaggtt tgttggaatt   2820
ggttgctatc aaggctgtta tcaacaacgg tttgaacaac gacttgtcta tcgctttccc   2880
aggtatcaac actatcttga ggcctgacac ttctttgcca caaatcttga acccattctg   2940
gttgtctggt ttcgttgacg ctgaaggttg tttctctgtt gttgttttca agtctaagac   3000
ttctaagttg ggtgaagctg ttaagttgtc tttcatcttg actcaatcta acagagacga   3060
atacttgatc aagtctttga tcgaatacct aggttgtggt aacacttctt tggacccaag   3120
aggtactatc gacttcaagg ttactaactt ctcttctatc aaggacatca tcgttccatt   3180
cttcatcaag tacccattga agggtaacaa gaacttggac ttcactgact tctgtgaagt   3240
tgttagattg atggaaaaca agtctcactt gactaaggaa ggtttggacc aaatcaagaa   3300
gatcagaaac agaatgaaca ctaacagaaa gggatccggt gagggcagag gaagtcttct   3360
aacatgcggt gacgtggagg agaatccggg cccctccgga tctgagccac ctcgggctga   3420
gacctttgta ttcctggacc tagaagccac tgggctccca aacatggacc ctgagattgc   3480
agagatatcc ctttttgctg ttcaccgctc ttccctggag aacccagaac gggatgattc   3540
tggttccttg gtgctgcccc gtgttctgga caagctcaca ctgtgcatgt gcccggagcg   3600
```

-continued

```
ccccttttact gccaaggcca gtgagattac tggtttgagc agcgaaagcc tgatgcactg   3660
cgggaaggct ggtttcaatg gcgctgtggt aaggacactg cagggcttcc taagccgcca   3720
ggagggcccc atctgccttg tggcccacaa tggcttcgat tatgacttcc cactgctgtg   3780
cacggagcta caacgtctgg gtgcccatct gccccaagac actgtctgcc tggacacact   3840
gcctgcattg cggggcctgg accgtgctca cagccacggc accagggctc aaggccgcaa   3900
aagctacagc ctggccagtc tcttccaccg ctacttccag gctgaaccca gtgctgccca   3960
ttcagcagaa ggtgatgtgc acaccctgct tctgatcttc ctgcatcgtg ctcctgagct   4020
gctcgcctgg gcagatgagc aggcccgcag ctgggctcat attgagccca tgtacgtgcc   4080
acctgatggt ccaagcctcg aagcctgacc tgcaggtcga gcatgcatct agggcggcca   4140
attccgcccc tctccctccc ccccccctaa cgttactggc cgaagccgct tggaataagg   4200
ccggtgtgcg tttgtctata tgtgattttc caccatattg ccgtcttttg gcaatgtgag   4260
ggcccggaaa cctggccctg tcttcttgac gagcattcct aggggtcttt cccctctcgc   4320
caaaggaatg caaggtctgt tgaatgtcgt gaaggaagca gttcctctgg aagcttcttg   4380
aagacaaaca acgtctgtag cgaccctttg caggcagcgg aaccccccac ctggcgacag   4440
gtgcctctgc ggccaaaagc cacgtgtata agatacacct gcaaaggcgg cacaacccca   4500
gtgccacgtt gtgagttgga tagttgtgga aagagtcaaa tggctctcct caagcgtatt   4560
caacaagggg ctgaaggatg cccagaaggt accccattgt atgggatctg atctggggcc   4620
tcggtgcaca tgctttacat gtgtttagtc gaggttaaaa aaacgtctag gccccccgaa   4680
ccacggggac gtggttttcc tttgaaaaac acgatgataa gcttgccaca acccttaccg   4740
gtcgccacca tgagcgagct gattaaggag aacatgcaca tgaagctgta catggagggc   4800
accgtggaca accatcactt caagtgcaca tccgagggcg aaggcaagcc ctacgagggc   4860
acccagacca tgagaatcaa ggtggtcgag ggcggccctc tcccctttcgc cttcgacatc   4920
ctggctacta gcttcctcta cggcagcaag accttcatca accacaccca gggcatcccc   4980
gacttcttca agcagtcctt ccctgagggc ttcacatggg agagagtcac cacatacgaa   5040
gacgggggcg tgctgaccgc tacccaggac accagcctcc aggacggctg cctcatctac   5100
aacgtcaaga tcagaggggt gaacttcaca tccaacggcc ctgtgatgca gaagaaaaca   5160
ctcggctggg aggccttcac cgagacgctg taccccgctg acggcggcct ggaaggcaga   5220
aacgacatgg ccctgaagct cgtgggcggg agccatctga tcgcaaacat caagaccaca   5280
tatagatcca agaaacccgc taagaacctc aagatgcctg gcgtctacta tgtggactac   5340
agactggaaa gaatcaagga ggccaacaac gagacctacg tcgagcagca cgaggtggca   5400
gtggccagat actgcgacct ccctagcaaa ctggggcaca agcttaattg attctagagt   5460
cgaccgagca tcttaccgcc atttataccc atatttgttc tgtttttctt gatttgggta   5520
tacatttaaa tgttaataga acaaaatggt ggggcaatca tttacatttt tagggatatg   5580
taattactag ttcaggtgta ttgccacaag acaaacatgt taagaaactt tcccgttatt   5640
tacgctctgt tcctgttaat caacctctgg attacaaaat ttgtgaaaga ttgactgata   5700
ttcttaacta tgttgctcct tttacgctgt gtggatatgc tgctttatag cctctgtatc   5760
tagctattgc ttcccgtacg gctttcgttt tctcctcctt gtataaatcc tggttgctgt   5820
ctcttttaga ggagttgtgg cccgttgtcc gtcaacgtgg cgtggtgtgc tctgtgtttg   5880
ctgacgcaac ccccactggc tggggcattg ccaccacctg tcaactcctt tctgggactt   5940
```

```
tcgctttccc cctcccgatc gccacggcag aactcatcgc cgcctgcctt gcccgctgct   6000
ggacaggggc taggttgctg ggcactgata attccgtggt gttgtcatcg gtaccttttt   6060
aaaagaaaag gggggactgg aagggctaat tcactcccaa cgaagacaag atatcataac   6120
ttcgtatagc atacattata cgaagttata atttatttgt gaaatttgtg atgctattgc   6180
tttatttgta accatatgtt tatttgtgaa atttgtgatg ctattgcttt atttgtaacc   6240
attgcttttt gcttgtactg ggtctctctg gttagaccag atctgagcct gggagctctc   6300
tggctaacta gggaacccac tgcttaagcc tcaataaagc ttgcctcgac cagcctcgac   6360
tgtgccttct agttgccagc catctgttgt ttgcccctcc cccgtgcctt ccttgaccct   6420
ggaaggtgcc actcccactg tcctttccta ataaaatgag gaaattgcat cgcattgtct   6480
gagtaggtgt cattctattc tggggggtgg ggtggggcag gacagcaagg gggaggattg   6540
ggaagacaat agcaggcatg ctggggatgc ggtgggctct atggcctgca gctgcattaa   6600
tgaatcggcc aacgcgcggg gagaggcggt ttgcgtattg ggcgctcttc cgcttcctcg   6660
ctcactgact cgctgcgctc ggtcgttcgg ctgcggcgag cggtatcagc tcactcaaag   6720
gcggtaatac ggttatccac agaatcaggg gataacgcag gaaagaacat gtgagcaaaa   6780
ggccagcaaa aggccaggaa ccgtaaaaag gccgcgttgc tggcgttttt ccataggctc   6840
cgcccccctg acgagcatca caaaaatcga cgctcaagtc agaggtggcg aaacccgaca   6900
ggactataaa gataccaggc gtttccccct ggaagctccc tcgtgcgctc tcctgttccg   6960
accctgccgc ttaccggata cctgtccgcc tttctccctt cgggaagcgt ggcgctttct   7020
catagctcac gctgtaggta tctcagttcg gtgtaggtcg ttcgctccaa gctgggctgt   7080
gtgcacgaac cccccgttca gcccgaccgc tgcgccttat ccggtaacta tcgtcttgag   7140
tccaacccgg taagacacga cttatcgcca ctggcagcag ccactggtaa caggattagc   7200
agagcgaggt atgtaggcgg tgctacagag ttcttgaagt ggtggcctaa ctacggctac   7260
actagaagga cagtatttgg tatctgcgct ctgctgaagc cagttacctt cggaaaaaga   7320
gttggtagct cttgatccgg caaacaaacc accgctggta gcggtggttt ttttgtttgc   7380
aagcagcaga ttacgcgcag aaaaaaagga tctcaagaag atcctttgat cttttctacg   7440
gggtctgacg ctcagtggaa cgaaaactca cgttaaggga ttttggtcat gagattatca   7500
aaaaggatct tcacctagat ccttttaaat taaaaatgaa gttttaaatc aatctaaagt   7560
atatatgagt aaacttggtc tgacagttac caatgcttaa tcagtgaggc acctatctca   7620
gcgatctgtc tatttcgttc atccatagtt gcctgactcc ccgtcgtgta gataactacg   7680
atacgggagg gcttaccatc tggccccagt gctgcaatga taccgcgaga cccacgctca   7740
ccggctccag atttatcagc aataaaccag ccagccggaa gggccgagcg cagaagtggt   7800
cctgcaactt tatccgcctc catccagtct attaattgtt gccgggaagc tagagtaagt   7860
agttcgccag ttaatagttt gcgcaacgtt gttgccattg ctacaggcat cgtggtgtca   7920
cgctcgtcgt ttggtatggc ttcattcagc tccggttccc aacgatcaag gcgagttaca   7980
tgatccccca tgttgtgcaa aaaagcggtt agctccttcg gtcctccgat cgttgtcaga   8040
agtaagttgg ccgcagtgtt atcactcatg gttatggcag cactgcataa ttctcttact   8100
gtcatgccat ccgtaagatg cttttctgtg actggtgagt actcaaccaa gtcattctga   8160
gaatagtgta tgcggcgacc gagttgctct tgcccggcgt caatacggga taataccgcg   8220
ccacatagca gaactttaaa agtgctcatc attggaaaac gttcttcggg gcgaaaactc   8280
tcaaggatct taccgctgtt gagatccagt tcgatgtaac ccactcgtgc acccaactga   8340
```

tcttcagcat cttttacttt caccagcgtt tctgggtgag caaaaacagg aaggcaaaat 8400
gccgcaaaaa agggaataag ggcgacacgg aaatgttgaa tactcatact cttccttttt 8460
caatattatt gaagcattta tcagggttat tgtctcatga gcggatacat atttgaatgt 8520
atttagaaaa ataaacaaat aggggttccg cgcacatttc cccgaaaagt gccacct 8577

<210> SEQ ID NO 125
<211> LENGTH: 7806
<212> TYPE: DNA
<213> ORGANISM: Artificial Sequence
<220> FEATURE:
<223> OTHER INFORMATION: Plasmid pCVL.SFFV.HA.NLS.I-OnuOpt.IRES.mTagBFP

<400> SEQUENCE: 125
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560
acaaattggc tgtggtatat aaaattattc ataatgatag taggaggctt ggtaggttta 1620
agaatagttt ttgctgtact ttctatagtg aatagagtta ggcagggata ttcaccatta 1680
tcgtttcaga cccacctccc aaccccgagg ggacccgaca ggcccgaagg aatagaagaa 1740
gaaggtggag agagagacag agacagatcc attcgattag tgaacggatc tcgacggtat 1800

-continued

```
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcagc cgccgcgaga gcatcaaccc   2460
ctggattctg accggcttcg ccgacgccga gggcagcttc ctgctgcgca tccgcaacaa   2520
caacaagagc agcgtgggct acagcaccga gctgggcttc cagatcaccc tgcacaacaa   2580
ggacaagagc atcctggaga acatccagag catctggaag gtgggcgtga tcgccaacag   2640
cggcgacaac gccgtgagcc tgaaggtgac ccgcttcgag gacctgaagg tgatcatcga   2700
ccacttcgag aagtaccccc tgatcaccca gaagctgggc gactacatgc tgttcaagca   2760
ggccttctgc gtgatggaga acaaggagca cctgaagatc aacggcatca aggagctggt   2820
gcgcatcaag gccaagctga actggggcct gaccgacgag ctgaagaagg ccttccccga   2880
gatcatcagc aaggagcgca gcctgatcaa caagaacatc cccaacttca agtggctggc   2940
cggcttcacc agcggcgagg gctgcttctt cgtgaacctg atcaagagca agagcaagct   3000
gggcgtgcag gtgcagctgg tgttcagcat cacccagcac atcaaggaca agaacctgat   3060
gaacagcctg atcacctacc tgggctgcgg ctacatcaag gagaagaaca agagcgagtt   3120
cagctggctg gacttcgtgg tgaccaagtt cagcgacatc aacgacaaga tcatccccgt   3180
gttccaggag aacaccctga tcggcgtgaa gctggaggac ttcgaggact ggtgcaaggt   3240
ggccaagctg atcgaggaga agaagcacct gaccgagagc ggcctggacg agatcaagaa   3300
gatcaagctg aacatgaaca agggccgcgt gttctagcct gcaggtcgag catgcatcta   3360
gggcggccaa ttccgcccct ctccctcccc ccccctaac gttactggcc gaagccgctt   3420
ggaataaggc cggtgtgcgt ttgtctatat gtgattttcc accatattgc cgtcttttgg   3480
caatgtgagg gcccggaaac ctggccctgt cttcttgacg agcattccta ggggtctttc   3540
ccctctcgcc aaaggaatgc aaggtctgtt gaatgtcgtg aaggaagcag ttcctctgga   3600
agcttcttga agacaaacaa cgtctgtagc gaccctttgc aggcagcgga acccccacc   3660
tggcgacagg tgcctctgcg gccaaaagcc acgtgtataa gatacacctg caaaggcggc   3720
acaaccccag tgccacgttg tgagttggat agttgtggaa agagtcaaat ggctctcctc   3780
aagcgtattc aacaaggggc tgaaggatgc ccagaaggta ccccattgta tgggatctga   3840
tctggggcct cggtgcacat gctttacatg tgtttagtcg aggttaaaaa aacgtctagg   3900
ccccccgaac cacggggacg tggttttcct ttgaaaaaca cgatgataag cttgccacaa   3960
cccttaccgg tcgccaccat gagcgagctg attaaggaga acatgcacat gaagctgtac   4020
atggagggca ccgtggacaa ccatcacttc aagtgcacat ccgagggcga aggcaagccc   4080
tacgagggca cccagaccat gagaatcaag gtggtcgagg gcggccctct ccccttcgcc   4140
ttcgacatcc tggctactag cttcctctac ggcagcaaga ccttcatcaa ccacacccag   4200
```

-continued

```
ggcatccccg acttcttcaa gcagtccttc cctgagggct tcacatggga gagagtcacc   4260
acatacgaag acgggggcgt gctgaccgct acccaggaca ccagcctcca ggacggctgc   4320
ctcatctaca acgtcaagat cagaggggtg aacttcacat ccaacggccc tgtgatgcag   4380
aagaaaacac tcggctggga ggccttcacc gagacgctgt accccgctga cggcggcctg   4440
gaaggcagaa acgacatggc cctgaagctc gtgggcggga gccatctgat cgcaaacatc   4500
aagaccacat atagatccaa gaaacccgct aagaacctca agatgcctgg cgtctactat   4560
gtggactaca gactggaaag aatcaaggag gccaacaacg agacctacgt cgagcagcac   4620
gaggtggcag tggccagata ctgcgacctc cctagcaaac tggggcacaa gcttaattga   4680
ttctagagtc gaccgagcat cttaccgcca tttataccca tatttgttct gtttttcttg   4740
atttgggtat acatttaaat gttaatagaa caaaatggtg ggcaatcat ttacattttt   4800
agggatatgt aattactagt tcaggtgtat tgccacaaga caaacatgtt aagaaacttt   4860
cccgttattt acgctctgtt cctgttaatc aacctctgga ttacaaaatt tgtgaaagat   4920
tgactgatat tcttaactat gttgctcctt ttacgctgtg tggatatgct gctttatagc   4980
ctctgtatct agctattgct tcccgtacgg ctttcgtttt ctcctccttg tataaatcct   5040
ggttgctgtc tcttttagag gagttgtggc ccgttgtccg tcaacgtggc gtggtgtgct   5100
ctgtgtttgc tgacgcaacc cccactggct ggggcattgc caccacctgt caactccttt   5160
ctgggacttt cgctttcccc ctcccgatcg ccacggcaga actcatcgcc gcctgccttg   5220
cccgctgctg gacaggggct aggttgctgg gcactgataa ttccgtggtg ttgtcatcgg   5280
tacctttta aaagaaaagg ggggactgga agggctaatt cactcccaac gaagacaaga   5340
tatcataact tcgtatagca tacattatac gaagttataa tttatttgtg aaatttgtga   5400
tgctattgct ttatttgtaa ccatatgttt atttgtgaaa tttgtgatgc tattgcttta   5460
tttgtaacca ttgcttttg cttgtactgg gtctctctgg ttagaccaga tctgagcctg   5520
ggagctctct ggctaactag ggaacccact gcttaagcct caataaagct tgcctcgacc   5580
agcctcgact gtgccttcta gttgccagcc atctgttgtt tgcccctccc ccgtgccttc   5640
cttgaccctg gaaggtgcca ctcccactgt cctttcctaa taaaatgagg aaattgcatc   5700
gcattgtctg agtaggtgtc attctattct ggggggtggg gtggggcagg acagcaaggg   5760
ggaggattgg gaagacaata gcaggcatgc tggggatgcg gtgggctcta tggcctgcag   5820
ctgcattaat gaatcggcca acgcgcgggg agaggcggtt tgcgtattgg gcgctcttcc   5880
gcttcctcgc tcactgactc gctgcgctcg gtcgttcggc tgcggcgagc ggtatcagct   5940
cactcaaagg cggtaatacg gttatccaca gaatcagggg ataacgcagg aaagaacatg   6000
tgagcaaaag gccagcaaaa ggccaggaac cgtaaaaagg ccgcgttgct ggcgtttttc   6060
cataggctcc gcccccctga cgagcatcac aaaaatcgac gctcaagtca gaggtggcga   6120
aacccgacag gactataaag ataccaggcg tttccccctg gaagctccct cgtgcgctct   6180
cctgttccga ccctgccgct taccggatac ctgtccgcct ttctcccttc gggaagcgtg   6240
gcgctttctc atagctcacg ctgtaggtat ctcagttcgg tgtaggtcgt tcgctccaag   6300
ctgggctgtg tgcacgaacc ccccgttcag cccgaccgct gcgccttatc cggtaactat   6360
cgtcttgagt ccaacccggt aagacacgac ttatcgccac tggcagcagc cactggtaac   6420
aggattagca gagcgaggta tgtaggcggt gctacagagt tcttgaagtg gtggcctaac   6480
tacggctaca ctagaaggac agtatttggt atctgcgctc tgctgaagcc agttaccttc   6540
```

-continued

```
ggaaaaagag ttggtagctc ttgatccggc aaacaaacca ccgctggtag cggtggtttt   6600

tttgtttgca agcagcagat tacgcgcaga aaaaaaggat ctcaagaaga tcctttgatc   6660

ttttctacgg ggtctgacgc tcagtggaac gaaaactcac gttaagggat tttggtcatg   6720

agattatcaa aaaggatctt cacctagatc cttttaaatt aaaaatgaag ttttaaatca   6780

atctaaagta tatatgagta aacttggtct gacagttacc aatgcttaat cagtgaggca   6840

cctatctcag cgatctgtct atttcgttca tccatagttg cctgactccc cgtcgtgtag   6900

ataactacga tacgggaggg cttaccatct ggccccagtg ctgcaatgat accgcgagac   6960

ccacgctcac cggctccaga tttatcagca ataaaccagc cagccggaag ggccgagcgc   7020

agaagtggtc ctgcaacttt atccgcctcc atccagtcta ttaattgttg ccgggaagct   7080

agagtaagta gttcgccagt taatagtttg cgcaacgttg ttgccattgc tacaggcatc   7140

gtggtgtcac gctcgtcgtt tggtatggct tcattcagct ccggttccca acgatcaagg   7200

cgagttacat gatcccccat gttgtgcaaa aaagcggtta gctccttcgg tcctccgatc   7260

gttgtcagaa gtaagttggc cgcagtgtta tcactcatgg ttatggcagc actgcataat   7320

tctcttactg tcatgccatc cgtaagatgc ttttctgtga ctggtgagta ctcaaccaag   7380

tcattctgag aatagtgtat gcggcgaccg agttgctctt gcccggcgtc aatacgggat   7440

aataccgcgc cacatagcag aactttaaaa gtgctcatca ttggaaaacg ttcttcgggg   7500

cgaaaactct caaggatctt accgctgttg agatccagtt cgatgtaacc cactcgtgca   7560

cccaactgat cttcagcatc ttttactttc accagcgttt ctgggtgagc aaaaacagga   7620

aggcaaaatg ccgcaaaaaa gggaataagg gcgacacgga aatgttgaat actcatactc   7680

ttcctttttc aatattattg aagcatttat cagggttatt gtctcatgag cggatacata   7740

tttgaatgta tttagaaaaa taaacaaata ggggttccgc gcacatttcc ccgaaaagtg   7800

ccacct                                                              7806
```

```
<210> SEQ ID NO 126
<211> LENGTH: 8580
<212> TYPE: DNA
<213> ORGANISM: Artificial Sequence
<220> FEATURE:
<223> OTHER INFORMATION: Plasmid
      pCVL.SFFV.HA.NLS.I-OnuOpt.T2A.Trex2.IRES.mTagBFP

<400> SEQUENCE: 126
```

```
gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720
```

-continued

```
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcagc cgccgcgaga gcatcaaccc   2460
ctggattctg accggcttcg ccgacgccga gggcagcttc ctgctgcgca tccgcaacaa   2520
caacaagagc agcgtgggct acagcaccga gctgggcttc cagatcaccc tgcacaacaa   2580
ggacaagagc atcctggaga acatccagag catctggaag gtgggcgtga tcgccaacag   2640
cggcgacaac gccgtgagcc tgaaggtgac ccgcttcgag gacctgaagg tgatcatcga   2700
ccacttcgag aagtaccccc tgatcaccca gaagctgggc gactacatgc tgttcaagca   2760
ggccttctgc gtgatggaga acaaggagca cctgaagatc aacggcatca aggagctggt   2820
gcgcatcaag gccaagctga actggggcct gaccgacgag ctgaagaagg ccttccccga   2880
gatcatcagc aaggagcgca gcctgatcaa caagaacatc cccaacttca agtggctggc   2940
cggcttcacc agcggcgagg gctgcttctt cgtgaacctg atcaagagca agagcaagct   3000
gggcgtgcag gtgcagctgg tgttcagcat cacccagcac atcaaggaca agaacctgat   3060
gaacagcctg atcacctacc tgggctgcgg ctacatcaag gagaagaaca agagcgagtt   3120
```

-continued

```
cagctggctg gacttcgtgg tgaccaagtt cagcgacatc aacgacaaga tcatccccgt   3180
gttccaggag aacaccctga tcggcgtgaa gctggaggac ttcgaggact ggtgcaaggt   3240
ggccaagctg atcgaggaga agaagcacct gaccgagagc ggcctggacg agatcaagaa   3300
gatcaagctg aacatgaaca agggccgcgt gttcggatcc ggtgagggca gaggaagtct   3360
tctaacatgc ggtgacgtgg aggagaatcc gggcccctcc ggatctgagc cacctcgggc   3420
tgagaccttt gtattcctgg acctagaagc cactgggctc ccaaacatgg accctgagat   3480
tgcagagata tccctttttg ctgttcaccg ctcttccctg gagaacccag aacgggatga   3540
ttctggttcc ttggtgctgc cccgtgttct ggacaagctc acactgtgca tgtgcccgga   3600
gcgccccttt actgccaagg ccagtgagat tactggtttg agcagcgaaa gcctgatgca   3660
ctgcgggaag gctggtttca atggcgctgt ggtaaggaca ctgcagggct tcctaagccg   3720
ccaggagggc cccatctgcc ttgtggccca caatggcttc gattatgact tcccactgct   3780
gtgcacggag ctacaacgtc tgggtgccca tctgccccaa gacactgtct gcctggacac   3840
actgcctgca ttgcggggcc tggaccgtgc tcacagccac ggcaccaggg ctcaaggccg   3900
caaaagctac agcctggcca gtctcttcca ccgctacttc caggctgaac ccagtgctgc   3960
ccattcagca gaaggtgatg tgcacaccct gcttctgatc ttcctgcatc gtgctcctga   4020
gctgctcgcc tgggcagatg agcaggcccg cagctgggct catattgagc ccatgtacgt   4080
gccacctgat ggtccaagcc tcgaagcctg acctgcaggt cgagcatgca tctagggcgg   4140
ccaattccgc ccctctccct cccccccccc taacgttact ggccgaagcc gcttggaata   4200
aggccggtgt gcgtttgtct atatgtgatt ttccaccata ttgccgtctt ttggcaatgt   4260
gagggcccgg aaacctggcc ctgtcttctt gacgagcatt cctaggggtc tttcccctct   4320
cgccaaagga atgcaaggtc tgttgaatgt cgtgaaggaa gcagttcctc tggaagcttc   4380
ttgaagacaa acaacgtctg tagcgaccct ttgcaggcag cggaaccccc cacctggcga   4440
caggtgcctc tgcggccaaa agccacgtgt ataagataca cctgcaaagg cggcacaacc   4500
ccagtgccac gttgtgagtt ggatagttgt ggaaagagtc aaatggctct cctcaagcgt   4560
attcaacaag gggctgaagg atgcccagaa ggtaccccat tgtatgggat ctgatctggg   4620
gcctcggtgc acatgcttta catgtgttta gtcgaggtta aaaaaacgtc taggcccccc   4680
gaaccacggg gacgtggttt tcctttgaaa aacacgatga taagcttgcc acaaccctta   4740
ccggtcgcca ccatgagcga gctgattaag gagaacatgc acatgaagct gtacatggag   4800
ggcaccgtgg acaaccatca cttcaagtgc acatccgagg gcgaaggcaa gccctacgag   4860
ggcacccaga ccatgagaat caaggtggtc gagggcggcc ctctcccctt cgccttcgac   4920
atcctggcta ctagcttcct ctacggcagc aagaccttca tcaaccacac ccagggcatc   4980
cccgacttct tcaagcagtc cttccctgag ggcttcacat gggagagagt caccacatac   5040
gaagacgggg gcgtgctgac cgctacccag gacaccagcc tccaggacgg ctgcctcatc   5100
tacaacgtca agatcagagg ggtgaacttc acatccaacg gccctgtgat gcagaagaaa   5160
acactcggct gggaggcctt caccgagacg ctgtaccccg ctgacggcgg cctggaaggc   5220
agaaacgaca tggccctgaa gctcgtgggc gggagccatc tgatcgcaaa catcaagacc   5280
acatatagat ccaagaaacc cgctaagaac ctcaagatgc ctggcgtcta ctatgtggac   5340
tacagactgg aaagaatcaa ggaggccaac aacgagacct acgtcgagca gcacgaggtg   5400
gcagtggcca gatactgcga cctccctagc aaactggggc acaagcttaa ttgattctag   5460
```

-continued

```
agtcgaccga gcatcttacc gccatttata cccatatttg ttctgttttt cttgatttgg   5520

gtatacattt aaatgttaat agaacaaaat ggtggggcaa tcatttacat ttttagggat   5580

atgtaattac tagttcaggt gtattgccac aagacaaaca tgttaagaaa ctttcccgtt   5640

atttacgctc tgttcctgtt aatcaacctc tggattacaa aatttgtgaa agattgactg   5700

atattcttaa ctatgttgct ccttttacgc tgtgtggata tgctgcttta tagcctctgt   5760

atctagctat tgcttcccgt acggctttcg ttttctcctc cttgtataaa tcctggttgc   5820

tgtctctttt agaggagttg tggcccgttg tccgtcaacg tggcgtggtg tgctctgtgt   5880

ttgctgacgc aacccccact ggctggggca ttgccaccac ctgtcaactc ctttctggga   5940

ctttcgcttt ccccctcccg atcgccacgg cagaactcat cgccgcctgc cttgcccgct   6000

gctggacagg ggctaggttg ctgggcactg ataattccgt ggtgttgtca tcggtacctt   6060

tttaaaagaa aaggggggac tggaagggct aattcactcc caacgaagac aagatatcat   6120

aacttcgtat agcatacatt atacgaagtt ataatttatt tgtgaaattt gtgatgctat   6180

tgctttattt gtaaccatat gtttatttgt gaaatttgtg atgctattgc tttatttgta   6240

accattgctt tttgcttgta ctgggtctct ctggttagac cagatctgag cctgggagct   6300

ctctggctaa ctagggaacc cactgcttaa gcctcaataa agcttgcctc gaccagcctc   6360

gactgtgcct tctagttgcc agccatctgt tgtttgcccc tcccccgtgc cttccttgac   6420

cctggaaggt gccactccca ctgtcctttc ctaataaaat gaggaaattg catcgcattg   6480

tctgagtagg tgtcattcta ttctgggggg tggggtgggg caggacagca agggggagga   6540

ttgggaagac aatagcaggc atgctgggga tgcggtgggc tctatggcct gcagctgcat   6600

taatgaatcg gccaacgcgc ggggagaggc ggtttgcgta ttgggcgctc ttccgcttcc   6660

tcgctcactg actcgctgcg ctcggtcgtt cggctgcggc gagcggtatc agctcactca   6720

aaggcggtaa tacggttatc cacagaatca ggggataacg caggaaagaa catgtgagca   6780

aaaggccagc aaaaggccag gaaccgtaaa aaggccgcgt tgctggcgtt tttccatagg   6840

ctccgccccc ctgacgagca tcacaaaaat cgacgctcaa gtcagaggtg gcgaaacccg   6900

acaggactat aaagatacca ggcgtttccc cctggaagct ccctcgtgcg ctctcctgtt   6960

ccgaccctgc cgcttaccgg atacctgtcc gcctttctcc cttcgggaag cgtggcgctt   7020

tctcatagct cacgctgtag gtatctcagt tcggtgtagg tcgttcgctc caagctgggc   7080

tgtgtgcacg aaccccccgt tcagcccgac cgctgcgcct tatccggtaa ctatcgtctt   7140

gagtccaacc cggtaagaca cgacttatcg ccactggcag cagccactgg taacaggatt   7200

agcagagcga ggtatgtagg cggtgctaca gagttcttga agtggtggcc taactacggc   7260

tacactagaa ggacagtatt tggtatctgc gctctgctga agccagttac cttcggaaaa   7320

agagttggta gctcttgatc cggcaaacaa accaccgctg gtagcggtgg tttttttgtt   7380

tgcaagcagc agattacgcg cagaaaaaaa ggatctcaag aagatccttt gatcttttct   7440

acggggtctg acgctcagtg gaacgaaaac tcacgttaag ggattttggt catgagatta   7500

tcaaaaagga tcttcaccta gatcctttta aattaaaaat gaagttttaa atcaatctaa   7560

agtatatatg agtaaacttg gtctgacagt taccaatgct taatcagtga ggcacctatc   7620

tcagcgatct gtctatttcg ttcatccata gttgcctgac tccccgtcgt gtagataact   7680

acgatacggg agggcttacc atctggcccc agtgctgcaa tgataccgcg agacccacgc   7740

tcaccggctc cagatttatc agcaataaac cagccagccg gaagggccga gcgcagaagt   7800

ggtcctgcaa ctttatccgc ctccatccag tctattaatt gttgccggga agctagagta   7860
```

agtagttcgc cagttaatag tttgcgcaac gttgttgcca ttgctacagg catcgtggtg 7920
tcacgctcgt cgtttggtat ggcttcattc agctccggtt cccaacgatc aaggcgagtt 7980
acatgatccc ccatgttgtg caaaaaagcg gttagctcct tcggtcctcc gatcgttgtc 8040
agaagtaagt tggccgcagt gttatcactc atggttatgg cagcactgca taattctctt 8100
actgtcatgc catccgtaag atgcttttct gtgactggtg agtactcaac caagtcattc 8160
tgagaatagt gtatgcggcg accgagttgc tcttgcccgg cgtcaatacg ggataatacc 8220
gcgccacata gcagaacttt aaaagtgctc atcattggaa aacgttcttc ggggcgaaaa 8280
ctctcaagga tcttaccgct gttgagatcc agttcgatgt aacccactcg tgcacccaac 8340
tgatcttcag catcttttac tttcaccagc gtttctgggt gagcaaaaac aggaaggcaa 8400
aatgccgcaa aaaagggaat aagggcgaca cggaaatgtt gaatactcat actcttcctt 8460
tttcaatatt attgaagcat ttatcagggt tattgtctca tgagcggata catatttgaa 8520
tgtatttaga aaaataaaca aataggggtt ccgcgcacat ttccccgaaa agtgccacct 8580

<210> SEQ ID NO 127
<211> LENGTH: 7833
<212> TYPE: DNA
<213> ORGANISM: Artificial Sequence
<220> FEATURE:
<223> OTHER INFORMATION: Plasmid pCVL.SFFV.HA.NLS.I-LTR I.IRES.mTagBFP

<400> SEQUENCE: 127
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320

-continued

```
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcttc ccagttcaag ctagaaacga   2460
caacatctct ccatggacta tcactggttt cgctgacgct gaatcttctt tcatgttgac   2520
tgtttctaag gactctaaga gaaacactgg ttggtctgtt agaccaagat tcagaatcgg   2580
tttgcacaac aaggacgtga ctatcttgaa gtctatcaga gaatacttgg gcgccggtat   2640
catcacttct gacaaggacg ctagaatcag attcgaatct ttgaaggaat tggaagttgt   2700
tatcaaccac ttcgacaagt acccattgat cactcaaaag agagctgact acttgttgtt   2760
caagaaggct ttctacttaa ttaagaacaa ggaacacttg actgaagaag gtttgaacca   2820
aatcttgact ttgaaggctt ctttgaactt gggtttgtct gaagaattga aggaagcatt   2880
cccaaacact atcccagctg aaaagttact agttactggt caagaaatcc cagactctaa   2940
ctgggttgct ggtttcactg ctggtgaagg ttctttctac atcagaatcg ctaagaactc   3000
tactttgaag actggttacc aagttcaatc tgttttccaa atcactcaag acacgcgtga   3060
catcgaattg atgaagaact tgatctctta cttgaactgt ggtaacatca gaatcagaaa   3120
gtacaagggt tctgaaggta tccacgacac ttgtgttgac ttggttgtta ctaacttgaa   3180
cgacatcaag gaaaagatca tcccattctt caacaagaac cacatcatcg gtgttaagtt   3240
gcaagactac agagactggt gtaaggttgt tactttgatc gacaacaagg aacacttgac   3300
ttctgaaggt ttggaaaaga tccaaaagat caaggaaggt atgaacagag gtagatcttt   3360
gtagcctgca ggtcgagcat gcatctaggg cggccaattc cgcccctctc cctccccccc   3420
ccctaacgtt actggccgaa gccgcttgga ataaggccgg tgtgcgtttg tctatatgtg   3480
attttccacc atattgccgt cttttggcaa tgtgagggcc cggaaacctg gccctgtctt   3540
cttgacgagc attcctaggg gtctttcccc tctcgccaaa ggaatgcaag gtctgttgaa   3600
tgtcgtgaag gaagcagttc ctctggaagc ttcttgaaga caaacaacgt ctgtagcgac   3660
cctttgcagg cagcggaacc ccccacctgg cgacaggtgc ctctgcggcc aaaagccacg   3720
```

-continued

```
tgtataagat acacctgcaa aggcggcaca accccagtgc cacgttgtga gttggatagt   3780
tgtggaaaga gtcaaatggc tctcctcaag cgtattcaac aaggggctga aggatgccca   3840
gaaggtaccc cattgtatgg gatctgatct ggggcctcgg tgcacatgct ttacatgtgt   3900
ttagtcgagg ttaaaaaaac gtctaggccc cccgaaccac ggggacgtgg ttttcctttg   3960
aaaaacacga tgataagctt gccacaaccc ttaccggtcg ccaccatgag cgagctgatt   4020
aaggagaaca tgcacatgaa gctgtacatg gagggcaccg tggacaacca tcacttcaag   4080
tgcacatccg agggcgaagg caagccctac gagggcaccc agaccatgag aatcaaggtg   4140
gtcgagggcg gccctctccc cttcgccttc gacatcctgg ctactagctt cctctacggc   4200
agcaagacct tcatcaacca cacccagggc atccccgact tcttcaagca gtccttccct   4260
gagggcttca catgggagag agtcaccaca tacgaagacg gggggcgtgct gaccgctacc   4320
caggacacca gcctccagga cggctgcctc atctacaacg tcaagatcag aggggtgaac   4380
ttcacatcca acggccctgt gatgcagaag aaaacactcg gctgggaggc cttcaccgag   4440
acgctgtacc ccgctgacgg cggcctggaa ggcagaaacg acatggccct gaagctcgtg   4500
ggcgggagcc atctgatcgc aaacatcaag accacatata gatccaagaa acccgctaag   4560
aacctcaaga tgcctggcgt ctactatgtg gactacagac tggaaagaat caaggaggcc   4620
aacaacgaga cctacgtcga gcagcacgag gtggcagtgg ccagatactg cgacctccct   4680
agcaaactgg ggcacaagct taattgattc tagagtcgac cgagcatctt accgccattt   4740
atacccatat ttgttctgtt tttcttgatt tgggtataca tttaaatgtt aatagaacaa   4800
aatggtgggg caatcattta catttttagg gatatgtaat tactagttca ggtgtattgc   4860
cacaagacaa acatgttaag aaactttccc gttatttacg ctctgttcct gttaatcaac   4920
ctctggatta caaaatttgt gaaagattga ctgatattct taactatgtt gctcctttta   4980
cgctgtgtgg atatgctgct ttatagcctc tgtatctagc tattgcttcc cgtacggctt   5040
tcgttttctc ctccttgtat aaatcctggt tgctgtctct tttagaggag ttgtggcccg   5100
ttgtccgtca acgtggcgtg gtgtgctctg tgtttgctga cgcaaccccc actggctggg   5160
gcattgccac cacctgtcaa ctcctttctg ggactttcgc tttccccctc ccgatcgcca   5220
cggcagaact catcgccgcc tgccttgccc gctgctggac aggggctagg ttgctgggca   5280
ctgataattc cgtggtgttg tcatcggtac ctttttaaaa gaaaaggggg gactggaagg   5340
gctaattcac tcccaacgaa gacaagatat cataacttcg tatagcatac attatacgaa   5400
gttataattt atttgtgaaa tttgtgatgc tattgcttta tttgtaacca tatgtttatt   5460
tgtgaaattt gtgatgctat tgctttattt gtaaccattg ctttttgctt gtactgggtc   5520
tctctggtta gaccagatct gagcctggga gctctctggc taactaggga acccactgct   5580
taagcctcaa taaagcttgc ctcgaccagc ctcgactgtg ccttctagtt gccagccatc   5640
tgttgtttgc ccctcccccg tgccttcctt gaccctggaa ggtgccactc ccactgtcct   5700
ttcctaataa aatgaggaaa ttgcatcgca ttgtctgagt aggtgtcatt ctattctggg   5760
gggtggggtg gggcaggaca gcaaggggga ggattgggaa gacaatagca ggcatgctgg   5820
ggatgcggtg ggctctatgg cctgcagctg cattaatgaa tcggccaacg cgcggggaga   5880
ggcggtttgc gtattgggcg ctcttccgct tcctcgctca ctgactcgct gcgctcggtc   5940
gttcggctgc ggcgagcggt atcagctcac tcaaaggcgg taatacggtt atccacagaa   6000
tcaggggata acgcaggaaa gaacatgtga gcaaaaggcc agcaaaaggc caggaaccgt   6060
```

aaaaaggccg cgttgctggc gtttttccat aggctccgcc cccctgacga gcatcacaaa 6120
aatcgacgct caagtcagag gtggcgaaac ccgacaggac tataaagata ccaggcgttt 6180
ccccctggaa gctccctcgt gcgctctcct gttccgaccc tgccgcttac cggatacctg 6240
tccgcctttc tcccttcggg aagcgtggcg ctttctcata gctcacgctg taggtatctc 6300
agttcggtgt aggtcgttcg ctccaagctg ggctgtgtgc acgaaccccc cgttcagccc 6360
gaccgctgcg ccttatccgg taactatcgt cttgagtcca acccggtaag acacgactta 6420
tcgccactgg cagcagccac tggtaacagg attagcagag cgaggtatgt aggcggtgct 6480
acagagttct tgaagtggtg gcctaactac ggctacacta gaaggacagt atttggtatc 6540
tgcgctctgc tgaagccagt taccttcgga aaaagagttg gtagctcttg atccggcaaa 6600
caaaccaccg ctggtagcgg tggttttttt gtttgcaagc agcagattac gcgcagaaaa 6660
aaaggatctc aagaagatcc tttgatcttt tctacggggt ctgacgctca gtggaacgaa 6720
aactcacgtt aagggatttt ggtcatgaga ttatcaaaaa ggatcttcac ctagatcctt 6780
ttaaattaaa aatgaagttt taaatcaatc taaagtatat atgagtaaac ttggtctgac 6840
agttaccaat gcttaatcag tgaggcacct atctcagcga tctgtctatt tcgttcatcc 6900
atagttgcct gactccccgt cgtgtagata actacgatac gggagggctt accatctggc 6960
cccagtgctg caatgatacc gcgagaccca cgctcaccgg ctccagattt atcagcaata 7020
aaccagccag ccggaagggc cgagcgcaga agtggtcctg caactttatc cgcctccatc 7080
cagtctatta attgttgccg ggaagctaga gtaagtagtt cgccagttaa tagtttgcgc 7140
aacgttgttg ccattgctac aggcatcgtg gtgtcacgct cgtcgtttgg tatggcttca 7200
ttcagctccg gttcccaacg atcaaggcga gttacatgat cccccatgtt gtgcaaaaaa 7260
gcggttagct ccttcggtcc tccgatcgtt gtcagaagta agttggccgc agtgttatca 7320
ctcatggtta tggcagcact gcataattct cttactgtca tgccatccgt aagatgcttt 7380
tctgtgactg gtgagtactc aaccaagtca ttctgagaat agtgtatgcg gcgaccgagt 7440
tgctcttgcc cggcgtcaat acgggataat accgcgccac atagcagaac tttaaaagtg 7500
ctcatcattg gaaaacgttc ttcggggcga aaactctcaa ggatcttacc gctgttgaga 7560
tccagttcga tgtaacccac tcgtgcaccc aactgatctt cagcatcttt tactttcacc 7620
agcgtttctg ggtgagcaaa aacaggaagg caaaatgccg caaaaaaggg aataagggcg 7680
acacggaaat gttgaatact catactcttc ctttttcaat attattgaag catttatcag 7740
ggttattgtc tcatgagcgg atacatattt gaatgtattt agaaaaataa acaaataggg 7800
gttccgcgca catttccccg aaaagtgcca cct 7833

<210> SEQ ID NO 128
<211> LENGTH: 8607
<212> TYPE: DNA
<213> ORGANISM: Artificial Sequence
<220> FEATURE:
<223> OTHER INFORMATION: Plasmid pCVL.SFFV.HA.NLS.I-LTR
I.T2A.Trex2.IRES.mTagBFP

<400> SEQUENCE: 128
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240

-continued

```
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc caggggggaaa gaaaaaatat   660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcttc ccagttcaag ctagaaacga   2460
caacatctct ccatggacta tcactggttt cgctgacgct gaatcttctt tcatgttgac   2520
tgtttctaag gactctaaga gaaacactgg ttggtctgtt agaccaagat tcagaatcgg   2580
tttgcacaac aaggacgtga ctatcttgaa gtctatcaga gaatacttgg gcgccggtat   2640
```

catcacttct gacaaggacg ctagaatcag attcgaatct ttgaaggaat tggaagttgt 2700
tatcaaccac ttcgacaagt acccattgat cactcaaaag agagctgact acttgttgtt 2760
caagaaggct ttctacttaa ttaagaacaa ggaacacttg actgaagaag gtttgaacca 2820
aatcttgact ttgaaggctt ctttgaactt gggtttgtct gaagaattga aggaagcatt 2880
cccaaacact atcccagctg aaaagttact agttactggt caagaaatcc cagactctaa 2940
ctgggttgct ggtttcactg ctggtgaagg ttctttctac atcagaatcg ctaagaactc 3000
tactttgaag actggttacc aagttcaatc tgttttccaa atcactcaag acacgcgtga 3060
catcgaattg atgaagaact tgatctctta cttgaactgt ggtaacatca gaatcagaaa 3120
gtacaagggt tctgaaggta tccacgacac ttgtgttgac ttggttgtta ctaacttgaa 3180
cgacatcaag gaaaagatca tcccattctt caacaagaac cacatcatcg gtgttaagtt 3240
gcaagactac agagactggt gtaaggttgt tactttgatc gacaacaagg aacacttgac 3300
ttctgaaggt ttggaaaaga tccaaaagat caaggaaggt atgaacagag gtagatcttt 3360
gggatccggt gagggcagag gaagtcttct aacatgcggt gacgtggagg agaatccggg 3420
cccctccgga tctgagccac ctcgggctga gacctttgta ttcctggacc tagaagccac 3480
tgggctccca aacatggacc ctgagattgc agagatatcc ctttttgctg ttcaccgctc 3540
ttccctggag aacccagaac gggatgattc tggttccttg gtgctgcccc gtgttctgga 3600
caagctcaca ctgtgcatgt gcccggagcg cccctttact gccaaggcca gtgagattac 3660
tggtttgagc agcgaaagcc tgatgcactg cgggaaggct ggtttcaatg gcgctgtggt 3720
aaggacactg cagggcttcc taagccgcca ggagggcccc atctgccttg tggcccacaa 3780
tggcttcgat tatgacttcc cactgctgtg cacggagcta caacgtctgg gtgcccatct 3840
gccccaagac actgtctgcc tggacacact gcctgcattg cggggcctgg accgtgctca 3900
cagccacggc accagggctc aaggccgcaa aagctacagc ctggccagtc tcttccaccg 3960
ctacttccag gctgaaccca gtgctgccca ttcagcagaa ggtgatgtgc acaccctgct 4020
tctgatcttc ctgcatcgtg ctcctgagct gctcgcctgg gcagatgagc aggcccgcag 4080
ctgggctcat attgagccca tgtacgtgcc acctgatggt ccaagcctcg aagcctgacc 4140
tgcaggtcga gcatgcatct agggcggcca attccgcccc tctccctccc ccccccctaa 4200
cgttactggc cgaagccgct tggaataagg ccggtgtgcg tttgtctata tgtgattttc 4260
caccatattg ccgtcttttg gcaatgtgag ggcccggaaa cctggccctg tcttcttgac 4320
gagcattcct aggggtcttt cccctctcgc caaaggaatg caaggtctgt tgaatgtcgt 4380
gaaggaagca gttcctctgg aagcttcttg aagacaaaca acgtctgtag cgaccctttg 4440
caggcagcgg aaccccccac ctggcgacag gtgcctctgc ggccaaaagc cacgtgtata 4500
agatacacct gcaaaggcgg cacaacccca gtgccacgtt gtgagttgga tagttgtgga 4560
aagagtcaaa tggctctcct caagcgtatt caacaagggg ctgaaggatg cccagaaggt 4620
accccattgt atgggatctg atctggggcc tcggtgcaca tgctttacat gtgtttagtc 4680
gaggttaaaa aaacgtctag gccccccgaa ccacggggac gtggttttcc tttgaaaaac 4740
acgatgataa gcttgccaca acccttaccg gtcgccacca tgagcgagct gattaaggag 4800
aacatgcaca tgaagctgta catggagggc accgtggaca accatcactt caagtgcaca 4860
tccgagggcg aaggcaagcc ctacgagggc acccagacca tgagaatcaa ggtggtcgag 4920
ggcggccctc tcccctcgc cttcgacatc ctggctacta gcttcctcta cggcagcaag 4980

-continued

```
accttcatca accacaccca gggcatcccc gacttcttca agcagtcctt ccctgagggc   5040
ttcacatggg agagagtcac cacatacgaa gacgggggcg tgctgaccgc tacccaggac   5100
accagcctcc aggacggctg cctcatctac aacgtcaaga tcagaggggt gaacttcaca   5160
tccaacggcc ctgtgatgca gaagaaaaca ctcggctggg aggccttcac cgagacgctg   5220
taccccgctg acggcggcct ggaaggcaga aacgacatgg ccctgaagct cgtgggcggg   5280
agccatctga tcgcaaacat caagaccaca tatagatcca agaaacccgc taagaacctc   5340
aagatgcctg gcgtctacta tgtggactac agactggaaa gaatcaagga ggccaacaac   5400
gagacctacg tcgagcagca cgaggtggca gtggccagat actgcgacct ccctagcaaa   5460
ctggggcaca agcttaattg attctagagt cgaccgagca tcttaccgcc atttataccc   5520
atatttgttc tgtttttctt gatttgggta tacatttaaa tgttaataga acaaaatggt   5580
ggggcaatca tttacatttt tagggatatg taattactag ttcaggtgta ttgccacaag   5640
acaaacatgt taagaaactt tcccgttatt tacgctctgt tcctgttaat caacctctgg   5700
attacaaaat ttgtgaaaga ttgactgata ttcttaacta tgttgctcct tttacgctgt   5760
gtggatatgc tgctttatag cctctgtatc tagctattgc ttcccgtacg gctttcgttt   5820
tctcctcctt gtataaatcc tggttgctgt ctcttttaga ggagttgtgg cccgttgtcc   5880
gtcaacgtgg cgtggtgtgc tctgtgtttg ctgacgcaac ccccactggc tggggcattg   5940
ccaccacctg tcaactcctt tctgggactt tcgctttccc cctcccgatc gccacggcag   6000
aactcatcgc cgcctgcctt gcccgctgct ggacaggggc taggttgctg ggcactgata   6060
attccgtggt gttgtcatcg gtaccttttt aaaagaaaag gggggactgg aagggctaat   6120
tcactcccaa cgaagacaag atatcataac ttcgtatagc atacattata cgaagttata   6180
atttatttgt gaaatttgtg atgctattgc tttatttgta accatatgtt tatttgtgaa   6240
atttgtgatg ctattgcttt atttgtaacc attgcttttt gcttgtactg ggtctctctg   6300
gttagaccag atctgagcct gggagctctc tggctaacta gggaacccac tgcttaagcc   6360
tcaataaagc ttgcctcgac cagcctcgac tgtgccttct agttgccagc catctgttgt   6420
ttgcccctcc cccgtgcctt ccttgaccct ggaaggtgcc actcccactg tcctttccta   6480
ataaaatgag gaaattgcat cgcattgtct gagtaggtgt cattctattc tggggggtgg   6540
ggtggggcag gacagcaagg gggaggattg ggaagacaat agcaggcatg ctggggatgc   6600
ggtgggctct atggcctgca gctgcattaa tgaatcggcc aacgcgcggg gagaggcggt   6660
ttgcgtattg ggcgctcttc cgcttcctcg ctcactgact cgctgcgctc ggtcgttcgg   6720
ctgcggcgag cggtatcagc tcactcaaag gcggtaatac ggttatccac agaatcaggg   6780
gataacgcag gaaagaacat gtgagcaaaa ggccagcaaa aggccaggaa ccgtaaaaag   6840
gccgcgttgc tggcgttttt ccataggctc cgcccccctg acgagcatca caaaaatcga   6900
cgctcaagtc agaggtggcg aaacccgaca ggactataaa gataccaggc gtttccccct   6960
ggaagctccc tcgtgcgctc tcctgttccg accctgccgc ttaccggata cctgtccgcc   7020
tttctccctt cgggaagcgt ggcgctttct catagctcac gctgtaggta tctcagttcg   7080
gtgtaggtcg ttcgctccaa gctgggctgt gtgcacgaac cccccgttca gcccgaccgc   7140
tgcgccttat ccggtaacta tcgtcttgag tccaacccgg taagacacga cttatcgcca   7200
ctggcagcag ccactggtaa caggattagc agagcgaggt atgtaggcgg tgctacagag   7260
ttcttgaagt ggtggcctaa ctacggctac actagaagga cagtatttgg tatctgcgct   7320
ctgctgaagc cagttacctt cggaaaaaga gttggtagct cttgatccgg caaacaaacc   7380
```

accgctggta gcggtggttt ttttgtttgc aagcagcaga ttacgcgcag aaaaaaagga 7440
tctcaagaag atcctttgat cttttctacg gggtctgacg ctcagtggaa cgaaaactca 7500
cgttaaggga ttttggtcat gagattatca aaaaggatct tcacctagat ccttttaaat 7560
taaaaatgaa gttttaaatc aatctaaagt atatatgagt aaacttggtc tgacagttac 7620
caatgcttaa tcagtgaggc acctatctca gcgatctgtc tatttcgttc atccatagtt 7680
gcctgactcc ccgtcgtgta gataactacg atacgggagg gcttaccatc tggccccagt 7740
gctgcaatga taccgcgaga cccacgctca ccggctccag atttatcagc aataaaccag 7800
ccagccggaa gggccgagcg cagaagtggt cctgcaactt tatccgcctc catccagtct 7860
attaattgtt gccgggaagc tagagtaagt agttcgccag ttaatagttt gcgcaacgtt 7920
gttgccattg ctacaggcat cgtggtgtca cgctcgtcgt ttggtatggc ttcattcagc 7980
tccggttccc aacgatcaag gcgagttaca tgatccccca tgttgtgcaa aaaagcggtt 8040
agctccttcg gtcctccgat cgttgtcaga agtaagttgg ccgcagtgtt atcactcatg 8100
gttatggcag cactgcataa ttctcttact gtcatgccat ccgtaagatg cttttctgtg 8160
actggtgagt actcaaccaa gtcattctga gaatagtgta tgcggcgacc gagttgctct 8220
tgcccggcgt caatacggga taataccgcg ccacatagca gaactttaaa agtgctcatc 8280
attggaaaac gttcttcggg gcgaaaactc tcaaggatct taccgctgtt gagatccagt 8340
tcgatgtaac ccactcgtgc acccaactga tcttcagcat cttttacttt caccagcgtt 8400
tctgggtgag caaaaacagg aaggcaaaat gccgcaaaaa agggaataag ggcgacacgg 8460
aaatgttgaa tactcatact cttccttttt caatattatt gaagcattta tcagggttat 8520
tgtctcatga gcggatacat atttgaatgt atttagaaaa ataaacaaat aggggttccg 8580
cgcacatttc cccgaaaagt gccacct 8607

<210> SEQ ID NO 129
<211> LENGTH: 7818
<212> TYPE: DNA
<213> ORGANISM: Artificial Sequence
<220> FEATURE:
<223> OTHER INFORMATION: Plasmid pCVL.SFFV.HA.NLS.I-GPI I.IRES.mTagBFP

<400> SEQUENCE: 129
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780

-continued

```
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgct actgttactc cattgatcga   2460
cccatggttc atcactggtt tcgctgacgc tgaatcttct ttcgttgttt ctatcaagag   2520
aaacaagaag atcaagtgtg gttggaacgt tgttactaga ttccaaatcg ccttaagtca   2580
aaaggacttg gctttgttgg aaagaatcaa gtcttacttc aaggacgctg gtaacatcta   2640
catcaagtct gacaaggttt ctgttgactg gcacgttact tctgttaagg acttgaagat   2700
catccttgat cacttcgaca agtacccatt gaagactgaa aagttggctg actacatctt   2760
gttcaaggaa gttttcaaca tcatcttgac taagcaacac ttgactgttg aaggtatcca   2820
aaagatcgtt gctatcagag cttctatcaa caagggtttg tacggtgaat tgaaggctgc   2880
attcccaaac atcatcccag ttcaaaggcc taagatcgac gacagattca tcatcgatat   2940
ccaaccatgg tgggttgctg gtttcactga aggtgaaggt tgtttctctg ttgttgttac   3000
taactctcca tctactaagt ctggtttctc tgcttctttg atcttccaaa tcactcaaca   3060
ctctcgtgac atcgttttga tgcaaaacat catcaagttc ctaggttgtg gtagaatcca   3120
caagagatct aaggaagaag ctgttgacat cttggttact aagttctctg acttgactga   3180
```

-continued

```
aaaggttatc ccattcttcg aatctatccc attgcaaggt ttgaagttga agaacttcac   3240
tgacttctct aaggctgctg acatcatcaa ggttaagggt cacttgactc caaagggttt   3300
ggacaagatc ttgcaaatca agttgggtat gaacactaga agaatctagc ctgcaggtcg   3360
agcatgcatc tagggcggcc aattccgccc ctctccctcc ccccccccta acgttactgg   3420
ccgaagccgc ttggaataag gccggtgtgc gtttgtctat atgtgatttt ccaccatatt   3480
gccgtctttt ggcaatgtga gggcccggaa acctggccct gtcttcttga cgagcattcc   3540
taggggtctt tcccctctcg ccaaaggaat gcaaggtctg ttgaatgtcg tgaaggaagc   3600
agttcctctg gaagcttctt gaagacaaac aacgtctgta gcgacccttt gcaggcagcg   3660
gaacccccca cctggcgaca ggtgcctctg cggccaaaag ccacgtgtat aagatacacc   3720
tgcaaaggcg gcacaacccc agtgccacgt tgtgagttgg atagttgtgg aaagagtcaa   3780
atggctctcc tcaagcgtat tcaacaaggg gctgaaggat gcccagaagg taccccattg   3840
tatgggatct gatctggggc ctcggtgcac atgctttaca tgtgtttagt cgaggttaaa   3900
aaaacgtcta ggccccccga accacgggga cgtggttttc ctttgaaaaa cacgatgata   3960
agcttgccac aacccttacc ggtcgccacc atgagcgagc tgattaagga gaacatgcac   4020
atgaagctgt acatggaggg caccgtggac aaccatcact tcaagtgcac atccgagggc   4080
gaaggcaagc cctacgaggg cacccagacc atgagaatca aggtggtcga gggcggccct   4140
ctccccttcg ccttcgacat cctggctact agcttcctct acggcagcaa gaccttcatc   4200
aaccacaccc agggcatccc cgacttcttc aagcagtcct tccctgaggg cttcacatgg   4260
gagagagtca ccacatacga agacgggggc gtgctgaccg ctacccagga caccagcctc   4320
caggacggct gcctcatcta caacgtcaag atcagagggg tgaacttcac atccaacggc   4380
cctgtgatgc agaagaaaac actcggctgg gaggccttca ccgagacgct gtaccccgct   4440
gacggcggcc tggaaggcag aaacgacatg gccctgaagc tcgtgggcgg gagccatctg   4500
atcgcaaaca tcaagaccac atatagatcc aagaaacccg ctaagaacct caagatgcct   4560
ggcgtctact atgtggacta cagactggaa agaatcaagg aggccaacaa cgagacctac   4620
gtcgagcagc acgaggtggc agtggccaga tactgcgacc tccctagcaa actggggcac   4680
aagcttaatt gattctagag tcgaccgagc atcttaccgc catttatacc catatttgtt   4740
ctgtttttct tgatttgggt atacatttaa atgttaatag aacaaaatgg tggggcaatc   4800
atttacattt ttagggatat gtaattacta gttcaggtgt attgccacaa gacaaacatg   4860
ttaagaaact ttcccgttat ttacgctctg ttcctgttaa tcaacctctg gattacaaaa   4920
tttgtgaaag attgactgat attcttaact atgttgctcc ttttacgctg tgtggatatg   4980
ctgctttata gcctctgtat ctagctattg cttcccgtac ggctttcgtt ttctcctcct   5040
tgtataaatc ctggttgctg tctcttttag aggagttgtg gcccgttgtc cgtcaacgtg   5100
gcgtggtgtg ctctgtgttt gctgacgcaa cccccactgg ctggggcatt gccaccacct   5160
gtcaactcct ttctgggact ttcgctttcc ccctcccgat cgccacggca gaactcatcg   5220
ccgcctgcct tgcccgctgc tggacagggg ctaggttgct gggcactgat aattccgtgg   5280
tgttgtcatc ggtacctttt taaaagaaaa ggggggactg gaagggctaa ttcactccca   5340
acgaagacaa gatatcataa cttcgtatag catacattat acgaagttat aatttatttg   5400
tgaaatttgt gatgctattg ctttatttgt aaccatatgt ttatttgtga aatttgtgat   5460
gctattgctt tatttgtaac cattgctttt tgcttgtact gggtctctct ggttagacca   5520
```

-continued

```
gatctgagcc tgggagctct ctggctaact agggaaccca ctgcttaagc ctcaataaag   5580
cttgcctcga ccagcctcga ctgtgccttc tagttgccag ccatctgttg tttgcccctc   5640
ccccgtgcct tccttgaccc tggaaggtgc cactcccact gtcctttcct aataaaatga   5700
ggaaattgca tcgcattgtc tgagtaggtg tcattctatt ctggggggtg gggtggggca   5760
ggacagcaag ggggaggatt gggaagacaa tagcaggcat gctggggatg cggtgggctc   5820
tatggcctgc agctgcatta atgaatcggc caacgcgcgg ggagaggcgg tttgcgtatt   5880
gggcgctctt ccgcttcctc gctcactgac tcgctgcgct cggtcgttcg gctgcggcga   5940
gcggtatcag ctcactcaaa ggcggtaata cggttatcca cagaatcagg ggataacgca   6000
ggaaagaaca tgtgagcaaa aggccagcaa aaggccagga accgtaaaaa ggccgcgttg   6060
ctggcgtttt tccataggct ccgcccccct gacgagcatc acaaaaatcg acgctcaagt   6120
cagaggtggc gaaacccgac aggactataa agataccagg cgtttccccc tggaagctcc   6180
ctcgtgcgct ctcctgttcc gaccctgccg cttaccggat acctgtccgc ctttctccct   6240
tcgggaagcg tggcgctttc tcatagctca cgctgtaggt atctcagttc ggtgtaggtc   6300
gttcgctcca agctgggctg tgtgcacgaa ccccccgttc agcccgaccg ctgcgcctta   6360
tccggtaact atcgtcttga gtccaacccg gtaagacacg acttatcgcc actggcagca   6420
gccactggta acaggattag cagagcgagg tatgtaggcg gtgctacaga gttcttgaag   6480
tggtggccta actacggcta cactagaagg acagtatttg gtatctgcgc tctgctgaag   6540
ccagttacct tcggaaaaag agttggtagc tcttgatccg gcaaacaaac caccgctggt   6600
agcggtggtt tttttgtttg caagcagcag attacgcgca gaaaaaaagg atctcaagaa   6660
gatcctttga tcttttctac ggggtctgac gctcagtgga acgaaaactc acgttaaggg   6720
attttggtca tgagattatc aaaaaggatc ttcacctaga tccttttaaa ttaaaaatga   6780
agttttaaat caatctaaag tatatatgag taaacttggt ctgacagtta ccaatgctta   6840
atcagtgagg cacctatctc agcgatctgt ctatttcgtt catccatagt tgcctgactc   6900
cccgtcgtgt agataactac gatacgggag ggcttaccat ctggccccag tgctgcaatg   6960
ataccgcgag acccacgctc accggctcca gatttatcag caataaacca gccagccgga   7020
agggccgagc gcagaagtgg tcctgcaact ttatccgcct ccatccagtc tattaattgt   7080
tgccgggaag ctagagtaag tagttcgcca gttaatagtt tgcgcaacgt tgttgccatt   7140
gctacaggca tcgtggtgtc acgctcgtcg tttggtatgg cttcattcag ctccggttcc   7200
caacgatcaa ggcgagttac atgatccccc atgttgtgca aaaaagcggt tagctccttc   7260
ggtcctccga tcgttgtcag aagtaagttg gccgcagtgt tatcactcat ggttatggca   7320
gcactgcata attctcttac tgtcatgcca tccgtaagat gcttttctgt gactggtgag   7380
tactcaacca agtcattctg agaatagtgt atgcggcgac cgagttgctc ttgcccggcg   7440
tcaatacggg ataataccgc gccacatagc agaactttaa aagtgctcat cattggaaaa   7500
cgttcttcgg ggcgaaaact ctcaaggatc ttaccgctgt tgagatccag ttcgatgtaa   7560
cccactcgtg cacccaactg atcttcagca tcttttactt tcaccagcgt ttctgggtga   7620
gcaaaaacag gaaggcaaaa tgccgcaaaa aagggaataa gggcgacacg gaaatgttga   7680
atactcatac tcttcctttt tcaatattat tgaagcattt atcagggtta ttgtctcatg   7740
agcggataca tatttgaatg tatttagaaa aataaacaaa taggggttcc gcgcacattt   7800
ccccgaaaag tgccacct                                                  7818
```

```
<210> SEQ ID NO 130
<211> LENGTH: 8592
<212> TYPE: DNA
<213> ORGANISM: Artificial Sequence
<220> FEATURE:
<223> OTHER INFORMATION: Plasmid pCVL.SFFV.HA.NLS.I-GPI
      I.T2A.Trex2.IRES.mTagBFP

<400> SEQUENCE: 130

gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc ctgatcttca gacctggagg aggagatatg    960

agggacaatt ggagaagtga attatataaa tataaagtag taaaaattga accattagga   1020

gtagcaccca ccaaggcaaa gagaagagtg gtgcagagag aaaaaagagc agtgggaata   1080

ggagctttgt tccttgggtt cttgggagca gcaggaagca ctatgggcgc agcgtcaatg   1140

acgctgacgg tacaggccag acaattattg tctggtatag tgcagcagca gaacaatttg   1200

ctgagggcta ttgaggcgca acagcatctg ttgcaactca cagtctgggg catcaagcag   1260

ctccaggcaa gaatcctggc tgtggaaaga tacctaaagg atcaacagct cctggggatt   1320

tggggttgct ctggaaaact catttgcacc actgctgtgc cttggaatgc tagttggagt   1380

aatgaatctc tggaacagat ttggaatcac acgacctgga tggagtggga cagagaaatt   1440

aacaattaca caagcttaat acactcctta attgaagaat cgcaaaacca gcaagaaaag   1500

aatgaacaag aattattgga attagataaa tgggcaagtt tgtggaattg gtttaacata   1560

acaaattggc tgtggtatat aaaattattc ataatgatag taggaggctt ggtaggttta   1620

agaatagttt ttgctgtact ttctatagtg aatagagtta ggcagggata ttcaccatta   1680

tcgtttcaga cccacctccc aaccccgagg ggacccgaca ggcccgaagg aatagaagaa   1740

gaaggtggag agagagacag agacagatcc attcgattag tgaacggatc tcgacggtat   1800

cggttaactt ttaaaagaaa aggggggatt ggggggtaca gtgcagggga aagaatagta   1860

gacataatag caacagacat acaaactaaa gaattacaaa aacaaattac aaaaattcaa   1920

aattttatcg attacgcgtc acgtgctagc tgcagtaacg ccattttgca aggcatggaa   1980

aaataccaaa ccaagaatag agaagttcag atcaagggcg ggtacatgaa aatagctaac   2040

gttgggccaa acaggatatc tgcggtgagc agtttcggcc ccggcccggg gccaagaaca   2100
```

-continued gatggtcacc gcagtttcgg ccccggcccg aggccaagaa cagatggtcc ccagatatgg 2160
cccaaccctc agcagtttct taagacccat cagatgtttc caggctcccc caaggacctg 2220
aaatgaccct gcgccttatt tgaattaacc aatcagcctg cttctcgctt ctgttcgcgc 2280
gcttctgctt cccgagctct ataaaagagc tcacaacccc tcactcggcg cgccagtcct 2340
ccgacagact gagtcgcccg ctcgagccgc caccatggga tatccatacg atgtcccaga 2400
ttatgcgcca cctaagaaga aacgcaaagt cgaattcgct actgttactc cattgatcga 2460
cccatggttc atcactggtt tcgctgacgc tgaatcttct ttcgttgttt ctatcaagag 2520
aaacaagaag atcaagtgtg gttggaacgt tgttactaga ttccaaatcg ccttaagtca 2580
aaaggacttg gctttgttgg aaagaatcaa gtcttacttc aaggacgctg gtaacatcta 2640
catcaagtct gacaaggttt ctgttgactg gcacgttact tctgttaagg acttgaagat 2700
catccttgat cacttcgaca agtacccatt gaagactgaa aagttggctg actacatctt 2760
gttcaaggaa gttttcaaca tcatcttgac taagcaacac ttgactgttg aaggtatcca 2820
aaagatcgtt gctatcagag cttctatcaa caagggtttg tacggtgaat tgaaggctgc 2880
attcccaaac atcatcccag ttcaaaggcc taagatcgac gacagattca tcatcgatat 2940
ccaaccatgg tgggttgctg gtttcactga aggtgaaggt tgtttctctg ttgttgttac 3000
taactctcca tctactaagt ctggtttctc tgcttctttg atcttccaaa tcactcaaca 3060
ctctcgtgac atcgttttga tgcaaaacat catcaagttc ctaggttgtg gtagaatcca 3120
caagagatct aaggaagaag ctgttgacat cttggttact aagttctctg acttgactga 3180
aaaggttatc ccattcttcg aatctatccc attgcaaggt ttgaagttga agaacttcac 3240
tgacttctct aaggctgctg acatcatcaa ggttaagggt cacttgactc caaagggttt 3300
ggacaagatc ttgcaaatca agttgggtat gaacactaga agaatcggat ccggtgaggg 3360
cagaggaagt cttctaacat gcggtgacgt ggaggagaat ccgggcccct ccggatctga 3420
gccacctcgg gctgagacct ttgtattcct ggacctagaa gccactgggc tcccaaacat 3480
ggaccctgag attgcagaga tatccctttt tgctgttcac cgctcttccc tggagaaccc 3540
agaacgggat gattctggtt ccttggtgct gccccgtgtt ctggacaagc tcacactgtg 3600
catgtgcccg gagcgcccct ttactgccaa ggccagtgag attactggtt tgagcagcga 3660
aagcctgatg cactgcggga aggctggttt caatggcgct gtggtaagga cactgcaggg 3720
cttcctaagc cgccaggagg gccccatctg ccttgtggcc cacaatggct tcgattatga 3780
cttcccactg ctgtgcacgg agctacaacg tctgggtgcc catctgcccc aagacactgt 3840
ctgcctggac acactgcctg cattgcgggg cctggaccgt gctcacagcc acggcaccag 3900
ggctcaaggc cgcaaaagct acagcctggc cagtctcttc caccgctact tccaggctga 3960
acccagtgct gcccattcag cagaaggtga tgtgcacacc ctgcttctga tcttcctgca 4020
tcgtgctcct gagctgctcg cctgggcaga tgagcaggcc cgcagctggg ctcatattga 4080
gcccatgtac gtgccacctg atggtccaag cctcgaagcc tgacctgcag gtcgagcatg 4140
catctagggc ggccaattcc gcccctctcc ctcccccccc cctaacgtta ctggccgaag 4200
ccgcttggaa taaggccggt gtgcgtttgt ctatatgtga ttttccacca tattgccgtc 4260
ttttggcaat gtgagggccc ggaaacctgg ccctgtcttc ttgacgagca ttcctagggg 4320
tctttcccct ctcgccaaag gaatgcaagg tctgttgaat gtcgtgaagg aagcagttcc 4380
tctggaagct tcttgaagac aaacaacgtc tgtagcgacc ctttgcaggc agcggaaccc 4440

-continued

```
cccacctggc gacaggtgcc tctgcggcca aaagccacgt gtataagata cacctgcaaa   4500
ggcggcacaa ccccagtgcc acgttgtgag ttggatagtt gtggaaagag tcaaatggct   4560
ctcctcaagc gtattcaaca aggggctgaa ggatgcccag aaggtacccc attgtatggg   4620
atctgatctg gggcctcggt gcacatgctt tacatgtgtt tagtcgaggt taaaaaaacg   4680
tctaggcccc ccgaaccacg gggacgtggt tttcctttga aaaacacgat gataagcttg   4740
ccacaaccct taccggtcgc caccatgagc gagctgatta aggagaacat gcacatgaag   4800
ctgtacatgg agggcaccgt ggacaaccat cacttcaagt gcacatccga gggcgaaggc   4860
aagccctacg agggcaccca gaccatgaga atcaaggtgg tcgagggcgg ccctctcccc   4920
ttcgccttcg acatcctggc tactagcttc ctctacggca gcaagacctt catcaaccac   4980
acccagggca tccccgactt cttcaagcag tccttccctg agggcttcac atgggagaga   5040
gtcaccacat acgaagacgg gggcgtgctg accgctaccc aggacaccag cctccaggac   5100
ggctgcctca tctacaacgt caagatcaga ggggtgaact tcacatccaa cggccctgtg   5160
atgcagaaga aaacactcgg ctgggaggcc ttcaccgaga cgctgtaccc cgctgacggc   5220
ggcctggaag gcagaaacga catggccctg aagctcgtgg gcgggagcca tctgatcgca   5280
aacatcaaga ccacatatag atccaagaaa cccgctaaga acctcaagat gcctggcgtc   5340
tactatgtgg actacagact ggaaagaatc aaggaggcca acaacgagac ctacgtcgag   5400
cagcacgagg tggcagtggc cagatactgc gacctcccta gcaaactggg gcacaagctt   5460
aattgattct agagtcgacc gagcatctta ccgccattta tacccatatt tgttctgttt   5520
ttcttgattt gggtatacat ttaaatgtta atagaacaaa atggtggggc aatcatttac   5580
atttttaggg atatgtaatt actagttcag gtgtattgcc acaagacaaa catgttaaga   5640
aactttcccg ttatttacgc tctgttcctg ttaatcaacc tctggattac aaaatttgtg   5700
aaagattgac tgatattctt aactatgttg ctccttttac gctgtgtgga tatgctgctt   5760
tatagcctct gtatctagct attgcttccc gtacggcttt cgttttctcc tccttgtata   5820
aatcctggtt gctgtctctt ttagaggagt tgtggcccgt tgtccgtcaa cgtggcgtgg   5880
tgtgctctgt gtttgctgac gcaaccccca ctggctgggg cattgccacc acctgtcaac   5940
tcctttctgg gactttcgct ttccccctcc cgatcgccac ggcagaactc atcgccgcct   6000
gccttgcccg ctgctggaca ggggctaggt tgctgggcac tgataattcc gtggtgttgt   6060
catcggtacc tttttaaaag aaaagggggg actggaaggg ctaattcact cccaacgaag   6120
acaagatatc ataacttcgt atagcataca ttatacgaag ttataattta tttgtgaaat   6180
ttgtgatgct attgctttat ttgtaaccat atgtttattt gtgaaatttg tgatgctatt   6240
gctttatttg taaccattgc tttttgcttg tactgggtct ctctggttag accagatctg   6300
agcctgggag ctctctggct aactagggaa cccactgctt aagcctcaat aaagcttgcc   6360
tcgaccagcc tcgactgtgc cttctagttg ccagccatct gttgtttgcc cctcccccgt   6420
gccttccttg accctggaag gtgccactcc cactgtcctt tcctaataaa atgaggaaat   6480
tgcatcgcat tgtctgagta ggtgtcattc tattctgggg ggtggggtgg ggcaggacag   6540
caagggggag gattgggaag acaatagcag gcatgctggg gatgcggtgg gctctatggc   6600
ctgcagctgc attaatgaat cggccaacgc gcggggagag gcggtttgcg tattgggcgc   6660
tcttccgctt cctcgctcac tgactcgctg cgctcggtcg ttcggctgcg gcgagcggta   6720
tcagctcact caaaggcggt aatacggtta tccacagaat caggggataa cgcaggaaag   6780
aacatgtgag caaaaggcca gcaaaaggcc aggaaccgta aaaaggccgc gttgctggcg   6840
```

```
tttttccata ggctccgccc ccctgacgag catcacaaaa atcgacgctc aagtcagagg   6900

tggcgaaacc cgacaggact ataaagatac caggcgtttc cccctggaag ctccctcgtg   6960

cgctctcctg ttccgaccct gccgcttacc ggatacctgt ccgcctttct cccttcggga   7020

agcgtggcgc tttctcatag ctcacgctgt aggtatctca gttcggtgta ggtcgttcgc   7080

tccaagctgg gctgtgtgca cgaacccccc gttcagcccg accgctgcgc cttatccggt   7140

aactatcgtc ttgagtccaa cccggtaaga cacgacttat cgccactggc agcagccact   7200

ggtaacagga ttagcagagc gaggtatgta ggcggtgcta cagagttctt gaagtggtgg   7260

cctaactacg gctacactag aaggacagta tttggtatct gcgctctgct gaagccagtt   7320

accttcggaa aaagagttgg tagctcttga tccggcaaac aaaccaccgc tggtagcggt   7380

ggtttttttg tttgcaagca gcagattacg cgcagaaaaa aaggatctca agaagatcct   7440

ttgatctttt ctacggggtc tgacgctcag tggaacgaaa actcacgtta agggattttg   7500

gtcatgagat tatcaaaaag gatcttcacc tagatccttt taaattaaaa atgaagtttt   7560

aaatcaatct aaagtatata tgagtaaact tggtctgaca gttaccaatg cttaatcagt   7620

gaggcaccta tctcagcgat ctgtctattt cgttcatcca tagttgcctg actccccgtc   7680

gtgtagataa ctacgatacg ggagggctta ccatctggcc ccagtgctgc aatgataccg   7740

cgagacccac gctcaccggc tccagattta tcagcaataa accagccagc cggaagggcc   7800

gagcgcagaa gtggtcctgc aactttatcc gcctccatcc agtctattaa ttgttgccgg   7860

gaagctagag taagtagttc gccagttaat agtttgcgca acgttgttgc cattgctaca   7920

ggcatcgtgg tgtcacgctc gtcgtttggt atggcttcat tcagctccgg ttcccaacga   7980

tcaaggcgag ttacatgatc ccccatgttg tgcaaaaaag cggttagctc cttcggtcct   8040

ccgatcgttg tcagaagtaa gttggccgca gtgttatcac tcatggttat ggcagcactg   8100

cataattctc ttactgtcat gccatccgta agatgctttt ctgtgactgg tgagtactca   8160

accaagtcat tctgagaata gtgtatgcgg cgaccgagtt gctcttgccc ggcgtcaata   8220

cgggataata ccgcgccaca tagcagaact ttaaaagtgc tcatcattgg aaaacgttct   8280

tcggggcgaa aactctcaag gatcttaccg ctgttgagat ccagttcgat gtaacccact   8340

cgtgcaccca actgatcttc agcatctttt actttcacca gcgtttctgg gtgagcaaaa   8400

acaggaaggc aaaatgccgc aaaaaaggga ataagggcga cacggaaatg ttgaatactc   8460

atactcttcc tttttcaata ttattgaagc atttatcagg gttattgtct catgagcgga   8520

tacatatttg aatgtattta gaaaaataaa caaatagggg ttccgcgcac atttccccga   8580

aaagtgccac ct                                                      8592
```

<210> SEQ ID NO 131
<211> LENGTH: 7818
<212> TYPE: DNA
<213> ORGANISM: Artificial Sequence
<220> FEATURE:
<223> OTHER INFORMATION: Plasmid pCVL.SFFV.HA.NLS.I-GZE I.IRES.mTagBFP

<400> SEQUENCE: 131

```
gacgtcaatg tagtcttatg caatactctt gtagtcttgc aacatggtaa cgatgagtta     60

gcaacatgcc ttacaaggag agaaaaagca ccgtgcatgc cgattggtgg aagtaaggtg    120

gtacgatcgt gccttattag gaaggcaaca gacgggtctg acatggattg gacgaaccac    180

tgaattgccg cattgcagag atattgtatt taagtgccta gctcgataca taaacgggtc    240
```

-continued

```
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgct agctctttgg aacaatcttc   2460
tttgccacca aagttggacc catcttacgt tactggtttc actgacggtg aaggttcttt   2520
catcttgact atcatcaagg acaacaagta caagttgggt tggagagttg catgcagatt   2580
cgttatctct ttgcacaaga aggacttggt tttgttgaac tctttgaaga acttcttcaa   2640
```

-continued

```
cactggttct gttttcttga tgggtaaggg cgccgctcaa tacagagttg aatctttgac   2700
tggtttgtct atcatcatca accacttcga cagataccca ttgaacacta agaagcaagc   2760
tgactacatg ttgttcaagt tggcttacaa cttgatcatc aacaagtctc acttgactga   2820
aaagggtttg tctgaactag tttctttgaa ggctgttatg aacaacggtt tgaaggacga   2880
attgaagatc gcttacccaa acatcactcc agttttgagg cctgaaatcc cattgtcttt   2940
gaacatcgat ccattgtggt tggctggttt cactgacgct gaaggttgtt tctctgttgt   3000
tgttttcaag tctaagactt ctaagatcgg tgaagctgtt aagttgtctt tcatcatcac   3060
tcaatctgtt agagacgaat ttttaattaa gtctttgatc gaatacttgg gttgtggtta   3120
cacttctttg gacggtagag gtgctatcga cttcaaggtt tctgacttct cttctcttaa   3180
gaacatcatc atcccattct acgacaagta ctacatccac ggtaacaagt ctttggactt   3240
caaggacttc tctcgtgttg ttactttgat ggaaaacaag aagcacttga ctaagcaagg   3300
tttggacgaa atcaagaaga tcagaaacgc tatgaacact aacagatagc ctgcaggtcg   3360
agcatgcatc tagggcggcc aattccgccc ctctccctcc cccccccta acgttactgg   3420
ccgaagccgc ttggaataag gccggtgtgc gtttgtctat atgtgatttt ccaccatatt   3480
gccgtctttt ggcaatgtga gggcccggaa acctggccct gtcttcttga cgagcattcc   3540
taggggtctt tcccctctcg ccaaaggaat gcaaggtctg ttgaatgtcg tgaaggaagc   3600
agttcctctg gaagcttctt gaagacaaac aacgtctgta gcgacccttt gcaggcagcg   3660
gaacccccca cctggcgaca ggtgcctctg cggccaaaag ccacgtgtat aagatacacc   3720
tgcaaaggcg gcacaacccc agtgccacgt tgtgagttgg atagttgtgg aaagagtcaa   3780
atggctctcc tcaagcgtat tcaacaaggg gctgaaggat gcccagaagg taccccattg   3840
tatgggatct gatctggggc ctcggtgcac atgctttaca tgtgtttagt cgaggttaaa   3900
aaaacgtcta ggccccccga accacgggga cgtggttttc ctttgaaaaa cacgatgata   3960
agcttgccac aacccttacc ggtcgccacc atgagcgagc tgattaagga gaacatgcac   4020
atgaagctgt acatggaggg caccgtggac aaccatcact tcaagtgcac atccgagggc   4080
gaaggcaagc cctacgaggg cacccagacc atgagaatca aggtggtcga gggcggccct   4140
ctccccttcg ccttcgacat cctggctact agcttcctct acggcagcaa gaccttcatc   4200
aaccacaccc agggcatccc cgacttcttc aagcagtcct tccctgaggg cttcacatgg   4260
gagagagtca ccacatacga agacgggggc gtgctgaccg ctacccagga caccagcctc   4320
caggacggct gcctcatcta caacgtcaag atcagagggg tgaacttcac atccaacggc   4380
cctgtgatgc agaagaaaac actcggctgg gaggccttca ccgagacgct gtaccccgct   4440
gacggcggcc tggaaggcag aaacgacatg gccctgaagc tcgtgggcgg gagccatctg   4500
atcgcaaaca tcaagaccac atatagatcc aagaaacccg ctaagaacct caagatgcct   4560
ggcgtctact atgtggacta cagactggaa agaatcaagg aggccaacaa cgagacctac   4620
gtcgagcagc acgaggtggc agtggccaga tactgcgacc tccctagcaa actggggcac   4680
aagcttaatt gattctagag tcgaccgagc atcttaccgc catttatacc catatttgtt   4740
ctgtttttct tgatttgggt atacatttaa atgttaatag aacaaaatgg tggggcaatc   4800
atttacattt ttagggatat gtaattacta gttcaggtgt attgccacaa gacaaacatg   4860
ttaagaaact ttcccgttat ttacgctctg ttcctgttaa tcaacctctg gattacaaaa   4920
tttgtgaaag attgactgat attcttaact atgttgctcc ttttacgctg tgtggatatg   4980
```

```
ctgctttata gcctctgtat ctagctattg cttcccgtac ggctttcgtt ttctcctcct   5040
tgtataaatc ctggttgctg tctcttttag aggagttgtg gcccgttgtc cgtcaacgtg   5100
gcgtggtgtg ctctgtgttt gctgacgcaa cccccactgg ctggggcatt gccaccacct   5160
gtcaactcct ttctgggact ttcgctttcc ccctcccgat cgccacggca gaactcatcg   5220
ccgcctgcct tgcccgctgc tggacagggg ctaggttgct gggcactgat aattccgtgg   5280
tgttgtcatc ggtacctttt taaaagaaaa ggggggactg gaagggctaa ttcactccca   5340
acgaagacaa gatatcataa cttcgtatag catacattat acgaagttat aatttatttg   5400
tgaaatttgt gatgctattg ctttatttgt aaccatatgt ttatttgtga aatttgtgat   5460
gctattgctt tatttgtaac cattgctttt tgcttgtact gggtctctct ggttagacca   5520
gatctgagcc tgggagctct ctggctaact agggaaccca ctgcttaagc ctcaataaag   5580
cttgcctcga ccagcctcga ctgtgccttc tagttgccag ccatctgttg tttgcccctc   5640
ccccgtgcct tccttgaccc tggaaggtgc cactcccact gtcctttcct aataaaatga   5700
ggaaattgca tcgcattgtc tgagtaggtg tcattctatt ctggggggtg gggtggggca   5760
ggacagcaag ggggaggatt gggaagacaa tagcaggcat gctggggatg cggtgggctc   5820
tatggcctgc agctgcatta atgaatcggc caacgcgcgg ggagaggcgg tttgcgtatt   5880
gggcgctctt ccgcttcctc gctcactgac tcgctgcgct cggtcgttcg gctgcggcga   5940
gcggtatcag ctcactcaaa ggcggtaata cggttatcca cagaatcagg ggataacgca   6000
ggaaagaaca tgtgagcaaa aggccagcaa aaggccagga accgtaaaaa ggccgcgttg   6060
ctggcgtttt tccataggct ccgcccccct gacgagcatc acaaaaatcg acgctcaagt   6120
cagaggtggc gaaacccgac aggactataa agataccagg cgtttccccc tggaagctcc   6180
ctcgtgcgct ctcctgttcc gaccctgccg cttaccggat acctgtccgc ctttctccct   6240
tcgggaagcg tggcgctttc tcatagctca cgctgtaggt atctcagttc ggtgtaggtc   6300
gttcgctcca agctgggctg tgtgcacgaa ccccccgttc agcccgaccg ctgcgcctta   6360
tccggtaact atcgtcttga gtccaacccg gtaagacacg acttatcgcc actggcagca   6420
gccactggta acaggattag cagagcgagg tatgtaggcg gtgctacaga gttcttgaag   6480
tggtggccta actacggcta cactagaagg acagtatttg gtatctgcgc tctgctgaag   6540
ccagttacct tcggaaaaag agttggtagc tcttgatccg gcaaacaaac caccgctggt   6600
agcggtggtt tttttgtttg caagcagcag attacgcgca gaaaaaaagg atctcaagaa   6660
gatcctttga tcttttctac ggggtctgac gctcagtgga acgaaaactc acgttaaggg   6720
attttggtca tgagattatc aaaaaggatc ttcacctaga tccttttaaa ttaaaaatga   6780
agttttaaat caatctaaag tatatatgag taaacttggt ctgacagtta ccaatgctta   6840
atcagtgagg cacctatctc agcgatctgt ctatttcgtt catccatagt tgcctgactc   6900
cccgtcgtgt agataactac gatacgggag ggcttaccat ctggccccag tgctgcaatg   6960
ataccgcgag acccacgctc accggctcca gatttatcag caataaacca gccagccgga   7020
agggccgagc gcagaagtgg tcctgcaact ttatccgcct ccatccagtc tattaattgt   7080
tgccgggaag ctagagtaag tagttcgcca gttaatagtt tgcgcaacgt tgttgccatt   7140
gctacaggca tcgtggtgtc acgctcgtcg tttggtatgg cttcattcag ctccggttcc   7200
caacgatcaa ggcgagttac atgatccccc atgttgtgca aaaaagcggt tagctccttc   7260
ggtcctccga tcgttgtcag aagtaagttg gccgcagtgt tatcactcat ggttatggca   7320
gcactgcata attctcttac tgtcatgcca tccgtaagat gcttttctgt gactggtgag   7380
```

tactcaacca agtcattctg agaatagtgt atgcggcgac cgagttgctc ttgcccggcg 7440
tcaatacggg ataataccgc gccacatagc agaactttaa aagtgctcat cattggaaaa 7500
cgttcttcgg ggcgaaaact ctcaaggatc ttaccgctgt tgagatccag ttcgatgtaa 7560
cccactcgtg cacccaactg atcttcagca tcttttactt tcaccagcgt ttctgggtga 7620
gcaaaaacag gaaggcaaaa tgccgcaaaa aagggaataa gggcgacacg gaaatgttga 7680
atactcatac tcttcctttt tcaatattat tgaagcattt atcagggtta ttgtctcatg 7740
agcggataca tatttgaatg tatttagaaa aataaacaaa taggggttcc gcgcacattt 7800
ccccgaaaag tgccacct 7818

<210> SEQ ID NO 132
<211> LENGTH: 8592
<212> TYPE: DNA
<213> ORGANISM: Artificial Sequence
<220> FEATURE:
<223> OTHER INFORMATION: Plasmid pCVL.SFFV.HA.NLS.I-GZE
I.T2A.Trex2.IRES.mTagBFP

<400> SEQUENCE: 132
gacgtcaatg tagtcttatg caatactctt gtagtcttgc aacatggtaa cgatgagtta 60
gcaacatgcc ttacaaggag agaaaaagca ccgtgcatgc cgattggtgg aagtaaggtg 120
gtacgatcgt gccttattag gaaggcaaca gacgggtctg acatggattg gacgaaccac 180
tgaattgccg cattgcagag atattgtatt taagtgccta gctcgataca taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560

-continued

```
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga aagaatagta   1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgct agctctttgg aacaatcttc   2460
tttgccacca aagttggacc catcttacgt tactggtttc actgacggtg aaggttcttt   2520
catcttgact atcatcaagg acaacaagta caagttgggt tggagagttg catgcagatt   2580
cgttatctct ttgcacaaga aggacttggt tttgttgaac tctttgaaga acttcttcaa   2640
cactggttct gttttcttga tgggtaaggg cgccgctcaa tacagagttg aatctttgac   2700
tggtttgtct atcatcatca accacttcga cagataccca ttgaacacta agaagcaagc   2760
tgactacatg ttgttcaagt tggcttacaa cttgatcatc aacaagtctc acttgactga   2820
aaagggtttg tctgaactag tttctttgaa ggctgttatg aacaacggtt tgaaggacga   2880
attgaagatc gcttacccaa acatcactcc agttttgagg cctgaaatcc cattgtcttt   2940
gaacatcgat ccattgtggt tggctggttt cactgacgct gaaggttgtt tctctgttgt   3000
tgttttcaag tctaagactt ctaagatcgg tgaagctgtt aagttgtctt tcatcatcac   3060
tcaatctgtt agagacgaat ttttaattaa gtctttgatc gaatacttgg gttgtggtta   3120
cacttctttg gacggtagag gtgctatcga cttcaaggtt tctgacttct cttctcttaa   3180
gaacatcatc atcccattct acgacaagta ctacatccac ggtaacaagt ctttggactt   3240
caaggacttc tctcgtgttg ttactttgat ggaaaacaag aagcacttga ctaagcaagg   3300
tttggacgaa atcaagaaga tcagaaacgc tatgaacact aacagaggat ccggtgaggg   3360
cagaggaagt cttctaacat gcggtgacgt ggaggagaat ccgggcccct ccggatctga   3420
gccacctcgg gctgagacct ttgtattcct ggacctagaa gccactgggc tcccaaacat   3480
ggaccctgag attgcagaga tatccctttt tgctgttcac cgctcttccc tggagaaccc   3540
agaacgggat gattctggtt ccttggtgct gccccgtgtt ctggacaagc tcacactgtg   3600
catgtgcccg gagcgcccct ttactgccaa ggccagtgag attactggtt tgagcagcga   3660
aagcctgatg cactgcggga aggctggttt caatggcgct gtggtaagga cactgcaggg   3720
cttcctaagc cgccaggagg gccccatctg ccttgtggcc cacaatggct tcgattatga   3780
cttcccactg ctgtgcacgg agctacaacg tctgggtgcc catctgcccc aagacactgt   3840
ctgcctggac acactgcctg cattgcgggg cctggaccgt gctcacagcc acggcaccag   3900
```

-continued

```
ggctcaaggc cgcaaaagct acagcctggc cagtctcttc caccgctact tccaggctga   3960
acccagtgct gcccattcag cagaaggtga tgtgcacacc ctgcttctga tcttcctgca   4020
tcgtgctcct gagctgctcg cctgggcaga tgagcaggcc cgcagctggg ctcatattga   4080
gcccatgtac gtgccacctg atggtccaag cctcgaagcc tgacctgcag gtcgagcatg   4140
catctagggc ggccaattcc gcccctctcc ctcccccccc cctaacgtta ctggccgaag   4200
ccgcttggaa taaggccggt gtgcgtttgt ctatatgtga ttttccacca tattgccgtc   4260
ttttggcaat gtgagggccc ggaaacctgg ccctgtcttc ttgacgagca ttcctagggg   4320
tctttcccct ctcgccaaag gaatgcaagg tctgttgaat gtcgtgaagg aagcagttcc   4380
tctggaagct tcttgaagac aaacaacgtc tgtagcgacc ctttgcaggc agcggaaccc   4440
cccacctggc gacaggtgcc tctgcggcca aaagccacgt gtataagata cacctgcaaa   4500
ggcggcacaa ccccagtgcc acgttgtgag ttggatagtt gtggaaagag tcaaatggct   4560
ctcctcaagc gtattcaaca aggggctgaa ggatgcccag aaggtacccc attgtatggg   4620
atctgatctg gggcctcggt gcacatgctt tacatgtgtt tagtcgaggt taaaaaaacg   4680
tctaggcccc ccgaaccacg gggacgtggt tttcctttga aaaacacgat gataagcttg   4740
ccacaaccct taccggtcgc caccatgagc gagctgatta aggagaacat gcacatgaag   4800
ctgtacatgg agggcaccgt ggacaaccat cacttcaagt gcacatccga gggcgaaggc   4860
aagccctacg agggcaccca gaccatgaga atcaaggtgg tcgagggcgg ccctctcccc   4920
ttcgccttcg acatcctggc tactagcttc ctctacggca gcaagacctt catcaaccac   4980
acccagggca tccccgactt cttcaagcag tccttccctg agggcttcac atgggagaga   5040
gtcaccacat acgaagacgg gggcgtgctg accgctaccc aggacaccag cctccaggac   5100
ggctgcctca tctacaacgt caagatcaga ggggtgaact tcacatccaa cggccctgtg   5160
atgcagaaga aaacactcgg ctgggaggcc ttcaccgaga cgctgtaccc cgctgacggc   5220
ggcctggaag gcagaaacga catggccctg aagctcgtgg gcgggagcca tctgatcgca   5280
aacatcaaga ccacatatag atccaagaaa cccgctaaga acctcaagat gcctggcgtc   5340
tactatgtgg actacagact ggaaagaatc aaggaggcca acaacgagac ctacgtcgag   5400
cagcacgagg tggcagtggc cagatactgc gacctcccta gcaaactggg gcacaagctt   5460
aattgattct agagtcgacc gagcatctta ccgccattta tacccatatt tgttctgttt   5520
ttcttgattt gggtatacat ttaaatgtta atagaacaaa atggtggggc aatcatttac   5580
atttttaggg atatgtaatt actagttcag gtgtattgcc acaagacaaa catgttaaga   5640
aactttcccg ttatttacgc tctgttcctg ttaatcaacc tctggattac aaaatttgtg   5700
aaagattgac tgatattctt aactatgttg ctccttttac gctgtgtgga tatgctgctt   5760
tatagcctct gtatctagct attgcttccc gtacggcttt cgttttctcc tccttgtata   5820
aatcctggtt gctgtctctt ttagaggagt tgtggcccgt tgtccgtcaa cgtggcgtgg   5880
tgtgctctgt gtttgctgac gcaaccccca ctggctgggg cattgccacc acctgtcaac   5940
tcctttctgg gactttcgct ttccccctcc cgatcgccac ggcagaactc atcgccgcct   6000
gccttgcccg ctgctggaca ggggctaggt tgctgggcac tgataattcc gtggtgttgt   6060
catcggtacc tttttaaaag aaaagggggg actggaaggg ctaattcact cccaacgaag   6120
acaagatatc ataacttcgt atagcataca ttatacgaag ttataattta tttgtgaaat   6180
ttgtgatgct attgctttat ttgtaaccat atgtttattt gtgaaatttg tgatgctatt   6240
gctttatttg taaccattgc tttttgcttg tactgggtct ctctggttag accagatctg   6300
```

-continued

```
agcctgggag ctctctggct aactagggaa cccactgctt aagcctcaat aaagcttgcc   6360
tcgaccagcc tcgactgtgc cttctagttg ccagccatct gttgtttgcc cctcccccgt   6420
gccttccttg accctggaag gtgccactcc cactgtcctt tcctaataaa atgaggaaat   6480
tgcatcgcat tgtctgagta ggtgtcattc tattctgggg ggtggggtgg ggcaggacag   6540
caagggggag gattgggaag acaatagcag gcatgctggg gatgcggtgg gctctatggc   6600
ctgcagctgc attaatgaat cggccaacgc gcggggagag gcggtttgcg tattgggcgc   6660
tcttccgctt cctcgctcac tgactcgctg cgctcggtcg ttcggctgcg gcgagcggta   6720
tcagctcact caaaggcggt aatacggtta tccacagaat caggggataa cgcaggaaag   6780
aacatgtgag caaaaggcca gcaaaaggcc aggaaccgta aaaaggccgc gttgctggcg   6840
tttttccata ggctccgccc ccctgacgag catcacaaaa atcgacgctc aagtcagagg   6900
tggcgaaacc cgacaggact ataaagatac caggcgtttc cccctggaag ctccctcgtg   6960
cgctctcctg ttccgaccct gccgcttacc ggatacctgt ccgcctttct cccttcggga   7020
agcgtggcgc tttctcatag ctcacgctgt aggtatctca gttcggtgta ggtcgttcgc   7080
tccaagctgg gctgtgtgca cgaacccccc gttcagcccg accgctgcgc cttatccggt   7140
aactatcgtc ttgagtccaa cccggtaaga cacgacttat cgccactggc agcagccact   7200
ggtaacagga ttagcagagc gaggtatgta ggcggtgcta cagagttctt gaagtggtgg   7260
cctaactacg gctacactag aaggacagta tttggtatct gcgctctgct gaagccagtt   7320
accttcggaa aaagagttgg tagctcttga tccggcaaac aaaccaccgc tggtagcggt   7380
ggtttttttg tttgcaagca gcagattacg cgcagaaaaa aaggatctca agaagatcct   7440
ttgatctttt ctacggggtc tgacgctcag tggaacgaaa actcacgtta agggattttg   7500
gtcatgagat tatcaaaaag gatcttcacc tagatccttt taaattaaaa atgaagtttt   7560
aaatcaatct aaagtatata tgagtaaact tggtctgaca gttaccaatg cttaatcagt   7620
gaggcaccta tctcagcgat ctgtctattt cgttcatcca tagttgcctg actccccgtc   7680
gtgtagataa ctacgatacg ggagggctta ccatctggcc ccagtgctgc aatgataccg   7740
cgagacccac gctcaccggc tccagattta tcagcaataa accagccagc cggaagggcc   7800
gagcgcagaa gtggtcctgc aactttatcc gcctccatcc agtctattaa ttgttgccgg   7860
gaagctagag taagtagttc gccagttaat agtttgcgca acgttgttgc cattgctaca   7920
ggcatcgtgg tgtcacgctc gtcgtttggt atggcttcat tcagctccgg ttcccaacga   7980
tcaaggcgag ttacatgatc ccccatgttg tgcaaaaaag cggttagctc cttcggtcct   8040
ccgatcgttg tcagaagtaa gttggccgca gtgttatcac tcatggttat ggcagcactg   8100
cataattctc ttactgtcat gccatccgta agatgctttt ctgtgactgg tgagtactca   8160
accaagtcat tctgagaata gtgtatgcgg cgaccgagtt gctcttgccc ggcgtcaata   8220
cgggataata ccgcgccaca tagcagaact ttaaaagtgc tcatcattgg aaaacgttct   8280
tcggggcgaa aactctcaag gatcttaccg ctgttgagat ccagttcgat gtaacccact   8340
cgtgcaccca actgatcttc agcatctttt actttcacca gcgtttctgg gtgagcaaaa   8400
acaggaaggc aaaatgccgc aaaaaaggga ataagggcga cacggaaatg ttgaatactc   8460
atactcttcc tttttcaata ttattgaagc atttatcagg gttattgtct catgagcgga   8520
tacatatttg aatgtattta gaaaaataaa caaatagggg ttccgcgcac atttccccga   8580
aaagtgccac ct                                                       8592
```

<210> SEQ ID NO 133
<211> LENGTH: 6955
<212> TYPE: DNA
<213> ORGANISM: Artificial Sequence
<220> FEATURE:
<223> OTHER INFORMATION: pExodus ExoI

<400> SEQUENCE: 133
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atggggatac agggattgct acaatttatc aaagaagctt cagaacccat ccatgtgagg 960
aagtataaag ggcaggtagt agctgtggat acatattgct ggcttcacaa aggagctatt 1020
gcttgtgctg aaaaactagc caaaggtgaa cctactgata ggtatgtagg attttgtatg 1080
aaatttgtaa atatgttact atctcatggg atcaagccta ttctcgtatt tgatggatgt 1140
actttacctt ctaaaaagga agtagagaga tctagaagag aaagacgaca agccaatctt 1200
cttaagggaa agcaacttct tcgtgagggg aaagtctcgg aagctcgaga gtgtttcacc 1260
cggtctatca atatcacaca tgccatggcc cacaaagtaa ttaaagctgc ccggtctcag 1320
ggggtagatt gcctcgtggc tccctatgaa gctgatgcgc agttggccta tcttaacaaa 1380
gcgggaattg tgcaagccat aattacagag gactcggatc tcctagcttt tggctgtaaa 1440
aaggtaattt taaagatgga ccagtttgga aatggacttg aaattgatca agctcggcta 1500
ggaatgtgca gacagcttgg ggatgtattc acggaagaga agtttcgtta catgtgtatt 1560
ctttcaggtt gtgactacct gtcatcactg cgtgggattg gattagcaaa ggcatgcaaa 1620
gtcctaagac tagccaataa tccagatata gtaaaggtta tcaagaaaat tggacattat 1680
ctcaagatga atatcacggt accagaggat tacatcaacg ggtttattcg ggccaacaat 1740
accttcctct atcagctagt ttttgatccc atcaaaagga aacttattcc tctgaacgcc 1800
tatgaagatg atgttgatcc tgaaacacta agctacgctg ggcaatatgt tgatgattcc 1860
atagctcttc aaatagcact tggaaataaa gatataaata cttttgaaca gatcgatgac 1920
tacaatccag acactgctat gcctgcccat tcaagaagtc atagttggga tgacaaaaca 1980
tgtcaaaagt cagctaatgt tagcagcatt tggcatagga attactctcc cagaccagag 2040
tcgggtactg tttcagatgc cccacaattg aaggaaaatc caagtactgt gggagtggaa 2100
cgagtgatta gtactaaagg gttaaatctc ccaaggaaat catccattgt gaaaagacca 2160
agaagtgcag agctgtcaga agatgacctg ttgagtcagt attctctttc atttacgaag 2220
aagaccaaga aaaatagctc tgaaggcaat aaatcattga gcttttctga agtgtttgtg 2280
cctgacctgg taaatggacc tactaacaaa aagagtgtaa gcactccacc taggacgaga 2340
aataaatttg caacattttt acaaaggaaa aatgaagaaa gtggtgcagt tgtggttcca 2400
gggaccagaa gcaggttttt ttgcagttca gattctactg actgtgtatc aaacaaagtg 2460
agcatccagc ctctggatga aactgctgtc acagataaag agaacaatct gcatgaatca 2520
gagtatggag accaagaagg caagagactg gttgacacag atgtagcacg taattcaagt 2580
gatgacattc cgaataatca tattccaggt gatcatattc cagacaaggc aacagtgttt 2640
acagatgaag agtcctactc ttttgagagc agcaaattta caaggaccat ttcaccaccc 2700
actttgggaa cactaagaag ttgttttagt tggtctggag gtcttggaga tttttcaaga 2760
acgccgagcc cctctccaag cacagcattg cagcagttcc gaagaaagag cgattccccc 2820
acctctttgc ctgagaataa tatgtctgat gtgtcgcagt taaagagcga ggagtccagt 2880
gacgatgagt ctcatccctt acgagaaggg gcatgttctt cacagtccca ggaaagtgga 2940
gaattctcac tgcagagttc aaatgcatca aagctttctc agtgctctag taaggactct 3000
gattcagagg aatctgattg caatattaag ttacttgaca gtcaaagtga ccagacctcc 3060
aagctatgtt tatctcattt ctcaaaaaaa gacacacctc taaggaacaa ggttcctggg 3120
ctatataagt ccagttctgc agactctctt tctacaacca agatcaaacc tctaggacct 3180
gccagagcca gtgggctgag caagaagccg gcaagcatcc agaagagaaa gcatcataat 3240
gccgagaaca agccggggtt acagatcaaa ctcaatgagc tctggaaaaa ctttggattt 3300
aaaaaagatt ctgaaaagct tcctccttgt aagaaacccc tgtccccagt cagagataac 3360
atccaactaa ctccagaagc ggaagaggat atatttaaca aacctgaatg tggccgtgtt 3420
caaagagcaa tattccagtg aggatccact agtccagtgt ggtggaattc tgcagatatc 3480
cagcacagtg gcggccgctc gagtctagag ggcccgttta aacccgctga tcagcctcga 3540
ctgtgccttc tagttgccag ccatctgttg tttgcccctc ccccgtgcct tccttgaccc 3600
tggaaggtgc cactcccact gtcctttcct aataaaatga ggaaattgca tcgcattgtc 3660
tgagtaggtg tcattctatt ctggggggtg gggtggggca ggacagcaag ggggaggatt 3720
gggaagacaa tagcaggcat gctggggatg cggtgggctc tatggcttct gaggcggaaa 3780
gaaccagctg gggctctagg gggtatcccc acgcgccctg tagcggcgca ttaagcgcgg 3840
cgggtgtggt ggttacgcgc agcgtgaccg ctacacttgc cagcgcccta gcgcccgctc 3900
ctttcgcttt cttcccttcc tttctcgcca cgttcgccgg ctttccccgt caagctctaa 3960
atcgggggct ccctttaggg ttccgattta gtgctttacg gcacctcgac cccaaaaaac 4020
ttgattaggg tgatggttca cgtagtgggc catcgccctg atagacggtt tttcgccctt 4080
tgacgttgga gtccacgttc tttaatagtg gactcttgtt ccaaactgga acaacactca 4140
accctatctc ggtctattct tttgatttat aagggatttt gccgatttcg gcctattggt 4200
taaaaaatga gctgatttaa caaaaattta acgcgaatta attctgtgga atgtgtgtca 4260
gttagggtgt ggaaagtccc caggctcccc agcaggcaga agtatgcaaa gcctatcagg 4320
acatagcgtt ggctacccgt gatattgctg aagagcttgg cggcgaatgg gctgaccgct 4380
tcctcgtgct ttacggtatc gccgctcccg attcgcagcg catcgccttc tatcgccttc 4440

-continued ttgacgagtt cttctgagcg ggactctggg gttcgaaatg accgaccaag cgacgcccaa 4500
cctgccatca cgagatttcg attccaccgc cgccttctat gaaaggttgg gcttcggaat 4560
cgttttccgg gacgccggct ggatgatcct ccagcgcggg gatctcatgc tggagttctt 4620
cgcccacccc aacttgttta ttgcagctta taatggttac aaataaagca atagcatcac 4680
aaatttcaca aataaagcat ttttttcact gcattctagt tgtggtttgt ccaaactcat 4740
caatgtatct tatcatgtct gtataccgtc gacctctagc tagagcttgg cgtaatcatg 4800
gtcatagctg tttcctgtgt gaaattgtta tccgctcaca attccacaca acatacgagc 4860
cggaagcata aagtgtaaag cctggggtgc ctaatgagtg agctaactca cattaattgc 4920
gttgcgctca ctgcccgctt tccagtcggg aaacctgtcg tgccagctgc attaatgaat 4980
cggccaacgc gcggggagag gcggtttgcg tattgggcgc tcttccgctt cctcgctcac 5040
tgactcgctg cgctcggtcg ttcggctgcg gcgagcggta tcagctcact caaaggcggt 5100
aatacggtta tccacagaat caggggataa cgcaggaaag aacatgtgag caaaaggcca 5160
gcaaaaggcc aggaaccgta aaaaggccgc gttgctggcg tttttccata ggctccgccc 5220
ccctgacgag catcacaaaa atcgacgctc aagtcagagg tggcgaaacc cgacaggact 5280
ataaagatac caggcgtttc cccctggaag ctccctcgtg cgctctcctg ttccgaccct 5340
gccgcttacc ggatacctgt ccgcctttct cccttcggga agcgtggcgc tttctcatag 5400
ctcacgctgt aggtatctca gttcggtgta ggtcgttcgc tccaagctgg gctgtgtgca 5460
cgaacccccc gttcagcccg accgctgcgc cttatccggt aactatcgtc ttgagtccaa 5520
cccggtaaga cacgacttat cgccactggc agcagccact ggtaacagga ttagcagagc 5580
gaggtatgta ggcggtgcta cagagttctt gaagtggtgg cctaactacg gctacactag 5640
aagaacagta tttggtatct gcgctctgct gaagccagtt accttcggaa aaagagttgg 5700
tagctcttga tccggcaaac aaaccaccgc tggtagcggt ttttttgttt gcaagcagca 5760
gattacgcgc agaaaaaaag gatctcaaga agatcctttg atcttttcta cggggtctga 5820
cgctcagtgg aacgaaaact cacgttaagg gattttggtc atgagattat caaaaaggat 5880
cttcacctag atccttttaa attaaaaatg aagttttaaa tcaatctaaa gtatatatga 5940
gtaaacttgg tctgacagtt accaatgctt aatcagtgag gcacctatct cagcgatctg 6000
tctatttcgt tcatccatag ttgcctgact ccccgtcgtg tagataacta cgatacggga 6060
gggcttacca tctggcccca gtgctgcaat gataccgcga gacccacgct caccggctcc 6120
agatttatca gcaataaacc agccagccgg aagggccgag cgcagaagtg gtcctgcaac 6180
tttatccgcc tccatccagt ctattaattg ttgccgggaa gctagagtaa gtagttcgcc 6240
agttaatagt ttgcgcaacg ttgttgccat tgctacaggc atcgtggtgt cacgctcgtc 6300
gtttggtatg gcttcattca gctccggttc ccaacgatca aggcgagtta catgatcccc 6360
catgttgtgc aaaaaagcgg ttagctcctt cggtcctccg atcgttgtca gaagtaagtt 6420
ggccgcagtg ttatcactca tggttatggc agcactgcat aattctctta ctgtcatgcc 6480
atccgtaaga tgcttttctg tgactggtga gtactcaacc aagtcattct gagaatagtg 6540
tatgcggcga ccgagttgct cttgcccggc gtcaatacgg gataataccg cgccacatag 6600
cagaacttta aaagtgctca tcattggaaa acgttcttcg gggcgaaaac tctcaaggat 6660
cttaccgctg ttgagatcca gttcgatgta acccactcgt gcacccaact gatcttcagc 6720
atcttttact ttcaccagcg tttctgggtg agcaaaaaca ggaaggcaaa atgccgcaaa 6780
aaagggaata agggcgacac ggaaatgttg aatactcata ctcttccttt ttcaatatta 6840
ttgaagcatt tatcagggtt attgtctcat gagcggatac atatttgaat gtatttagaa 6900
aaataaacaa ataggggttc cgcgcacatt tccccgaaaa gtgccacctg acgtc 6955

<210> SEQ ID NO 134
<211> LENGTH: 5036
<212> TYPE: DNA
<213> ORGANISM: Artificial Sequence
<220> FEATURE:
<223> OTHER INFORMATION: pExodus Lambda exonuclease

<400> SEQUENCE: 134
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atgacacccg acattattct ccagcggaca ggtattgacg tgagggccgt ggaacagggg 960
gatgatgctt ggcacaaact gaggctcggc gtgatcaccg catctgaggt gcacaacgtc 1020
attgccaaac cccgctctgg aaagaaatgg cctgacatga agatgagtta cttccatact 1080
ctgctcgccg aggtgtgcac cggagtcgct cccgaagtga acgccaaggc tctggcatgg 1140
ggtaaacagt acgagaatga cgctcgaacc ctcttcgagt tcaccagtgg ggtgaacgtc 1200
acagagtcac caatcatcta ccgggatgaa agcatgcgca ctgcatgctc ccccgacggt 1260
ctgtgttctg atgggaatgg tctggagctc aagtgtcctt tcacctcccg agatttcatg 1320
aagttcaggc tcggcggatt tgaagctatc aagagcgcat acatggccca ggtccagtat 1380
tccatgtggg tgacaagaaa aaacgcttgg tactttgcaa attatgaccc taggatgaag 1440
agagagggcc tgcactacgt ggtcatcgag cgggacgaaa aatatatggc cagcttcgat 1500
gaaatcgtgc cagagtttat tgaaaagatg gatgaggccc tggctgaaat tggcttcgtg 1560
tttggagagc agtggcggct cgagtctaga gggcccgttt aaacccgctg atcagcctcg 1620
actgtgcctt ctagttgcca gccatctgtt gtttgcccct cccccgtgcc ttccttgacc 1680
ctggaaggtg ccactcccac tgtcctttcc taataaaatg aggaaattgc atcgcattgt 1740
ctgagtaggt gtcattctat tctggggggt ggggtggggc aggacagcaa gggggaggat 1800
tgggaagaca atagcaggca tgctggggat gcggtgggct ctatggcttc tgaggcggaa 1860
agaaccagct ggggctctag gggtatcccc cacgcgccct gtagcggcgc attaagcgcg 1920

-continued gcgggtgtgg tggttacgcg cagcgtgacc gctacacttg ccagcgccct agcgcccgct 1980
cctttcgctt tcttcccttc ctttctcgcc acgttcgccg gctttccccg tcaagctcta 2040
aatcgggggc tccctttagg gttccgattt agtgctttac ggcacctcga ccccaaaaaa 2100
cttgattagg gtgatggttc acgtagtggg ccatcgccct gatagacggt ttttcgccct 2160
ttgacgttgg agtccacgtt ctttaatagt ggactcttgt tccaaactgg aacaacactc 2220
aaccctatct cggtctattc ttttgattta taagggattt tgccgatttc ggcctattgg 2280
ttaaaaaatg agctgattta acaaaaattt aacgcgaatt aattctgtgg aatgtgtgtc 2340
agttagggtg tggaaagtcc ccaggctccc cagcaggcag aagtatgcaa agcctatcag 2400
gacatagcgt tggctacccg tgatattgct gaagagcttg gcggcgaatg ggctgaccgc 2460
ttcctcgtgc tttacggtat cgccgctccc gattcgcagc gcatcgcctt ctatcgcctt 2520
cttgacgagt tcttctgagc gggactctgg ggttcgaaat gaccgaccaa gcgacgccca 2580
acctgccatc acgagatttc gattccaccg ccgccttcta tgaaaggttg ggcttcggaa 2640
tcgttttccg ggacgccggc tggatgatcc tccagcgcgg ggatctcatg ctggagttct 2700
tcgcccaccc caacttgttt attgcagctt ataatggtta caaataaagc aatagcatca 2760
caaatttcac aaataaagca tttttttcac tgcattctag ttgtggtttg tccaaactca 2820
tcaatgtatc ttatcatgtc tgtataccgt cgacctctag ctagagcttg gcgtaatcat 2880
ggtcatagct gtttcctgtg tgaaattgtt atccgctcac aattccacac aacatacgag 2940
ccggaagcat aaagtgtaaa gcctggggtg cctaatgagt gagctaactc acattaattg 3000
cgttgcgctc actgcccgct ttccagtcgg gaaacctgtc gtgccagctg cattaatgaa 3060
tcggccaacg cgcggggaga ggcggtttgc gtattgggcg ctcttccgct tcctcgctca 3120
ctgactcgct gcgctcggtc gttcggctgc ggcgagcggt atcagctcac tcaaaggcgg 3180
taatacggtt atccacagaa tcaggggata acgcaggaaa gaacatgtga gcaaaaggcc 3240
agcaaaaggc caggaaccgt aaaaaggccg cgttgctggc gtttttccat aggctccgcc 3300
cccctgacga gcatcacaaa aatcgacgct caagtcagag gtggcgaaac ccgacaggac 3360
tataaagata ccaggcgttt ccccctggaa gctccctcgt gcgctctcct gttccgaccc 3420
tgccgcttac cggatacctg tccgcctttc tcccttcggg aagcgtggcg ctttctcata 3480
gctcacgctg taggtatctc agttcggtgt aggtcgttcg ctccaagctg ggctgtgtgc 3540
acgaaccccc cgttcagccc gaccgctgcg ccttatccgg taactatcgt cttgagtcca 3600
acccggtaag acacgactta tcgccactgg cagcagccac tggtaacagg attagcagag 3660
cgaggtatgt aggcggtgct acagagttct tgaagtggtg gcctaactac ggctacacta 3720
gaagaacagt atttggtatc tgcgctctgc tgaagccagt taccttcgga aaaagagttg 3780
gtagctcttg atccggcaaa caaaccaccg ctggtagcgg tttttttgtt tgcaagcagc 3840
agattacgcg cagaaaaaaa ggatctcaag aagatccttt gatcttttct acggggtctg 3900
acgctcagtg gaacgaaaac tcacgttaag ggattttggt catgagatta tcaaaaagga 3960
tcttcaccta gatcctttta aattaaaaat gaagttttaa atcaatctaa agtatatatg 4020
agtaaacttg gtctgacagt taccaatgct taatcagtga ggcacctatc tcagcgatct 4080
gtctatttcg ttcatccata gttgcctgac tccccgtcgt gtagataact acgatacggg 4140
agggcttacc atctggcccc agtgctgcaa tgataccgcg agacccacgc tcaccggctc 4200
cagatttatc agcaataaac cagccagccg gaagggccga gcgcagaagt ggtcctgcaa 4260
ctttatccgc ctccatccag tctattaatt gttgccggga agctagagta agtagttcgc 4320

```
cagttaatag tttgcgcaac gttgttgcca ttgctacagg catcgtggtg tcacgctcgt   4380

cgtttggtat ggcttcattc agctccggtt cccaacgatc aaggcgagtt acatgatccc   4440

ccatgttgtg caaaaaagcg gttagctcct tcggtcctcc gatcgttgtc agaagtaagt   4500

tggccgcagt gttatcactc atggttatgg cagcactgca taattctctt actgtcatgc   4560

catccgtaag atgcttttct gtgactggtg agtactcaac caagtcattc tgagaatagt   4620

gtatgcggcg accgagttgc tcttgcccgg cgtcaatacg ggataatacc gcgccacata   4680

gcagaacttt aaaagtgctc atcattggaa aacgttcttc ggggcgaaaa ctctcaagga   4740

tcttaccgct gttgagatcc agttcgatgt aacccactcg tgcacccaac tgatcttcag   4800

catcttttac tttcaccagc gtttctgggt gagcaaaaac aggaaggcaa aatgccgcaa   4860

aaaagggaat aagggcgaca cggaaatgtt gaatactcat actcttcctt tttcaatatt   4920

attgaagcat ttatcagggt tattgtctca tgagcggata catatttgaa tgtatttaga   4980

aaaataaaca aataggggtt ccgcgcacat ttccccgaaa agtgccacct gacgtc       5036
```

<210> SEQ ID NO 135
<211> LENGTH: 5816
<212> TYPE: DNA
<213> ORGANISM: Artificial Sequence
<220> FEATURE:
<223> OTHER INFORMATION: pExodus Sox

<400> SEQUENCE: 135

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

atggaagcaa cccctacacc cgccgacctg tttagcgaag attacctcgt ggataccctc    960

gacggactga ttgtggatga ccagcaggct gtgctggcat ctctcagttt ctcaaagttt   1020

ctgaaacacg ccaaggtgcg agattggtgc gcacaggcca agatccagcc aagcatgccc   1080

gccctcagga tggcttacaa ttatttcctg ttttccaaag tgggcgagtt cattggatct   1140

gaagacgtct gcaacttctt tgtggataga gtctttggag gagtgcggct gctcgacgtg   1200

gcctctgtct acgccgcttg tagtcagatg aatgctcatc agaggcacca tatctgctgt   1260

ctggtggaga gagcaacaag ctcccagtcc ctcaacccag tctgggacgc actgcgagat   1320
```

```
gggatcattt ctagttcaaa attccactgg gccgtgaagc agcagaatac aagcaagaaa   1380
atcttttccc cctggcctat tactaacaat catttcgtgg caggacccct cgcctttgga   1440
ctgcgatgcg aggaagtggt caagacactg ctcgctactc tgctccaccc cgacgaggca   1500
aactgtctgg attacggctt catgcagagt cctcagaatg ggatcttcgg tgtgtccctg   1560
gactttgcag ccaacgtcaa aactgatacc gagggacggc tgcagttcga ccccaactgc   1620
aaggtgtacg aaatcaaatg tcgcttcaag tatacttttg ctaaaatgga gtgcgatcct   1680
atctacgctg catatcagag gctgtatgaa gccccaggaa aactggctct caaggacttc   1740
ttttacagca tctccaaacc agccgtggag tatgtcggcc tgggaaagct cccctctgaa   1800
agtgactacc tggtggccta cgaccaggag tgggaagcct gcccccggaa gaaacgcaag   1860
ctgacccctc tccacaacct gatcagagag tgtattctgc ataatagtac cacagaatca   1920
gacgtgtacg tcctgaccga ccctcaggat acacgcgggc agatcagcat caaggctcga   1980
ttcaaggcaa acctgtttgt gaatgtcaga cacagctact tctatcaggt gctgctccag   2040
agctccatcg tcgaggaata cattgggctc gattcaggta tcccacggct gggtagcccc   2100
aaatactata ttgctaccgg gttctttagg aagagaggtt atcaggaccc tgtgaactgt   2160
acaatcggag gtgacgccct ggacccccac gtcgagatcc caactctgct cattgtgacc   2220
cccgtctact tccccagggg cgctaagcac aggctgctcc atcaggccgc taatttttgg   2280
tcacggagcg caaaagatac cttcccatac attaagtggg acttttccta tctgtctgcc   2340
aacgtgcctc attctccact cgagtctaga gggcccgttt aaacccgctg atcagcctcg   2400
actgtgcctt ctagttgcca gccatctgtt gtttgcccct cccccgtgcc ttccttgacc   2460
ctggaaggtg ccactcccac tgtcctttcc taataaaatg aggaaattgc atcgcattgt   2520
ctgagtaggt gtcattctat tctggggggt ggggtggggc aggacagcaa gggggaggat   2580
tgggaagaca atagcaggca tgctggggat gcggtgggct ctatggcttc tgaggcggaa   2640
agaaccagct ggggctctag ggggtatccc cacgcgccct gtagcggcgc attaagcgcg   2700
gcgggtgtgg tggttacgcg cagcgtgacc gctacacttg ccagcgccct agcgcccgct   2760
cctttcgctt tcttcccttc ctttctcgcc acgttcgccg gctttccccg tcaagctcta   2820
aatcgggggc tccctttagg gttccgattt agtgctttac ggcacctcga ccccaaaaaa   2880
cttgattagg gtgatggttc acgtagtggg ccatcgccct gatagacggt ttttcgccct   2940
ttgacgttgg agtccacgtt ctttaatagt ggactcttgt tccaaactgg aacaacactc   3000
aaccctatct cggtctattc ttttgattta taagggattt tgccgatttc ggcctattgg   3060
ttaaaaaatg agctgattta acaaaaattt aacgcgaatt aattctgtgg aatgtgtgtc   3120
agttagggtg tggaaagtcc ccaggctccc cagcaggcag aagtatgcaa agcctatcag   3180
gacatagcgt tggctacccg tgatattgct gaagagcttg gcggcgaatg ggctgaccgc   3240
ttcctcgtgc tttacggtat cgccgctccc gattcgcagc gcatcgcctt ctatcgcctt   3300
cttgacgagt tcttctgagc gggactctgg ggttcgaaat gaccgaccaa gcgacgccca   3360
acctgccatc acgagatttc gattccaccg ccgccttcta tgaaaggttg ggcttcggaa   3420
tcgttttccg ggacgccggc tggatgatcc tccagcgcgg ggatctcatg ctggagttct   3480
tcgcccaccc caacttgttt attgcagctt ataatggtta caaataaagc aatagcatca   3540
caaatttcac aaataaagca tttttttcac tgcattctag ttgtggtttg tccaaactca   3600
tcaatgtatc ttatcatgtc tgtataccgt cgacctctag ctagagcttg gcgtaatcat   3660
ggtcatagct gtttcctgtg tgaaattgtt atccgctcac aattccacac aacatacgag   3720
```

-continued

```
ccggaagcat aaagtgtaaa gcctggggtg cctaatgagt gagctaactc acattaattg   3780
cgttgcgctc actgcccgct ttccagtcgg gaaacctgtc gtgccagctg cattaatgaa   3840
tcggccaacg cgcggggaga ggcggtttgc gtattgggcg ctcttccgct tcctcgctca   3900
ctgactcgct gcgctcggtc gttcggctgc ggcgagcggt atcagctcac tcaaaggcgg   3960
taatacggtt atccacagaa tcaggggata acgcaggaaa gaacatgtga gcaaaaggcc   4020
agcaaaaggc caggaaccgt aaaaaggccg cgttgctggc gtttttccat aggctccgcc   4080
cccctgacga gcatcacaaa aatcgacgct caagtcagag gtggcgaaac ccgacaggac   4140
tataaagata ccaggcgttt ccccctggaa gctccctcgt gcgctctcct gttccgaccc   4200
tgccgcttac cggatacctg tccgcctttc tcccttcggg aagcgtggcg ctttctcata   4260
gctcacgctg taggtatctc agttcggtgt aggtcgttcg ctccaagctg ggctgtgtgc   4320
acgaaccccc cgttcagccc gaccgctgcg ccttatccgg taactatcgt cttgagtcca   4380
acccggtaag acacgactta tcgccactgg cagcagccac tggtaacagg attagcagag   4440
cgaggtatgt aggcggtgct acagagttct tgaagtggtg gcctaactac ggctacacta   4500
gaagaacagt atttggtatc tgcgctctgc tgaagccagt taccttcgga aaaagagttg   4560
gtagctcttg atccggcaaa caaaccaccg ctggtagcgg tttttttgtt tgcaagcagc   4620
agattacgcg cagaaaaaaa ggatctcaag aagatccttt gatcttttct acggggtctg   4680
acgctcagtg gaacgaaaac tcacgttaag ggattttggt catgagatta tcaaaaagga   4740
tcttcaccta gatcctttta aattaaaaat gaagttttaa atcaatctaa agtatatatg   4800
agtaaacttg gtctgacagt taccaatgct taatcagtga ggcacctatc tcagcgatct   4860
gtctatttcg ttcatccata gttgcctgac tccccgtcgt gtagataact acgatacggg   4920
agggcttacc atctggcccc agtgctgcaa tgataccgcg agacccacgc tcaccggctc   4980
cagatttatc agcaataaac cagccagccg gaagggccga gcgcagaagt ggtcctgcaa   5040
ctttatccgc ctccatccag tctattaatt gttgccggga agctagagta agtagttcgc   5100
cagttaatag tttgcgcaac gttgttgcca ttgctacagg catcgtggtg tcacgctcgt   5160
cgtttggtat ggcttcattc agctccggtt cccaacgatc aaggcgagtt acatgatccc   5220
ccatgttgtg caaaaaagcg gttagctcct tcggtcctcc gatcgttgtc agaagtaagt   5280
tggccgcagt gttatcactc atggttatgg cagcactgca taattctctt actgtcatgc   5340
catccgtaag atgcttttct gtgactggtg agtactcaac caagtcattc tgagaatagt   5400
gtatgcggcg accgagttgc tcttgcccgg cgtcaatacg ggataatacc gcgccacata   5460
gcagaacttt aaaagtgctc atcattggaa aacgttcttc ggggcgaaaa ctctcaagga   5520
tcttaccgct gttgagatcc agttcgatgt aacccactcg tgcacccaac tgatcttcag   5580
catcttttac tttcaccagc gtttctgggt gagcaaaaac aggaaggcaa aatgccgcaa   5640
aaaagggaat aagggcgaca cggaaatgtt gaatactcat actcttcctt tttcaatatt   5700
attgaagcat ttatcagggt tattgtctca tgagcggata catatttgaa tgtatttaga   5760
aaaataaaca aataggggtt ccgcgcacat ttccccgaaa agtgccacct gacgtc       5816
```

<210> SEQ ID NO 136
<211> LENGTH: 6236
<212> TYPE: DNA
<213> ORGANISM: Artificial Sequence
<220> FEATURE:
<223> OTHER INFORMATION: pExodus UL12

<400> SEQUENCE: 136

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
atggaaagca ctgggggtcc tgcctgtcct cctgggcgaa ccgtgactaa aaggtcctgg    960
gctctggctg aagatacacc aagggggcct gacagccccc ctaagaggcc aagacccaac   1020
tccctgccac tcaccacaac tttcaggcca ctgccaccac ctccacagac cacaagtgcc   1080
gtcgatccaa gctcccactc acccgtgaat ccccccaggg accagcatgc cactgacacc   1140
gctgatgaga aacctcgcgc cgcttcacca gcactgtctg atgccagtgg accacccacc   1200
cccgacattc ctctgagccc aggcggaaca cacgcaagag acccagatgc cgaccccgat   1260
agccctgacc tggattccat gtggagtgct tcagtgattc ccaacgcact ccctagccac   1320
atcctggccg agaccttcga acgacatctg aggggactgc tcagaggggt gcgggcaccc   1380
ctcgctatcg gacctctgtg ggcccggctg gattacctct gctccctggc cgtggtgctg   1440
gaggaagctg gaatggtgga ccgaggactg ggacgccacc tctggcgact gaccaggaga   1500
gcacctccag cagccgctga tgcagtggca cctcggccac tgatgggttt ctatgaggca   1560
gccactcaga atcaggcaga ctgccagctg tgggcactgc tccgacgagg actcactacc   1620
gcctctaccc tgcgatgggg accacagggt ccctgttttt ctccccagtg gctcaagcat   1680
aacgctagtc tgcggcctga cgtgcagtct agtgcagtca tgttcggacg agtgaatgag   1740
ccaacagcac ggagcctgct ctttcgctac tgcgtgggtc gagctgacga tgggggcgag   1800
gctggcgcag atactcgaag gttcatcttt cacgaaccta gtgacctggc cgaggaaaac   1860
gtccacacat gcggggtgct gatggatggc catactggaa tggtcggggc ttctctcgat   1920
attctggtgt gtccaaggga catccacggc tacctggcac ccgtgcctaa aactcccctg   1980
gctttctacg aggtcaagtg tagagcaaaa tatgcctttg accctatgga cccctctgac   2040
cccacagcca gtgcttacga ggacctgatg gcccacagat cccctgaggc cttcagggcc   2100
ttcatcagat caattccaaa gcccagcgtc aggtatttcg ctccaggtag agtgcctggc   2160
ccagaggaag ctctggtcac ccaggatcag gcatggtccg aggcacacgc ctctggtgaa   2220
aaaagacgat gcagcgctgc agaccgagca ctcgtggagc tgaacagtgg cgtggtctca   2280
gaagtgctgc tctttggagc tcctgatctg ggcgcccata caatctcacc agtgagctgg   2340
```

-continued

```
tcaagcggcg acctggtccg ccgagagcca gtgttcgcca accctcggca cccaaatttt   2400
aagcagattc tcgtgcaggg atacgtcctg gattcccatt tccccgactg tccccctcac   2460
cctcatctgg tgaccttcat cggacggcac cgcacttctg ccgaggaagg ggtgaccttc   2520
aggctggagg atggagctgg tgcactgggt gcagctggac catccaaggc ttctattctc   2580
ccaaatcagg ctgtgcccat cgcactgatc attacccctg tcaggatcga cccagaaatc   2640
tacaaagcaa tccagcgctc ctctcgactg gcctttgacg atacactcgc cgagctgtgg   2700
gccagcagga gcccaggccc tggaccagca gccgctgaaa caactagttc aagccctacc   2760
acaggaagga gcagcaggct cgagtctaga gggcccgttt aaacccgctg atcagcctcg   2820
actgtgcctt ctagttgcca gccatctgtt gtttgcccct cccccgtgcc ttccttgacc   2880
ctggaaggtg ccactcccac tgtcctttcc taataaaatg aggaaattgc atcgcattgt   2940
ctgagtaggt gtcattctat tctggggggt ggggtggggc aggacagcaa gggggaggat   3000
tgggaagaca atagcaggca tgctggggat gcggtgggct ctatggcttc tgaggcggaa   3060
agaaccagct ggggctctag ggggtatccc cacgcgccct gtagcggcgc attaagcgcg   3120
gcgggtgtgg tggttacgcg cagcgtgacc gctacacttg ccagcgccct agcgcccgct   3180
cctttcgctt tcttcccttc ctttctcgcc acgttcgccg gctttccccg tcaagctcta   3240
aatcgggggc tccctttagg gttccgattt agtgctttac ggcacctcga ccccaaaaaa   3300
cttgattagg gtgatggttc acgtagtggg ccatcgccct gatagacggt ttttcgccct   3360
ttgacgttgg agtccacgtt ctttaatagt ggactcttgt tccaaactgg aacaacactc   3420
aaccctatct cggtctattc ttttgattta taagggattt tgccgatttc ggcctattgg   3480
ttaaaaaatg agctgattta acaaaaattt aacgcgaatt aattctgtgg aatgtgtgtc   3540
agttagggtg tggaaagtcc ccaggctccc cagcaggcag aagtatgcaa agcctatcag   3600
gacatagcgt tggctacccg tgatattgct gaagagcttg gcggcgaatg ggctgaccgc   3660
ttcctcgtgc tttacggtat cgccgctccc gattcgcagc gcatcgcctt ctatcgcctt   3720
cttgacgagt tcttctgagc gggactctgg ggttcgaaat gaccgaccaa gcgacgccca   3780
acctgccatc acgagatttc gattccaccg ccgccttcta tgaaaggttg ggcttcggaa   3840
tcgttttccg ggacgccggc tggatgatcc tccagcgcgg ggatctcatg ctggagttct   3900
tcgcccaccc caacttgttt attgcagctt ataatggtta caaataaagc aatagcatca   3960
caaatttcac aaataaagca tttttttcac tgcattctag ttgtggtttg tccaaactca   4020
tcaatgtatc ttatcatgtc tgtataccgt cgacctctag ctagagcttg gcgtaatcat   4080
ggtcatagct gtttcctgtg tgaaattgtt atccgctcac aattccacac aacatacgag   4140
ccggaagcat aaagtgtaaa gcctggggtg cctaatgagt gagctaactc acattaattg   4200
cgttgcgctc actgcccgct ttccagtcgg gaaacctgtc gtgccagctg cattaatgaa   4260
tcggccaacg cgcggggaga ggcggtttgc gtattgggcg ctcttccgct tcctcgctca   4320
ctgactcgct gcgctcggtc gttcggctgc ggcgagcggt atcagctcac tcaaaggcgg   4380
taatacggtt atccacagaa tcaggggata acgcaggaaa gaacatgtga gcaaaaggcc   4440
agcaaaaggc caggaaccgt aaaaaggccg cgttgctggc gtttttccat aggctccgcc   4500
cccctgacga gcatcacaaa aatcgacgct caagtcagag gtggcgaaac ccgacaggac   4560
tataaagata ccaggcgttt ccccctggaa gctccctcgt gcgctctcct gttccgaccc   4620
tgccgcttac cggatacctg tccgcctttc tcccttcggg aagcgtggcg ctttctcata   4680
```

```
gctcacgctg taggtatctc agttcggtgt aggtcgttcg ctccaagctg ggctgtgtgc   4740

acgaaccccc cgttcagccc gaccgctgcg ccttatccgg taactatcgt cttgagtcca   4800

acccggtaag acacgactta tcgccactgg cagcagccac tggtaacagg attagcagag   4860

cgaggtatgt aggcggtgct acagagttct tgaagtggtg gcctaactac ggctacacta   4920

gaagaacagt atttggtatc tgcgctctgc tgaagccagt taccttcgga aaaagagttg   4980

gtagctcttg atccggcaaa caaaccaccg ctggtagcgg tttttttgtt tgcaagcagc   5040

agattacgcg cagaaaaaaa ggatctcaag aagatccttt gatcttttct acggggtctg   5100

acgctcagtg gaacgaaaac tcacgttaag ggattttggt catgagatta tcaaaaagga   5160

tcttcaccta gatcctttta aattaaaaat gaagttttaa atcaatctaa agtatatatg   5220

agtaaacttg gtctgacagt taccaatgct taatcagtga ggcacctatc tcagcgatct   5280

gtctatttcg ttcatccata gttgcctgac tccccgtcgt gtagataact acgatacggg   5340

agggcttacc atctggcccc agtgctgcaa tgataccgcg agacccacgc tcaccggctc   5400

cagatttatc agcaataaac cagccagccg gaagggccga gcgcagaagt ggtcctgcaa   5460

ctttatccgc ctccatccag tctattaatt gttgccggga agctagagta agtagttcgc   5520

cagttaatag tttgcgcaac gttgttgcca ttgctacagg catcgtggtg tcacgctcgt   5580

cgtttggtat ggcttcattc agctccggtt cccaacgatc aaggcgagtt acatgatccc   5640

ccatgttgtg caaaaaagcg gttagctcct tcggtcctcc gatcgttgtc agaagtaagt   5700

tggccgcagt gttatcactc atggttatgg cagcactgca taattctctt actgtcatgc   5760

catccgtaag atgcttttct gtgactggtg agtactcaac caagtcattc tgagaatagt   5820

gtatgcggcg accgagttgc tcttgcccgg cgtcaatacg ggataatacc gcgccacata   5880

gcagaacttt aaaagtgctc atcattggaa aacgttcttc ggggcgaaaa ctctcaagga   5940

tcttaccgct gttgagatcc agttcgatgt aacccactcg tgcacccaac tgatcttcag   6000

catcttttac tttcaccagc gtttctgggt gagcaaaaac aggaaggcaa aatgccgcaa   6060

aaaagggaat aagggcgaca cggaaatgtt gaatactcat actcttcctt tttcaatatt   6120

attgaagcat ttatcagggt tattgtctca tgagcggata catatttgaa tgtatttaga   6180

aaaataaaca aataggggtt ccgcgcacat ttccccgaaa agtgccacct gacgtc       6236
```

<210> SEQ ID NO 137
<211> LENGTH: 5954
<212> TYPE: DNA
<213> ORGANISM: Artificial Sequence
<220> FEATURE:
<223> OTHER INFORMATION: pExodus Apollo

<400> SEQUENCE: 137

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540
```

-continued atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atgaacggcg tgctgattcc tcacactcct attgctgtgg acttctggtc tctccggcga 960
gctgggactg cccgactctt ctttctgagt cacatgcatt cagatcacac tgtgggactg 1020
agctccacct gggcccgacc actgtactgc tcccccatca cagctcatct gctccacagg 1080
catctgcagg tgagcaagca gtggattcag gccctggagg tcggcgaatc ccacgtcctg 1140
cctctcgatg agatcggaca ggaaaccatg acagtgactc tgctcgacgc taatcattgc 1200
ccagggtccg tcatgttcct gtttgagggc tacttcggaa caattctgta tactggcgat 1260
tttcggtaca ctccatctat gctgaaggaa cccgccctga ccctcggaaa acagatccac 1320
acactgtacc tcgacaacac taattgtaac cctgctctgg tgctcccatc caggcaggag 1380
gccgctcacc agatcgtcca gctgattaga aagcacccac agcataacat caaaattggg 1440
ctgtatagtc tcggcaagga gtcactgctc gaacagctgg ccctggagtt ccagacatgg 1500
gtggtcctgt ctcccaggag actggaactc gtgcagctgc tcgggctggc tgatgtgttt 1560
actgtcgagg aaaaggctgg tagaatccac gcagtggacc acatggagat ttgtcacagc 1620
aatatgctga gatggaacca gacccatcct acaatcgcca ttctgccaac tagccggaag 1680
atccactcta gtcatcccga tatccacgtg attccttatt ctgaccattc aagctacagt 1740
gagctgcgag cattcgtggc agccctcaag ccatgccagg tggtccctat cgtcagccgg 1800
cgcccttgtg gaggatttca ggattcactg agcccacgca tctcagtgcc actgattccc 1860
gacagcgtcc agcagtacat gtcctctagt tcacgaaagc ccagcctgct ctggctgctg 1920
gagcgaaggc tgaaacgccc ccgaacccag ggagtggtct tcgaaagccc tgaggaatcc 1980
gccgatcagt ctcaggctga tagggactcc aagaaagcaa agaaagagaa gctgtctccc 2040
tggcctgccg atctcgaaaa acagcccagc caccatcctc tgaggatcaa gaaacagctg 2100
ttcccagacc tctattctaa ggagtggaac aaggctgtgc ccttttgcga aagtcagaag 2160
agagtcacta tgctgaccgc acctctcggc ttcagcgtgc acctgcggtc caccgacgag 2220
gagttcatca gtcagaaaac acgcgaggaa attggcctgg gatcacctct cgtgccaatg 2280
ggcgacgatg acgggggtcc agaggcaacc ggaaatcaga gcgcctggat ggggcacggt 2340
tccccactgt ctcatagctc caaggggacc cccctgctcg ctacagagtt caggggtctg 2400
gcactcaaat atctgctcac acccgtgaac ttctttcagg ccggctactc tagtagacgg 2460
tttgaccagc aggtcgagaa gtatcacaaa ccttgtctcg agtctagagg gcccgtttaa 2520
acccgctgat cagcctcgac tgtgccttct agttgccagc catctgttgt ttgcccctcc 2580
cccgtgcctt ccttgaccct ggaaggtgcc actcccactg tcctttccta ataaaatgag 2640
gaaattgcat cgcattgtct gagtaggtgt cattctattc tggggggtgg ggtggggcag 2700
gacagcaagg gggaggattg ggaagacaat agcaggcatg ctggggatgc ggtgggctct 2760
atggcttctg aggcggaaag aaccagctgg ggctctaggg ggtatcccca cgcgccctgt 2820
agcggcgcat taagcgcggc gggtgtggtg gttacgcgca gcgtgaccgc tacacttgcc 2880

-continued agcgccctag cgcccgctcc tttcgctttc ttcccttcct ttctcgccac gttcgccggc 2940
tttccccgtc aagctctaaa tcgggggctc cctttagggt tccgatttag tgctttacgg 3000
cacctcgacc ccaaaaaact tgattagggt gatggttcac gtagtgggcc atcgccctga 3060
tagacggttt ttcgcccttt gacgttggag tccacgttct ttaatagtgg actcttgttc 3120
caaactggaa caacactcaa ccctatctcg gtctattctt ttgatttata agggattttg 3180
ccgatttcgg cctattggtt aaaaaatgag ctgatttaac aaaaatttaa cgcgaattaa 3240
ttctgtggaa tgtgtgtcag ttagggtgtg gaaagtcccc aggctcccca gcaggcagaa 3300
gtatgcaaag cctatcagga catagcgttg gctacccgtg atattgctga agagcttggc 3360
ggcgaatggg ctgaccgctt cctcgtgctt tacggtatcg ccgctcccga ttcgcagcgc 3420
atcgccttct atcgccttct tgacgagttc ttctgagcgg gactctgggg ttcgaaatga 3480
ccgaccaagc gacgcccaac ctgccatcac gagatttcga ttccaccgcc gccttctatg 3540
aaaggttggg cttcggaatc gttttccggg acgccggctg gatgatcctc cagcgcgggg 3600
atctcatgct ggagttcttc gcccacccca acttgtttat tgcagcttat aatggttaca 3660
aataaagcaa tagcatcaca aatttcacaa ataaagcatt tttttcactg cattctagtt 3720
gtggtttgtc caaactcatc aatgtatctt atcatgtctg tataccgtcg acctctagct 3780
agagcttggc gtaatcatgg tcatagctgt ttcctgtgtg aaattgttat ccgctcacaa 3840
ttccacacaa catacgagcc ggaagcataa agtgtaaagc ctggggtgcc taatgagtga 3900
gctaactcac attaattgcg ttgcgctcac tgcccgcttt ccagtcggga aacctgtcgt 3960
gccagctgca ttaatgaatc ggccaacgcg cggggagagg cggtttgcgt attgggcgct 4020
cttccgcttc ctcgctcact gactcgctgc gctcggtcgt tcggctgcgg cgagcggtat 4080
cagctcactc aaaggcggta atacggttat ccacagaatc aggggataac gcaggaaaga 4140
acatgtgagc aaaaggccag caaaaggcca ggaaccgtaa aaaggccgcg ttgctggcgt 4200
ttttccatag gctccgcccc cctgacgagc atcacaaaaa tcgacgctca agtcagaggt 4260
ggcgaaaccc gacaggacta taaagatacc aggcgtttcc ccctggaagc tccctcgtgc 4320
gctctcctgt tccgaccctg ccgcttaccg gatacctgtc cgcctttctc ccttcgggaa 4380
gcgtggcgct ttctcatagc tcacgctgta ggtatctcag ttcggtgtag gtcgttcgct 4440
ccaagctggg ctgtgtgcac gaaccccccg ttcagcccga ccgctgcgcc ttatccggta 4500
actatcgtct tgagtccaac ccggtaagac acgacttatc gccactggca gcagccactg 4560
gtaacaggat tagcagagcg aggtatgtag gcggtgctac agagttcttg aagtggtggc 4620
ctaactacgg ctacactaga agaacagtat ttggtatctg cgctctgctg aagccagtta 4680
ccttcggaaa aagagttggt agctcttgat ccggcaaaca aaccaccgct ggtagcggtt 4740
tttttgtttg caagcagcag attacgcgca gaaaaaaagg atctcaagaa gatcctttga 4800
tcttttctac ggggtctgac gctcagtgga acgaaaactc acgttaaggg attttggtca 4860
tgagattatc aaaaaggatc ttcacctaga tccttttaaa ttaaaaatga agttttaaat 4920
caatctaaag tatatatgag taaacttggt ctgacagtta ccaatgctta atcagtgagg 4980
cacctatctc agcgatctgt ctatttcgtt catccatagt tgcctgactc cccgtcgtgt 5040
agataactac gatacgggag ggcttaccat ctggccccag tgctgcaatg ataccgcgag 5100
acccacgctc accggctcca gatttatcag caataaacca gccagccgga agggccgagc 5160
gcagaagtgg tcctgcaact ttatccgcct ccatccagtc tattaattgt tgccgggaag 5220
ctagagtaag tagttcgcca gttaatagtt tgcgcaacgt tgttgccatt gctacaggca 5280

```
tcgtggtgtc acgctcgtcg tttggtatgg cttcattcag ctccggttcc caacgatcaa   5340

ggcgagttac atgatccccc atgttgtgca aaaaagcggt tagctccttc ggtcctccga   5400

tcgttgtcag aagtaagttg gccgcagtgt tatcactcat ggttatggca gcactgcata   5460

attctcttac tgtcatgcca tccgtaagat gcttttctgt gactggtgag tactcaacca   5520

agtcattctg agaatagtgt atgcggcgac cgagttgctc ttgcccggcg tcaatacggg   5580

ataataccgc gccacatagc agaactttaa aagtgctcat cattggaaaa cgttcttcgg   5640

ggcgaaaact ctcaaggatc ttaccgctgt tgagatccag ttcgatgtaa cccactcgtg   5700

cacccaactg atcttcagca tcttttactt tcaccagcgt ttctgggtga gcaaaaacag   5760

gaaggcaaaa tgccgcaaaa aagggaataa gggcgacacg gaaatgttga atactcatac   5820

tcttcctttt tcaatattat tgaagcattt atcagggtta ttgtctcatg agcggataca   5880

tatttgaatg tatttagaaa aataaacaaa taggggttcc gcgcacattt ccccgaaaag   5940

tgccacctga cgtc                                                     5954
```

<210> SEQ ID NO 138
<211> LENGTH: 5498
<212> TYPE: DNA
<213> ORGANISM: Artificial Sequence
<220> FEATURE:
<223> OTHER INFORMATION: pExodus FenI

<400> SEQUENCE: 138

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

atgggcatcc aggggctcgc aaaactcatc gcagacgtgg ctccttccgc aattagagag    960

aacgacatca agtcctattt cggcagaaag gtggctatcg acgcatctat gagtatctac   1020

cagttcctga ttgccgtgag gcagggcgga gatgtcctcc agaacgagga aggcgagacc   1080

acaagccacc tgatgggaat gttctacaga acaatccgga tgatggagaa tggcattaag   1140

ccagtgtatg tctttgacgg gaaaccccct cagctgaagt caggcgagct cgccaaaaga   1200

agcgaaagga gagccgaagc tgagaagcag ctgcagcagg cacaggcagc tggagccgaa   1260

caggaggtgg aaaaattcac aaagcggctg gtgaaagtca ctaagcagca caacgacgag   1320
```

-continued

```
tgcaagcatc tgctcagcct gatgggaatc ccctacctcg atgctccttc cgaggcagaa   1380
gcctcttgcg cagccctggt gaaagcaggg aaggtctatg ctgcagccac cgaggacatg   1440
gattgtctga catttggttc ccctgtgctg atgcgacacc tcaccgcctc tgaggctaag   1500
aaactgccaa tccaggagtt ccatctgtcc cgcattctcc aggagctggg gctcaatcag   1560
gaacagtttg tggacctgtg catcctgctc ggtagtgatt actgtgagtc aatcaggggg   1620
attggtccca agagagctgt ggacctgatt cagaaacata agtctatcga ggaaattgtg   1680
aggaggctgg accccaacaa atatccagtc cccgagaatt ggctccacaa ggaagcccat   1740
cagctgttcc tggagccaga agtgctggac cccgagagcg tcgaactcaa gtggtccgag   1800
cccaacgagg aagagctgat caaattcatg tgtggcgaga agcagttttc tgaagagcga   1860
attaggagtg gagtgaaacg cctgtcaaag agccgacagg ggagtactca gggtcggctg   1920
gacgatttct ttaaggtcac cggcagcctc agctccgcta aacgcaagga gcctgaacca   1980
aaaggaagca ctaagaaaaa ggccaagacc ggcgctgccg gcaagttcaa gagaggaaag   2040
ctcgagtcta gagggcccgt ttaaacccgc tgatcagcct cgactgtgcc ttctagttgc   2100
cagccatctg ttgtttgccc ctcccccgtg ccttccttga ccctggaagg tgccactccc   2160
actgtccttt cctaataaaa tgaggaaatt gcatcgcatt gtctgagtag gtgtcattct   2220
attctggggg gtggggtggg gcaggacagc aagggggagg attgggaaga caatagcagg   2280
catgctgggg atgcggtggg ctctatggct tctgaggcgg aaagaaccag ctggggctct   2340
agggggtatc cccacgcgcc ctgtagcggc gcattaagcg cggcgggtgt ggtggttacg   2400
cgcagcgtga ccgctacact tgccagcgcc ctagcgcccg ctcctttcgc tttcttccct   2460
tcctttctcg ccacgttcgc cggctttccc cgtcaagctc taaatcgggg gctcccttta   2520
gggttccgat ttagtgcttt acggcacctc gaccccaaaa aacttgatta gggtgatggt   2580
tcacgtagtg ggccatcgcc ctgatagacg gtttttcgcc ctttgacgtt ggagtccacg   2640
ttctttaata gtggactctt gttccaaact ggaacaacac tcaaccctat ctcggtctat   2700
tcttttgatt tataagggat tttgccgatt tcggcctatt ggttaaaaaa tgagctgatt   2760
taacaaaaat ttaacgcgaa ttaattctgt ggaatgtgtg tcagttaggg tgtggaaagt   2820
ccccaggctc cccagcaggc agaagtatgc aaagcctatc aggacatagc gttggctacc   2880
cgtgatattg ctgaagagct tggcggcgaa tgggctgacc gcttcctcgt gctttacggt   2940
atcgccgctc ccgattcgca gcgcatcgcc ttctatcgcc ttcttgacga gttcttctga   3000
gcgggactct ggggttcgaa atgaccgacc aagcgacgcc caacctgcca tcacgagatt   3060
tcgattccac cgccgccttc tatgaaaggt tgggcttcgg aatcgttttc cgggacgccg   3120
gctggatgat cctccagcgc ggggatctca tgctggagtt cttcgcccac cccaacttgt   3180
ttattgcagc ttataatggt tacaaataaa gcaatagcat cacaaatttc acaaataaag   3240
catttttttc actgcattct agttgtggtt tgtccaaact catcaatgta tcttatcatg   3300
tctgtatacc gtcgacctct agctagagct tggcgtaatc atggtcatag ctgtttcctg   3360
tgtgaaattg ttatccgctc acaattccac acaacatacg agccggaagc ataaagtgta   3420
aagcctgggg tgcctaatga gtgagctaac tcacattaat tgcgttgcgc tcactgcccg   3480
ctttccagtc gggaaacctg tcgtgccagc tgcattaatg aatcggccaa cgcgcgggga   3540
gaggcggttt gcgtattggg cgctcttccg cttcctcgct cactgactcg ctgcgctcgg   3600
tcgttcggct gcggcgagcg gtatcagctc actcaaaggc ggtaatacgg ttatccacag   3660
aatcagggga taacgcagga aagaacatgt gagcaaaagg ccagcaaaag gccaggaacc   3720
```

-continued gtaaaaaggc cgcgttgctg gcgtttttcc ataggctccg cccccctgac gagcatcaca 3780
aaaatcgacg ctcaagtcag aggtggcgaa acccgacagg actataaaga taccaggcgt 3840
ttccccctgg aagctccctc gtgcgctctc ctgttccgac cctgccgctt accggatacc 3900
tgtccgcctt tctcccttcg ggaagcgtgg cgctttctca tagctcacgc tgtaggtatc 3960
tcagttcggt gtaggtcgtt cgctccaagc tgggctgtgt gcacgaaccc cccgttcagc 4020
ccgaccgctg cgccttatcc ggtaactatc gtcttgagtc caacccggta agacacgact 4080
tatcgccact ggcagcagcc actggtaaca ggattagcag agcgaggtat gtaggcggtg 4140
ctacagagtt cttgaagtgg tggcctaact acggctacac tagaagaaca gtatttggta 4200
tctgcgctct gctgaagcca gttaccttcg gaaaaagagt tggtagctct tgatccggca 4260
aacaaaccac cgctggtagc ggtttttttg tttgcaagca gcagattacg cgcagaaaaa 4320
aaggatctca agaagatcct ttgatctttt ctacggggtc tgacgctcag tggaacgaaa 4380
actcacgtta agggattttg gtcatgagat tatcaaaaag gatcttcacc tagatccttt 4440
taaattaaaa atgaagtttt aaatcaatct aaagtatata tgagtaaact tggtctgaca 4500
gttaccaatg cttaatcagt gaggcaccta tctcagcgat ctgtctattt cgttcatcca 4560
tagttgcctg actccccgtc gtgtagataa ctacgatacg ggagggctta ccatctggcc 4620
ccagtgctgc aatgataccg cgagacccac gctcaccggc tccagattta tcagcaataa 4680
accagccagc cggaagggcc gagcgcagaa gtggtcctgc aactttatcc gcctccatcc 4740
agtctattaa ttgttgccgg gaagctagag taagtagttc gccagttaat agtttgcgca 4800
acgttgttgc cattgctaca ggcatcgtgg tgtcacgctc gtcgtttggt atggcttcat 4860
tcagctccgg ttcccaacga tcaaggcgag ttacatgatc ccccatgttg tgcaaaaaag 4920
cggttagctc cttcggtcct ccgatcgttg tcagaagtaa gttggccgca gtgttatcac 4980
tcatggttat ggcagcactg cataattctc ttactgtcat gccatccgta agatgctttt 5040
ctgtgactgg tgagtactca accaagtcat tctgagaata gtgtatgcgg cgaccgagtt 5100
gctcttgccc ggcgtcaata cgggataata ccgcgccaca tagcagaact ttaaaagtgc 5160
tcatcattgg aaaacgttct tcggggcgaa aactctcaag gatcttaccg ctgttgagat 5220
ccagttcgat gtaacccact cgtgcaccca actgatcttc agcatctttt actttcacca 5280
gcgtttctgg gtgagcaaaa acaggaaggc aaaatgccgc aaaaaaggga ataagggcga 5340
cacggaaatg ttgaatactc atactcttcc tttttcaata ttattgaagc atttatcagg 5400
gttattgtct catgagcgga tacatatttg aatgtattta gaaaaataaa caaatagggg 5460
ttccgcgcac atttccccga aaagtgccac ctgacgtc 5498

<210> SEQ ID NO 139
<211> LENGTH: 6341
<212> TYPE: DNA
<213> ORGANISM: Artificial Sequence
<220> FEATURE:
<223> OTHER INFORMATION: pExodus RecE

<400> SEQUENCE: 139
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240

-continued

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
atgtccacta aacccctctt cctcctgaga aaagccaaaa aatcaagcgg cgaacccgat    960
gtcgtcctct gggcaagcaa tgacttcgag tctacatgcg ctactctgga ctacctcatc   1020
gtgaagagtg ggaagaaact gagctcctat ttcaaagctg tcgcaacaaa ttttccagtg   1080
gtcaacgacc tgcctgcaga gggagaaatt gatttcacct ggtccgagag ataccagctg   1140
tccaaggact ctatgacatg ggaactgaaa ccaggagccg ctcccgataa tgctcactat   1200
cagggaaaca ccaatgtgaa cggggaggac atgacagaaa tcgaggaaaa catgctgctc   1260
ccaatctctg gacaggagct gcccattaga tggctcgccc agcacgggag tgaaaagcct   1320
gtgacccatg tctcaaggga cggtctgcag gctctccata ttgccagagc tgaggaactg   1380
ccagcagtga ctgcactggc cgtcagtcac aagacctcac tgctcgatcc cctggagatc   1440
cgggaactgc ataagctcgt gcgcgatact gacaaagtct ttccaaaccc cggaaatagc   1500
aacctggggc tcattaccgc tttctttgag gcatacctga atgccgatta tacagaccgc   1560
ggactgctca ctaaggaatg gatgaaaggg aacagggtgt ctcacatcac aagaactgcc   1620
agtggggcta atgcaggcgg agggaacctg acagaccgag gcgagggctt cgtgcatgac   1680
ctgacatcac tcgctcgcga tgtggcaact ggcgtcctgg ctcgaagcat ggatctggac   1740
atctacaatc tccaccccgc ccatgctaag cggattgagg aaatcattgc cgagaacaag   1800
ccccctttct ccgtgtttcg ggacaagttc atcaccatgc ctggtggcct ggattactca   1860
cgcgccattg tggtcgccag cgtgaaggag gcccctatcg gaattgaagt gatcccagct   1920
cacgtcacag agtatctgaa caaggtgctc accgaaacag atcatgcaaa ccctgaccca   1980
gagatcgtcg atattggatg cggcaggagc agcgcaccaa tgcctcagcg ggtgaccgag   2040
gaaggcaagc aggacgatga ggaaaaacca cagccctctg gcaccacagc agtggagcag   2100
ggagaggcag aaacaatgga gcccgacgcc acagaacacc atcaggacac tcagcctctg   2160
gatgcacaga gccaggtgaa cagcgtcgat gccaagtacc aggagctgcg agctgagctc   2220
cacgaagcaa ggaagaatat ccctagcaaa aacccagtgg acgatgacaa actgctcgca   2280
gccagccgag gtgagttcgt ggacggcatc tccgatccca acgaccctaa gtgggtgaaa   2340
ggcatccaga ctagggactg tgtctaccag aatcagcccg agaccgaaaa gacaagtcct   2400
gatatgaacc agcctgagcc agtggtccag caggagcctg aaatcgcatg caatgcctgt   2460
gggcagaccg gagggggataa ctgcccagac tgtggagccg tgatgggggga cgctacttat   2520
caggagacct ttgatgagga atcccaggtc gaggccaagg aaaacgaccc tgaggaaatg   2580
gagggtgctg aacacccaca taatgagaac gcaggctccg atccccacag ggattgctct   2640
```

gacgagaccg gagaagtggc tgacccagtg atcgtcgagg atattgaacc cggtatctac 2700
tatggcattt ctaatgagaa ctaccatgcc ggtccaggca tctcaaagag ccagctggat 2760
gacattgcag acacacctgc cctgtatctc tggagaaaaa acgccccagt ggacactacc 2820
aagactaaaa ccctggatct cggcactgct ttccactgtc gggtgctgga gcccgaggaa 2880
tttctcgagt ctagagggcc cgtttaaacc cgctgatcag cctcgactgt gccttctagt 2940
tgccagccat ctgttgtttg cccctccccc gtgccttcct tgaccctgga aggtgccact 3000
cccactgtcc tttcctaata aaatgaggaa attgcatcgc attgtctgag taggtgtcat 3060
tctattctgg ggggtggggt ggggcaggac agcaaggggg aggattggga agacaatagc 3120
aggcatgctg gggatgcggt gggctctatg gcttctgagg cggaaagaac cagctggggc 3180
tctagggggt atccccacgc gccctgtagc ggcgcattaa gcgcggcggg tgtggtggtt 3240
acgcgcagcg tgaccgctac acttgccagc gccctagcgc ccgctccttt cgctttcttc 3300
ccttcctttc tcgccacgtt cgccggcttt ccccgtcaag ctctaaatcg gggctccct 3360
ttagggttcc gatttagtgc tttacggcac ctcgacccca aaaaacttga ttagggtgat 3420
ggttcacgta gtgggccatc gccctgatag acggtttttc gccctttgac gttggagtcc 3480
acgttcttta atagtggact cttgttccaa actggaacaa cactcaaccc tatctcggtc 3540
tattcttttg atttataagg gattttgccg atttcggcct attggttaaa aaatgagctg 3600
atttaacaaa aatttaacgc gaattaattc tgtggaatgt gtgtcagtta gggtgtggaa 3660
agtccccagg ctccccagca ggcagaagta tgcaaagcct atcaggacat agcgttggct 3720
acccgtgata ttgctgaaga gcttggcggc gaatgggctg accgcttcct cgtgctttac 3780
ggtatcgccg ctcccgattc gcagcgcatc gccttctatc gccttcttga cgagttcttc 3840
tgagcgggac tctggggttc gaaatgaccg accaagcgac gcccaacctg ccatcacgag 3900
atttcgattc caccgccgcc ttctatgaaa ggttgggctt cggaatcgtt ttccgggacg 3960
ccggctggat gatcctccag cgcggggatc tcatgctgga gttcttcgcc caccccaact 4020
tgtttattgc agcttataat ggttacaaat aaagcaatag catcacaaat ttcacaaata 4080
aagcattttt ttcactgcat tctagttgtg gtttgtccaa actcatcaat gtatcttatc 4140
atgtctgtat accgtcgacc tctagctaga gcttggcgta atcatggtca tagctgtttc 4200
ctgtgtgaaa ttgttatccg ctcacaattc cacacaacat acgagccgga agcataaagt 4260
gtaaagcctg gggtgcctaa tgagtgagct aactcacatt aattgcgttg cgctcactgc 4320
ccgctttcca gtcgggaaac ctgtcgtgcc agctgcatta atgaatcggc caacgcgcgg 4380
ggagaggcgg tttgcgtatt gggcgctctt ccgcttcctc gctcactgac tcgctgcgct 4440
cggtcgttcg gctgcggcga gcggtatcag ctcactcaaa ggcggtaata cggttatcca 4500
cagaatcagg ggataacgca ggaaagaaca tgtgagcaaa aggccagcaa aaggccagga 4560
accgtaaaaa ggccgcgttg ctggcgtttt tccataggct ccgcccccct gacgagcatc 4620
acaaaaatcg acgctcaagt cagaggtggc gaaacccgac aggactataa agataccagg 4680
cgtttccccc tggaagctcc ctcgtgcgct ctcctgttcc gaccctgccg cttaccggat 4740
acctgtccgc ctttctccct tcgggaagcg tggcgctttc tcatagctca cgctgtaggt 4800
atctcagttc ggtgtaggtc gttcgctcca agctgggctg tgtgcacgaa ccccccgttc 4860
agcccgaccg ctgcgcctta tccggtaact atcgtcttga gtccaacccg gtaagacacg 4920
acttatcgcc actggcagca gccactggta acaggattag cagagcgagg tatgtaggcg 4980
gtgctacaga gttcttgaag tggtggccta actacggcta cactagaaga acagtatttg 5040
gtatctgcgc tctgctgaag ccagttacct tcggaaaaag agttggtagc tcttgatccg 5100
gcaaacaaac caccgctggt agcggttttt ttgtttgcaa gcagcagatt acgcgcagaa 5160
aaaaaggatc tcaagaagat cctttgatct tttctacggg gtctgacgct cagtggaacg 5220
aaaactcacg ttaagggatt ttggtcatga gattatcaaa aaggatcttc acctagatcc 5280
ttttaaatta aaaatgaagt tttaaatcaa tctaaagtat atatgagtaa acttggtctg 5340
acagttacca atgcttaatc agtgaggcac ctatctcagc gatctgtcta tttcgttcat 5400
ccatagttgc ctgactcccc gtcgtgtaga taactacgat acgggagggc ttaccatctg 5460
gccccagtgc tgcaatgata ccgcgagacc cacgctcacc ggctccagat ttatcagcaa 5520
taaaccagcc agccggaagg gccgagcgca gaagtggtcc tgcaacttta tccgcctcca 5580
tccagtctat taattgttgc cgggaagcta gagtaagtag ttcgccagtt aatagtttgc 5640
gcaacgttgt tgccattgct acaggcatcg tggtgtcacg ctcgtcgttt ggtatggctt 5700
cattcagctc cggttcccaa cgatcaaggc gagttacatg atcccccatg ttgtgcaaaa 5760
aagcggttag ctccttcggt cctccgatcg ttgtcagaag taagttggcc gcagtgttat 5820
cactcatggt tatggcagca ctgcataatt ctcttactgt catgccatcc gtaagatgct 5880
tttctgtgac tggtgagtac tcaaccaagt cattctgaga atagtgtatg cggcgaccga 5940
gttgctcttg cccggcgtca atacgggata ataccgcgcc acatagcaga actttaaaag 6000
tgctcatcat tggaaaacgt tcttcggggc gaaaactctc aaggatctta ccgctgttga 6060
gatccagttc gatgtaaccc actcgtgcac ccaactgatc ttcagcatct tttactttca 6120
ccagcgtttc tgggtgagca aaaacaggaa ggcaaaatgc cgcaaaaaag ggaataaggg 6180
cgacacggaa atgttgaata ctcatactct tcctttttca atattattga agcatttatc 6240
agggttattg tctcatgagc ggatacatat ttgaatgtat ttagaaaaat aaacaaatag 6300
gggttccgcg cacatttccc cgaaaagtgc cacctgacgt c 6341

<210> SEQ ID NO 140
<211> LENGTH: 6434
<212> TYPE: DNA
<213> ORGANISM: Artificial Sequence
<220> FEATURE:
<223> OTHER INFORMATION: pExodus Artemis

<400> SEQUENCE: 140
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720

-continued

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
atgtcctcat ttgaagggca gatggcagaa taccccacca ttagcattga tagatttgat    960
agggaaaacc tcagggcacg ggcttatttc ctgagccact gccataagga ccacatgaaa   1020
gggctcaggg cacctaccct caagaggaga ctggagtgct ccctcaaagt ctacctgtat   1080
tgttctccag tgacaaagga gctgctcctg acttccccca aatatcgctt ttggaagaaa   1140
cgaatcattt ctatcgagat tgaaactcca acccagatca gtctggtgga tgaggcttca   1200
ggcgaaaagg aggaaattgt ggtcaccctc ctgccagcag gacactgtcc aggtagcgtc   1260
atgttcctgt ttcagggcaa caatggaacc gtgctgtaca caggcgactt ccgcctcgct   1320
cagggagagg cagctcgaat ggaactcctg cattctggcg gacgggtcaa ggatatccag   1380
agtgtgtatc tggacaccac attctgcgat ccccggtttt accagattcc tagccgcgag   1440
gaatgtctgt ccggagtgct ggagctggtg aggtcatgga tcaccagaag cccatatcac   1500
gtggtctggc tgaactgcaa ggcagcctac gggtatgagt acctcttcac aaatctgtcc   1560
gaggaactcg gtgtgcaggt ccatgtgaac aaactggaca tgtttcgcaa tatgcccgag   1620
atcctccacc atctgactac cgataggaac acccagattc acgcttgcag acatcccaag   1680
gcagaggaat acttccagtg gagtaaactg ccttgtggca tcacttcacg gaaccgcatt   1740
cccctccaca tcattagcat caagccttcc accatgtggt ttggcgagcg atccaggaaa   1800
accaatgtca ttgtgcgaac aggagaaagc tcctataggg cctgcttctc ttttcattct   1860
agttacagtg agatcaagga cttcctctct tatctgtgtc ctgtgaacgc ttaccctaat   1920
gtcatcccag tgggcacaac tatggataag gtggtcgaga ttctcaaacc actgtgtcgg   1980
tcaagccaga gcacagaacc caagtacaaa cctctcggaa agctgaaaag agcccggact   2040
gtgcaccgag acagcgagga agaggacgat tatctgtttg acgatcccct gcctatccca   2100
ctcagacaca aggtgcccta ccctgagact ttccatcccg aagtcttttc catgaccgct   2160
gtgtctgaga agcagccaga aaaactgaga cagaccccag gatgctgtcg agcagagtgc   2220
atgcagtcct ctaggttcac aaactttgtg gactgtgaag agtccaattc tgagagtgaa   2280
gaggaagtgg gcatccccgc ctcactgcag ggggatctcg gtagcgtgct ccacctgcag   2340
aaggctgacg gcgacgtccc acagtgggag gtgttcttta aaagaaacga cgaaatcacc   2400
gatgagtccc tggaaaattt ccctagttca acagtggccg gggcttcaca gagcccaaag   2460
ctgttttccg actctgatgg ggagtctact cacatcagct cccagaactc tagtcagagc   2520
acacatatta ctgagcaggg ctcccaggga tgggacagtc agtcagatac agtcctggtg   2580
tcaagccagg agcggaacag tggtgacatc acatcactgg acaaggcaga ttatcgccct   2640
actatcaaag agaacattcc agccagcctg atggaacaga atgtgatttg ccctaaggac   2700
acctactctg atctgaagag tagagacaaa gatgtcacta tcgtgcctag caccggcgag   2760
ccaaccacac tgtcctctga aactcacatt cccgaggaaa agagcctcct gaacctgtcc   2820
accaatgcag actctcagag ttcaagcgat ttcgaggtgc catctacacc cgaggccgaa   2880
ctgcctaagc gggaacatct ccagtatctg tacgagaaac tggccacagg agaaagcatc   2940
gctgtgaaga aacgcaagtg tagcctcctg gacactctcg agtctagagg gcccgtttaa   3000
acccgctgat cagcctcgac tgtgccttct agttgccagc catctgttgt ttgcccctcc   3060
```

-continued

```
cccgtgcctt ccttgaccct ggaaggtgcc actcccactg tcctttccta ataaaatgag   3120
gaaattgcat cgcattgtct gagtaggtgt cattctattc tggggggtgg ggtggggcag   3180
gacagcaagg gggaggattg ggaagacaat agcaggcatg ctggggatgc ggtgggctct   3240
atggcttctg aggcggaaag aaccagctgg ggctctaggg ggtatcccca cgcgccctgt   3300
agcggcgcat taagcgcggc gggtgtggtg gttacgcgca gcgtgaccgc tacacttgcc   3360
agcgccctag cgcccgctcc tttcgctttc ttcccttcct ttctcgccac gttcgccggc   3420
tttccccgtc aagctctaaa tcgggggctc cctttagggt tccgatttag tgctttacgg   3480
cacctcgacc ccaaaaaact tgattagggt gatggttcac gtagtgggcc atcgccctga   3540
tagacggttt ttcgcccttt gacgttggag tccacgttct ttaatagtgg actcttgttc   3600
caaactggaa caacactcaa ccctatctcg gtctattctt ttgatttata agggattttg   3660
ccgatttcgg cctattggtt aaaaaatgag ctgatttaac aaaaatttaa cgcgaattaa   3720
ttctgtggaa tgtgtgtcag ttagggtgtg gaaagtcccc aggctcccca gcaggcagaa   3780
gtatgcaaag cctatcagga catagcgttg gctacccgtg atattgctga agagcttggc   3840
ggcgaatggg ctgaccgctt cctcgtgctt tacggtatcg ccgctcccga ttcgcagcgc   3900
atcgccttct atcgccttct tgacgagttc ttctgagcgg gactctgggg ttcgaaatga   3960
ccgaccaagc gacgcccaac ctgccatcac gagatttcga ttccaccgcc gccttctatg   4020
aaaggttggg cttcggaatc gttttccggg acgccggctg gatgatcctc cagcgcgggg   4080
atctcatgct ggagttcttc gcccacccca acttgtttat tgcagcttat aatggttaca   4140
aataaagcaa tagcatcaca aatttcacaa ataaagcatt tttttcactg cattctagtt   4200
gtggtttgtc caaactcatc aatgtatctt atcatgtctg tataccgtcg acctctagct   4260
agagcttggc gtaatcatgg tcatagctgt ttcctgtgtg aaattgttat ccgctcacaa   4320
ttccacacaa catacgagcc ggaagcataa agtgtaaagc ctggggtgcc taatgagtga   4380
gctaactcac attaattgcg ttgcgctcac tgcccgcttt ccagtcggga aacctgtcgt   4440
gccagctgca ttaatgaatc ggccaacgcg cggggagagg cggtttgcgt attgggcgct   4500
cttccgcttc ctcgctcact gactcgctgc gctcggtcgt tcggctgcgg cgagcggtat   4560
cagctcactc aaaggcggta atacggttat ccacagaatc aggggataac gcaggaaaga   4620
acatgtgagc aaaaggccag caaaaggcca ggaaccgtaa aaaggccgcg ttgctggcgt   4680
ttttccatag gctccgcccc cctgacgagc atcacaaaaa tcgacgctca agtcagaggt   4740
ggcgaaaccc gacaggacta taaagatacc aggcgtttcc ccctggaagc tccctcgtgc   4800
gctctcctgt tccgaccctg ccgcttaccg gatacctgtc cgcctttctc ccttcgggaa   4860
gcgtggcgct ttctcatagc tcacgctgta ggtatctcag ttcggtgtag gtcgttcgct   4920
ccaagctggg ctgtgtgcac gaaccccccg ttcagcccga ccgctgcgcc ttatccggta   4980
actatcgtct tgagtccaac ccggtaagac acgacttatc gccactggca gcagccactg   5040
gtaacaggat tagcagagcg aggtatgtag gcggtgctac agagttcttg aagtggtggc   5100
ctaactacgg ctacactaga agaacagtat ttggtatctg cgctctgctg aagccagtta   5160
ccttcggaaa aagagttggt agctcttgat ccggcaaaca aaccaccgct ggtagcggtt   5220
tttttgtttg caagcagcag attacgcgca gaaaaaaagg atctcaagaa gatcctttga   5280
tcttttctac ggggtctgac gctcagtgga acgaaaactc acgttaaggg attttggtca   5340
tgagattatc aaaaaggatc ttcacctaga tccttttaaa ttaaaaatga agttttaaat   5400
caatctaaag tatatatgag taaacttggt ctgacagtta ccaatgctta atcagtgagg   5460
```

cacctatctc agcgatctgt ctatttcgtt catccatagt tgcctgactc cccgtcgtgt 5520
agataactac gatacgggag ggcttaccat ctggccccag tgctgcaatg ataccgcgag 5580
acccacgctc accggctcca gatttatcag caataaacca gccagccgga agggccgagc 5640
gcagaagtgg tcctgcaact ttatccgcct ccatccagtc tattaattgt tgccgggaag 5700
ctagagtaag tagttcgcca gttaatagtt tgcgcaacgt tgttgccatt gctacaggca 5760
tcgtggtgtc acgctcgtcg tttggtatgg cttcattcag ctccggttcc caacgatcaa 5820
ggcgagttac atgatccccc atgttgtgca aaaaagcggt tagctccttc ggtcctccga 5880
tcgttgtcag aagtaagttg gccgcagtgt tatcactcat ggttatggca gcactgcata 5940
attctcttac tgtcatgcca tccgtaagat gcttttctgt gactggtgag tactcaacca 6000
agtcattctg agaatagtgt atgcggcgac cgagttgctc ttgcccggcg tcaatacggg 6060
ataataccgc gccacatagc agaactttaa aagtgctcat cattggaaaa cgttcttcgg 6120
ggcgaaaact ctcaaggatc ttaccgctgt tgagatccag ttcgatgtaa cccactcgtg 6180
cacccaactg atcttcagca tcttttactt tcaccagcgt ttctgggtga gcaaaaacag 6240
gaaggcaaaa tgccgcaaaa aagggaataa gggcgacacg gaaatgttga atactcatac 6300
tcttcctttt tcaatattat tgaagcattt atcagggtta ttgtctcatg agcggataca 6360
tatttgaatg tatttagaaa aataaacaaa taggggttcc gcgcacattt ccccgaaaag 6420
tgccacctga cgtc 6434

<210> SEQ ID NO 141
<211> LENGTH: 6419
<212> TYPE: DNA
<213> ORGANISM: Artificial Sequence
<220> FEATURE:
<223> OTHER INFORMATION: pExodus Dna2

<400> SEQUENCE: 141
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atggaacagc tcaacgaact ggaactcctc atggagaagt ccttttggga agaagccgaa 960
ctgcctgccg aactgtttca gaagaaggtg gtcgcttctt tcccccgcac cgtgctgagt 1020

-continued

```
acagggatgg acaaccgata cctcgtcctg gcagtgaata ccgtccagaa caaagagggt   1080

aattgcgaaa agcgactggt catcacagcc agccagtccc tggagaataa ggaactgtgc   1140

attctcagaa acgactggtg ttccgtgcca gtcgagcccg gcgatatcat tcacctggaa   1200

ggagactgca catctgatac ttggatcatt gacaaggatt tcggctacct catcctgtat   1260

cctgacatgc tgattagcgg aacttccatc gccagctcca ttaggtgtat gaggagagct   1320

gtgctgagcg agacctttcg ctctagtgat cccgctaccc gacagatgct catcggcaca   1380

gtgctgcacg aggtcttcca gaaagccatt aacaatagct ttgctcctga gaagctgcag   1440

gaactcgcat ttcagacaat ccaggagatt aggcatctga aagaaatgta cagactcaat   1500

ctgtctcagg acgagatcaa gcaggaggtg gaagattatc tgccaagttt ctgcaaatgg   1560

gccggagact ttatgcataa gaacactagc accgatttcc cacagatgca gctctctctg   1620

cccagtgaca actcaaaaga taattccacc tgtaacatcg aggtggtcaa gcctatggac   1680

atcgaggaaa gcatttggtc cccacggttt gggctgaagg gtaaaatcga tgtgactgtc   1740

ggggtgaaga ttcaccgcgg ttacaagacc aaatataaga tcatgcccct ggagctgaag   1800

acaggcaagg agtctaacag tattgaacat cggtcccagg tggtcctgta cacactgctc   1860

tctcaggagc gacgagccga ccccgaagct ggactgctcc tgtacctgaa gactggacag   1920

atgtatcccg tgcctgcaaa tcacctggat aaaagagagc tcctgaagct gcggaaccag   1980

atggccttca gcctgtttca tcggatctca aaaagcgcaa ctcgccagaa gacccagctg   2040

gccagcctcc ctcagatcat tgaggaagag aaaacatgca agtactgtag tcagatcgga   2100

aattgcgcac tgtattcaag agccgtggag cagcagatgg actgttcaag cgtgcccatc   2160

gtcatgctgc ctaaaattga agaggaaaca cagcacctca agcagactca tctggagtat   2220

ttctccctct ggtgcctcat gctgaccctc gaatcccagt ctaaggacaa caagaaaaat   2280

caccagaaca tctggctgat gcctgcttct gagatggaaa agagtggctc atgtatcgga   2340

aacctgatta ggatggagca tgtgaagatt gtctgcgacg ggcagtacct gcacaatttc   2400

cagtgtaagc atggtgctat cccagtgacc aacctgatgg caggggatag agtcattgtg   2460

tctggcgagg aacgaagtct gtttgccctc tcaaggggat atgtgaagga gatcaatatg   2520

accacagtca catgcctcct ggacaggaac ctgagcgtgc tcccagaatc cactctgttc   2580

agactcgatc aggaggagaa gaactgtgac atcgatactc ccctggggaa tctcagcaag   2640

ctgatggaga acacctttgt gtccaagaaa ctcagagacc tgatcattga tttccgggaa   2700

ccccagttta tctcctacct ctcctctgtg ctgcctcacg acgctaagga taccgtcgca   2760

tgcattctca aagggctgaa caagcctcag cggcaggcta tgaagaaagt gctcctgtct   2820

aaagactata ctctgatcgt cggcatgcca ggcaccggaa agactaccac aatctgtaca   2880

ctggtgcgct tccgaaggtt tattcagctc agttcaaatc tgcagtcaaa gaaattcgcc   2940

gatcagagcc ctctgaaccc actcgagtct agagggcccg tttaaacccg ctgatcagcc   3000

tcgactgtgc cttctagttg ccagccatct gttgtttgcc cctcccccgt gccttccttg   3060

accctggaag gtgccactcc cactgtcctt tcctaataaa atgaggaaat tgcatcgcat   3120

tgtctgagta ggtgtcattc tattctgggg ggtggggtgg ggcaggacag caagggggag   3180

gattgggaag acaatagcag gcatgctggg gatgcggtgg gctctatggc ttctgaggcg   3240

gaaagaacca gctggggctc tagggggtat ccccacgcgc cctgtagcgg cgcattaagc   3300

gcggcgggtg tggtggttac gcgcagcgtg accgctacac ttgccagcgc cctagcgccc   3360

gctcctttcg ctttcttccc ttcctttctc gccacgttcg ccggctttcc ccgtcaagct   3420
```

-continued

```
ctaaatcggg ggctcccttt agggttccga tttagtgctt tacggcacct cgaccccaaa   3480
aaacttgatt agggtgatgg ttcacgtagt gggccatcgc cctgatagac ggtttttcgc   3540
cctttgacgt tggagtccac gttctttaat agtggactct tgttccaaac tggaacaaca   3600
ctcaacccta tctcggtcta ttcttttgat ttataaggga ttttgccgat ttcggcctat   3660
tggttaaaaa atgagctgat ttaacaaaaa tttaacgcga attaattctg tggaatgtgt   3720
gtcagttagg gtgtggaaag tccccaggct ccccagcagg cagaagtatg caaagcctat   3780
caggacatag cgttggctac ccgtgatatt gctgaagagc ttggcggcga atgggctgac   3840
cgcttcctcg tgctttacgg tatcgccgct cccgattcgc agcgcatcgc cttctatcgc   3900
cttcttgacg agttcttctg agcgggactc tggggttcga aatgaccgac caagcgacgc   3960
ccaacctgcc atcacgagat ttcgattcca ccgccgcctt ctatgaaagg ttgggcttcg   4020
gaatcgtttt ccgggacgcc ggctggatga tcctccagcg cggggatctc atgctggagt   4080
tcttcgccca ccccaacttg tttattgcag cttataatgg ttacaaataa agcaatagca   4140
tcacaaattt cacaaataaa gcattttttt cactgcattc tagttgtggt ttgtccaaac   4200
tcatcaatgt atcttatcat gtctgtatac cgtcgacctc tagctagagc ttggcgtaat   4260
catggtcata gctgtttcct gtgtgaaatt gttatccgct cacaattcca cacaacatac   4320
gagccggaag cataaagtgt aaagcctggg gtgcctaatg agtgagctaa ctcacattaa   4380
ttgcgttgcg ctcactgccc gctttccagt cgggaaacct gtcgtgccag ctgcattaat   4440
gaatcggcca acgcgcgggg agaggcggtt tgcgtattgg gcgctcttcc gcttcctcgc   4500
tcactgactc gctgcgctcg gtcgttcggc tgcggcgagc ggtatcagct cactcaaagg   4560
cggtaatacg gttatccaca gaatcagggg ataacgcagg aaagaacatg tgagcaaaag   4620
gccagcaaaa ggccaggaac cgtaaaaagg ccgcgttgct ggcgtttttc cataggctcc   4680
gcccccctga cgagcatcac aaaaatcgac gctcaagtca gaggtggcga aacccgacag   4740
gactataaag ataccaggcg tttccccctg gaagctccct cgtgcgctct cctgttccga   4800
ccctgccgct taccggatac ctgtccgcct ttctcccttc gggaagcgtg gcgctttctc   4860
atagctcacg ctgtaggtat ctcagttcgg tgtaggtcgt tcgctccaag ctgggctgtg   4920
tgcacgaacc ccccgttcag cccgaccgct gcgccttatc cggtaactat cgtcttgagt   4980
ccaacccggt aagacacgac ttatcgccac tggcagcagc cactggtaac aggattagca   5040
gagcgaggta tgtaggcggt gctacagagt tcttgaagtg gtggcctaac tacggctaca   5100
ctagaagaac agtatttggt atctgcgctc tgctgaagcc agttaccttc ggaaaaagag   5160
ttggtagctc ttgatccggc aaacaaacca ccgctggtag cggttttttt gtttgcaagc   5220
agcagattac gcgcagaaaa aaaggatctc aagaagatcc tttgatcttt tctacggggt   5280
ctgacgctca gtggaacgaa aactcacgtt aagggatttt ggtcatgaga ttatcaaaaa   5340
ggatcttcac ctagatcctt ttaaattaaa aatgaagttt taaatcaatc taaagtatat   5400
atgagtaaac ttggtctgac agttaccaat gcttaatcag tgaggcacct atctcagcga   5460
tctgtctatt tcgttcatcc atagttgcct gactccccgt cgtgtagata actacgatac   5520
gggagggctt accatctggc cccagtgctg caatgatacc gcgagaccca cgctcaccgg   5580
ctccagattt atcagcaata aaccagccag ccggaagggc cgagcgcaga agtggtcctg   5640
caactttatc cgcctccatc cagtctatta attgttgccg ggaagctaga gtaagtagtt   5700
cgccagttaa tagtttgcgc aacgttgttg ccattgctac aggcatcgtg gtgtcacgct   5760
```

-continued

```
cgtcgtttgg tatggcttca ttcagctccg gttcccaacg atcaaggcga gttacatgat   5820

cccccatgtt gtgcaaaaaa gcggttagct ccttcggtcc tccgatcgtt gtcagaagta   5880

agttggccgc agtgttatca ctcatggtta tggcagcact gcataattct cttactgtca   5940

tgccatccgt aagatgcttt tctgtgactg gtgagtactc aaccaagtca ttctgagaat   6000

agtgtatgcg gcgaccgagt tgctcttgcc cggcgtcaat acgggataat accgcgccac   6060

atagcagaac tttaaaagtg ctcatcattg gaaaacgttc ttcggggcga aaactctcaa   6120

ggatcttacc gctgttgaga tccagttcga tgtaacccac tcgtgcaccc aactgatctt   6180

cagcatcttt tactttcacc agcgtttctg ggtgagcaaa aacaggaagg caaaatgccg   6240

caaaaaaggg aataagggcg acacggaaat gttgaatact catactcttc ctttttcaat   6300

attattgaag catttatcag ggttattgtc tcatgagcgg atacatattt gaatgtattt   6360

agaaaaataa acaaataggg gttccgcgca catttccccg aaaagtgcca cctgacgtc    6419
```

<210> SEQ ID NO 142
<211> LENGTH: 6482
<212> TYPE: DNA
<213> ORGANISM: Artificial Sequence
<220> FEATURE:
<223> OTHER INFORMATION: pExodus MreII

<400> SEQUENCE: 142

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

atgagcaccg cagacgccct ggacgatgag aacacattca aaatcctggt cgcaacagac    960

attcacctcg ggtttatgga gaaagacgcc gtgagaggga acgatacttt cgtcaccctg   1020

gacgagatcc tgcggctcgc tcaggagaac gaagtggatt tcattctgct cggcggagac   1080

ctgtttcacg aaaataagcc aagcagaaaa acactccata cttgcctgga gctgctccgc   1140

aagtactgta tgggcgatcg accagtgcag ttcgagatcc tgtctgacca gagtgtcaac   1200

ttcggatttt ccaagtttcc ctgggtgaat tatcaggatg ggaacctgaa tatctcaatt   1260

cccgtgttca gcatccacgg caaccatgac gatcctaccg gagcagatgc cctgtgcgcc   1320

ctcgacatcc tgagctgtgc tgggttcgtg aatcactttg gcaggtccat gtctgtggag   1380

aagatcgaca tttctcccgt cctgctccag aagggcagta ccaaaatcgc cctctacggc   1440
```

-continued ctgggaagca ttcctgatga gcgcctctat cgaatgtttg tgaacaagaa agtcacaatg 1500
ctgcgcccaa aggaggacga aaactcctgg ttcaatctct ttgtgatcca ccagaaccgg 1560
tctaaacatg gcagtacaaa tttcattcct gagcagttcc tcgacgattt tatcgacctg 1620
gtcatctggg gacacgagca tgaatgcaag atcgctccaa caaaaaacga acagcagctg 1680
ttttacattt ctcagcctgg gagctccgtg gtcactagtc tgtcaccagg cgaggcagtg 1740
aagaaacacg tcggcctgct ccggatcaag ggacgcaaaa tgaacatgca caagattccc 1800
ctgcatactg tgagacagtt ctttatggag gatatcgtcc tggccaatca tcctgatatt 1860
ttcaaccccg acaatcctaa ggtgacccag gctatccaga gcttttgtct cgaaaaaatt 1920
gaggaaatgc tggagaacgc agagcgcgaa cgactgggaa attcccacca gccagaaaag 1980
cccctcgtga ggctgagagt ggactattct gggggtttcg agccattttc cgtgctgaga 2040
ttctctcaga agtttgtgga tcgggtcgct aaccccaaag acatcattca cttctttcgg 2100
catcgcgagc agaaggaaaa aacaggggag gaaatcaatt tcggcaagct gattactaaa 2160
ccttctgaag ggaccacact cagggtggag gacctggtca agcagtactt tcagaccgcc 2220
gagaagaacg tgcagctgag cctgctcaca gagagaggga tgggtgaagc tgtgcaggag 2280
ttcgtcgata aggaggaaaa agacgcaatc gaggaactcg tgaagtatca gctggagaaa 2340
acccagcgat tcctcaagga aaggcacatc gacgctctgg aggataaaat tgacgaggaa 2400
gtcaggaggt tcagggagac cagacagaag aacacaaatg aggaagacga tgaggtgcgc 2460
gaagcaatga cacgagctag ggcactgagg agccagtccg aggaatctgc cagtgctttc 2520
agtgccgacg atctcatgtc aatcgatctg gctgagcaga tggcaaacga ctccgacgat 2580
tcaatcagcg ccgctactaa taagggcaga ggacgggggc gcggtcggcg cggcggacgc 2640
ggacagaact ccgcatctag gggggggttct cagcgaggca gggcagatac tggactggag 2700
acctcaacaa gaagccggaa ctccaagacc gcagtgagtg cctcacggaa tatgagcatc 2760
attgacgcct tcaagagcac cagacagcag ccctcccgga acgtcactac caaaaaattac 2820
tcagaagtga tcgaagtcga tgagagcgac gtggaggaag atatttttcc tacaactagt 2880
aagactgacc agaggtggtc tagtacctca agctccaaga tcatgagcca gtcccaggtg 2940
tccaaaggag tggacttcga atctagtgag gacgatgacg atgacccctt catgaacaca 3000
tcaagcctgc gaaggaatag acggctcgag tctagagggc ccgtttaaac ccgctgatca 3060
gcctcgactg tgccttctag ttgccagcca tctgttgttt gcccctcccc cgtgccttcc 3120
ttgaccctgg aaggtgccac tcccactgtc ctttcctaat aaaatgagga aattgcatcg 3180
cattgtctga gtaggtgtca ttctattctg gggggtgggg tggggcagga cagcaagggg 3240
gaggattggg aagacaatag caggcatgct ggggatgcgg tgggctctat ggcttctgag 3300
gcggaaagaa ccagctgggg ctctaggggg tatccccacg cgccctgtag cggcgcatta 3360
agcgcggcgg gtgtggtggt tacgcgcagc gtgaccgcta cacttgccag cgccctagcg 3420
cccgctcctt tcgctttctt cccttccttt ctcgccacgt tcgccggctt tccccgtcaa 3480
gctctaaatc gggggctccc tttagggttc cgatttagtg ctttacggca cctcgacccc 3540
aaaaaacttg attagggtga tggttcacgt agtgggccat cgccctgata gacggttttt 3600
cgccctttga cgttggagtc cacgttcttt aatagtggac tcttgttcca aactggaaca 3660
acactcaacc ctatctcggt ctattctttt gatttataag ggattttgcc gatttcggcc 3720
tattggttaa aaaatgagct gatttaacaa aaatttaacg cgaattaatt ctgtggaatg 3780

-continued

```
tgtgtcagtt agggtgtgga aagtccccag gctccccagc aggcagaagt atgcaaagcc   3840
tatcaggaca tagcgttggc tacccgtgat attgctgaag agcttggcgg cgaatgggct   3900
gaccgcttcc tcgtgcttta cggtatcgcc gctcccgatt cgcagcgcat cgccttctat   3960
cgccttcttg acgagttctt ctgagcggga ctctggggtt cgaaatgacc gaccaagcga   4020
cgcccaacct gccatcacga gatttcgatt ccaccgccgc cttctatgaa aggttgggct   4080
tcggaatcgt tttccgggac gccggctgga tgatcctcca gcgcggggat ctcatgctgg   4140
agttcttcgc ccaccccaac ttgtttattg cagcttataa tggttacaaa taaagcaata   4200
gcatcacaaa tttcacaaat aaagcatttt tttcactgca ttctagttgt ggtttgtcca   4260
aactcatcaa tgtatcttat catgtctgta taccgtcgac ctctagctag agcttggcgt   4320
aatcatggtc atagctgttt cctgtgtgaa attgttatcc gctcacaatt ccacacaaca   4380
tacgagccgg aagcataaag tgtaaagcct ggggtgccta atgagtgagc taactcacat   4440
taattgcgtt gcgctcactg cccgctttcc agtcgggaaa cctgtcgtgc cagctgcatt   4500
aatgaatcgg ccaacgcgcg gggagaggcg gtttgcgtat tgggcgctct tccgcttcct   4560
cgctcactga ctcgctgcgc tcggtcgttc ggctgcggcg agcggtatca gctcactcaa   4620
aggcggtaat acggttatcc acagaatcag gggataacgc aggaaagaac atgtgagcaa   4680
aaggccagca aaaggccagg aaccgtaaaa aggccgcgtt gctggcgttt ttccataggc   4740
tccgcccccc tgacgagcat cacaaaaatc gacgctcaag tcagaggtgg cgaaacccga   4800
caggactata aagataccag gcgtttcccc ctggaagctc cctcgtgcgc tctcctgttc   4860
cgaccctgcc gcttaccgga tacctgtccg cctttctccc ttcgggaagc gtggcgcttt   4920
ctcatagctc acgctgtagg tatctcagtt cggtgtaggt cgttcgctcc aagctgggct   4980
gtgtgcacga accccccgtt cagcccgacc gctgcgcctt atccggtaac tatcgtcttg   5040
agtccaaccc ggtaagacac gacttatcgc cactggcagc agccactggt aacaggatta   5100
gcagagcgag gtatgtaggc ggtgctacag agttcttgaa gtggtggcct aactacggct   5160
acactagaag aacagtattt ggtatctgcg ctctgctgaa gccagttacc ttcggaaaaa   5220
gagttggtag ctcttgatcc ggcaaacaaa ccaccgctgg tagcggtttt tttgtttgca   5280
agcagcagat tacgcgcaga aaaaaaggat ctcaagaaga tcctttgatc ttttctacgg   5340
ggtctgacgc tcagtggaac gaaaactcac gttaagggat tttggtcatg agattatcaa   5400
aaaggatctt cacctagatc cttttaaatt aaaaatgaag ttttaaatca atctaaagta   5460
tatatgagta aacttggtct gacagttacc aatgcttaat cagtgaggca cctatctcag   5520
cgatctgtct atttcgttca tccatagttg cctgactccc cgtcgtgtag ataactacga   5580
tacgggaggg cttaccatct ggccccagtg ctgcaatgat accgcgagac ccacgctcac   5640
cggctccaga tttatcagca ataaaccagc cagccggaag ggccgagcgc agaagtggtc   5700
ctgcaacttt atccgcctcc atccagtcta ttaattgttg ccgggaagct agagtaagta   5760
gttcgccagt taatagtttg cgcaacgttg ttgccattgc tacaggcatc gtggtgtcac   5820
gctcgtcgtt tggtatggct tcattcagct ccggttccca acgatcaagg cgagttacat   5880
gatcccccat gttgtgcaaa aaagcggtta gctccttcgg tcctccgatc gttgtcagaa   5940
gtaagttggc cgcagtgtta tcactcatgg ttatggcagc actgcataat tctcttactg   6000
tcatgccatc cgtaagatgc ttttctgtga ctggtgagta ctcaaccaag tcattctgag   6060
aatagtgtat gcggcgaccg agttgctctt gcccggcgtc aatacgggat aataccgcgc   6120
cacatagcag aactttaaaa gtgctcatca ttggaaaacg ttcttcgggg cgaaaactct   6180
```

-continued caaggatctt accgctgttg agatccagtt cgatgtaacc cactcgtgca cccaactgat 6240
cttcagcatc ttttactttc accagcgttt ctgggtgagc aaaaacagga aggcaaaatg 6300
ccgcaaaaaa gggaataagg gcgacacgga aatgttgaat actcatactc ttcctttttc 6360
aatattattg aagcatttat cagggttatt gtctcatgag cggatacata tttgaatgta 6420
tttagaaaaa taaacaaata ggggttccgc gcacatttcc ccgaaaagtg ccacctgacg 6480
tc 6482

<210> SEQ ID NO 143
<211> LENGTH: 5885
<212> TYPE: DNA
<213> ORGANISM: Artificial Sequence
<220> FEATURE:
<223> OTHER INFORMATION: pExodus TdT

<400> SEQUENCE: 143
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atggacccac caagggcatc acatctctcc cccaggaaga aaagaccaag acagacaggc 960
gctctcatgg caagttcacc tcaggatatc aagttccagg acctcgtggt ctttattctg 1020
gaaaagaaaa tgggaaccac aaggagagca ttcctcatgg agctggcccg gcgcaagggg 1080
tttagggtgg aaaacgagct gtccgactct gtcacacaca tcgtggctga gaacaatagt 1140
ggttcagatg tgctcgaatg gctgcaggca cagaaggtgc aggtcagctc ccagcccgag 1200
ctgctcgatg tcagctggct gatcgaatgc attagagctg gcaagcctgt ggagatgact 1260
ggcaaacatc agctggtggt ccgaagggac tacagcgatt ccactaaccc aggaccacct 1320
aagaccccac caatcgctgt gcagaaaatt agtcagtatg catgccagag acggactacc 1380
ctgaacaatt gtaatcagat tttcaccgac gcctttgata ttctggctga aaactgcgag 1440
ttccgagaaa atgaggactc ctgtgtcacc ttcatgagag ccgcttccgt gctcaagtct 1500
ctgcctttca caatcatctc aatgaaggat actgagggca tcccatgcct gggaagcaag 1560
gtgaaaggga tcattgagga aatcattgaa gacggagagt ctagtgaagt caaggccgtg 1620
ctgaacgatg agagatacca gagcttcaag ctgttcacct cagtcttcgg ggtgggtctg 1680

-continued

```
aagacatccg agaaatggtt cagaatggga tttcggactc tctctaaggt gcggtctgac   1740
aagagtctga aattcacccg catgcagaaa gcagggtttc tctactatga ggatctggtc   1800
tcttgtgtga cccgcgcaga agccgaggct gtgagtgtcc tcgtgaagga ggctgtctgg   1860
gcattcctgc ctgacgcctt tgtgacaatg actggcggat tccgccgagg gaagaaaatg   1920
ggtcacgacg tggattttct gatcacctca ccaggtagca cagaagacga ggaacagctg   1980
ctccagaaag tgatgaatct gtgggagaag aaaggcctgc tcctgtacta tgatctggtc   2040
gagagcactt tcgaaaagct ccgcctgcca tcccgaaaag tggacgccct ggatcatttt   2100
cagaagtgct tcctcatctt taaactgccc cgacagaggg tggactctga tcagtcaagc   2160
tggcaggaag gaaagacctg gaaagctatt cgggtggacc tggtgctgtg tccctacgag   2220
aggagagcat tcgcactcct gggatggaca ggcagcaggc agtttgaaag ggacctgcgg   2280
cgctacgcaa ctcacgagcg gaagatgatc ctcgacaacc atgccctgta tgataagaca   2340
aaacgcattt tcctgaaggc cgagagcgag gaagaaatct tcgctcacct cggcctggac   2400
tatattgagc cttgggaaag aaatgctctc gagtctagag ggcccgttta aacccgctga   2460
tcagcctcga ctgtgccttc tagttgccag ccatctgttg tttgcccctc ccccgtgcct   2520
tccttgaccc tggaaggtgc cactcccact gtcctttcct aataaaatga ggaaattgca   2580
tcgcattgtc tgagtaggtg tcattctatt ctggggggtg gggtggggca ggacagcaag   2640
ggggaggatt gggaagacaa tagcaggcat gctggggatg cggtgggctc tatggcttct   2700
gaggcggaaa gaaccagctg gggctctagg gggtatcccc acgcgccctg tagcggcgca   2760
ttaagcgcgg cgggtgtggt ggttacgcgc agcgtgaccg ctacacttgc cagcgcccta   2820
gcgcccgctc ctttcgcttt cttcccttcc tttctcgcca cgttcgccgg ctttccccgt   2880
caagctctaa atcgggggct ccctttaggg ttccgattta gtgctttacg gcacctcgac   2940
cccaaaaaac ttgattaggg tgatggttca cgtagtgggc catcgccctg atagacggtt   3000
tttcgccctt tgacgttgga gtccacgttc tttaatagtg gactcttgtt ccaaactgga   3060
acaacactca accctatctc ggtctattct tttgatttat aagggatttt gccgatttcg   3120
gcctattggt taaaaaatga gctgatttaa caaaaattta acgcgaatta attctgtgga   3180
atgtgtgtca gttagggtgt ggaaagtccc caggctcccc agcaggcaga agtatgcaaa   3240
gcctatcagg acatagcgtt ggctacccgt gatattgctg aagagcttgg cggcgaatgg   3300
gctgaccgct tcctcgtgct ttacggtatc gccgctcccg attcgcagcg catcgccttc   3360
tatcgccttc ttgacgagtt cttctgagcg ggactctggg gttcgaaatg accgaccaag   3420
cgacgcccaa cctgccatca cgagatttcg attccaccgc cgccttctat gaaaggttgg   3480
gcttcggaat cgttttccgg gacgccggct ggatgatcct ccagcgcggg gatctcatgc   3540
tggagttctt cgcccacccc aacttgttta ttgcagctta taatggttac aaataaagca   3600
atagcatcac aaatttcaca aataaagcat ttttttcact gcattctagt tgtggtttgt   3660
ccaaactcat caatgtatct tatcatgtct gtataccgtc gacctctagc tagagcttgg   3720
cgtaatcatg gtcatagctg tttcctgtgt gaaattgtta tccgctcaca attccacaca   3780
acatacgagc cggaagcata aagtgtaaag cctggggtgc ctaatgagtg agctaactca   3840
cattaattgc gttgcgctca ctgcccgctt tccagtcggg aaacctgtcg tgccagctgc   3900
attaatgaat cggccaacgc gcggggagag gcggtttgcg tattgggcgc tcttccgctt   3960
cctcgctcac tgactcgctg cgctcggtcg ttcggctgcg gcgagcggta tcagctcact   4020
caaaggcggt aatacggtta tccacagaat caggggataa cgcaggaaag aacatgtgag   4080
```

-continued caaaaggcca gcaaaaggcc aggaaccgta aaaaggccgc gttgctggcg tttttccata 4140
ggctccgccc ccctgacgag catcacaaaa atcgacgctc aagtcagagg tggcgaaacc 4200
cgacaggact ataaagatac caggcgtttc cccctggaag ctccctcgtg cgctctcctg 4260
ttccgaccct gccgcttacc ggatacctgt ccgcctttct cccttcggga agcgtggcgc 4320
tttctcatag ctcacgctgt aggtatctca gttcggtgta ggtcgttcgc tccaagctgg 4380
gctgtgtgca cgaacccccc gttcagcccg accgctgcgc cttatccggt aactatcgtc 4440
ttgagtccaa cccggtaaga cacgacttat cgccactggc agcagccact ggtaacagga 4500
ttagcagagc gaggtatgta ggcggtgcta cagagttctt gaagtggtgg cctaactacg 4560
gctacactag aagaacagta tttggtatct gcgctctgct gaagccagtt accttcggaa 4620
aaagagttgg tagctcttga tccggcaaac aaaccaccgc tggtagcggt ttttttgttt 4680
gcaagcagca gattacgcgc agaaaaaaag gatctcaaga agatcctttg atcttttcta 4740
cggggtctga cgctcagtgg aacgaaaact cacgttaagg gattttggtc atgagattat 4800
caaaaaggat cttcacctag atccttttaa attaaaaatg aagttttaaa tcaatctaaa 4860
gtatatatga gtaaacttgg tctgacagtt accaatgctt aatcagtgag gcacctatct 4920
cagcgatctg tctatttcgt tcatccatag ttgcctgact ccccgtcgtg tagataacta 4980
cgatacggga gggcttacca tctggcccca gtgctgcaat gataccgcga gacccacgct 5040
caccggctcc agatttatca gcaataaacc agccagccgg aagggccgag cgcagaagtg 5100
gtcctgcaac tttatccgcc tccatccagt ctattaattg ttgccgggaa gctagagtaa 5160
gtagttcgcc agttaatagt ttgcgcaacg ttgttgccat tgctacaggc atcgtggtgt 5220
cacgctcgtc gtttggtatg gcttcattca gctccggttc ccaacgatca aggcgagtta 5280
catgatcccc catgttgtgc aaaaaagcgg ttagctcctt cggtcctccg atcgttgtca 5340
gaagtaagtt ggccgcagtg ttatcactca tggttatggc agcactgcat aattctctta 5400
ctgtcatgcc atccgtaaga tgcttttctg tgactggtga gtactcaacc aagtcattct 5460
gagaatagtg tatgcggcga ccgagttgct cttgcccggc gtcaatacgg gataataccg 5520
cgccacatag cagaacttta aaagtgctca tcattggaaa acgttcttcg gggcgaaaac 5580
tctcaaggat cttaccgctg ttgagatcca gttcgatgta acccactcgt gcacccaact 5640
gatcttcagc atcttttact ttcaccagcg tttctgggtg agcaaaaaca ggaaggcaaa 5700
atgccgcaaa aaagggaata agggcgacac ggaaatgttg aatactcata ctcttccttt 5760
ttcaatatta ttgaagcatt tatcagggtt attgtctcat gagcggatac atatttgaat 5820
gtatttagaa aaataaacaa ataggggttc cgcgcacatt tccccgaaaa gtgccacctg 5880
acgtc 5885

<210> SEQ ID NO 144
<211> LENGTH: 7412
<212> TYPE: DNA
<213> ORGANISM: Artificial Sequence
<220> FEATURE:
<223> OTHER INFORMATION: pExodus Vaccinia Polymerase

<400> SEQUENCE: 144
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
atggatgtcc gctgtattaa ctggtttgaa tctcatggtg aaaatcggtt cctgtatctg    960
aaaagtcggt gtagaaatgg cgagaccgtg ttcatcaggt ttcctcacta cttttactat   1020
gtggtcactg acgaaatcta ccagtctctg agtccccctc cattcaatgc tcgcccactc   1080
gggaagatgc gaactatcga cattgatgag accatcagtt acaacctgga cattaaggat   1140
cgaaaatgct cagtggcaga catgtggctg atcgaggaac caaagaaacg cagcattcag   1200
aacgccacaa tggatgaatt tctgaatatc tcctggttct atatcagtaa cgggatttca   1260
cccgacggtt gctacagcct ggatgagcag tatctcacta agatcaacaa tggatgctac   1320
cattgtgacg atcctagaaa ctgttttgca aagaaaatcc cccgattcga cattcctagg   1380
agctatctgt tcctcgacat cgagtgccac ttcgataaga aatttccaag cgtgttcatc   1440
aatcccatct cccatacatc ttactgttac attgatctga gcggcaagcg gctgctcttc   1500
actctgatca acgaggaaat gctcaccgag caggaaattc aggaggcagt ggaccgagga   1560
tgcctgcgca tccagtctct catggagatg gattacgaga gggaactggt gctctgtagt   1620
gaaatcgtcc tgctcagaat tgccaagcag ctgctggagc tgacatttga ctacgtggtc   1680
acttttaacg ggcacaattt cgatctgaga tatatcacca acaggctgga gctgctcaca   1740
ggtgaaaaga tcattttccg gtcccccgac aagaaagagg ctgtgtacct gtgcatctat   1800
gaacgcaatc agagctccca caaaggcgtg ggcggaatgg caaacaccac atttcatgtc   1860
aacaataaca atggaaccat cttctttgac ctgtacagct tcattcagaa gtccgaaaaa   1920
ctggactctt ataagctcga ttcaatcagc aagaacgctt tttcttgtat gggcaaggtg   1980
ctgaacaggg gagtcagaga gatgacattc attggggacg atactaccga cgccaagggt   2040
aaagccgctg catttgccaa agtgctgaca actggcgctg ataacaattt cacccaggag   2100
acagctactg gtaactacgt gactgtggac gaggacatta tctgtaaagt gattagaaag   2160
gacatttggg agaacggctt caaggtggtg ctcctgtgcc ccactctccc taacgacacc   2220
tacaaactca gcttcggaaa ggacgatgtg gacctggccc agatgtacaa ggattataac   2280
ctgaatatcg ccctcgacat ggctaggtac tgtattcacg atgcttgcct gtgtcagtat   2340
ctctgggagt actatggggt ggaaactaag accgatgccg gtgcttctac ctacgtcctg   2400
cctcagagta tggtgtttga gtatcgagca tccacagtca tcaaagggcc actgctcaag   2460
ctgctcctgg agacaaagac tattctggtg aggagcgaga ccaaacagaa gttcccttac   2520
gaaggcggaa aggtcttcgc tccaaaacag aagatgtttt caaacaatgt gctcatcttc   2580
```

-continued

```
gactacaaca gcctgtatcc caatgtctgc atttttggca acctgtcccc tgagactctc   2640
gtgggagtgg tcgtgtctac caataggctg gaggaagaga tcaacaatca gctcctgctc   2700
cagaagtacc cccctccaag gtatatcaca gtgcattgtg agccaagact gcccaacctc   2760
attagtgaaa tcgccatttt tgacagatca atcgagggca ccattccacg actgctcagg   2820
acattcctgg ctgaacgagc aaggtacaag aaaatgctga aacaggctac cagctccaca   2880
gagaaggcaa tctacgattc catgcagtac acatataaga ttgtcgcaaa cagtgtgtat   2940
gggctcatgg gcttcaggaa cagcgccctg tacagttatg catcagccaa gagctgcact   3000
tccatcggga ggagaatgat tctgtacctg gagagcgtgc tgaacggcgc cgaactctcc   3060
aatggaatgc tgcggtttgc taaccctctg tctaatccat tctatatgga cgatcgcgac   3120
atcaacccaa ttgtcaagac cagcctgccc atcgattaca gattccggtt tcgctcagtc   3180
tatggtgaca cagatagcgt gtttactgaa atcgacagcc aggacgtgga taaatccatc   3240
gagattgcca aggaactgga gagactcatt aacaatcggg tcctgttcaa caattttaaa   3300
atcgagttcg aggctgtgta caagaacctg attatgcaga gcaagaaaaa gtacaccaca   3360
atgaaatatt ccgcatctag taactccaag tctgtccccg agaggatcaa caaggggact   3420
tccgaaaccc ggcgcgacgt gtctaagttc cacaagaaca tgatcaaaac atataagact   3480
cggctgtctg agatgctcag tgaaggtcgc atgaactcta atcaagtgtg tatcgatatt   3540
ctgaggagcc tggagaccga cctgcgctca gaatttgata gccgatcaag ccctctggag   3600
ctcttcatgc tgagccgcat gcaccattcc aactacaagt ctgccgacaa cccaaatatg   3660
tacctggtga cagagtataa caagaacaat cccgaaacta tcgagctggg cgaacggtac   3720
tattttgcat acatttgccc cgccaacgtc ccttggacaa aaaagctggt gaatatcaag   3780
acctatgaga caatcattga ccgaagtttc aaactgggat cagatcagag gatcttctac   3840
gaagtgtatt ttaagagact gacttccgag atcgtcaacc tgctcgataa caaggtgctg   3900
tgtatttctt tctttgaacg catgttcgga agtaaaccca ccttttacga ggctctcgag   3960
tctagagggc ccgtttaaac ccgctgatca gcctcgactg tgccttctag ttgccagcca   4020
tctgttgttt gcccctcccc cgtgccttcc ttgaccctgg aaggtgccac tcccactgtc   4080
ctttcctaat aaaatgagga aattgcatcg cattgtctga gtaggtgtca ttctattctg   4140
gggggtgggg tggggcagga cagcaagggg gaggattggg aagacaatag caggcatgct   4200
ggggatgcgg tgggctctat ggcttctgag gcggaaagaa ccagctgggg ctctaggggg   4260
tatccccacg cgccctgtag cggcgcatta agcgcggcgg gtgtggtggt tacgcgcagc   4320
gtgaccgcta cacttgccag cgccctagcg cccgctcctt tcgctttctt cccttccttt   4380
ctcgccacgt tcgccggctt tccccgtcaa gctctaaatc gggggctccc tttagggttc   4440
cgatttagtg ctttacggca cctcgacccc aaaaaacttg attagggtga tggttcacgt   4500
agtgggccat cgccctgata gacggttttt cgccctttga cgttggagtc cacgttcttt   4560
aatagtggac tcttgttcca aactggaaca acactcaacc ctatctcggt ctattctttt   4620
gatttataag ggattttgcc gatttcggcc tattggttaa aaaatgagct gatttaacaa   4680
aaatttaacg cgaattaatt ctgtggaatg tgtgtcagtt agggtgtgga aagtccccag   4740
gctccccagc aggcagaagt atgcaaagcc tatcaggaca tagcgttggc tacccgtgat   4800
attgctgaag agcttggcgg cgaatgggct gaccgcttcc tcgtgcttta cggtatcgcc   4860
gctcccgatt cgcagcgcat cgccttctat cgccttcttg acgagttctt ctgagcggga   4920
```

-continued

```
ctctggggtt cgaaatgacc gaccaagcga cgcccaacct gccatcacga gatttcgatt   4980
ccaccgccgc cttctatgaa aggttgggct tcggaatcgt tttccgggac gccggctgga   5040
tgatcctcca gcgcggggat ctcatgctgg agttcttcgc ccaccccaac ttgtttattg   5100
cagcttataa tggttacaaa taaagcaata gcatcacaaa tttcacaaat aaagcatttt   5160
tttcactgca ttctagttgt ggtttgtcca aactcatcaa tgtatcttat catgtctgta   5220
taccgtcgac ctctagctag agcttggcgt aatcatggtc atagctgttt cctgtgtgaa   5280
attgttatcc gctcacaatt ccacacaaca tacgagccgg aagcataaag tgtaaagcct   5340
ggggtgccta atgagtgagc taactcacat taattgcgtt gcgctcactg cccgctttcc   5400
agtcgggaaa cctgtcgtgc cagctgcatt aatgaatcgg ccaacgcgcg gggagaggcg   5460
gtttgcgtat tgggcgctct tccgcttcct cgctcactga ctcgctgcgc tcggtcgttc   5520
ggctgcggcg agcggtatca gctcactcaa aggcggtaat acggttatcc acagaatcag   5580
gggataacgc aggaaagaac atgtgagcaa aaggccagca aaaggccagg aaccgtaaaa   5640
aggccgcgtt gctggcgttt ttccataggc tccgcccccc tgacgagcat cacaaaaatc   5700
gacgctcaag tcagaggtgg cgaaacccga caggactata aagataccag gcgtttcccc   5760
ctggaagctc cctcgtgcgc tctcctgttc cgaccctgcc gcttaccgga tacctgtccg   5820
cctttctccc ttcgggaagc gtggcgcttt ctcatagctc acgctgtagg tatctcagtt   5880
cggtgtaggt cgttcgctcc aagctgggct gtgtgcacga accccccgtt cagcccgacc   5940
gctgcgcctt atccggtaac tatcgtcttg agtccaaccc ggtaagacac gacttatcgc   6000
cactggcagc agccactggt aacaggatta gcagagcgag gtatgtaggc ggtgctacag   6060
agttcttgaa gtggtggcct aactacggct acactagaag aacagtattt ggtatctgcg   6120
ctctgctgaa gccagttacc ttcggaaaaa gagttggtag ctcttgatcc ggcaaacaaa   6180
ccaccgctgg tagcggtttt tttgtttgca agcagcagat tacgcgcaga aaaaaaggat   6240
ctcaagaaga tcctttgatc ttttctacgg ggtctgacgc tcagtggaac gaaaactcac   6300
gttaagggat tttggtcatg agattatcaa aaaggatctt cacctagatc cttttaaatt   6360
aaaaatgaag ttttaaatca atctaaagta tatatgagta aacttggtct gacagttacc   6420
aatgcttaat cagtgaggca cctatctcag cgatctgtct atttcgttca tccatagttg   6480
cctgactccc cgtcgtgtag ataactacga tacgggaggg cttaccatct ggccccagtg   6540
ctgcaatgat accgcgagac ccacgctcac cggctccaga tttatcagca ataaaccagc   6600
cagccggaag ggccgagcgc agaagtggtc ctgcaacttt atccgcctcc atccagtcta   6660
ttaattgttg ccgggaagct agagtaagta gttcgccagt taatagtttg cgcaacgttg   6720
ttgccattgc tacaggcatc gtggtgtcac gctcgtcgtt tggtatggct tcattcagct   6780
ccggttccca acgatcaagg cgagttacat gatcccccat gttgtgcaaa aaagcggtta   6840
gctccttcgg tcctccgatc gttgtcagaa gtaagttggc cgcagtgtta tcactcatgg   6900
ttatggcagc actgcataat tctcttactg tcatgccatc cgtaagatgc ttttctgtga   6960
ctggtgagta ctcaaccaag tcattctgag aatagtgtat gcggcgaccg agttgctctt   7020
gcccggcgtc aatacgggat aataccgcgc cacatagcag aactttaaaa gtgctcatca   7080
ttggaaaacg ttcttcgggg cgaaaactct caaggatctt accgctgttg agatccagtt   7140
cgatgtaacc cactcgtgca cccaactgat cttcagcatc ttttactttc accagcgttt   7200
ctgggtgagc aaaaacagga aggcaaaatg ccgcaaaaaa gggaataagg gcgacacgga   7260
aatgttgaat actcatactc ttcctttttc aatattattg aagcatttat cagggttatt   7320
```

gtctcatgag cggatacata tttgaatgta tttagaaaaa taaacaaata ggggttccgc 7380
gcacatttcc ccgaaaagtg ccacctgacg tc 7412

<210> SEQ ID NO 145
<211> LENGTH: 5601
<212> TYPE: DNA
<213> ORGANISM: Artificial Sequence
<220> FEATURE:
<223> OTHER INFORMATION: pExodus Rad2

<400> SEQUENCE: 145
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atggggatac agggattgct acaatttatc aaagaagctt cagaacccat ccatgtgagg 960
aagtataaag ggcaggtagt agctgtggat acatattgct ggcttcacaa aggagctatt 1020
gcttgtgctg aaaaactagc caaaggtgaa cctactgata ggtatgtagg attttgtatg 1080
aaatttgtaa atatgttact atctcatggg atcaagccta ttctcgtatt tgatggatgt 1140
actttacctt ctaaaaagga agtagagaga tctagaagag aaagacgaca agccaatctt 1200
cttaagggaa agcaacttct tcgtgagggg aaagtctcgg aagctcgaga gtgtttcacc 1260
cggtctatca atatcacaca tgccatggcc cacaaagtaa ttaaagctgc ccggtctcag 1320
ggggtagatt gcctcgtggc tccctatgaa gctgatgcgc agttggccta tcttaacaaa 1380
gcgggaattg tgcaagccat aattacagag gactcggatc tcctagcttt tggctgtaaa 1440
aaggtaattt taaagatgga ccagtttgga aatggacttg aaattgatca agctcggcta 1500
ggaatgtgca gacagcttgg ggatgtattc acggaagaga agtttcgtta catgtgtatt 1560
ctttcaggtt gtgactacct gtcatcactg cgtgggattg gattagcaaa ggcatgcaaa 1620
gtcctaagac tagccaataa tccagatata gtaaaggtta tcaagaaaat tggacattat 1680
ctcaagatga atatcacggt accagaggat tacatcaacg ggtttattcg ggccaacaat 1740
accttcctct atcagctagt ttttgatccc atcaaaagga aacttattcc tctgaacgcc 1800
tatgaagatg atgttgatcc tgaaacacta agctacgctg ggcaatatgt tgatgattcc 1860
atagctcttc aaatagcact tggaaataaa gatataaata cttttgaaca gatcgatgac 1920

-continued

```
tacaatccag acactgctat gcctgcccat tcaagaagtc atagttggga tgacaaaaca   1980
tgtcaaaagt cagctaatgt tagcagcatt tggcatagga attactctcc cagaccagag   2040
tcgggtactg tttcagatgc ccccacaattg aaggaaaatc caagtgagga tccactagtc   2100
cagtgtggtg gaattctgca gatatccagc acagtggcgg ccgctcgagt ctagagggcc   2160
cgtttaaacc cgctgatcag cctcgactgt gccttctagt tgccagccat ctgttgtttg   2220
cccctccccc gtgccttcct tgaccctgga aggtgccact cccactgtcc tttcctaata   2280
aaatgaggaa attgcatcgc attgtctgag taggtgtcat tctattctgg ggggtggggt   2340
ggggcaggac agcaaggggg aggattggga agacaatagc aggcatgctg gggatgcggt   2400
gggctctatg gcttctgagg cggaaagaac cagctggggc tctagggggt atccccacgc   2460
gccctgtagc ggcgcattaa gcgcggcggg tgtggtggtt acgcgcagcg tgaccgctac   2520
acttgccagc gccctagcgc ccgctccttt cgctttcttc ccttcctttc tcgccacgtt   2580
cgccggcttt ccccgtcaag ctctaaatcg ggggctccct ttagggttcc gatttagtgc   2640
tttacggcac ctcgacccca aaaaacttga ttagggtgat ggttcacgta gtgggccatc   2700
gccctgatag acggtttttc gccctttgac gttggagtcc acgttcttta atagtggact   2760
cttgttccaa actggaacaa cactcaaccc tatctcggtc tattcttttg atttataagg   2820
gattttgccg atttcggcct attggttaaa aaatgagctg atttaacaaa aatttaacgc   2880
gaattaattc tgtggaatgt gtgtcagtta gggtgtggaa agtccccagg ctccccagca   2940
ggcagaagta tgcaaagcct atcaggacat agcgttggct acccgtgata ttgctgaaga   3000
gcttggcggc gaatgggctg accgcttcct cgtgctttac ggtatcgccg ctcccgattc   3060
gcagcgcatc gccttctatc gccttcttga cgagttcttc tgagcgggac tctggggttc   3120
gaaatgaccg accaagcgac gcccaacctg ccatcacgag atttcgattc caccgccgcc   3180
ttctatgaaa ggttgggctt cggaatcgtt ttccgggacg ccggctggat gatcctccag   3240
cgcggggatc tcatgctgga gttcttcgcc caccccaact tgtttattgc agcttataat   3300
ggttacaaat aaagcaatag catcacaaat ttcacaaata aagcattttt ttcactgcat   3360
tctagttgtg gtttgtccaa actcatcaat gtatcttatc atgtctgtat accgtcgacc   3420
tctagctaga gcttggcgta atcatggtca tagctgtttc ctgtgtgaaa ttgttatccg   3480
ctcacaattc cacacaacat acgagccgga agcataaagt gtaaagcctg gggtgcctaa   3540
tgagtgagct aactcacatt aattgcgttg cgctcactgc ccgctttcca gtcgggaaac   3600
ctgtcgtgcc agctgcatta atgaatcggc caacgcgcgg ggagaggcgg tttgcgtatt   3660
gggcgctctt ccgcttcctc gctcactgac tcgctgcgct cggtcgttcg gctgcggcga   3720
gcggtatcag ctcactcaaa ggcggtaata cggttatcca cagaatcagg ggataacgca   3780
ggaaagaaca tgtgagcaaa aggccagcaa aaggccagga accgtaaaaa ggccgcgttg   3840
ctggcgtttt tccataggct ccgcccccct gacgagcatc acaaaaatcg acgctcaagt   3900
cagaggtggc gaaacccgac aggactataa agataccagg cgtttccccc tggaagctcc   3960
ctcgtgcgct ctcctgttcc gaccctgccg cttaccggat acctgtccgc ctttctccct   4020
tcgggaagcg tggcgctttc tcatagctca cgctgtaggt atctcagttc ggtgtaggtc   4080
gttcgctcca agctgggctg tgtgcacgaa ccccccgttc agcccgaccg ctgcgcctta   4140
tccggtaact atcgtcttga gtccaacccg gtaagacacg acttatcgcc actggcagca   4200
gccactggta acaggattag cagagcgagg tatgtaggcg gtgctacaga gttcttgaag   4260
tggtggccta actacggcta cactagaaga acagtatttg gtatctgcgc tctgctgaag   4320
```

```
ccagttacct tcggaaaaag agttggtagc tcttgatccg gcaaacaaac caccgctggt   4380

agcggttttt ttgtttgcaa gcagcagatt acgcgcagaa aaaaaggatc tcaagaagat   4440

cctttgatct tttctacggg gtctgacgct cagtggaacg aaaactcacg ttaagggatt   4500

ttggtcatga gattatcaaa aaggatcttc acctagatcc ttttaaatta aaaatgaagt   4560

tttaaatcaa tctaaagtat atatgagtaa acttggtctg acagttacca atgcttaatc   4620

agtgaggcac ctatctcagc gatctgtcta tttcgttcat ccatagttgc ctgactcccc   4680

gtcgtgtaga taactacgat acgggagggc ttaccatctg gccccagtgc tgcaatgata   4740

ccgcgagacc cacgctcacc ggctccagat ttatcagcaa taaaccagcc agccggaagg   4800

gccgagcgca gaagtggtcc tgcaacttta tccgcctcca tccagtctat taattgttgc   4860

cgggaagcta gagtaagtag ttcgccagtt aatagtttgc gcaacgttgt tgccattgct   4920

acaggcatcg tggtgtcacg ctcgtcgttt ggtatggctt cattcagctc cggttcccaa   4980

cgatcaaggc gagttacatg atcccccatg ttgtgcaaaa aagcggttag ctccttcggt   5040

cctccgatcg ttgtcagaag taagttggcc gcagtgttat cactcatggt tatggcagca   5100

ctgcataatt ctcttactgt catgccatcc gtaagatgct tttctgtgac tggtgagtac   5160

tcaaccaagt cattctgaga atagtgtatg cggcgaccga gttgctcttg cccggcgtca   5220

atacgggata ataccgcgcc acatagcaga actttaaaag tgctcatcat tggaaaacgt   5280

tcttcggggc gaaaactctc aaggatctta ccgctgttga gatccagttc gatgtaaccc   5340

actcgtgcac ccaactgatc ttcagcatct tttactttca ccagcgtttc tgggtgagca   5400

aaaacaggaa ggcaaaatgc cgcaaaaaag ggaataaggg cgacacggaa atgttgaata   5460

ctcatactct tcctttttca atattattga agcatttatc agggttattg tctcatgagc   5520

ggatacatat ttgaatgtat ttagaaaaat aaacaaatag gggttccgcg cacatttccc   5580

cgaaaagtgc cacctgacgt c                                             5601
```

<210> SEQ ID NO 146
<211> LENGTH: 30
<212> TYPE: DNA
<213> ORGANISM: Artificial Sequence
<220> FEATURE:
<223> OTHER INFORMATION: Cleavage site for I-SceI

<400> SEQUENCE: 146

```
agttacgcta gggataacag ggtaatatag                                      30
```

<210> SEQ ID NO 147
<211> LENGTH: 24
<212> TYPE: DNA
<213> ORGANISM: Artificial Sequence
<220> FEATURE:
<223> OTHER INFORMATION: Target site for zinc finger nuclease VF2468.

<400> SEQUENCE: 147

```
accatcttct tcaaggacga cggc                                            24
```

COUPLING ENDONUCLEASES WITH END-PROCESSING ENZYMES DRIVES HIGH EFFICIENCY GENE DISRUPTION

RELATED APPLICATION

The present application is a continuation application of U.S. application Ser. No. 14/949,744, filed Nov. 23, 2015, which is a divisional application of U.S. application Ser. No. 14/173,705, filed on Feb. 5, 2014, which is a divisional application of U.S. application Ser. No. 13,405,183, filed on Feb. 24, 2012, now issued as U.S. Pat. No. 8,673,557, which in turn claims the benefit of priority to U.S. Provisional Patent Application No. 61/447,672, filed Feb. 28, 2011, and the disclosures for each of these related applications are incorporated herein by reference in their entireties.

REFERENCE TO SEQUENCE LISTING

The present application is being filed along with a Sequence Listing in electronic format. The Sequence Listing is provided as a file entitled SCRI-025D1_SUBSTITUTE.TXT, created Feb. 5, 2014, which is 350 kb III Size. The information is the electronic format of the Sequence Listing is incorporated herein by reference in its entirety.

STATEMENT REGARDING FEDERALLY SPONSORED R&D

This invention was made with government support under Grant No. T32 GM07270 awarded by the U.S. National Institute of General Medical Sciences and Grant Nos. RL1CA133832, UL1DE019582, R01-HL075453, PL1-HL092557, RL1-HL092553, RL1-HL92554, and U19-AI96111 awarded by the National Institutes of Health.

FIELD

The present disclosure relates to molecular and cellular biology. Some embodiments relate to genome engineering and the introduction of targeted, site-specific DNA breaks mediated by endonucleases to achieve gene disruption or site-specific recombination. Several embodiments relate to compositions and methods for partial or complete inactivation of a target gene. Some embodiments relate to inactivation of a targeted gene for therapeutic purposes and/or to produce cell lines in which a target gene is inactivated.

BACKGROUND

Targeted gene disruption has wide applicability for research, therapeutic, agricultural, and industrial uses. One strategy for producing targeted gene disruption is through the generation of double-strand DNA breaks caused by site-specific endonucleases. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. One limitation of the zinc finger endonucleases is that low specificity for a target site or the presence of multiple target sites in a genome can result in off-target cleavage events. As Fok1 endonuclease cleaves as a dimer, one strategy to prevent off-target cleavage events has been to design zinc finger domains that bind at adjacent 9 base pair sites.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease.

The mutagenicity of the double strand DNA breaks generated by both the naturally occurring and artificial endonucleases depend upon the precision of DNA repair. The double strand breaks caused by endonucleases are commonly repaired through non-homologous end joining (NHEJ), which is the major DNA double-strand break repair pathway for many organisms. NHEJ is referred to as "non-homologous" because the break ends are ligated directly without the need for a homologous template, in contrast to homologous recombination, which utilizes a homologous sequence to guide repair. Imprecise repair through this pathway can result in mutations at the break site, such as DNA base deletions and insertions as well as translocations and telomere fusion. When the mutations are made within the coding sequence of a gene, they can render the gene and its subsequent protein product non-functional, creating a targeted gene disruption or "knockout" of the gene.

Double strand DNA break repair through the NHEJ pathway is often not mutagenic. The majority of endonuclease-induced breaks repaired by the NHEJ pathway involve precise re-ligation, resulting in the restoration of the original DNA sequence. This is especially true of the types of DNA breaks created by the current endonuclease platforms available for engineering site-specificity, namely homing endonucleases (meganucleases) and zinc finger nucleases. Both of these types of enzymes leave compatible base pair overhangs that do not require processing prior to re-ligation by the NHEJ pathway. When the overhangs are compatible, NHEJ repairs the break with a high degree of accuracy. Thus, from a genome engineering standpoint, many of the cleavage events generated by the current site-specific endonuclease platforms are unproductive.

The need for additional solutions to these problems is manifest.

SUMMARY

Mutagenesis of cellular DNA can occur when a DNA cleavage event is followed by imprecise end joining during DNA repair. As disclosed herein, one strategy for increasing the frequency of imprecise DNA repair events is by modifying compatible overhangs generated at double-strand DNA breaks with an end-processing enzyme. The methods and compositions described herein are broadly applicable and may involve any agent of interest which generates either blunt ends or compatible overhangs upon cleaving double stranded DNA, for example, nucleases, ionizing radiation, such as x-rays and gamma rays, as well as drugs such as bleomycin, cisplatin, and mitomycin C. Several embodiments disclosed herein relate to methods for coupling the generation of double-strand DNA breaks to modification of compatible overhangs generated at the cleavage site with a DNA end-processing enzyme. Several embodiments disclosed herein relate to methods for coupling the generation of double-strand DNA breaks to modification of blunt ends generated at the cleavage site with an end-processing enzyme. Some embodiments disclosed herein relate to methods for coupling the generation of double-strand DNA breaks to cleavage of the exposed phosphodiester bonds at the DNA break site by an exonuclease. Some embodiments disclosed herein relate to methods for coupling the generation of double-strand DNA breaks to the addition of DNA bases to an exposed DNA end by a non-template polymerase.

In yet another aspect, the methods and compositions described herein are broadly applicable and may involve any agent of interest which generates breaks in a polynucleatide. Several embodiments disclosed herein relate to methods for coupling the generation of polynucleotide breaks to modification of polynucleotide ends generated at the cleavage site with an end-processing enzyme. In some embodiments, the polynucleotide may be double stranded DNA, single stranded DNA, stranded RNA, single stranded RNA, double stranded DNA/RNA hybrids and synthetic polynucleotides.

Several embodiments disclosed herein relate to a strategy for increasing the frequency of imprecise DNA repair events by modifying compatible overhangs generated at exonuclease-induced DNA breaks with a DNA end-processing enzyme. Several embodiments disclosed herein relate to methods for coupling site-specific cleavage of a targeted DNA sequence to modification of compatible overhangs generated at the cleavage site with a DNA end-processing enzyme. Several embodiments disclosed herein relate to methods for coupling site-specific cleavage of a targeted DNA sequence to modification of blunt DNA ends generated at the cleavage site with a DNA end-processing enzyme. Some embodiments disclosed herein relate to methods for coupling site-specific cleavage of a targeted DNA sequence by an endonuclease to cleavage of the exposed phosphodiester bonds at the DNA cleavage site by an exonuclease. Some embodiments disclosed herein relate to methods for coupling site-specific cleavage of a targeted DNA sequence by an endonuclease to the addition of DNA bases to an exposed DNA end by a non-template polymerase. Some embodiments disclosed herein relate to methods for coupling site-specific cleavage of a targeted DNA sequence by an endonuclease to removal of a 5'phosphate at the DNA cleavage site by a 5'-phosphatase. Some embodiments disclosed herein relate to methods for coupling site-specific cleavage of a targeted DNA sequence by an endonuclease to removal of a 3'phosphate at the DNA cleavage site by a 3'phosphatase. Further disclosed herein are fusion proteins, comprising one or more site-specific endonuclease domains tethered to one or more DNA end-processing domains.

Non-limiting examples of endonucleases include homing endonucleases (meganucleases), zinc finger nucleases and TAL effector nucleases. The endonucleases may comprise heterologous DNA-binding and cleavage domains (e.g., zinc finger nucleases; homing endonuclease DNA-binding domains with heterologous cleavage domains or TAL-effector domain nuclease fusions) or, alternatively, the DNA-binding domain of a naturally-occurring nuclease may be altered to bind to a selected target site (e.g., a homing endonuclease that has been engineered to bind to site different than the cognate binding site or a TAL-effector domain nuclease fusion).

Non-limiting examples of DNA end-processing enzymes include 5-3'exonucleases, 3-5'exonucleases, 5-3' alkaline exonucleases, 5' flap endonucleases, helicases, phosphatases, hydrolases and template-independent DNA polymerases. The exonucleases may comprise heterologous DNA-binding and end-processing domains (e.g., a zinc finger and an exonuclease domain).

Several embodiments relate to co-expression of one or more endonucleases (enzymes that incise DNA at a specific internal target site) with one or more end-processing enzymes, in order to achieve enhanced processing of the polynucleotide ends produced by endonuclease-mediated polynucleotide cleavage. Several embodiments relate to co-expression of one or more endonucleases with one or more exonucleases (enzymes that catalyzes the removal of polynucleotide bases from an exposed polynucleotide end) in order to achieve enhanced processing of the polynucleotide ends produced by endonuclease-mediated polynucleotide cleavage. Several embodiments relate to co-expression of one or more endonucleases with one or more non-templative polymerases (enzymes that catalyze the addition of DNA bases to an exposed DNA end) in order to achieve enhanced processing of the DNA ends produced by endonuclease-mediated DNA cleavage. Several embodiments relate to co-expression of one or more endonucleases with one or more phosphatases that catalyze the removal of a 5' phosphate in order to achieve enhanced processing of the polynucleotide ends produced by endonuclease-mediated polynucleotide cleavage. Several embodiments relate to co-expression of one or more endonucleases with one or more phosphatases that catalyze the removal of a 3' phosphate in order to achieve enhanced processing of the polynucleotide ends produced by endonuclease-mediated polynucleotide cleavage. In some embodiments, an endonuclease is coupled to an end-processing enzyme.

Several embodiments relate to co-expression of one or more endonucleases (enzymes that incise DNA at a specific internal target site) with one or more DNA end-processing enzymes, in order to achieve enhanced processing of the DNA ends produced by endonuclease-mediated DNA cleavage. Several embodiments relate to co-expression of one or more endonucleases with one or more exonucleases (enzymes that catalyzes the removal of DNA bases from an exposed DNA end) in order to achieve enhanced processing of the DNA ends produced by endonuclease-mediated DNA cleavage. Several embodiments relate to co-expression of one or more endonucleases with one or more non-templative polymerases (enzymes that catalyze the addition of DNA bases to an exposed DNA end) in order to achieve enhanced processing of the DNA ends produced by endonuclease-mediated DNA cleavage. Several embodiments relate to co-expression of one or more endonucleases with one or more phosphatases that catalyze the removal of a 5' phosphate in order to achieve enhanced processing of the DNA ends produced by endonuclease-mediated DNA cleavage. Several embodiments relate to co-expression of one or more endonucleases with one or more phosphatases that catalyze the removal of a 3' phosphate in order to achieve enhanced processing of the DNA ends produced by endonuclease-mediated DNA cleavage. In some embodiments, an endonuclease is coupled to a DNA end-processing enzyme.

In one aspect, a method for improving the mutation frequency associated with endonuclease mediated cleavage of cellular DNA in a region of interest (e.g., a method for targeted disruption of genomic sequences) is provided, the method comprising: (a) selecting a sequence in the region of interest; (b) selecting a site-specific endonuclease which cleaves the sequence within the region of interest; and (c) delivering one or more fusion proteins to the cell, the fusion protein(s) comprising one or more site-specific endonuclease domains and one or more DNA end-processing domains; wherein the endonuclease domain cleaves the DNA in the region of interest. In some embodiments, a fusion protein can be delivered to a cell by delivering a polynucleotide encoding the fusion protein to a cell. In some embodiments the polynucleotide is DNA. In other embodiments, the polynucleotide is RNA. In some embodiments, a fusion protein can be expressed in a cell by delivering a DNA vector encoding the fusion protein to a cell, wherein the DNA vector is transcribed and the mRNA transcription product is translated to generate the fusion protein. In some embodiments, a fusion protein can be expressed in a cell by delivering an RNA molecule encoding the fusion protein to the cell wherein the RNA molecule is translated to generate the fusion protein. In some embodiments, a fusion protein may be delivered directly to the cell.

In another aspect, a method for improving the mutation frequency associated with endonuclease mediated cleavage of cellular DNA in a region of interest (e.g., a method for targeted disruption of genomic sequences) is provided, the method comprising: (a) selecting a sequence in the region of interest; (b) selecting one or more site-specific endonucleases which cleaves the sequence within the region of interest; and (c) co-expressing the one or more selected endonuclease and one or more end-processing enzyme in the cell; wherein the endonuclease cleaves the DNA in the region of interest and the end-processing enzyme modifies the DNA ends exposed by the endonuclease. The nucleases and end-processing enzymes can be expressed in a cell, e.g., by delivering the proteins to the cell or by delivering one or more polynucleotides encoding the nucleases to a cell. In some embodiments, a single polynucleotide encodes both the one or more endonucleases and the one or more end-processing enzymes under the control of a single promoter. In some embodiments, one or more endonucleases and one or more end-processing enzymes are coupled by one or more T2A “skip” peptide motifs. In some embodiments, one or more endonucleases and one or more end-processing enzymes are encoded by separate polynucleotides. In some embodiments, expression of the DNA end-processing enzyme precedes that of the endonuclease.

In yet another aspect, a method for improving the mutation frequency associated with endonuclease mediated cleavage of cellular DNA in multiple regions of interest (e.g., a method for targeted disruption of multiple genomic sequences) is provided, the method comprising: (a) selecting a first sequence in a first region of interest; (b) selecting a first site-specific endonuclease which cleaves the first sequence within the first region of interest; (c) selecting a second sequence in a second region of interest; (d) selecting a second site-specific endonuclease which cleaves the second sequence within the second region of interest and (c) co-expressing the selected endonucleases and one or more end-processing enzymes in the cell; wherein the first endonuclease cleaves the DNA in the first region of interest, the second endonuclease cleaves the DNA in the second region of interest and the one or more end-processing enzymes modify the exposed DNA ends. The nucleases and end-processing enzyme(s) can be expressed in a cell, e.g., by delivering the proteins to the cell or by delivering one or more polynucleotides encoding the nucleases and end-processing enzyme(s) to a cell. In some embodiments, a single polynucleotide encodes both the first and second endonucleases and the one or more end-processing enzyme under the control of a single promoter. In some embodiments, the endonucleases and the end-processing enzyme(s) are coupled by one or more T2A “skip” peptide motifs. In some embodiments, the first and second regions of interest are in the same gene. In other embodiments, the first and second regions of interest are in different genes. In some embodiments the method further comprises co-expression of a third, fourth, fifth, sixth, seventh, eighth, ninth, and/or tenth endonuclease in the cell.

In yet another aspect, the disclosure provides a method for treating or preventing, or inhibiting HIV infection or ameliorating a condition associated with HIV in a subject, the method comprising: (a) introducing, into a cell, a first nucleic acid encoding a first polypeptide, wherein the first polypeptide comprises: (i) a zinc finger DNA-binding domain that is engineered to bind to a first target site in the CCR5 gene; and (ii) a cleavage domain; and (iii) an end-processing domain under conditions such that the polypeptide is expressed in the cell, whereby the polypeptide binds to the target site and cleaves the CCR5 gene and end-processing enzyme domain modifies the endonuclease cleavage site; and (b) introducing the cell into the subject. In certain embodiments, the cell is selected from the group consisting of a hematopoietic stem cell, a T-cell, a macrophage, a dendritic cell, and an antigen-presenting cell.

In yet another aspect, the disclosure provides a method for treating or preventing or inhibiting HIV infection or ameliorating a condition associated with HIV in a subject, the method comprising: (a) introducing, into a cell, a first nucleic acid encoding a first polypeptide and a second polypeptide, wherein the first polypeptide comprises: (i) a zinc finger DNA-binding domain that is engineered to bind to a first target site in the CCR5 gene; and (ii) a cleavage domain; and the second polypeptide comprises a end-processing enzyme under conditions such that the polypeptides are co-expressed in the cell, whereby the first polypeptide binds to the target site and cleaves the CCR5 gene and the end-processing enzyme modifies the exposed DNA ends created at the endonuclease cleavage site; and (b) introducing the cell into the subject. In certain embodiments, the cell is selected from the group consisting of a hematopoietic stem cell, a T-cell, a macrophage, a dendritic cell and an antigen-presenting cell.

In another aspect, the disclosure provides a method for treating or preventing or inhibiting HIV infection or ameliorating a condition associated with HIV in a subject, the method comprising: (a) introducing, into a cell, a nucleic acid encoding a polypeptide, wherein the polypeptide comprises: (i) a homing endonuclease domain that is engineered to bind to a first target site in the CCR5 gene; and (ii) a end-processing domain under conditions such that the polypeptide is expressed in the cell, whereby the polypeptide binds to the target site and cleaves the CCR5 gene and modifies the exposed DNA ends created at the cleavage site; and (b) introducing the cell into the subject. In certain embodiments, the DNA end-processing domain comprises an exonuclease.

In another aspect, the disclosure provides a method for treating or preventing or inhibiting HIV infection or ameliorating a condition associated with HIV in a subject, the method comprising: (a) introducing, into a cell, a nucleic acid encoding a first polypeptide and a second polypeptide, wherein the first polypeptide comprises a homing endonuclease that is engineered to bind to a target site in the CCR5 gene; and the second polypeptide comprises a end-processing enzyme under conditions such that the polypeptides are co-expressed in the cell, whereby the first polypeptide binds to the target site and cleaves the CCR5 gene and the end-processing enzyme modifies the exposed DNA ends created at the endonuclease cleavage site; and (b) introducing the cell into the subject. In certain embodiments, the end-processing enzyme comprises an exonuclease. In some embodiments, the homing endonuclease and the end-processing enzyme are coupled by one or more T2A "skip" peptide motifs.

In yet another aspect, the disclosure provides a method for treating or preventing or inhibiting HIV infection or ameliorating a condition associated with HIV in a subject, the method comprising: (a) introducing, into a cell, a first nucleic acid encoding a first polypeptide, wherein the first polypeptide comprises: a homing endonuclease that is engineered to bind to a first target site in the CCR5 gene; and (b) introducing, into the cell, a second nucleic acid encoding a second polypeptide, wherein the second polypeptide comprises: a end-processing enzyme; under conditions such that the polypeptides are expressed in the cell, whereby the homing endonuclease binds to the target site and cleaves the CCR5 gene and the end-processing enzyme modifies the exposed DNA ends created at the endonuclease cleavage site; and (b) introducing the cell into the subject. In certain embodiments, the end-processing enzyme comprises an exonuclease. In some embodiments, expression of the end-processing enzyme precedes that of the endonuclease.

In another aspect, the disclosure provides a method for treating or preventing or inhibiting hyper IGE syndrome or ameliorating a condition associated with hyper IGE syndrome a subject, the method comprising: (a) introducing, into one or more cells, a nucleic acid encoding a polypeptide, wherein the polypeptide comprises: (i) a homing endonuclease domain that is engineered to bind to a first target site in the Stat3 gene; and (ii) a end-processing domain under conditions such that the polypeptide is expressed in the cell, whereby the polypeptide binds to the target site and cleaves the Stat3 gene and modifies the exposed DNA ends created at the endonuclease cleavage site. In certain embodiments, the end-processing enzyme domain comprises an exonuclease.

In yet another aspect, the disclosure provides a method for treating or preventing or inhibiting hyper IGE syndrome or ameliorating a condition associated with hyper IGE syndrome a subject, the method comprising: (a) introducing, into a cell, a first nucleic acid encoding a first polypeptide, wherein the first polypeptide comprises: a homing endonuclease that is engineered to bind to a first target site in the STAT3 gene; and (b) introducing, into the cell, a second nucleic acid encoding a second polypeptide, wherein the second polypeptide comprises: a end-processing enzyme; under conditions such that the polypeptides are expressed in the cell, whereby the homing endonuclease binds to the target site and cleaves the STAT3 gene and the end-processing enzyme modifies the exposed DNA ends created at the endonuclease cleavage site. In certain embodiments, the end-processing enzyme comprises an exonuclease. In some embodiments, the expression of the end-processing enzyme precedes that of the endonuclease.

In yet another aspect, the disclosure provides a method for treating or preventing or inhibiting hyper IGE syndrome or ameliorating a condition associated with hyper IGE syndrome a subject, the method comprising: (a) introducing, into a cell, a nucleic acid encoding a first polypeptide and a second polypeptide, wherein the first polypeptide comprises a homing endonuclease that is engineered to bind to a first target site in the STAT3 gene and the second polypeptide comprises a end-processing enzyme; under conditions such that the polypeptides are co-expressed in the cell, whereby the homing endonuclease binds to the target site and cleaves the STAT3 gene and the end-processing enzyme modifies the exposed DNA ends created at the endonuclease cleavage site. In certain embodiments, the end-processing enzyme comprises an exonuclease. In some embodiments, the homing endonuclease and the end-processing enzyme are coupled by one or more T2A "skip" peptide motifs.

BRIEF DESCRIPTION OF THE DRAWINGS

FIGS. 6A and 6B shows the results of DNA sequencing of amplicons surrounding the I-SceI target site in HEK293

Traffic Light Reporter cells treated with I-SceI-IRES-BFP or I-SceI-T2A-Trex2-IRES-BFP.

Figure 5A:
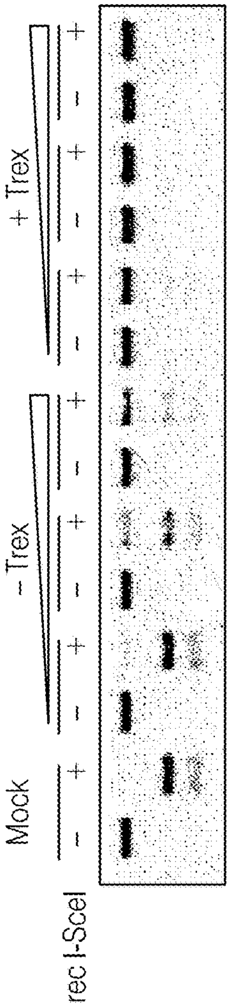
FIG. 5A shows an I-SceI restriction digest of amplicons flanking the I-SceI target site from HEK293 cells harboring traffic light reporter sorted by BFP expression levels follow transfection with expression constructs as indicated in FIG. 4A and FIG. 4B.
Figure 5B:
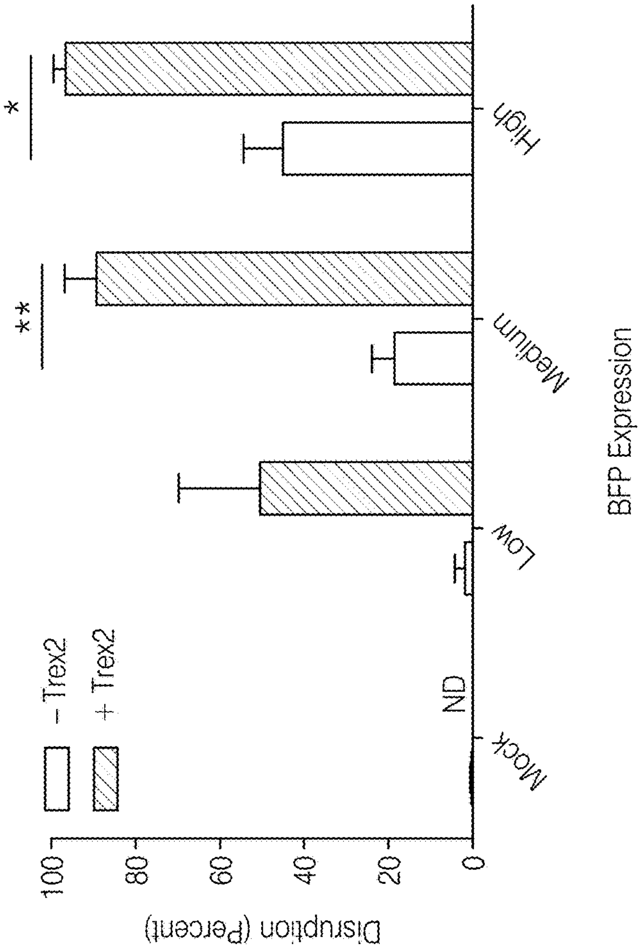
FIG. 5B shows quantification of three independent experiments as described in FIG. 5A.
Figure 7:
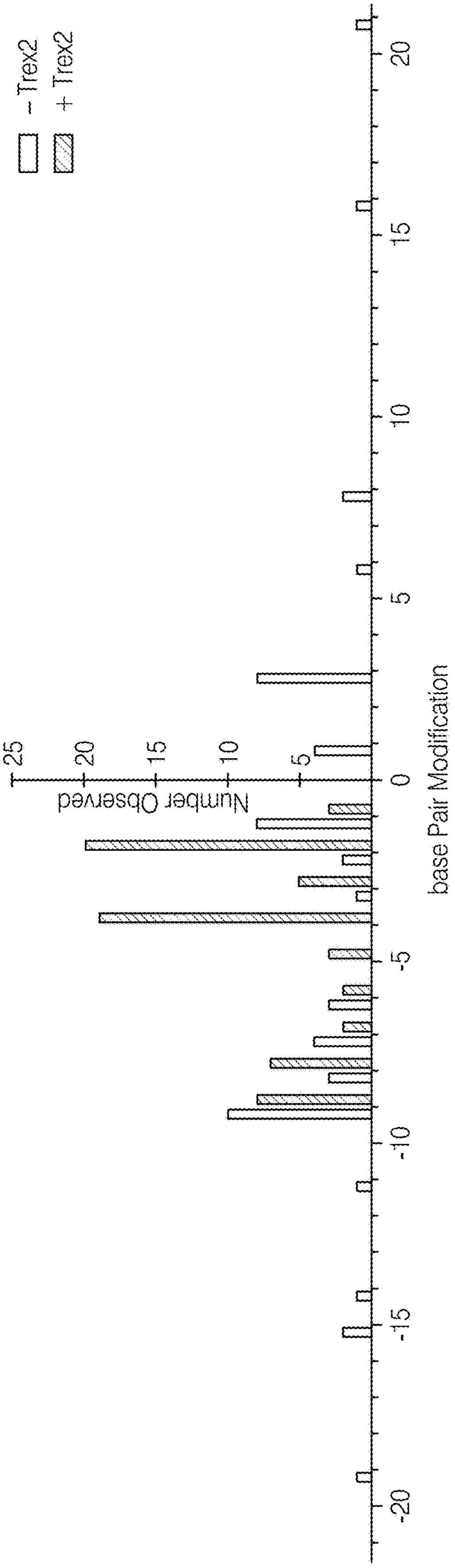

FIG. 7 shows a graph scoring observed mutations (deletions are negative, insertions are positive) at the I-SceI target site following transfection of HEK293 Traffic Light Reporter cells with I-SceI-IRES-BFP or I-SceI-T2A-Trex2-IRES-BFP as described in FIG. 5.

Figure 8A:
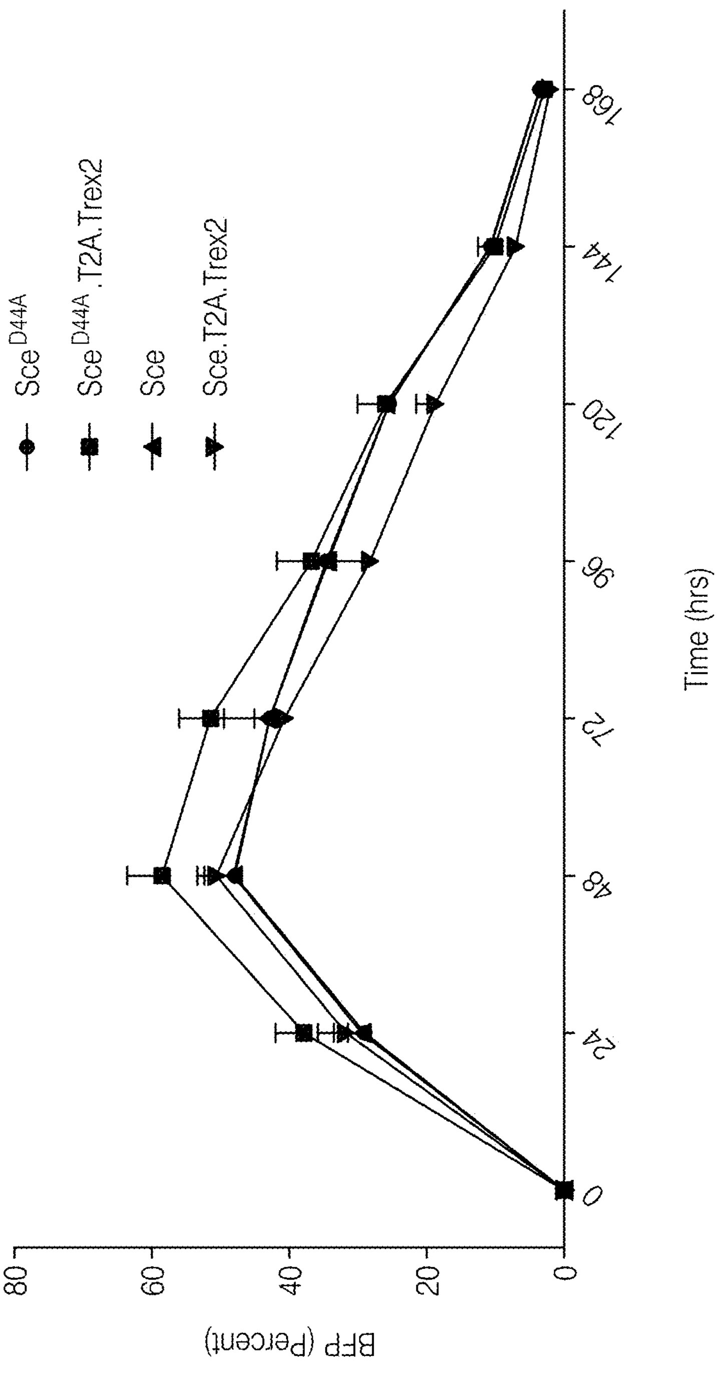
Figure 8B:
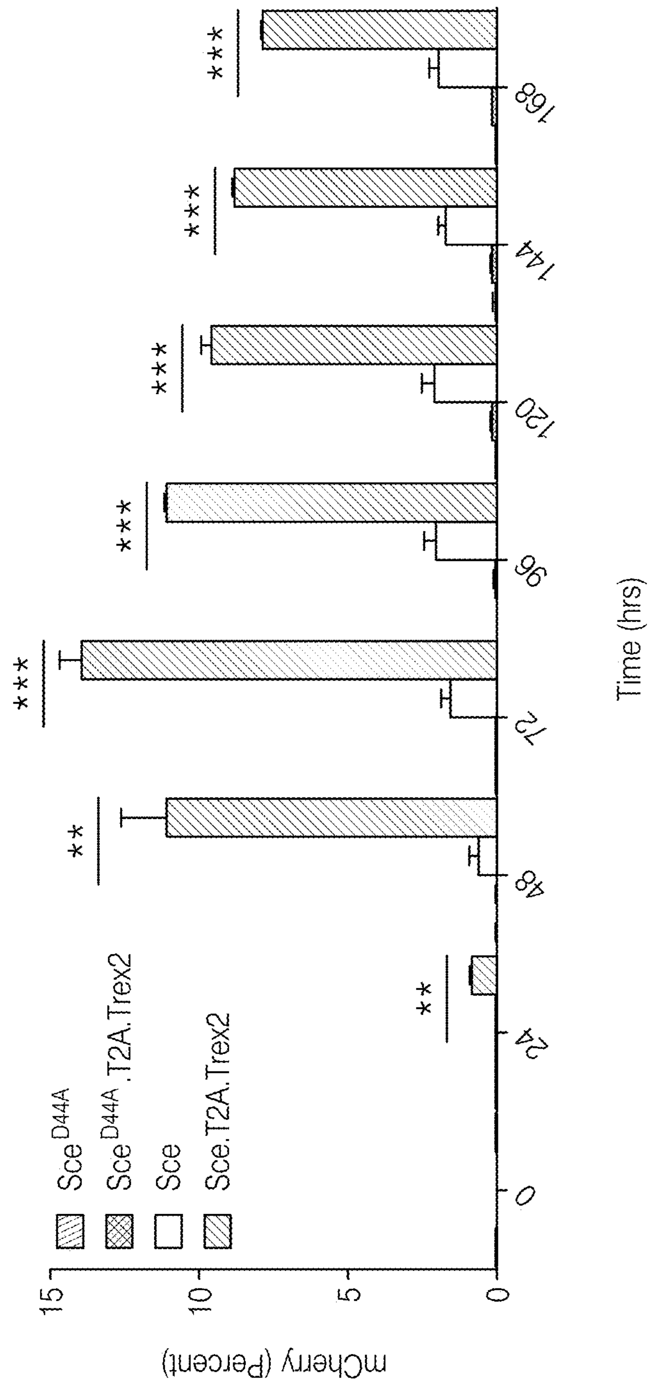
Figure 9A:
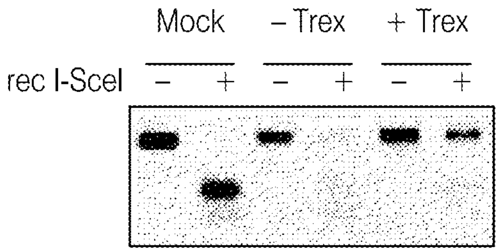
Figure 9B:
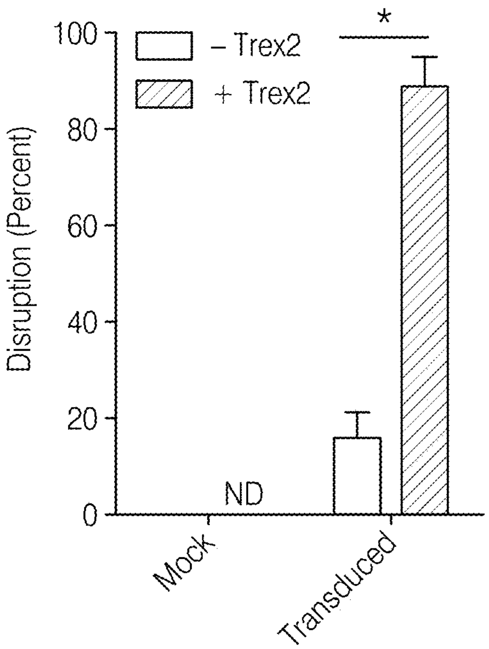
Figure 9C:
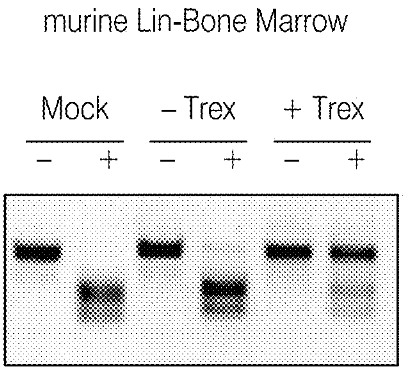
Figure 9D:
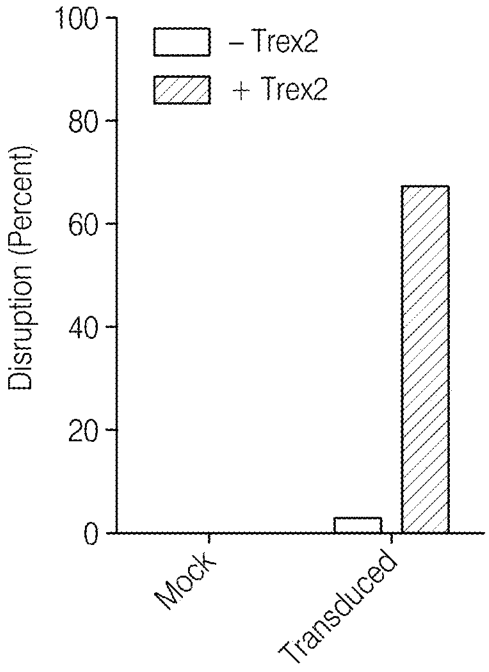

FIG. 8A shows a kinetic time course analysis demonstrating transient expression of I-SceI-T2A-Trex2-IRES-BFP after transfection into HEK293 cells harboring Traffic Light Reporter. The constructs shown are tagged to BFP by an IRES sequence downstream of either I-SceI or Trex2. FIG. 8B shows a graph quantifying 3 experiments of HEK293T cells transfected with the vectors indicated in FIG. 8A, analyzed at the indicated time-points. Cherry indicates gene disruption rates observed in transfected cells. FIG. 9A shows an I-SceI restriction digest of amplicons from primary murine embryonic fibroblasts spanning an I-SceI target site 72 hours post transduction with I-SceI-IRES BFP or I-SceI-T2A-Trex2-IRES-BFP. FIG. 9B shows a graph quantifying cleavage site disruption in 2 independent experiments. FIG. 9C shows an I-SceI restriction digest of amplicons from lineage depleted bone marrow spanning an I-SceI target site 72 hours post transduction with I-SceI-IRES BFP or I-SceI-T2A-Trex2-IRES-BFP. FIG. 9D shows quantification of bands from FIG. 9C.

Figure 10:
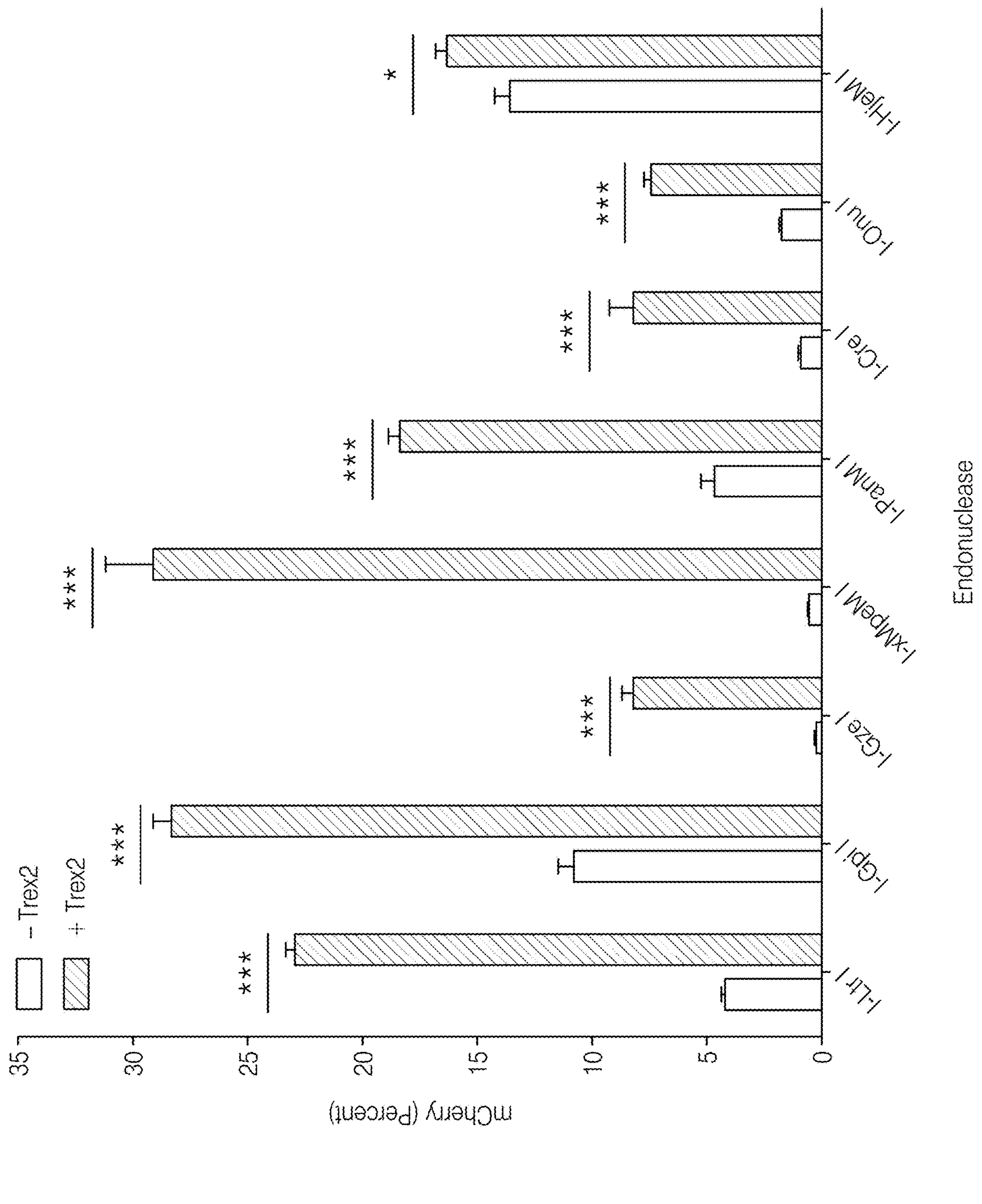

FIG. 10 shows a graph quantifying gene disruption rates of several different homing endonucleases with and without Trex2 exonuclease as measured by HEK293 cells harboring Traffic Light Reporters with respective target sites for the indicated homing endonucleases.

Figure 11A:
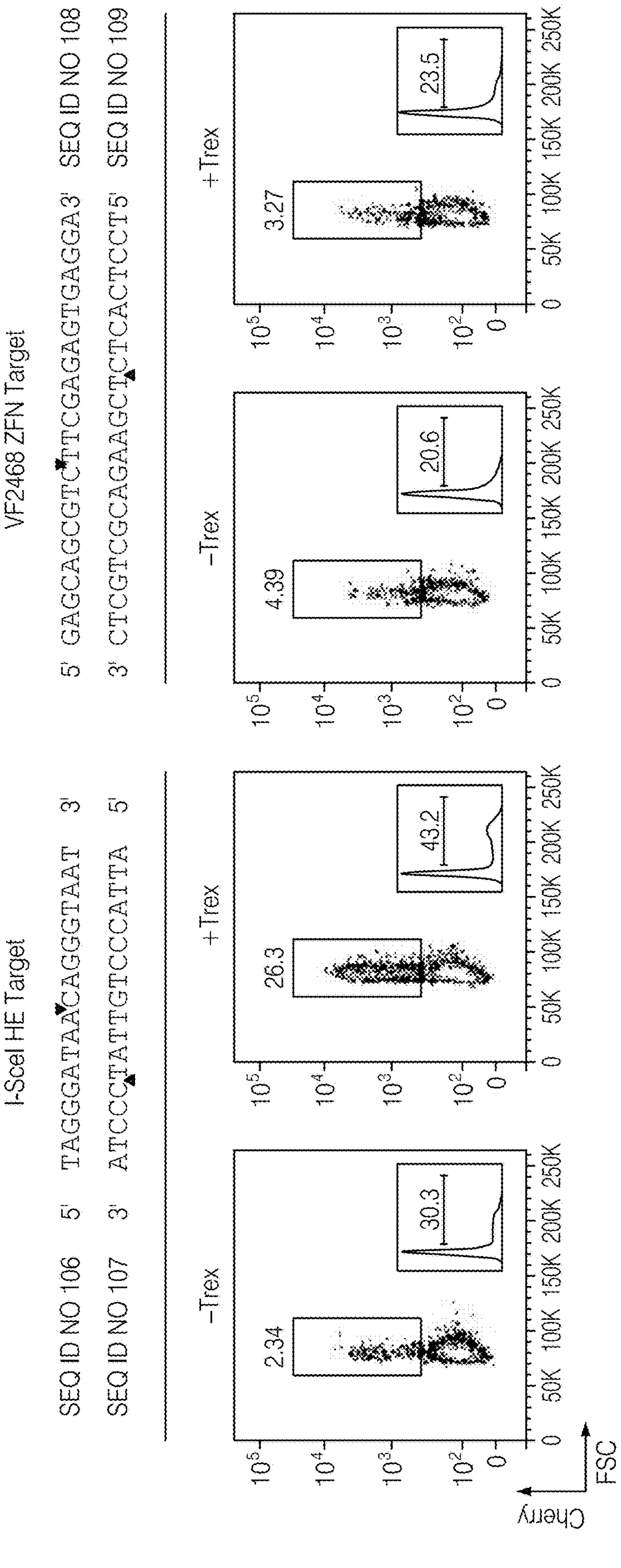
Figure 11C:
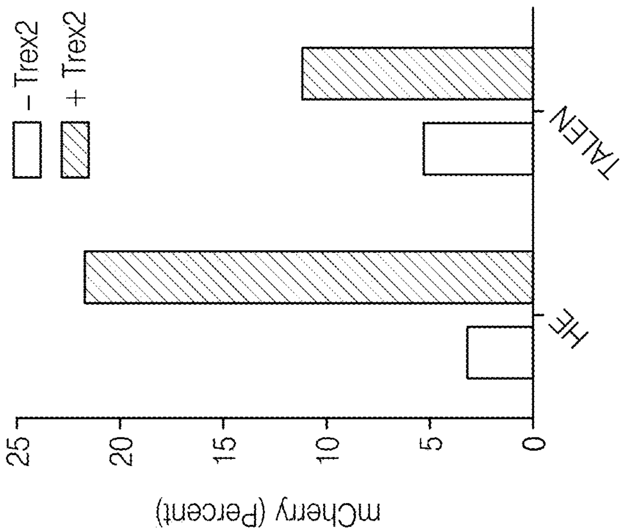
Figure 11B:
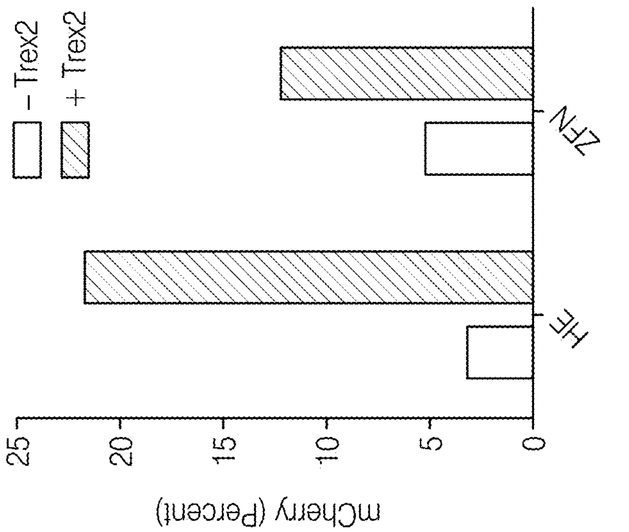

FIG. 11A shows representative flow plots and targets sites of HEK293 Traffic Light Reporter cells following transfection with a homing endonuclease with and without Trex2 and a zinc finger nuclease with and without Trex2. FIG. 11B shows a graph of an independent experiment examining cleavage site mutation for I-SceI and Zinc Finger Nuclease in the presence and absence of Trex2. FIG. 11C shows a graph of HEK293 Traffic Light Reporter cells following co-transfection of an HE with Trex2 or a TALEN with Trex2.

Figure 12A:
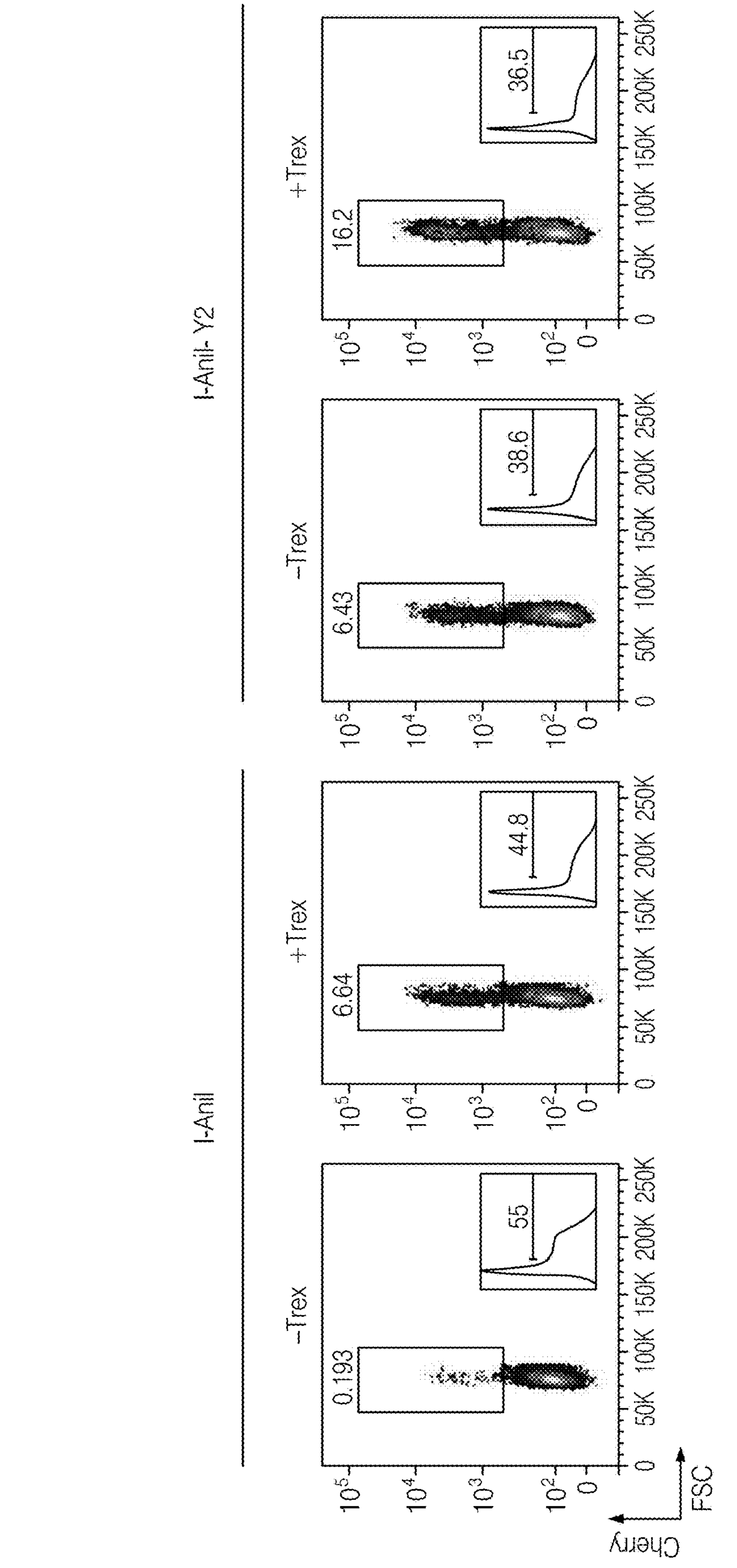
Figure 12B:
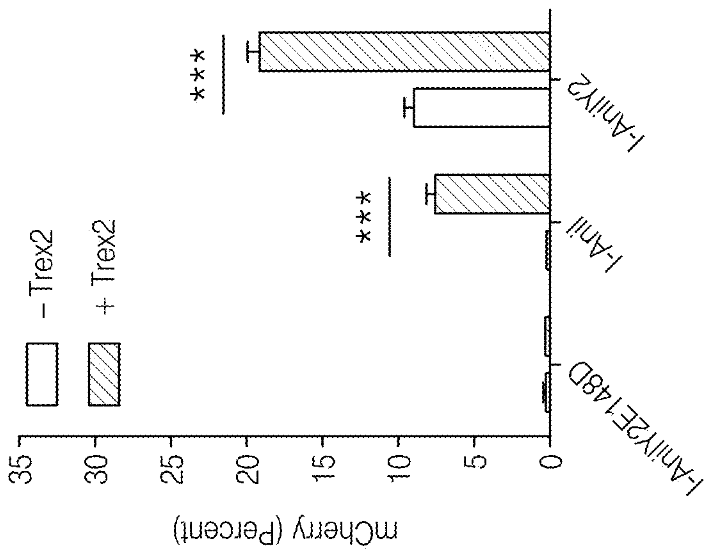

FIG. 12A shows representative flow plots of HEK293 cells harboring Traffic Light Reporters with an I-AniI target site following transfection with either I-AniI-IRES-BFP, I-AniI-T2A-Trex2-IRES-BFP, I-AniIY2-IRES-BFP, I-AniIY2-T2A-Trex2-IRES-BFP. FIG. 12B shows a graph quantitating 3 independent experiments as performed in FIG. 12A.

Figure 13:
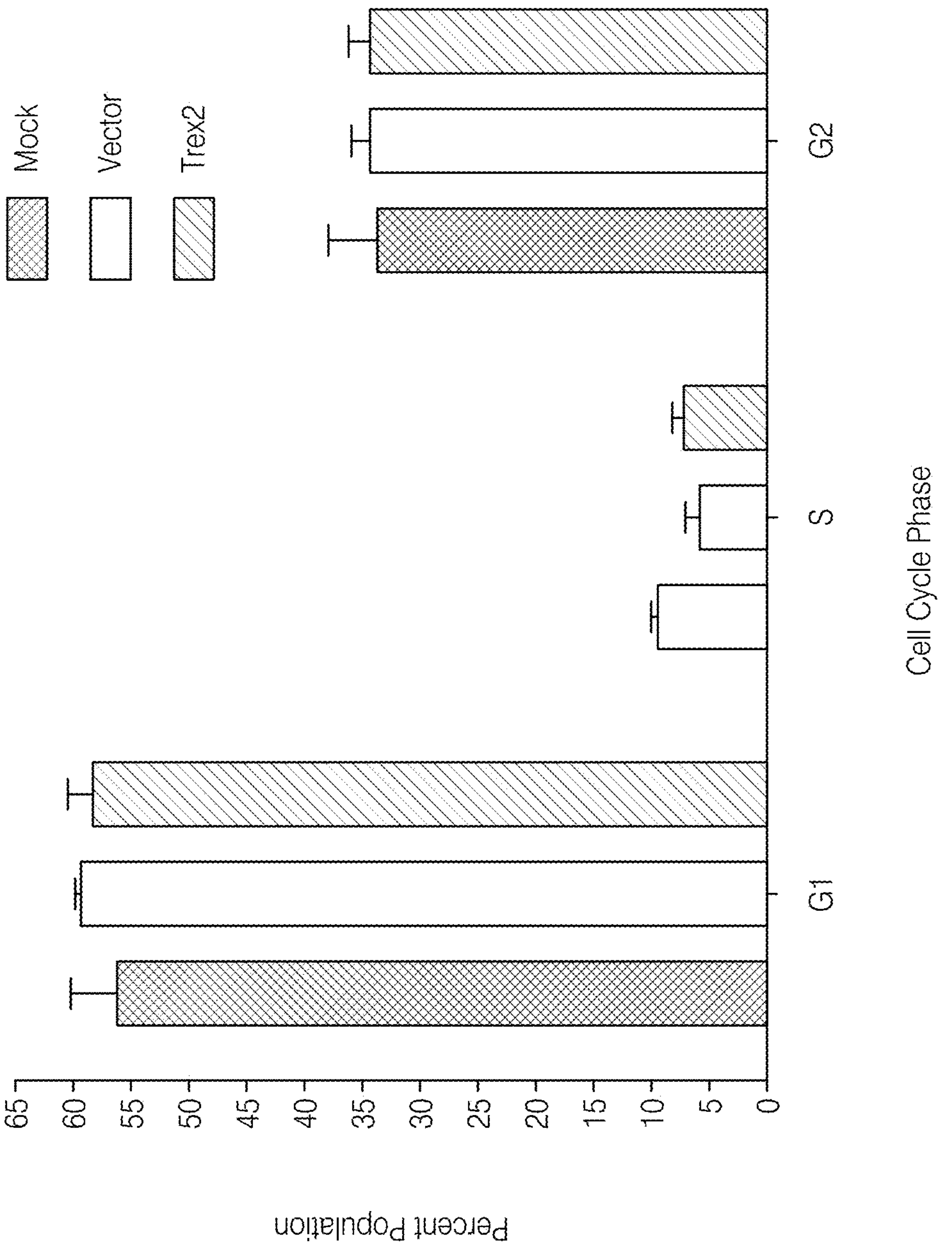

FIG. 13 shows graph depicting cell cycle analysis of murine embryonic fibroblasts transduced with Mock, I-SceI-IRES-BFP, or I-SceI-T2A-Trex2-IRES-BFP viruses.

Figure 14:
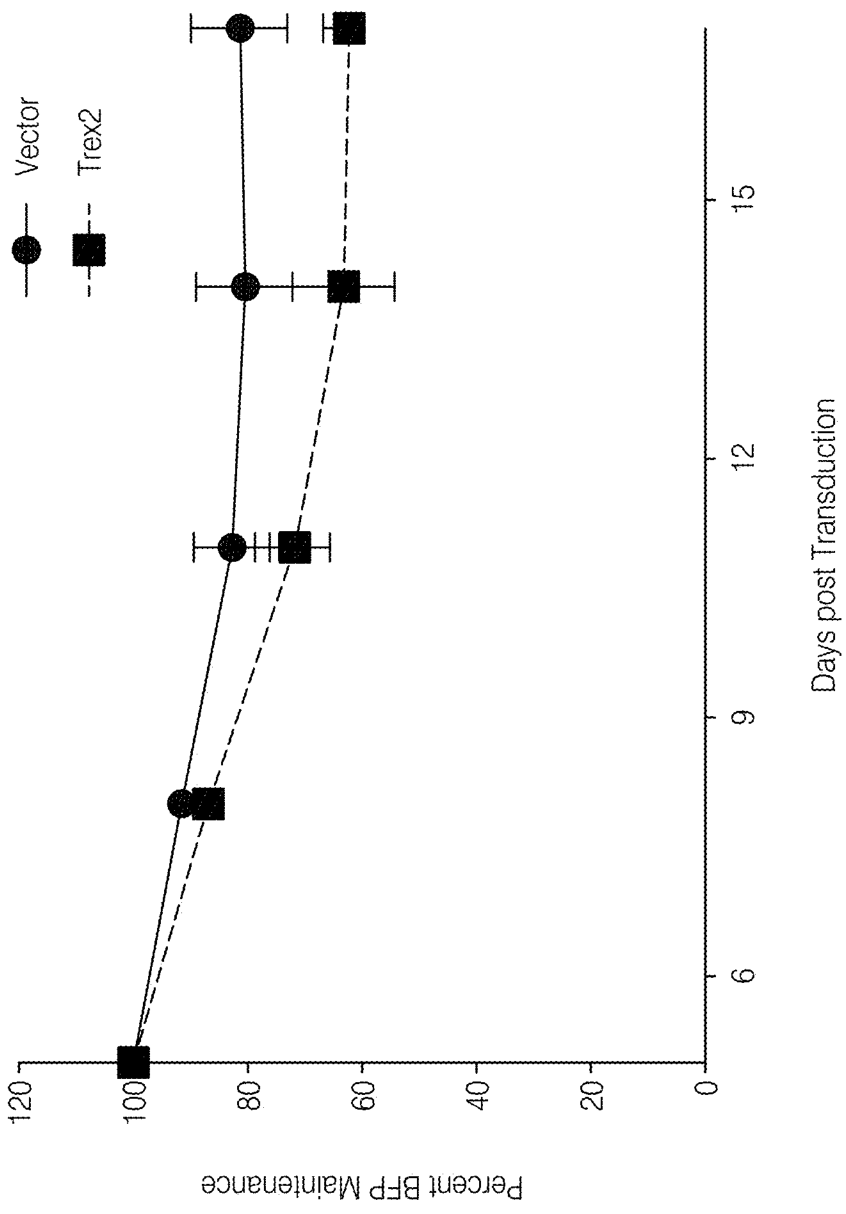

FIG. 14 shows a graph depicting maintenance of BFP expression in cells transduced with an integrating lentivirus containing I-SceID44A-IRES-BFP or I-SceID44A-T2A-Trex2-IRES-BFP.

Figure 15A:
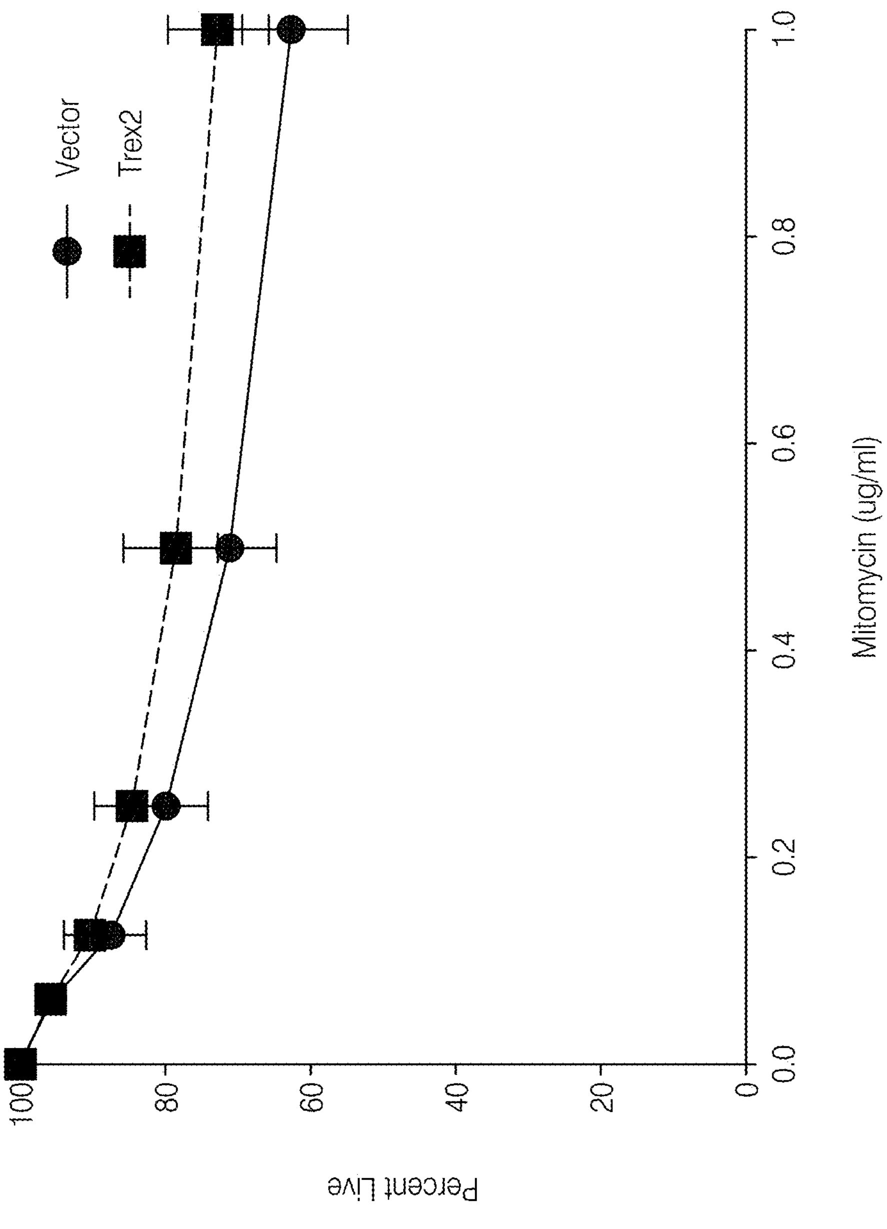
Figure 15B:
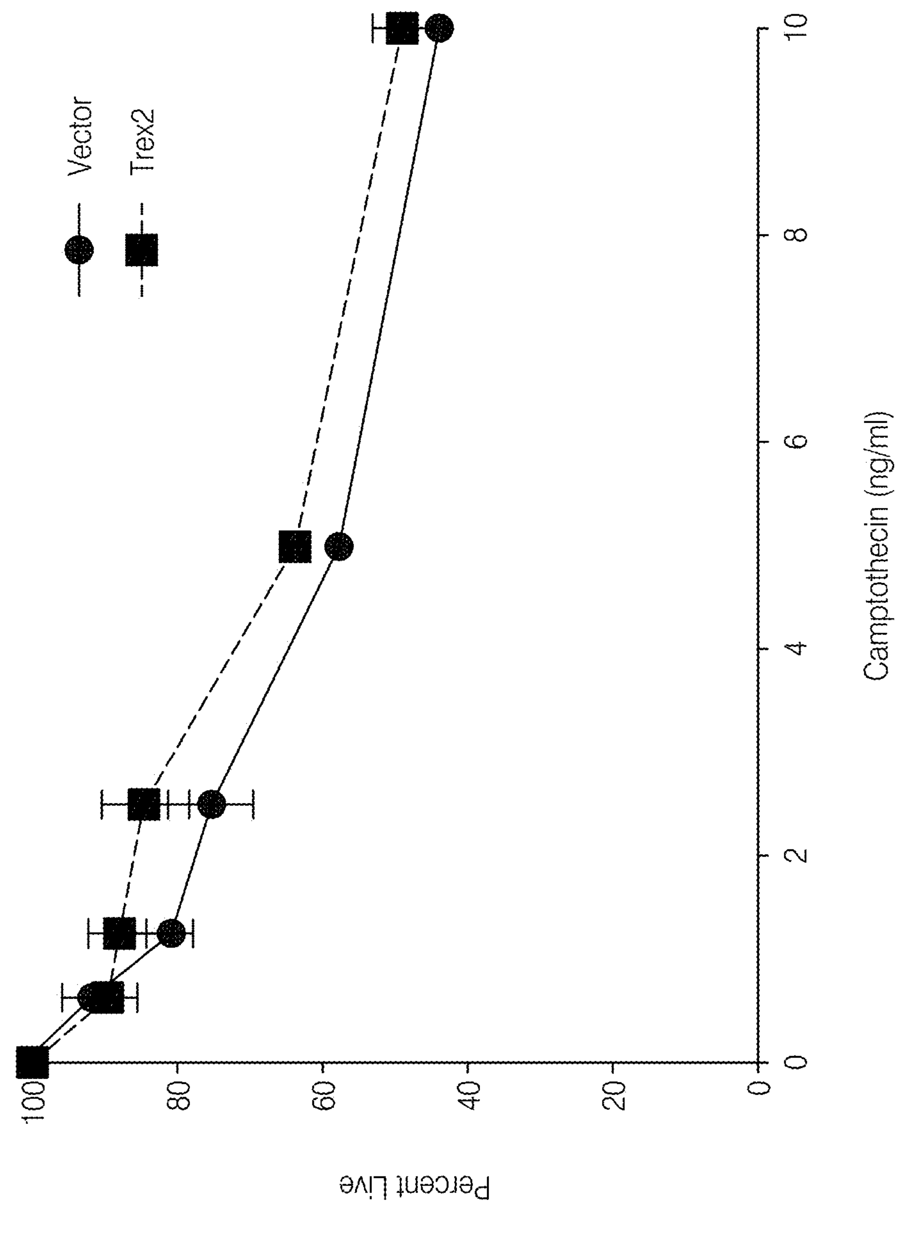
Figure 15C:
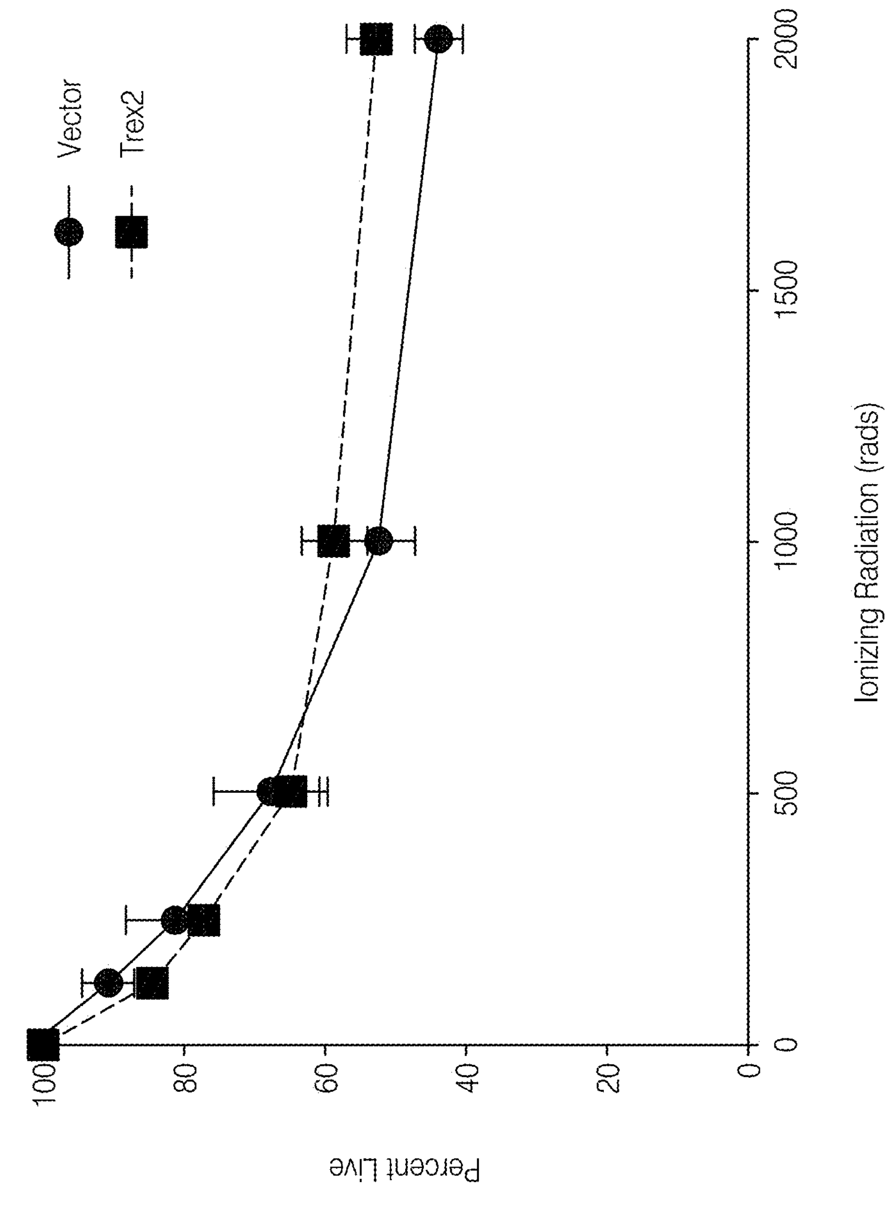

FIG. 15A shows a graph measuring human CD34+ hematopietic stem cell survival when transduced with I-SceID44A-IRES-BFP or I-SceID44A-T2A-Trex2-IRES-BFP and challenged with Mitomycin C. FIG. 15B shows a graph measuring human CD34+ hematopietic stem cell survival when transduced with I-SceID44A-IRES-BFP or I-SceID44A-T2A-Trex2-IRES-BFP and challenged with camptothecin. FIG. 15C shows a graph measuring human CD34+ hematopietic stem cell survival when transduced with I-SceID44A-IRES-BFP or I-SceID44A-T2A-Trex2-IRES-BFP and challenged with ionizing radiation.

Figure 16A:
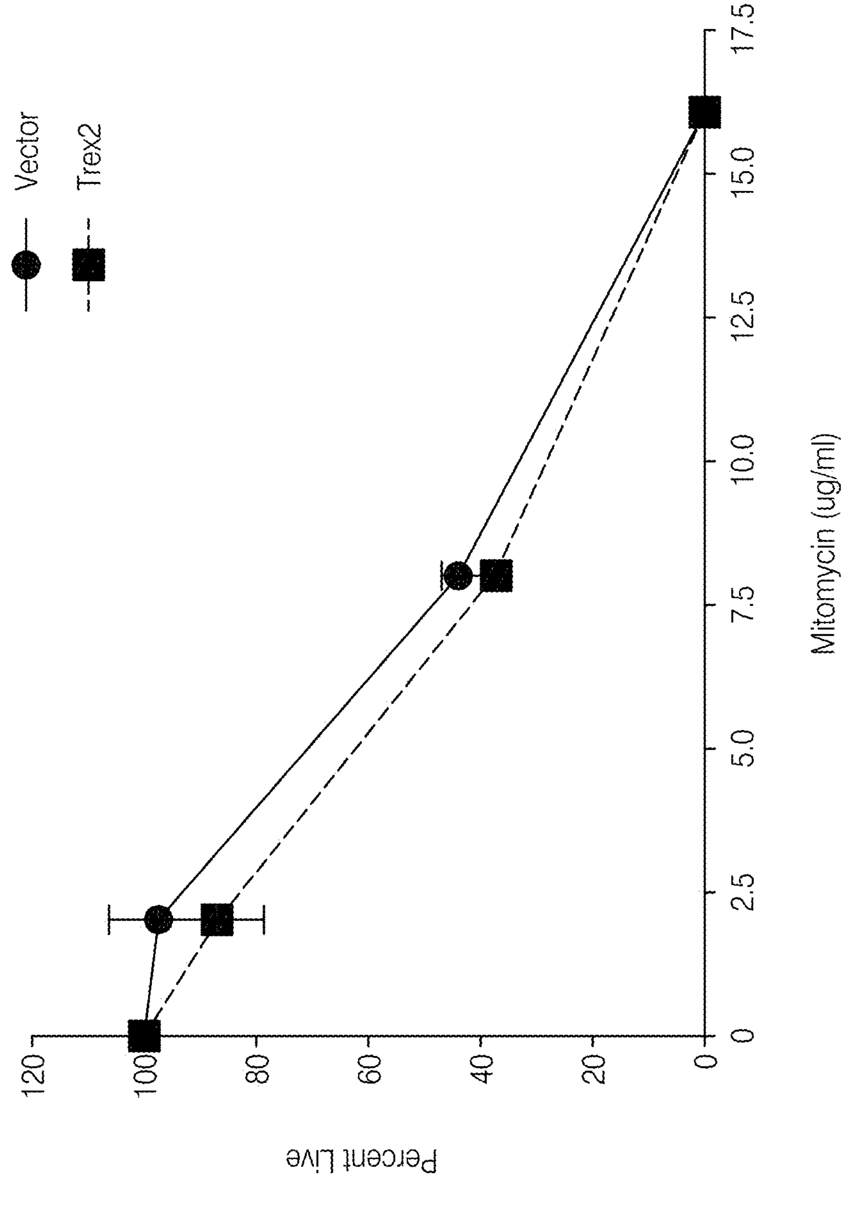
Figure 16B:
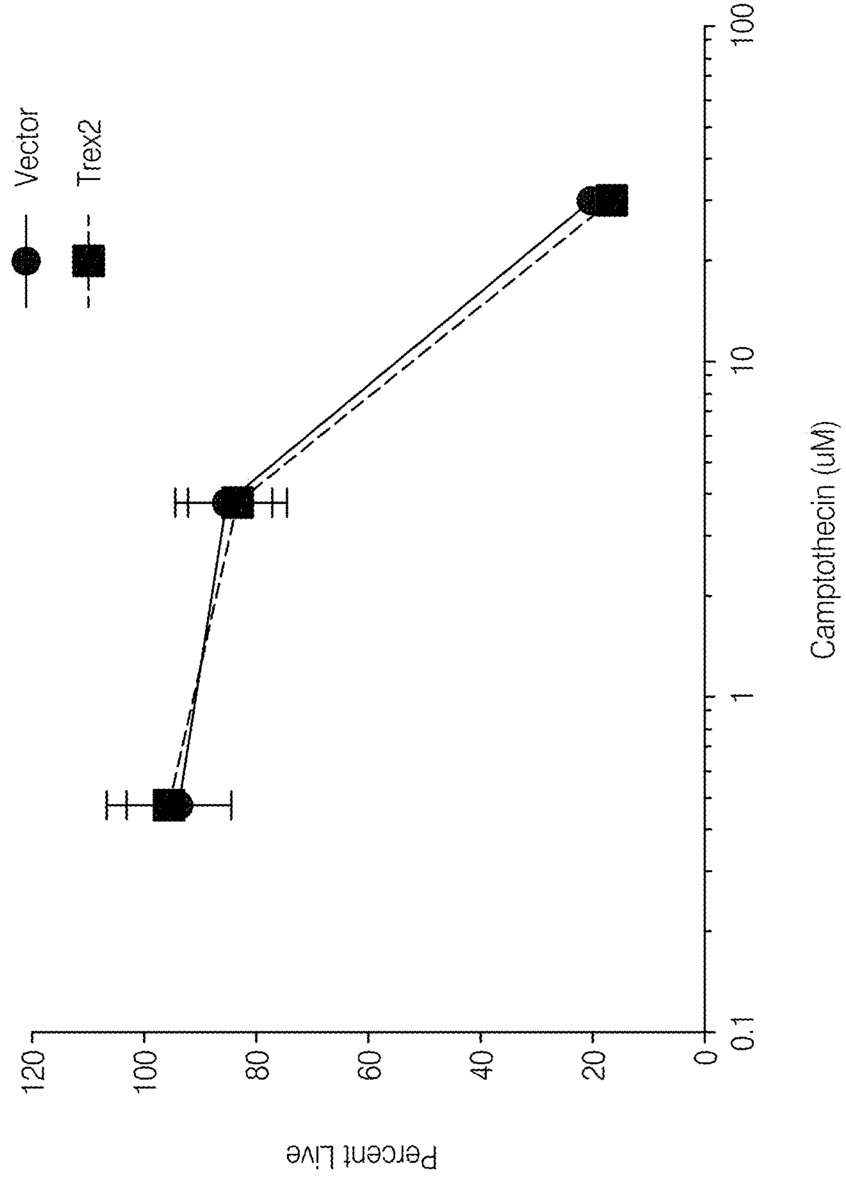

FIG. 16A shows a graph measuring murine embryonic fibroblast cell survival when transduced with I-SceID44A-IRES-BFP or I-SceID44A-T2A-Trex2-IRES-BFP and challenged with Mitomycin C. FIG. 16B shows a graph measuring murine embryonic fibroblast cell survival when transduced with I-SceID44A-IRES-BFP or I-SceID44A-T2A-Trex2-IRES-BFP and challenged with camptothecin.

Figure 17B:
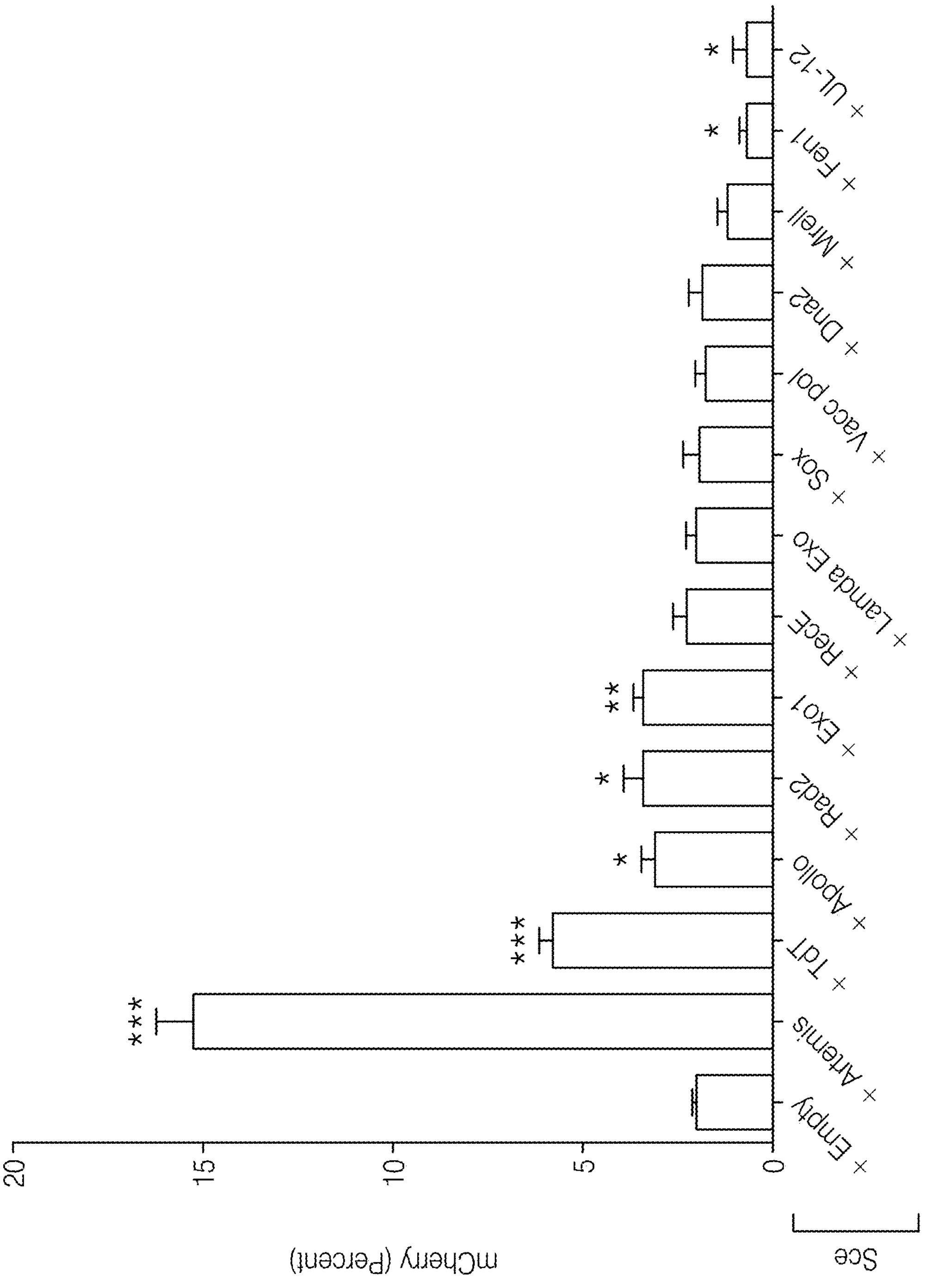

FIG. 17$A_1$ and FIG. 17$A_2$ show representative flow plots of HEK293 Traffic Light Reporter cells following co-transfection of I-SceI-IRES-BFP and an expression plasmid coding for the indicated end-processing enzyme. FIG. 17B shows a graph quantifying 3 independent experiments as performed in FIG. 17$A_1$ and FIG. 17$A_2$.

Figure 18A:
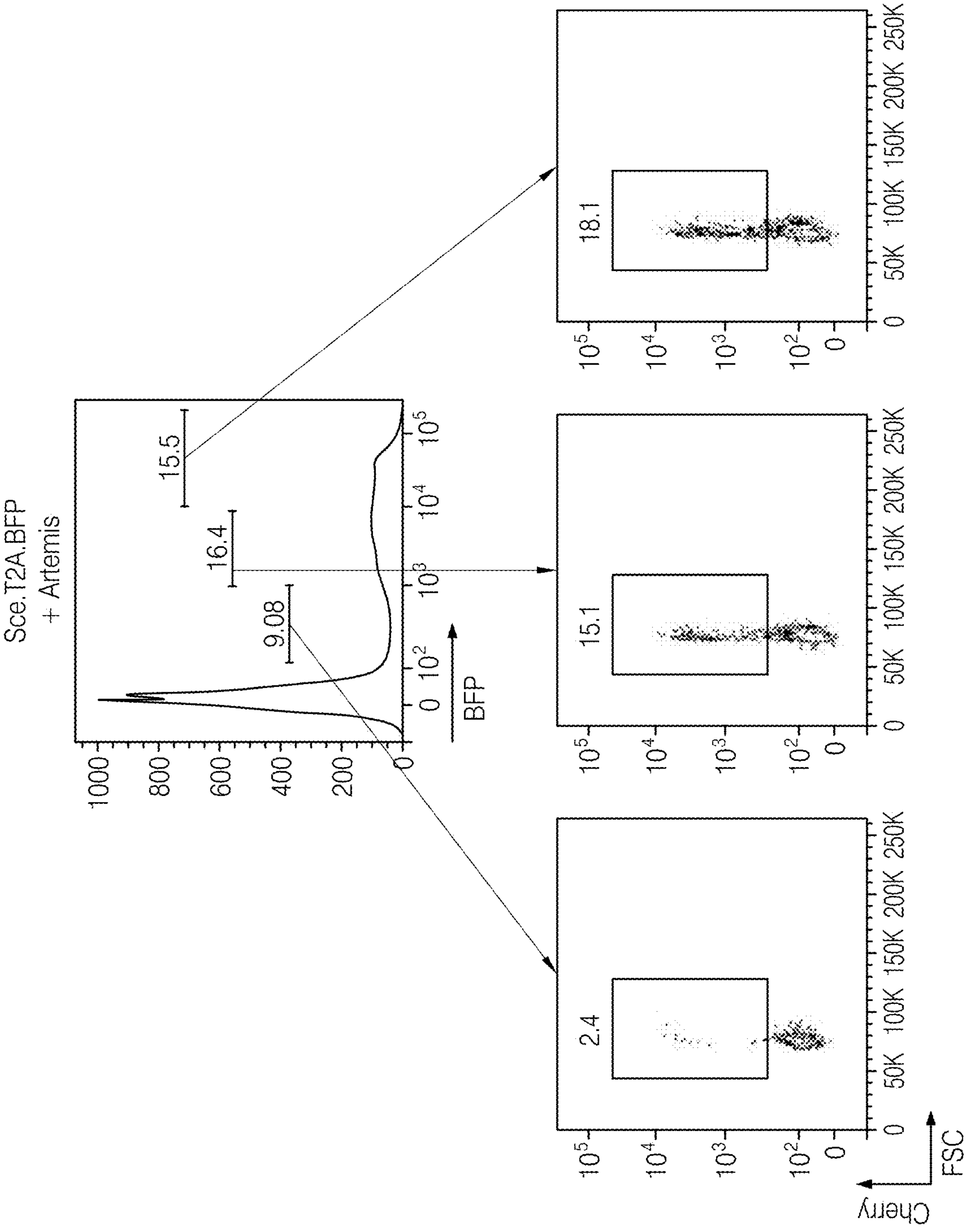
Figure 18B:
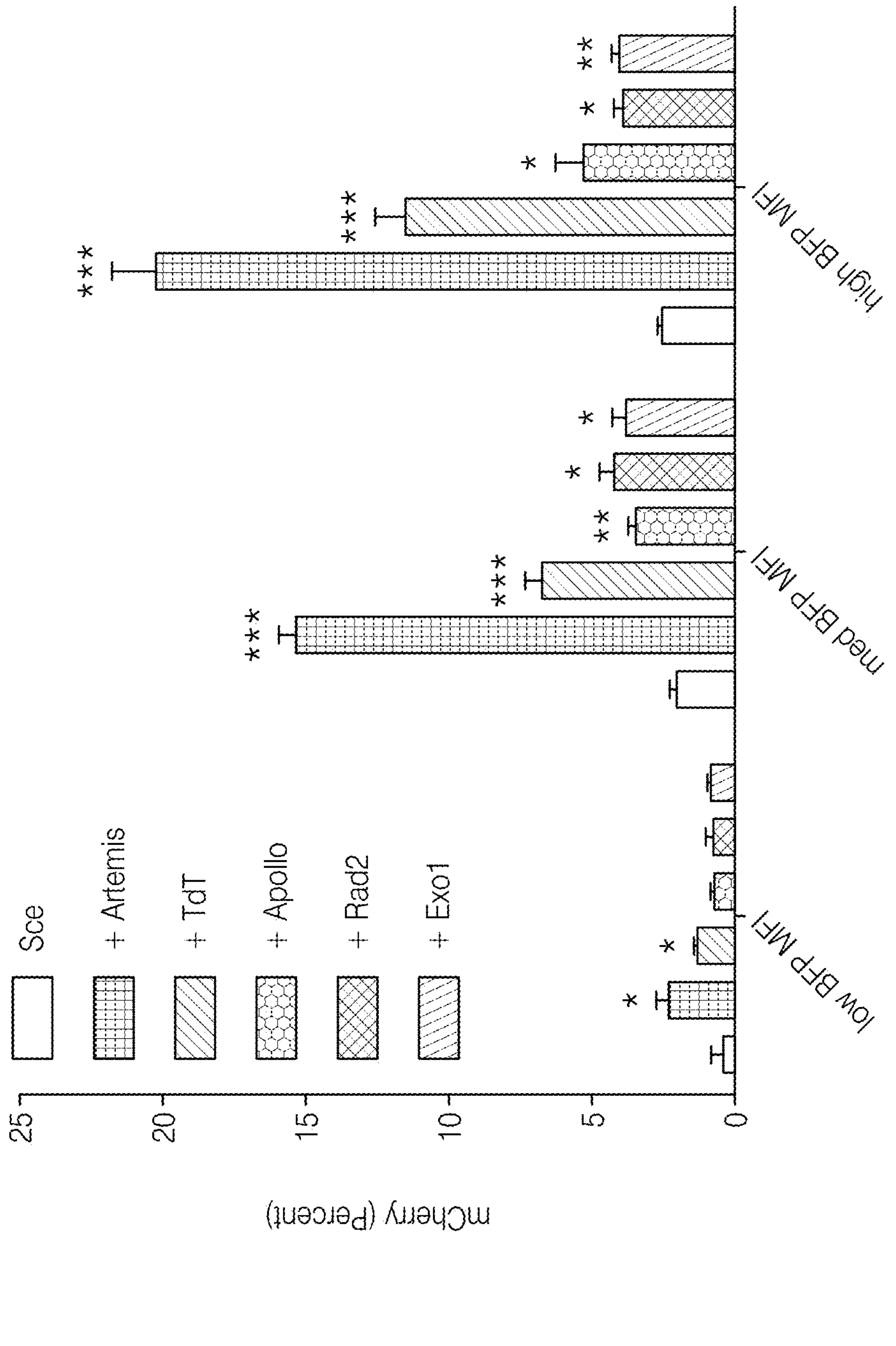

FIG. 18A shows representative flow plots of a gating analysis of I-SceI-IRES-BFP co-transfected with ARTEMIS expression plasmid as indicated in FIG. 17$A_1$ and FIG. 17$A_2$. FIG. 18B shows a graph quantifying gating analysis of several end-processing enzymes from 3 independent experiments as indicated in FIG. 18$A_1$ and FIG. 17$A_2$.

Figure 19A:
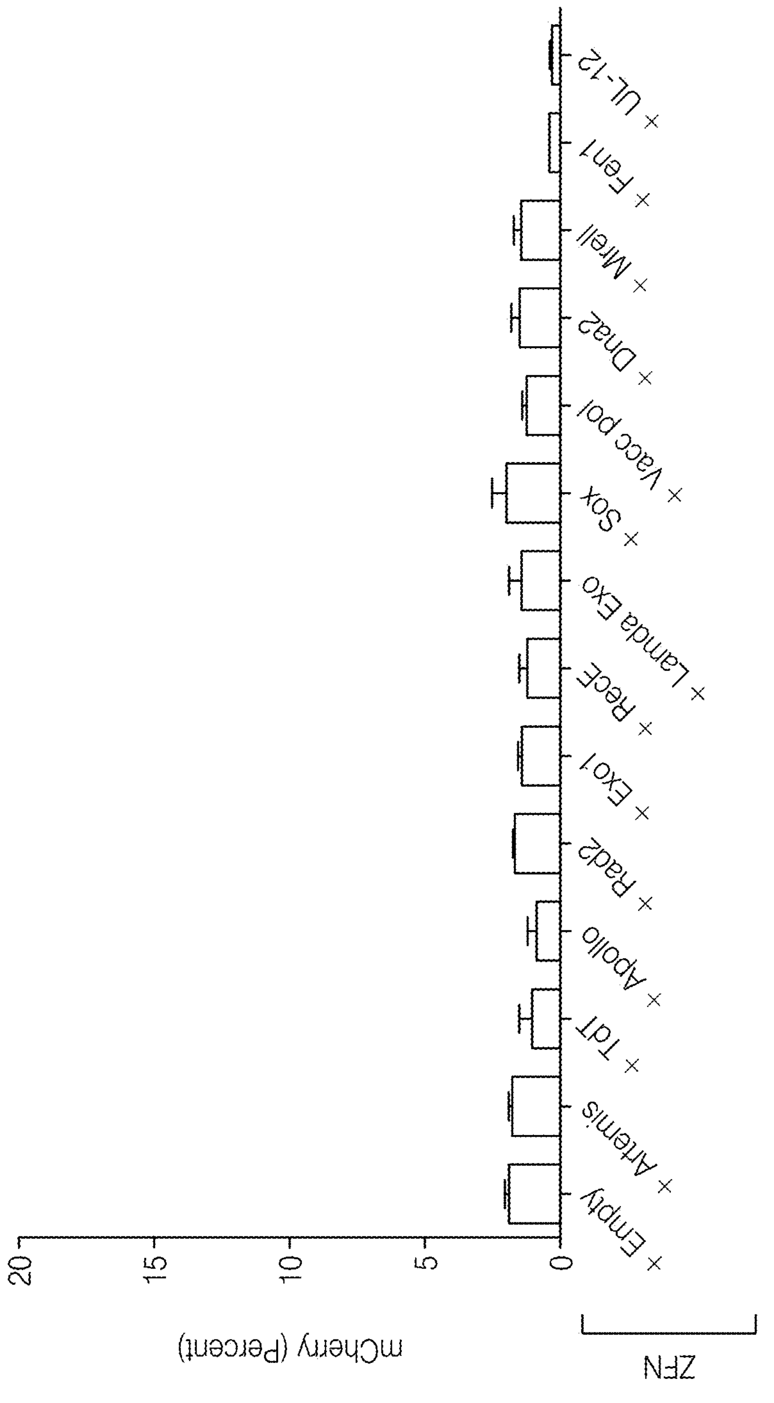
Figure 19B:
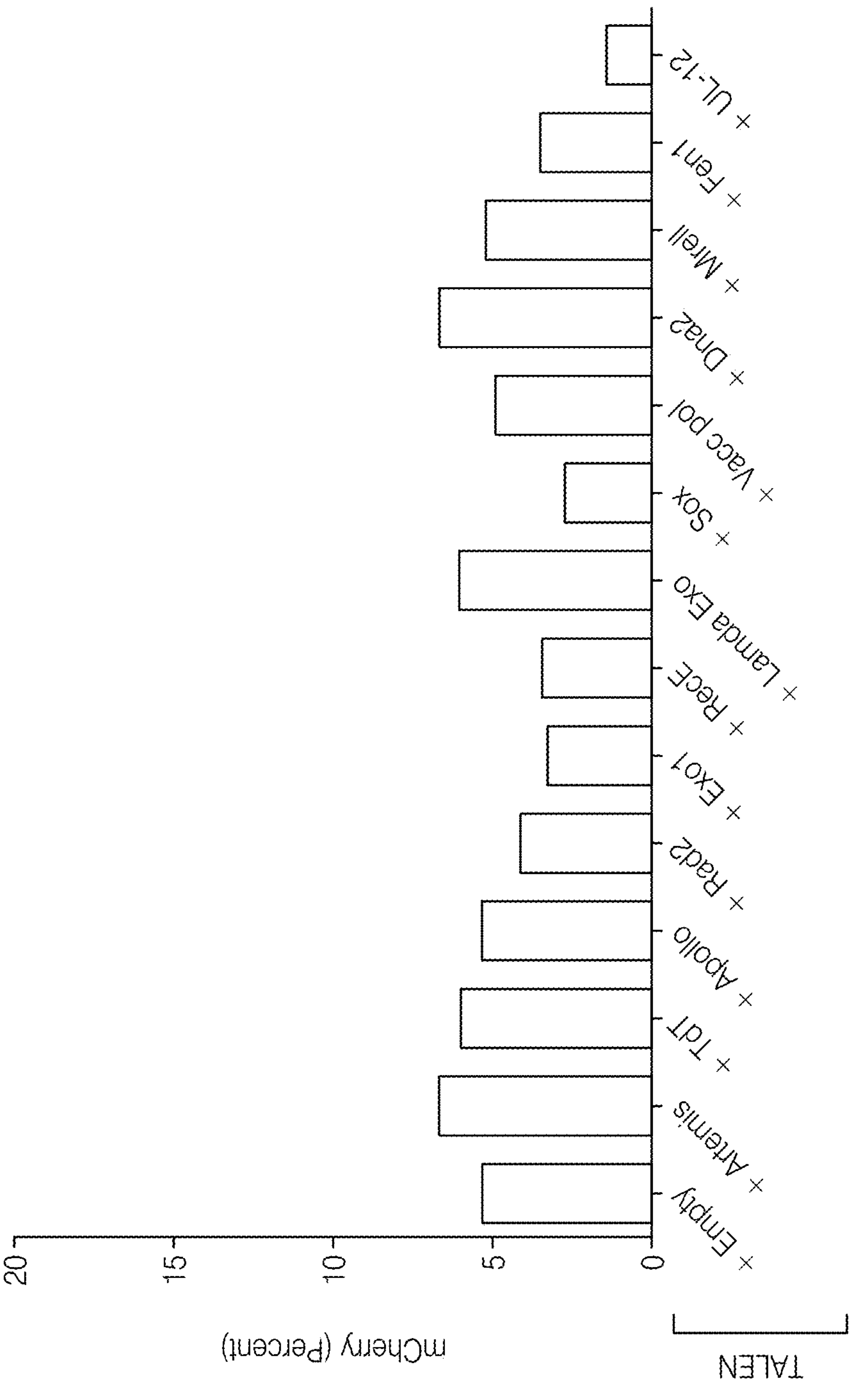

FIG. 19A shows a graph of HEK293 Traffic Light Reporter cells following co-transfection with a zinc finger nuclease and the indicated end-processing enzyme expression plasmid. FIG. 19B shows a graph of HEK293 Traffic Light Reporter cells following co-transfection with a TALEN and the indicated end-processing enzyme expression plasmid.

Figure 20A:
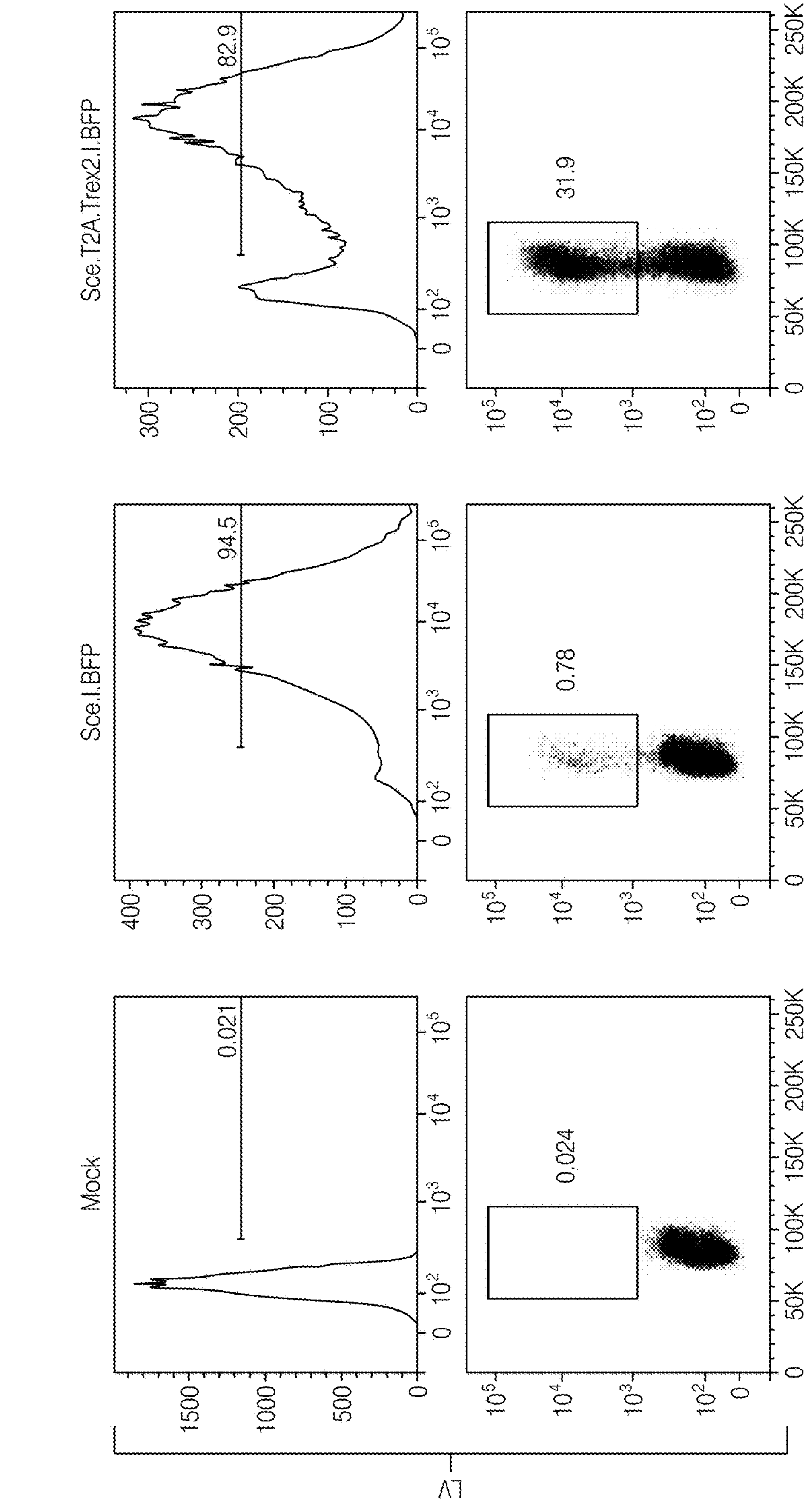
Figure 20B:
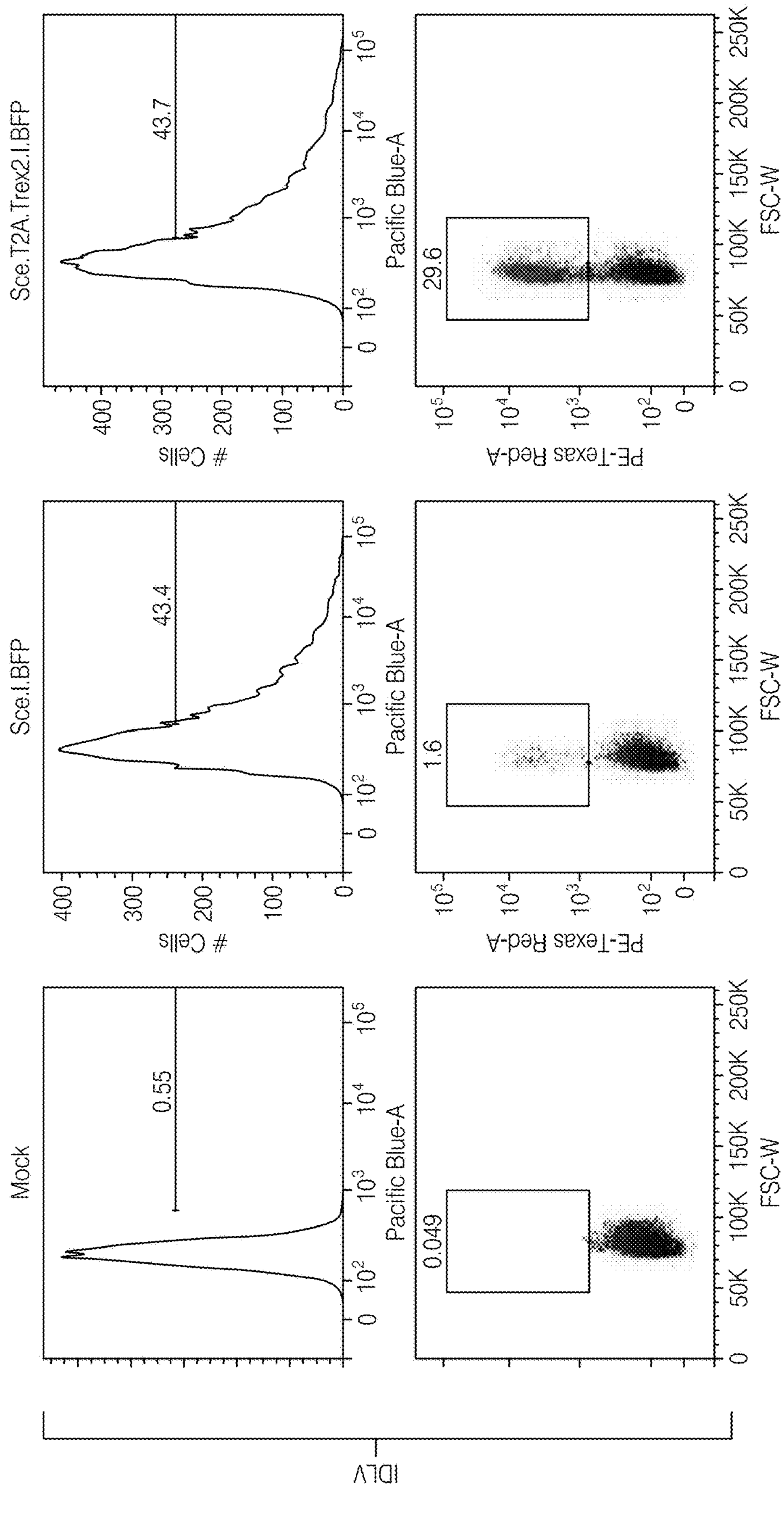

FIGS. 20A and 20B show a comparison of expression levels and gene disruption rates between integrating lentivirus and integrase deficient lentivirus from I-SceI with and without exonuclease coupling on HEK293 Traffic Light reporter cells.

Figure 21A:
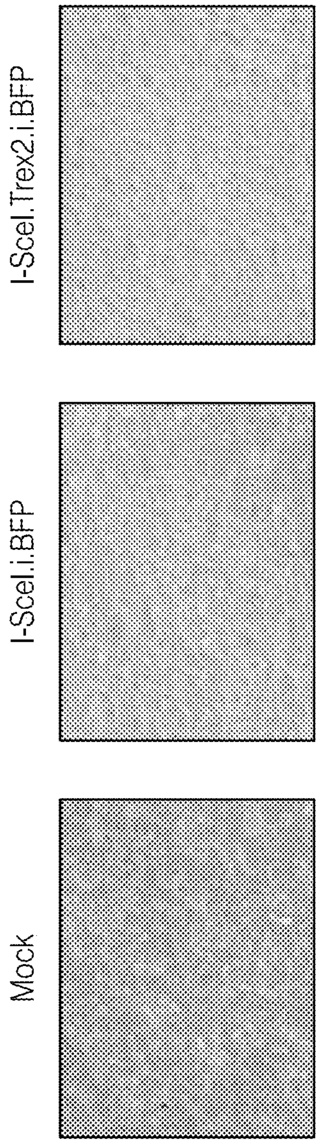
Figure 21B:
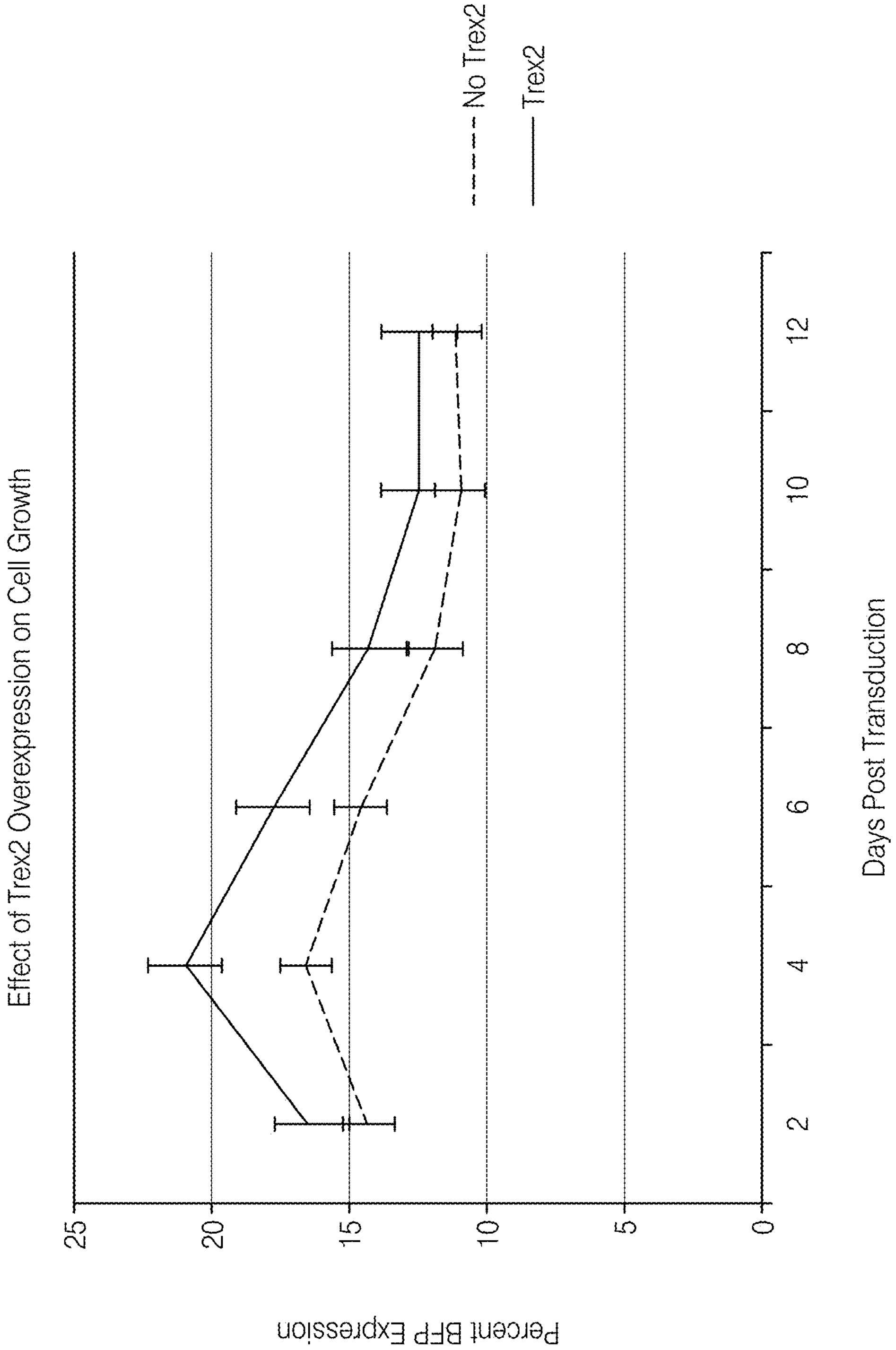

FIG. 21A shows live cell image of cells 72 hrs post mock transfection or transfection with an expression vectors encoding I-SceI-IRES-BFP or I-SceI-T2A-Trex2-IRES-BFP. FIG. 21B shows a graph depicting maintenance of BFP expression in cells transduced with an integrating lentivirus containing BFP alone (no Trex2) or Trex2-BFP.

DETAILED DESCRIPTION

Definitions

In the description that follows, a number of terms are used extensively. The following definitions are provided to facilitate understanding of the present embodiments.

As used herein, "a" or "an" may mean one or more than one.

As used herein, the term "about" indicates that a value includes the inherent variation of error for the method being employed to determine a value, or the variation that exists among experiments.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (e.g., GAU and GAC triplets each encode Asp). It will be understood that, as a result of the degeneracy of the genetic code, a multitude of nucleotide sequences encoding a given protein such as an endonuclease, end-processing enzyme, or endonuclease/end-processing enzyme fusion protein of the present embodiments may be produced.

The term "complementary to" means that the complementary sequence is homologous to all or a portion of a reference polynucleotide sequence. For illustration, the nucleotide sequence "CATTAG" corresponds to a reference sequence "CATTAG" and is complementary to a reference sequence "GTAATC."

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another non-limiting example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art may also use the term "cDNA" to refer to a double-stranded DNA molecule consisting of such a single-stranded DNA molecule and its complementary DNA strand. The term "cDNA" may also refer to a clone of a cDNA molecule synthesized from an RNA template.

A "promoter" is a nucleotide sequence that directs the transcription of a structural gene. In some embodiments, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). As used herein, a promoter may be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (e.g., endogenous DNA) so long as that host DNA is combined with non-host DNA (e.g., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptide components, such as carbohydrate groups. Carbohydrates and other non-peptide sub stituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present embodiments, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, plastome, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transduced with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, "transient transfection" refers to the introduction of exogenous nucleic acid(s) into a host cell by a method that does not generally result in the integration of the exogenous nucleic into the genome of the transiently transfected host cell.

By the term "host cell" is meant a cell that contains one or more nucleases, for example endonucleases, end-processing enzymes, and/or endonuclease/end-processing enzyme fusion proteins encompassed by the present embodiments or a vector encoding the same that supports the replication, and/or transcription or transcription and translation (expression) of one or more nucleases, for example endonucleases, end-processing enzymes, and/or endonuclease/end-processing enzyme fusion proteins. Host cells for use in the present invention can be prokaryotic cells or eukaryotic cells. Examples of prokaryotic host cells include, but are not limited to *E. coli*, nitrogen fixing bacteria, *Staphylococcus aureus, Staphylococcus albus, Lactobacillus acidophilus, Bacillus anthracis, Bacillus subtilis, Bacillus thuringiensis, Clostridium tetani, Clostridium botulinum, Streptococcus mutans, Streptococcus pneumoniae*, mycoplasmas, and cyanobacteria. Examples of eukaryotic host cells include, but are not limited to, protozoa, fungi, algae, plant, insect, amphibian, avian and mammalian cells.

"Integrative transformants" are recombinant host cells, in which heterologous DNA has become integrated into the genomic DNA of the cells.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, e.g., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers, or alternatively glycosylated or derivative forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "gene expression" refers to the biosynthesis of a gene product. For example, in the case of a structural gene, gene expression involves transcription of the structural gene into mRNA and the translation of mRNA into one or more polypeptides.

The term "endonuclease" refers to enzymes that cleave the phosphodiester bond within a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An endonuclease may cut a polynucleotide symmetrically, leaving "blunt" ends, or in positions that are not directly opposing, creating overhangs, which may be referred to as "sticky ends." The methods and compositions described herein may be applied to cleavage sites generated by endonucleases.

The term "homing endonuclease" refers to double stranded DNases that have large, asymmetric recognition sites (12-40 base pairs). Homing endonuclease recognition sites are extremely rare. For example, an 18 base pair recognition sequence will occur only once in every $7\times10^{10}$ base pairs of random sequence. This is equivalent to only one site in 20 mammalian-sized genomes. Unlike standard restriction endonucleases, however, homing endonucleases tolerate some sequence degeneracy within their recognition sequence. As a result, their observed sequence specificity is typically in the range of 10-12 base pairs. Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. Examples of homing endonucleases include, but are not limited to, I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TeeI, I-TevII, and I-TevIII. Their recognition sequences are known. The specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66. The methods and compositions described herein may be applied to cleavage sites generated by homing endonucleases.

The term "TAL effector nuclease" (TALEN) refers to a nuclease comprising a TAL-effector domain fused to a nuclease domain. TAL-effector DNA binding domains, isolated from the plant pathogen Xanthomonas have been described (see Boch et al., (2009) Science 29 Oct. 2009 (10.1126/science.117881) and Moscou and Bogdanove, (2009) Science 29 Oct. 2009 (10.1126/science.1178817)). These DNA binding domains may be engineered to bind to a desired target and fused to a nuclease domain, such as the FokI nuclease domain, to derive a TAL effector domain-nuclease fusion protein. The methods and compositions described herein may be applied to cleavage sites generated by TAL effector nucleases.

The term "Zinc-finger nuclease" (ZFN) refers to artificial restriction enzymes generated by fusing a zinc finger DNA-binding domain to a DNA-cleavage domain. Zinc finger domains can be engineered to bind to a desired target site. In some embodiments, the cleavage domain comprises the non-specific cleavage domain of FokI. In other embodiments, the cleavage domain comprises all or an active portion of another nuclease. In some embodiments, the cleavage domain may comprise Trex2 or an active fragment thereof. The methods and compositions described herein may be applied to cleavage sites generated by zinc-finger nucleases The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. A end-processing enzyme may modify may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents. DNA end-processing enzyme may modify exposed DNA ends by adding one or more nucleotides, removing one or more nucleotides, removing or modifying a phosphate group and/or removing or modifying a hydroxyl group. Non-limiting examples of types of DNA end-processing enzymes include 5-3' exonucleases, 5-3' alkaline exonucleases, 3-5' exonucleases, 5' flap endonucleases, helicases, phosphatases, hydrolases and template-independent DNA polymerases. Examples of DNA end-processing enzymes include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. Many DNA end-processing enzymes are highly conserved throughout evolution, and thus likely to function in several different species. Further, homologues of DNA end-processing enzymes may be readily identifiable in organisms of biotechnological interest, including plants, animals, and algae. Contemplated herein are methods of modifying DNA end-processing enzymes to optimize activity or processivity.

The term "exonuclease" refers to enzymes that cleave phosphodiester bonds at the end of a polynucleotide chain via a hydrolyzing reaction that breaks phosphodiester bonds at either the 3' or 5' end. The polynucleotide may be double-stranded DNA (dsDNA), single-stranded DNA (ssDNA), RNA, double-stranded hybrids of DNA and RNA, and synthetic DNA (for example, containing bases other than A, C, G, and T). The term "5' exonuclease" refers to exonucleases that cleave the phosphodiester bond at the 5' end. The term "3' exonuclease" refers to exonucleases that cleave the phosphodiester bond at the 3' end. Exonucleases may cleave the phosphodiester bonds at the end of a polynucleotide chain at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents. Exonucleases may cleave the phosphodiester bonds at blunt ends or sticky ends. *E. coli* exonuclease I and exonuclease III are two commonly used 3'-exonucleases that have 3'-exonucleolytic single-strand degradation activity. Other examples of 3'-exonucleases include Nucleoside diphosphate kinases (NDKs), NDK1 (NM23-H1), NDK5, NDK7, and NDK8 (Yoon J-H, et al., Characterization of the 3' to 5' exonuclease activity found in human nucleoside diphosphate kinase 1 (NDK1) and several of its homologues. *Biochemistry* 2005: 44(48):15774-15786.), WRN (Ahn, B., et al., Regulation of WRN helicase activity in human base excision repair. *J. Biol. Chem.* 2004, 279:53465-53474) and Three prime repair exonuclease 2 (Trex2) (Mazur, D. J., Perrino, F. W., Excision of 3' termini by the Trex1 and TREX2 3'→5' exonucleases. Characterization of the recombinant proteins. *J. Biol. Chem.* 2001, 276:17022-17029.). *E. coli* exonuclease VII and T7-exonuclease Gene 6 are two commonly used 5'-3' exonucleases that have 5% exonucleolytic single-strand degradation activity. The exonuclease can be originated from prokaryotes, such as *E. coli* exonucleases, or eukaryotes, such as yeast, worm, murine, or human exonucleases.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

The terms "target site" or "target sequence" refers to a nucleic acid sequence that defines a portion of a nucleic acid to which a binding molecule will bind, provided sufficient conditions for binding exist. For example, the target sites for several homing endonucleases are shown in Table 1.

TABLE 1

Examples of Homing Endonucleases and their Target Sites.

| Homing Endo-nucleases | Target |
|---|---|
| I-SceI | TAGGGATAACAGGGTAAT (SEQ ID No. 1) |
| I-LtrI | AATGCTCCTATACGACGTTTAG (SEQ ID No. 2) |
| I-GpiI | TTTTCCTGTATATGACTTAAAT (SEQ ID No. 3) |
| I-GzeI | GCCCCTCATAACCCGTATCAAG (SEQ ID No. 4) |
| I-xMpeMI | TAGATAACCATAAGTGCTAAT (SEQ ID No. 5) |
| I-PanMI | GCTCCTCATAATCCTTATCAAG (SEQ ID No. 6) |
| I-CreI | TCAAAACGTCGTGAGACAGTTTGG (SEQ ID No. 7) |
| I-OnuI | TTTCCACTTATTCAACCTTTTA (SEQ ID No. 8) |
| I-HjeMI | TTGAGGAGGTTTCTCTGTTAAT (SEQ ID No. 9) |
| I-AniI | TGAGGAGGTTTCTCTGTAAA (SEQ ID No. 10) |

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a host cell as a single protein. A fusion protein can comprise at least part of one polypeptide fused with another polypeptide. In some embodiments, a fusion protein can comprise at least a part of one polypeptide fused with at least a part of the same polypeptide. One example of a fusion protein is monomorized Trex2 (at least a part of Trex2 fused to at least a part of Trex2).

The term "endonuclease/end-processing enzyme fusion protein" or "fusion protein having endonuclease and end-processing activity" refers to an enzyme, which has an endonuclease catalytic domain and an end-processing catalytic domain and exhibits endonuclease and end-processing activity.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., an endonuclease domain, a polynucleotide binding domain, such as a DNA-binding domain, or an end-processing domain).

"Prokaryotic" cells lack a true nuclease. Examples of prokaryotic cells are bacteria (e.g., cyanobacteria, *Lactobacillus acidophilus*, Nitrogen-Fixing Bacteria, *Helicobacter pylori, Bifidobacterium, Staphylococcus aureus, Bacillus anthrax, Clostridium tetani, Streptococcus pyogenes, Staphylococcus pneumoniae, Klebsiella pneumoniae* and *Escherichia coli*) and archaea (e.g., Crenarchaeota, Euryarchaeota, and Korarchaeota).

"Eukaryotic" cells include, but are not limited to, algae cells, fungal cells (such as yeast), plant cells, animal cells, mammalian cells, and human cells (e.g., T-cells).

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

"Algae" are predominantly aquatic organisms that carry out oxygen-evolving photosynthesis but lack specialized water-conducting and food-conducting tissues. Algae may be unicellular or multicellular. Algae may be adapted to live in salt water, fresh water and on land. Example of algae include, but are not limited to, diatoms, chlorophyta (for example, volvox, spirogyra), euglenophyta, dinoflagellata, chrysophyta, phaephyta (for example, fucus, kelp, sargassum), and rhodophyta (for example, lemanae).

The term "subject" as used herein includes all members of the animal kingdom including non-human primates and humans.

Overview

Several embodiments described herein relate to a method of improving the rate of gene disruptions caused by imprecise repair of DNA double-strand breaks. In some embodiments, DNA end-processing enzymes are provided to enhance the rate of gene disruption. Some aspects of the present embodiments include, without limitation, enhanced rates of DNA end-processing enzyme-mediated processing of DNA ends at the site of a double-strand break.

Targeted DNA double-strand breaks introduced by rare-cleaving endonucleases can be harnessed for gene disruption applications in diverse cell types by engaging non-homologous end joining DNA repair pathways. However, endonucleases create chemically clean breaks that are often subject to precise repair, limiting the efficiency of targeted gene disruption. Several embodiments described herein relate to a method of improving the rate of targeted gene disruptions caused by imprecise repair of endonuclease-induced site-specific DNA double-strand breaks. In some embodiments, site specific endonucleases are coupled with end-processing enzymes to enhance the rate of targeted gene disruption. Coupling may be, for example, physical, spatial, and/or temporal.

Some aspects of the present embodiments include, without limitation, enhanced rates of end-processing enzyme-mediated processing of endonuclease-produced DNA ends, leading to enhanced targeted gene disruption at the genomic target site. Using this strategy, embodiments described herein show over 25 fold increased endonuclease-induced disruption rates. Certain embodiments described herein can achieve complete knockout of a target gene within a population. This technology further has the potential to dramatically increase the utility of rare-cleaving endonucleases for genetic knockout applications. Improving the mutation rate associated with endonucleases facilitates endonuclease engineering, as enzymes with different levels of activity can be utilized. In some embodiments, endo-end-processor coupling is used modify DNA ends for endonuclease-induced genome engineering. In some embodiments, expression of exonucleases capable of processive 5' end resection coupled with manipulation of the DNA repair environment can be used to enhance homologous recombination-mediated gene targeting.

Not to be bound by any particular theory, the resolution of a double-strand DNA breaks by "error-prone" non-homologous end-joining (NHEJ) can be harnessed to create targeted disruptions and genetic knockouts, as the NHEJ process can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, and ligates ends back together with minimal processing. As the DNA breaks created by designer endonuclease platforms (zinc-finger nucleases (ZFNs), TAL effector nucleases (TALENs), and homing endonucleases (HEs)) all leave chemically clean, compatible overhang breaks that do not require processing prior to ligation, they are excellent substrates for precise repair by the cNHEJ pathway. In the absence or failure of the classical NHEJ pathway to resolve a break, alternative NHEJ pathways (altNHEJ) can substitute: however, these pathways are considerably more mutagenic.

Not to be bound by any particular theory, modification of DNA double-strand breaks by end-processing enzymes may bias repair towards an altNHEJ pathway. Further, different subsets of end-processing enzymes may enhance disruption by different mechanisms. For example, Trex2, an exonuclease that specifically hydrolyzes the phosphodiester bonds which are exposed at 3' overhangs, biases repair at break sites toward mutagenic deletion. By contrast, terminal deoxynucleotidyl transferase (TdT), a non-templative polymerase, is expected to bias repair at break sites toward mutagenic insertions by promoting the addition of nucleotide bases to alter DNA ends prior to ligation. Accordingly, one of skill in the art may use end-processing enzymes with different activities to provide for a desired engineering outcome. Further one of skill in the art may use synergy between different end-processing enzymes to achieve maximal or unique types of knockout effects.

Several embodiments described herein couple DNA breaks created by endonucleases with end-processing enzymes is a robust way to improve the rates of targeted disruption in a variety of cell types and species, without associated toxicity to the host. This is an important advance at least because: 1) Double-strand breaks (DSBs) trigger cell cycle checkpoints to arrest division until the break has been resolved; in the case of a "persistent break" (a repetitive cycle of cleaving and precise repair), cells may arrest indefinitely, leading to apoptosis. 2) Engineering applications often utilize transient delivery of an endonuclease, providing only a short window in which enzyme concentration is sufficient to achieve breaks. 3) Persistent breaks can be a source of translocations. Coupling endonucleases to end-processing enzymes prevents the establishment of a persistent break and reduces the incidence of gross chromosomal rearrangements, thereby potentially improving the safety of endonuclease-induced targeted disruption. 4) Multiple changes in a single round of mutagenesis may be achieved, for use for example, in multi-allelic knockouts and multiplexing, as data described herein suggests that coupling endonucleases to end-processing enzymes improves the mutagenic rate of two given endonucleases 5-fold at their respective targets, a 25-fold improvement may be realized in disrupting both targets simultaneously.

Any suitable method may be used to provide endonucleases, end-processing enzymes, and/or fusion proteins having endonuclease and end-processing activity to host cells. In some embodiments one or more polypeptides having endonuclease and/or end-processing activity may be provided directly to cells. In some embodiments, expression of endonucleases, end-processing enzymes and/or fusion proteins having endonuclease and end-processing activity in a host cell can result from delivery of one or more polynucleotides encoding one or more endonucleases, end-processing enzymes, and/or fusion proteins having endonuclease and end-processing activity to the host cell. In some embodiments, one or more polynucleotides is a DNA expression vector. In some embodiments, one or more polynucleotides is an RNA expression vector. In some embodiments, trans-splicing, polypeptide cleavage and/or polypeptide ligation can be involved in expression of one or more proteins in a cell. Methods for polynucleotide and polypeptide delivery to cells are well known in the art.

The compositions and methods described herein are useful for generating targeted disruptions of the coding sequences of genes and in some embodiments, creating gene knockouts. Targeted cleavage by the compositions and methods described herein can also be used to alter non-coding sequences (e.g., regulatory sequences such as promoters, enhancers, initiators, terminators, splice sites) to alter the levels of expression of a gene product. Such methods can be used, for example, for biological research, for biotechnology applications such as crop modification, for therapeutic purposes, functional genomics, and/or target validation studies.

Targeted mutations resulting from the methods and compositions described herein include, but are not limited to, point mutations (e.g., conversion of a single base pair to a different base pair), substitutions (e.g., conversion of a plurality of base pairs to a different sequence of identical length), insertions of one or more base pairs, deletions of one or more base pairs and any combination of the aforementioned sequence alterations.

Some embodiments relate to coupling the activity of one or more site-specific endonucleases with one or more end-processing enzymes. In some embodiments, the endonucleases and end-processing enzymes are provided as separate proteins. In some embodiments, the endonucleases and end-processing enzymes are co-expressed in a cell. If expression of the separate endonucleases and end-processing enzymes is by polynucleotide delivery, each of the endonucleases and end-processing enzymes can be encoded by separate polynucleotides, or by a single polynucleotide. In some embodiments, the endonucleases and end-processing enzymes are encoded by a single polynucleotide and expressed by a single promoter. In some embodiments, an endonuclease and end-processing enzymes are linked by a T2A sequence which allows for two separate proteins to be produced from a single translation. In some embodiments, a different linker sequence can be used. In other embodiments a single polynucleotide encodes the endonucleases and end-processing enzymes separated by an Internal Ribosome Entry Sequence (IRES).

Several embodiments relate to coupling the activity of one or more site-specific endonucleases selected from the group consisting of: homing endonucleases (meganucleases) (including engineered homing edonucleases), zinc finger nucleases, and TAL effector nucleases with one or more end-processing enzymes. The endonucleases may comprise heterologous DNA-binding and cleavage domains (e.g., zinc finger nucleases; homing endonuclease DNA-binding domains with heterologous cleavage domains or TAL-effector domain nuclease fusions) or, alternatively, the DNA-binding domain of a naturally-occurring nuclease may be altered to bind to a selected target site (e.g., a homing endonuclease that has been engineered to bind to site different than the cognate binding site or a TAL-effector domain nuclease fusion). In some embodiments, the endonucleases and end-processing enzymes are provided as a fusion protein. In some embodiments, the endonucleases and end-processing enzymes are provided as separate proteins. In some embodiments, the endonucleases and end-processing enzymes are co-expressed in a cell.

Several embodiments relate to coupling the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

Several embodiments relate to coupling the activity of one or more ZFNs with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some embodiments, the ZFNs and DNA end-processing enzymes are provided as a fusion protein. In some embodiments, the ZFNs and DNA end-processing enzymes are provided as separate proteins. In some embodiments, the ZFNs and DNA end-processing enzymes are co-expressed in a host cell.

Several embodiments relate to coupling the activity of one or more TALENs with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some embodiments, the TALENs and DNA end-processing enzymes are provided as a fusion protein. In some embodiments, the TALENs and DNA end-processing enzymes are provided as separate proteins. In some embodiments, the TALENs and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Apollo, Artemis, Dna2, Exo1, Mre11, Rad2, RecE, Lambda exonuclease, Sox, exonuclease VII, T7-exonuclease Gene 6 and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Sox and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Trex2, Vaccinia DNA polymerase, Mre11, exonuclease I, exonuclease III, NDK1, NDK5, NDK7, NDK8, and WRN. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of Fen1. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of TdT. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

Some embodiments relate to coupling the activity of multiple site-specific endonucleases with the activity of one or more end-processing enzymes. The site specific endonucleases may cleave target sites within the same gene or in different genes. In some embodiments, 1, 2, 3, 4, 5, 6, 7, 8, 9, or 10 site-specific endonucleases may be provided to a cell along with one or more end-processing enzymes. In some embodiments, a combination of homing endonucleases, zinc finger endonucleases, and/or TAL effector endonucleases may be provided to a cell with one or more end-processing enzymes. In some embodiments, the end-processing enzyme is an exonuclease. In some embodiments, a 5' and a 3' exonuclease may be provided. If expression of the multiple endonucleases and one or more exonucleases is by polynucleotide delivery, each of the endonucleases and exonucleases can be encoded by separate polynucleotides, or by a single polynucleotide. In some embodiments, the endonucleases and exonucleases are encoded by a single polynucleotide and expressed by a single promoter. In some embodiments, the endonucleases and exonucleases are linked by a T2A sequence which allows for separate proteins to be produced from a single translation. In some embodiments, different linker sequences can be used. In other embodiments, a single polynucleotide encodes the endonucleases and exonucleases separated by IRESs.

Several embodiments relate to a heterologous fusion protein, which comprises an endonuclease domain and an end-processing domain or portions thereof. Several embodiments relate to a heterologous fusion construct, which encodes a fusion protein having endonuclease and end-processing activity. The present embodiments also relate to vectors and host cells comprising the heterologous fusion construct as well as methods for producing a fusion protein having endonuclease and end-processing activity and compositions thereof. In one embodiment, the endonuclease domain is coupled to the end-processing domain by recombinant means (e.g., the fusion protein is generated by translation of a nucleic acid in which a polynucleotide encoding all or a portion of a endonuclease is joined in-frame with a polynucleotide encoding all or a portion of a end-processing enzyme). In other embodiments, the endonuclease domain and end-processing domain of a fusion protein may be linked chemically. This chemical linkage can be carried out, for example, by using bifunctional linker molecules, such as, B S3 (Bis[sulfosuccinimidyl] suberate).

Some embodiments relate to a fusion protein comprising an endonuclease domain and exonuclease domain. In some embodiments the fusion protein comprises at least a fragment or variant of a homing endonuclease and at least a fragment or variant of an exonuclease, for example a 3' exonuclease, which are associated with one another by genetic or chemical conjugation to one another. In several embodiments, the 3' exonuclease is a Trex2 monomer, dimer, or a variant thereof. In other embodiments, the fusion protein comprises at least a fragment or variant of a zinc finger endonuclease and at least a fragment or variant of a 5' exonuclease, which are associated with one another, by genetic fusion or chemical conjugation to one another. The endonuclease and exonuclease, once part of the fusion protein, may be referred to as a "portion", "region," "domain" or "moiety" of the endo/exo-nuclease fusion protein.

In some embodiments, an end-processing enzyme (or fragment or variant thereof) is fused directly to an endonuclease (or fragment or variant thereof). The end-processing enzyme (or fragment or variant thereof) may be fused to the amino terminus or the carboxyl terminus of the endonuclease (or fragment or variant thereof).

An endonuclease/end-processing enzyme fusion protein may optionally include a linker peptide between the endonuclease and end-processing enzyme domains to provide greater physical separation between the moieties and thus maximize the accessibility of the endonuclease portion, for instance, for binding to its target sequence. The linker peptide may consist of amino acids selected to make it more flexible or more rigid depending on the relevant function. The linker sequence may be cleavable by a protease or cleavable chemically to yield separate endonuclease and end-processing enzyme moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the endonuclease moiety with respect to the end-processing enzyme moiety so that the endonuclease domain can recognize and cleave its target sequence and the end-processing domain can modify the DNA ends exposed at the cleavage site. The linker may also be a simple amino acid sequence of a sufficient length to prevent any steric hindrance between the endonuclease domain and the end-processing domain. In addition, the linker sequence may provide for post-translational modification including, but not limited to, e.g., phosphorylation sites, biotinylation sites, sulfation sites, γ-carboxylation sites, and the like.

In some embodiments the linker sequence comprises from about 4 to 30 amino acids, more preferably from about 8 to 22 amino acids. That is, the linker sequence can be any number of amino acids from about 4 to 30, such as at least or equal to 4, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the linker sequence is flexible so as not hold the biologically active peptide in a single undesired conformation. The linker may be predominantly comprised of amino acids with small side chains, such as glycine, alanine, and serine, to provide for flexibility. In some embodiments about 80 or 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a T2A linker sequence allows for two separate proteins to be produced from a single translation. Suitable linker sequences can be readily identified empirically. Additionally, suitable size and sequences of linker sequences also can be determined by conventional computer modeling techniques.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are well known in the art.

A variety of DNA molecules encoding the above-described endonucleases, end-processing enzymes and fusion proteins may be constructed for providing the selected proteins or peptides to a cell. The DNA molecules encoding the endonucleases, end-processing enzyme, and fusion proteins may be modified to contain different codons to optimize expression in a selected host cell, as is known in the art.

A variety of RNA molecules encoding the above-described endonucleases, end-processing enzymes and fusion proteins may be constructed for providing the selected proteins or peptides to a cell. The RNA molecules encoding the endonucleases, end-processing enzyme, and fusion proteins may be modified to contain different codons to optimize expression in a selected host cell, as is known in the art.

Several embodiments relate to the prevention of precise cNHEJ mediated repair of endonuclease-induced double strand breaks by simultaneous expression of end-processing enzymes capable of recognizing the post-endonuclease break structure, resulting in the modification of DNA ends prior to ligation, promoting a mutagenic outcome. Some embodiments relate to the simultaneous expression exonucleases capable of recognizing the post-endonuclease break structure, resulting in the trimming of DNA ends prior to ligation, promoting a mutagenic outcome. Simultaneous expression of a site-specific endonuclease and an end-processing enzyme improves the efficiency of targeted gene disruption by up to ~70 fold, essentially fixing a mutagenic outcome in 100% of a population of cells containing the target site in less than 72 hours.

In some embodiments, effective amounts of endonucleases and end-processing enzymes or an effective amount of a fusion protein are delivered to a cell either directly by contacting the cell will the protein(s) or by transient expression from an expression construct. In such embodiments, cell division reduces the concentration of the nucleases to sub-active levels within a few cell divisions.

Several embodiments relate to a method of conferring site specificity on a DNA end-processing enzyme by physically tethering an end-processing enzyme domain to a site specific DNA binding domain. In some embodiments, the end-processing enzyme domain is tethered to a DNA binding domain through a linker peptide. The composition and structure of the linker peptide is not especially limited and in some embodiments the linker may be chemically or enzymaticly cleavable. The linker peptide may be flexible or rigid and may comprise from about 4 to 30 amino acids. In other embodiments, the end-processing enzyme domain is chemically fused to a DNA binding domain. Not wishing to be bound by a particular theory, imparting site specificity to a end-processing enzyme through tethering the end-processing enzyme to a site specific DNA binding domain decreases toxicity associated with indiscriminate end-processing activity, such as exonuclease activity, and reduces the effective amount of end-processing enzyme required for efficient modification of the exposed double stranded DNA break caused by endonuclease activity compared to untethered end-processing enzyme. In some embodiments, the end-processing enzyme is tethered to a homing endonuclease. In other embodiments, the end-processing enzyme is tethered to zinc finger endonuclease. In some embodiments, an end-processing enzyme domain is tethered to a zinc finger DNA binding domain which binds to a DNA sequence adjacent to the cleavage site of a homing endonuclease or zinc finger endonuclease.

Several embodiments relate to coupling the activity of one or more site-specific endonucleases with Trex2. Trex2 may be provided as a monomer or dimer. The Trex2 enzyme specifically hydrolyzes the phosphodiester bonds which are exposed at 3' overhangs. While the homing endonucleases generate 3' overhangs which are susceptible to Trex2 exonuclease activity, the zinc finger nucleases, which utilize the Fok1 cleavage domain, generate double strand DNA breaks with 5' overhangs. The homing endonucleases and zinc finger nucleases generate mutations at their cleavage sites at a baseline rate. Co-expression of Trex2 with homing endonucleases increased the mutation rate 70 fold. Co-expression of Trex2 with zinc finger endonucleases was also observed to effect on the rate of mutation. See FIGS. 11A and 11B. Accordingly, several embodiments described herein relate to improving the mutation rate associated zinc finger endonuclease targeted cleavage events by coupling zinc finger endonuclease to exonucleases which cleave 5' overhangs. Some embodiments relate to coupling 3' exonucleases to zinc finger endonucleases wherein the nuclease domain of the zinc finger endonuclease generates 3' overhangs.

Some embodiments relate to the co-expression of a homing endonuclease and the exonuclease, Trex2, via a single promoter linked by a T2A sequence that enables separate polypeptides to be produced from a single translation event. In this way, the endonuclease and exonuclease are provided in a 1 to 1 ratio. Higher rates of modification are achieved using T2A linked expression of the homing endonuclease, I-SceI, and Trex2 than is achieved through co-transduction of separate I-SceI, and Trex2 expression constructs. In some embodiments, a fusion protein comprising one or more endonuclease domains and one or more Trex2 domains may be provided.

In another aspect, methods of co-expressing an end-processing enzyme with a zinc finger endonuclease capable of mutating the CCR-5 gene and/or inactivating CCR-5 function in a cell or cell line are provided. In some embodiments, a method for improving the inactivation of a CCR-5 gene in a human cell is provided, the method comprising administering to the cell any site specific endonuclease having a target site in a CCR5 coupled to an end-processing enzyme. In some embodiments, a method for improving the inactivation of a CCR-5 gene in a human cell is provided, the method comprising administering to the cell any site specific endonuclease having a target site in a CCR5 coupled to an exonuclease capable of cleaving the phosphodiester bonds created at the site of endonuclease cleavage. In some embodiments, a method for improving the inactivation of a CCR-5 gene in a human cell is provided, the method comprising administering to the cell any site specific endonuclease having a target site in a CCR5 and contemporaneously administering an exonuclease capable of cleaving the phosphodiester bonds created at the site of endonuclease cleavage. Examples of suitable endonucleases include engineered homing endonucleases and meganucleases, which have very long recognition sequences, some of which are likely to be present, on a statistical basis, once in a human-sized genome. Any such nuclease having a unique target site in a CCR5 gene can be used instead of, or in addition to, a zinc finger nuclease, in conjunction with an exonuclease for targeted cleavage in a CCR5 gene. Some embodiments relate to administration of a fusion protein comprising a CCR5-site-specific endonuclease and an exonuclease capable of cleaving the phosphodiester bonds created at the site of endonuclease cleavage.

Expression Vectors

Expression constructs can be readily designed using methods known in the art. Examples of nucleic acid expression vectors include, but are not limited to: recombinant viruses, lentiviruses, adenoviruses, plasmids, bacterial artificial chromosomes, yeast artificial chromosomes, human artificial chromosomes, minicircle DNA, episomes, cDNA, RNA, and PCR products. In some embodiments, nucleic acid expression vectors encode a single peptide (e.g., an endonuclease, an end-processing enzyme, or a fusion protein having endonuclease and end-processing activity). In some embodiments, nucleic acid expression vectors encode one or more endonucleases and one or more end-processing enzymes in a single, polycistronic expression cassette. In some embodiments, one or more endonucleases and one or more end-processing enzymes are linked to each other by a 2A peptide sequence or equivalent "autocleavage" sequence. In some embodiments, a polycistronic expression cassette may incorporate one or more internal ribosomal entry site (IRES) sequences between open reading frames. In some embodiments, the nucleic acid expression vectors are DNA expression vectors. In some embodiments, the nucleic acid expression vectors are RNA expression vectors.

In some embodiments, a nucleic acid expression vector may further comprise one or more selection markers that facilitate identification or selection of host cells that have received and express the endonuclease(s), end-processing enzyme(s), and/or fusion protein(s) having endonuclease and end-processing activity along with the selection marker. Examples of selection markers include, but are not limited to, genes encoding fluorescent proteins, e.g., EGFP, DS-Red, YFP, and CFP; genes encoding proteins conferring resistance to a selection agent, e.g., $Puro^R$ gene, $Zeo^R$ gene, $Hygro^R$ gene, $neo^R$ gene, and the blasticidin resistance gene. In some cases, the selection marker comprises a fluorescent reporter and a selection marker.

In some embodiments, a DNA expression vector may comprise a promoter capable of driving expression of one or more endonuclease(s), end-processing enzyme(s), and/or fusion protein(s) having endonuclease and end-processing activity. Examples of promoters include, but are not limited to, retroviral LTR elements; constitutive promoters such as CMV, HSV1-TK, SV40, EF-1$\alpha$, $\beta$-actin; inducible promoters, such as those containing Tet-operator elements; and tissue specific promoters. Suitable bacterial and eukaryotic promoters are well known in the art and described, e.g., in Sambrook et al., Molecular Cloning, A Laboratory Manual (2nd ed. 2001); Kriegler, Gene Transfer and Expression: A Laboratory Manual (1990); and Current Protocols in Molecular Biology (2010). Non-limiting examples of plant promoters include promoter sequences derived from *A. thaliana* ubiquitin-3 (ubi-3).

In some embodiments, a nucleic acid encoding one or more endonucleases, end-processing enzymes, and/or fusion proteins having endonuclease and end-processing activity can be cloned into a vector for transformation into prokaryotic or eukaryotic cells. In some embodiments, nucleic acids encoding different endonucleases and end-processing enzymes are cloned into the same vector. In such cases, the nucleic acids encoding different endonucleases and end-processing enzymes may optionally be separated by T2A or IRES sequences. Vectors can be prokaryotic vectors, e.g., plasmids, or shuttle vectors, insect vectors, or eukaryotic vectors, including plant vectors described herein. Expression of the nucleases and fusion proteins may be under the control of a constitutive promoter or an inducible promoter.

Introduction of polypeptides having endonuclease and/or end-processing activity and/or polynucleotides encoding polypeptides having endonuclease and/or end-processing activity into host cells may use any suitable methods for nucleic acid or protein delivery as described herein or as would be known to one of ordinary skill in the art. The polypeptides and polynucleotides described herein can be delivered into cultured cells in vitro, as well as in situ into tissues and whole organisms. Introduction of the polypeptides and polynucleotides of the present embodiments into a host cell can be accomplished chemically, biologically, or mechanically. This may include, but is not limited to, electroporation, sonoporation, use of a gene gun, lipotransfection, calcium phosphate transfection, use of dendrimers, microinjection, polybrene, protoplast fusion, the use of viral vectors including adenoviral, AAV, and retroviral vectors, and group II ribozymes.

Organisms

The present invention is applicable to any prokaryotic or eukaryotic organism in which it is desired to create a targeted genetic mutation. Examples of eukaryotic organisms include, but are not limited to, algae, plants, animals (e.g., mammals such as mice, rats, primates, pigs, cows, sheep, rabbits, etc.), fish, and insects. In some embodiments, isolated cells from the organism can be genetically modified as described herein. In some embodiments, the modified cells can develop into reproductively mature organisms. Eukaryotic (e.g., algae, yeast, plant, fungal, piscine, avian, and mammalian cells) cells can be used. Cells from organisms containing one or more additional genetic modifications can also be used.

Examples of mammalian cells include any cell or cell line of the organism of interest, for example oocytes, somatic cells, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells and myeloma cells like SP2 or NS0. Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, muscle stem cells, skin stem cells, and neuronal stem cells.

Examples of target plants and plant cells include, but are not limited to, monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, roots, etc. The present disclosure also encompasses seeds of the plants described above. The present disclosure further encompasses the progeny, clones, cell lines, or cells of the plants described.

Generating Homozygously Modified Organisms

Cells in which one or more endonucleases are co-expressed with one or more end-processing enzyme(s) and/or cells in which one or more fusion proteins having endonuclease and end-processing activity are expressed are then assayed for the presence of mutations at the endonuclease cleavage site(s). Such modified cells can be identified using any suitable method known to the skilled artisan, including sequencing, PCR analysis, southern blotting, and the like. In some embodiments, an amplicon spanning the endonuclease target site is generated by PCR. The amplicon is then exposed to the endonuclease and the ability of the endonuclease to cut the amplicon is assessed. Mutation of the target site is indicated by the absence of endonuclease generated cleavage products.

Subsequently, cells containing the mutated target site(s) are cultured or otherwise treated such that they generate a whole organism with the mutated target site. For example, traditional methods of pro-nuclear injection or oocyte injection can be used to generate animals with the mutated target site. Likewise, plant cells containing the mutated target site(s) can be cultured to regenerate a whole plant which possesses the mutant genotype and thus the desired phenotype. Regeneration can also be obtained from plant callus, explants, organs, pollens, embryos, or parts thereof. Once the heterozygous organisms containing the mutated target site(s) reach reproductive maturity, they can be crossed to each other, or in some instances, spores may be grown into haploids. Of the resulting progeny from crosses, approximately 25% will be homozygous mutant/mutant at the target locus.

Pharmaceutical Compositions and Administration

Endonucleases, end-processing enzymes and fusion proteins having endonuclease and end-processing activity and expression vectors encoding endonucleases, end-processing enzymes and fusion proteins having endonuclease and end-processing activity can be administered directly to a patient for targeted cleavage of a DNA sequence and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia and the like. In some embodiments, the compositions described herein (e.g., endonucleases, end-processing enzymes and fusion proteins having endonuclease and end-processing activity and expression vectors encoding endonucleases, end-processing enzymes and fusion proteins having endonuclease and end-processing activity) can be used in methods of treating, preventing, or inhibiting a disease (e.g., cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia) or ameliorating a disease condition or symptom associated with a disease, such as, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis or ameliorate a disease condition or symptom associated with an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit a disease caused by misregulation of genes. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit a cancer, such as BCL-2, Bcl-XI, and FLIP, or ameliorate a disease condition or symptom associated with a cancer, such as BCL-2, Bcl-XI, and FLIP, by, for example, increasing the mutation rate of genes with anti-apoptotic activity.

Examples of microorganisms that can be inhibited (e.g., inhibiting the growth or infection) by provision of endonucleases, end-processing enzymes and fusion proteins having endonuclease and end-processing activity include pathogenic bacteria, e.g., chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria; infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia*, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing homing endonucleases or zinc finger endonucleases into ultimate contact with the tissue to be treated. The endonucleases, end-processing enzymes and fusion proteins having endonuclease and end-processing activity are administered in any suitable manner, and in some embodiments with pharmaceutically acceptable carriers. Suitable methods of administering such proteins or polynucleotides are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences).

The endonucleases, end-processing enzymes and fusion proteins having endonuclease and end-processing activity or vectors encoding endonucleases, end-processing enzymes and fusion proteins having endonuclease and end-processing activity, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Kits

Also provided are kits for performing any of the above methods. The kits typically contain one or more endonucleases, end-processing enzymes and/or fusion proteins having endonuclease and end-processing activity or expression vectors encoding endonucleases, end-processing enzymes and/or fusion proteins having endonuclease and end-processing activity as described herein. The kits may also contain a reporter construct, such as the mCherry+ reporter construct described herein, containing a cloning site for insertion of the target site for a selected endonuclease of interest. In some embodiments, kits may contain one or more plasmids according to SEQ ID NOs: 110-145. For example, kits for screening mutagenesis produced by coupled endonuclease and end-processing activity and/or fusion proteins with activity to a particular gene are provided with one or more reporter constructs containing the desired target site(s). Similarly, kits for enriching cells for a population of cells having a endonuclease-mediated genomic modification may comprise a reporter construct comprising a target site present in the genome of the cells and one or more endonuclease specific to the target site of interest and one or more selected end-processing enzymes and/or one or more fusion proteins specific to the target site of interest.

The kits can also contain cells, buffers for transformation of cells, culture media for cells, and/or buffers for performing assays. Typically, the kits also contain a label, which includes any material such as instructions, packaging or advertising leaflet that is attached to or otherwise accompanies the other components of the kit.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The present embodiments should therefore not be limited by the above described embodiment, method, and examples, but by all embodiments and methods within the scope and spirit of the present embodiments.

The following Examples are presented for the purposes of illustration and should not be construed as limitations.

Example 1

Co-Expression of the Homing Endonuclease, I-SceI, and Trex2 Exonuclease Increases the Rate at which I-SceI Induces Mutations To determine if coupling an exonuclease with a site-specific endonuclease could enhance targeted gene disruption efficiency, we assessed the effect of Trex2 on the mutagenic repair of DSBs generated by I-SceI. To ensure that Trex2 would be co-expressed with I-SceI, we developed expression vectors that drive coupled expression of both an endonuclease and an end-processing enzyme from a single promoter via a T2A "skip" peptide motif. We also included mTagBFP fluorescent protein co-expression by an internal ribosomal entry site (IRES) for tracking transfection efficiency.

Figures 1A, 1B, 1C:
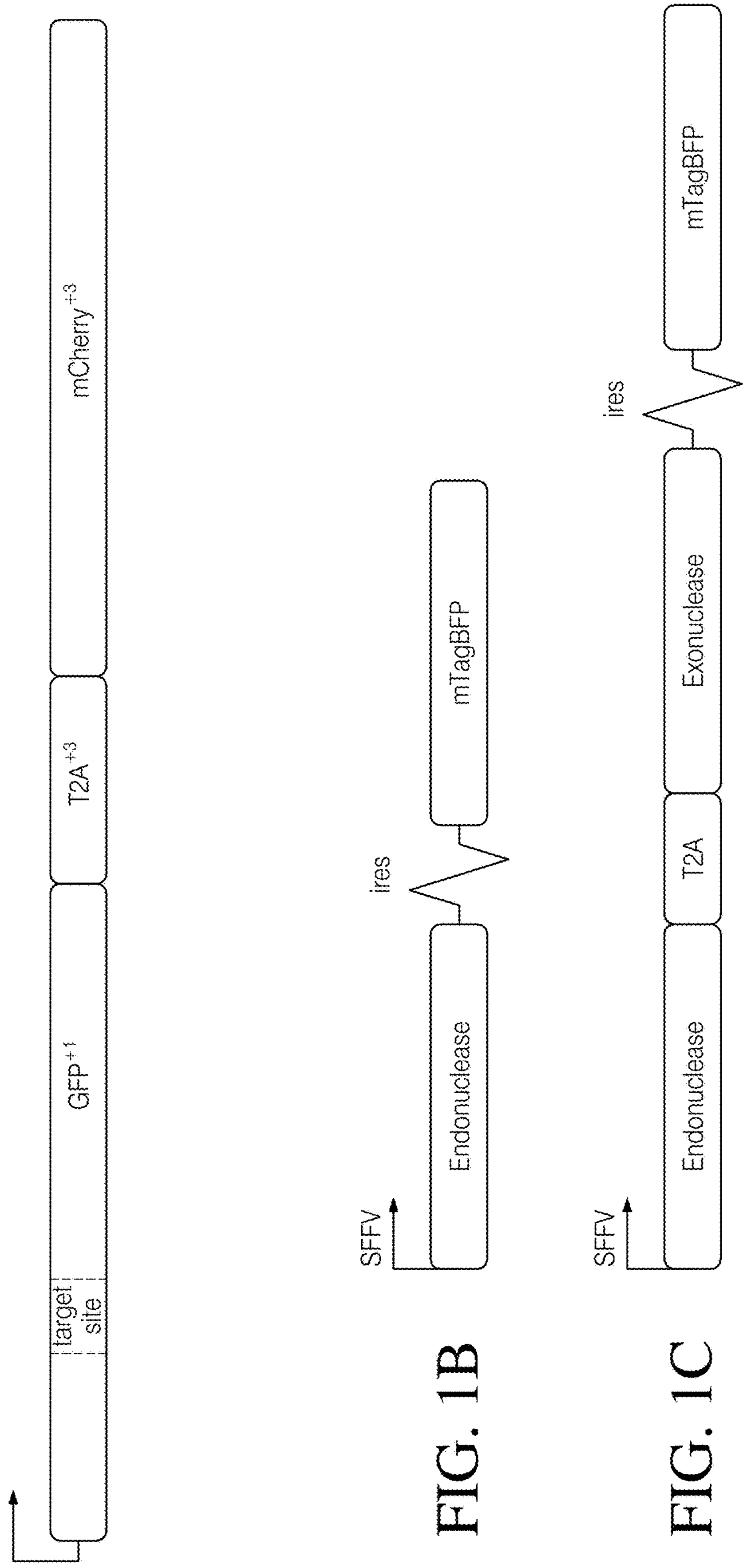
FIG. 1A shows a schematic of the Traffic Light Reporter system (TLR) for measuring the effectiveness of exonuclease induced gene disruption. mCherry positive cells represent a proportion of the total cells that have undergone gene disruption.
FIGS. 1B-1H show schematic representations of expression vectors for delivery of endonucleases and DNA end-processing enzymes.
Figure 1D:
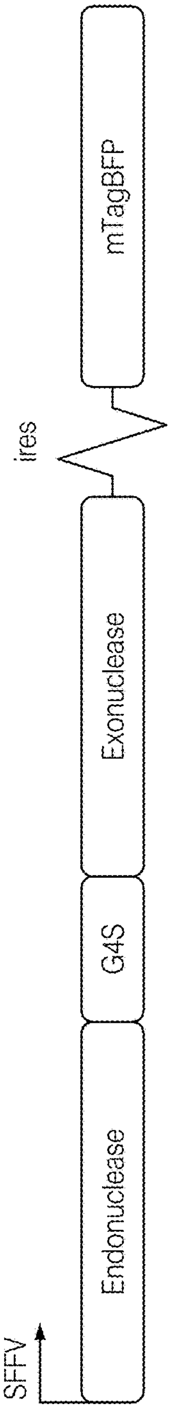
Figure 1E:
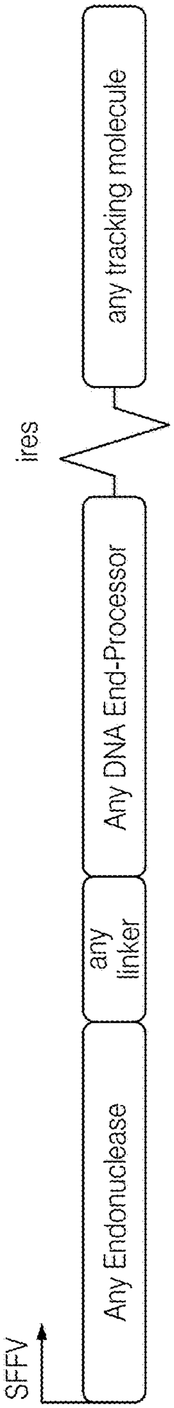
Figure 1F:
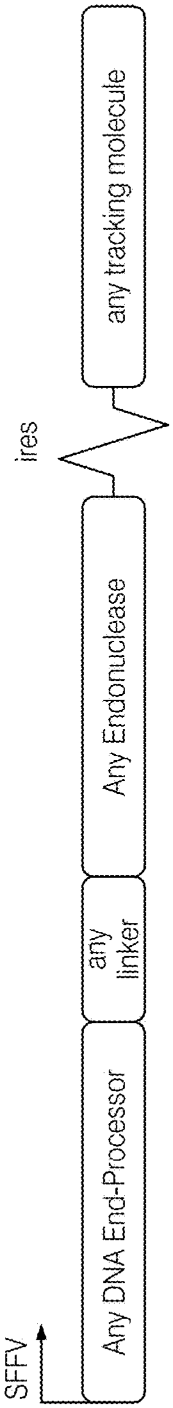
Figure 1G:
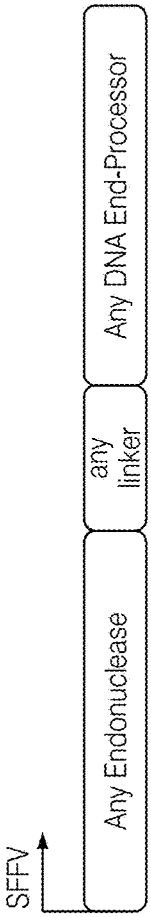
Figure 1H:
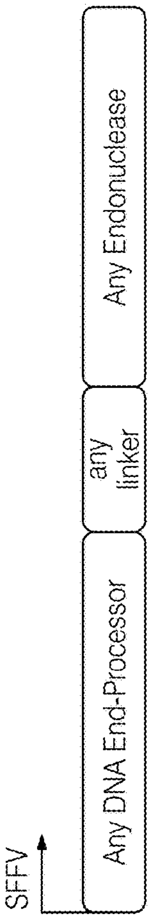

To measure the rate of nuclease-induced targeted disruption, a mutNHEJ reporter construct (Traffic Light Reporter (TLR)) was constructed by placing the I-SceI target site, SEQ ID NO: 146 5'-AGTTACGCTAGGGATAACAGGGTAATATAG-3', in front of the mCherry fluorescent protein ORF in the +3 reading frame. See FIG. 1A. When an endonuclease-induced DNA cleavage event results in a frameshift into the +3 reading frame, the mCherry fluorescent protein is placed in frame and correctly translated, resulting in red fluorescent cells that may be easily detected by flow cytometry. HEK cell lines harboring the TLR were generated by plating $0.1\times10^6$ HEK293 cells 24 hrs prior to transduction in a 24 well plate. mutNHEJ (TLR) reporter cell lines were made by transducing HEK293 cells at limiting titer (~5%) with ~25 ngs of an integrating lentivirus containing the reporter construct with 4 ug/ml polybrene. Media was changed 24 hrs after transduction.

Expression vectors comprising the homing endonuclease, I-SceI, a fluorescent protein (BFP), and optionally Trex2 with either a T2A or G4S linker peptide were constructed according to the schematics provided in FIGS. 1B-H.

0.1×10^6 HEK293 cells containing a genomically-integrated mutNHEJ (TLR) reporter cassette were plated 24 hrs prior to transfection in a 24 well plate. The HEK 293 cells were transfected with expression constructs comprising the I-SceI mutant D44A alone, the I-SceI mutant D44A coupled to Trex2 via a T2A linker, I-SceI alone or I-SceI coupled to Trex2 via a T2A linker using Fugene transfection reagent according to manufacture's protocol. 72 hours following transduction of the cell line with the expression vectors, the cells were analyzed by flow cytometry on a BD LSRII or BD FACS ARIAII. The mCherry fluorophore was excited using a 561 nm laser and acquired with a 610/20 filter. The mTagBFP fluorophore was excited on a 405 nm laser with a 450/50 filter. Data was analyzed using FlowJo software (FlowJo, Ashland Oreg.).

Figure 2A:
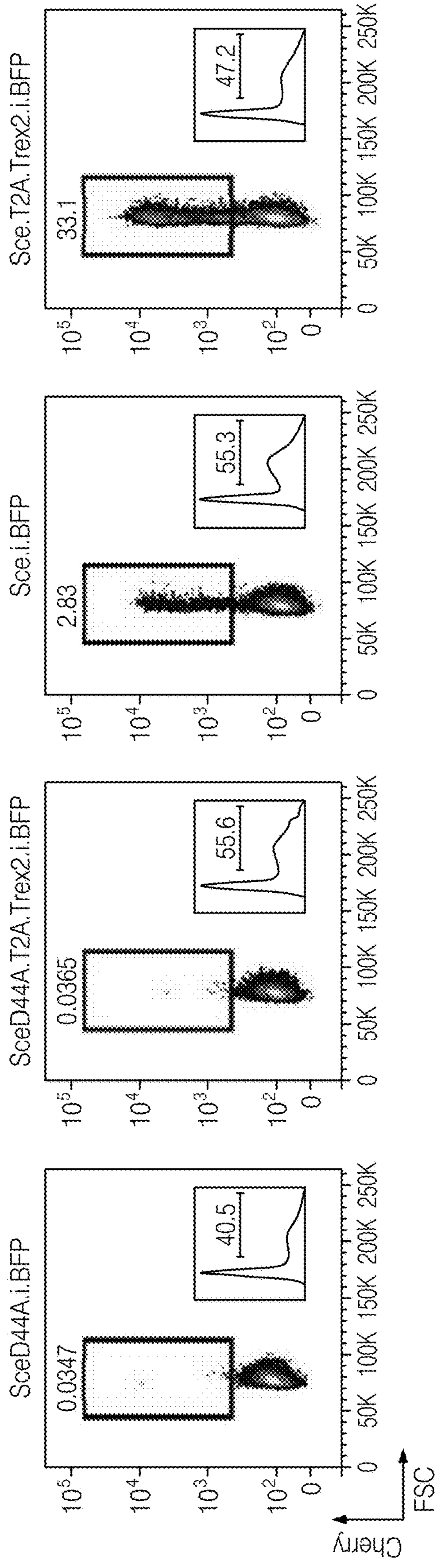
FIG. 2A shows representative flow plots of HEK293 cells harboring Traffic light Reporter transfected with expression vectors encoding SceD44A-IRES-BFP, SceD44A-T2A-Trex2-IRES-BFP, I-SceI-IRES-BFP, and I-SceI-T2A-Trex2-IRES-BFP. SceD44A corresponds to an inactive mutant form of I-SceI.
Figure 2B:
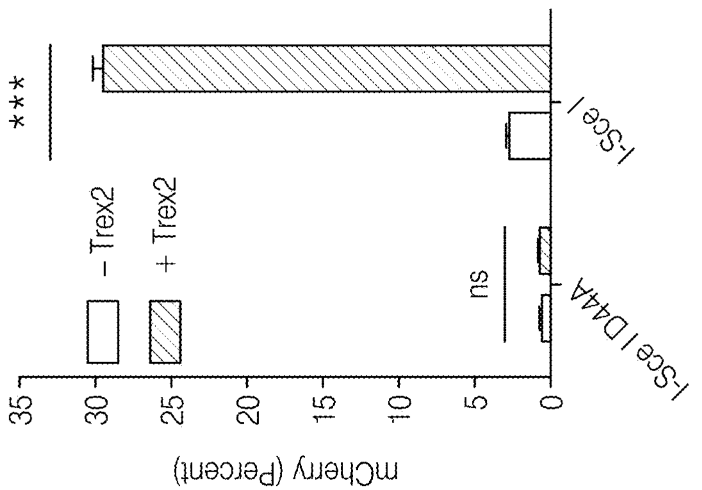
FIG. 2B shows quantification of gene disruption in three independent transfections of the vectors indicated in FIG. 2A. Error bars represent standard error of the mean (SEM), and p-values (with * representing $p<0.05$, $p<0.005$, and *$p<0.0005$) were calculated using the Student's two-tailed unpaired t-test to compare the samples indicated in this and all subsequent figures.

The plot shown in FIG. 2A demonstrates that I-SceI expression induced mutagenic NHEJ events as visualized by mCherry+ expression and that the rate of mutagenic NHEJ events (mCherry+) was significantly increased following co-expression of I-SceI with the exonuclease Trex2. See FIG. 2A. While neither I-SceI D44A (catalytically inactive) nor I-SceI D44A coupled to Trex2 was able to induce any measurable gene disruption, I-SceI coupled to Trex2 via T2A linkage exhibited a substantial increase in mCherry positive cells compared to I-SceI alone. See FIG. 2A.

Following co-expression of I-SceI endonuclease and Trex2 exonuclease, genomic DNA was extracted from the HEK 293 reporter cells using Qiagen's DNA easy kit. Amplicons spanning the I-SceI target site were generated by PCR, cloned into a shuttle vector and subjected to DNA sequencing of the I-SceI target site. The sequencing demonstrated that essentially every cell in the population contains a mutated I-SceI target site, as predicted by the reporter readout. See FIGS. 6A and 6B.

HEK 293 cells were transduced with expression constructs comprising the I-SceI mutant D44A alone, I-SceI alone or I-SceI coupled to Trex2 via a T2A linker. Following transduction of the cell line with the expression vectors, the cells were analyzed by visual inspection daily. Live cell images were taken 72 hours post transduction with the expression vectors. The cells treated in each manner appeared indistinguishable, and there is no overt toxicity associated with Trex2 co-expression. See FIG. 21B.

Figure 4A:
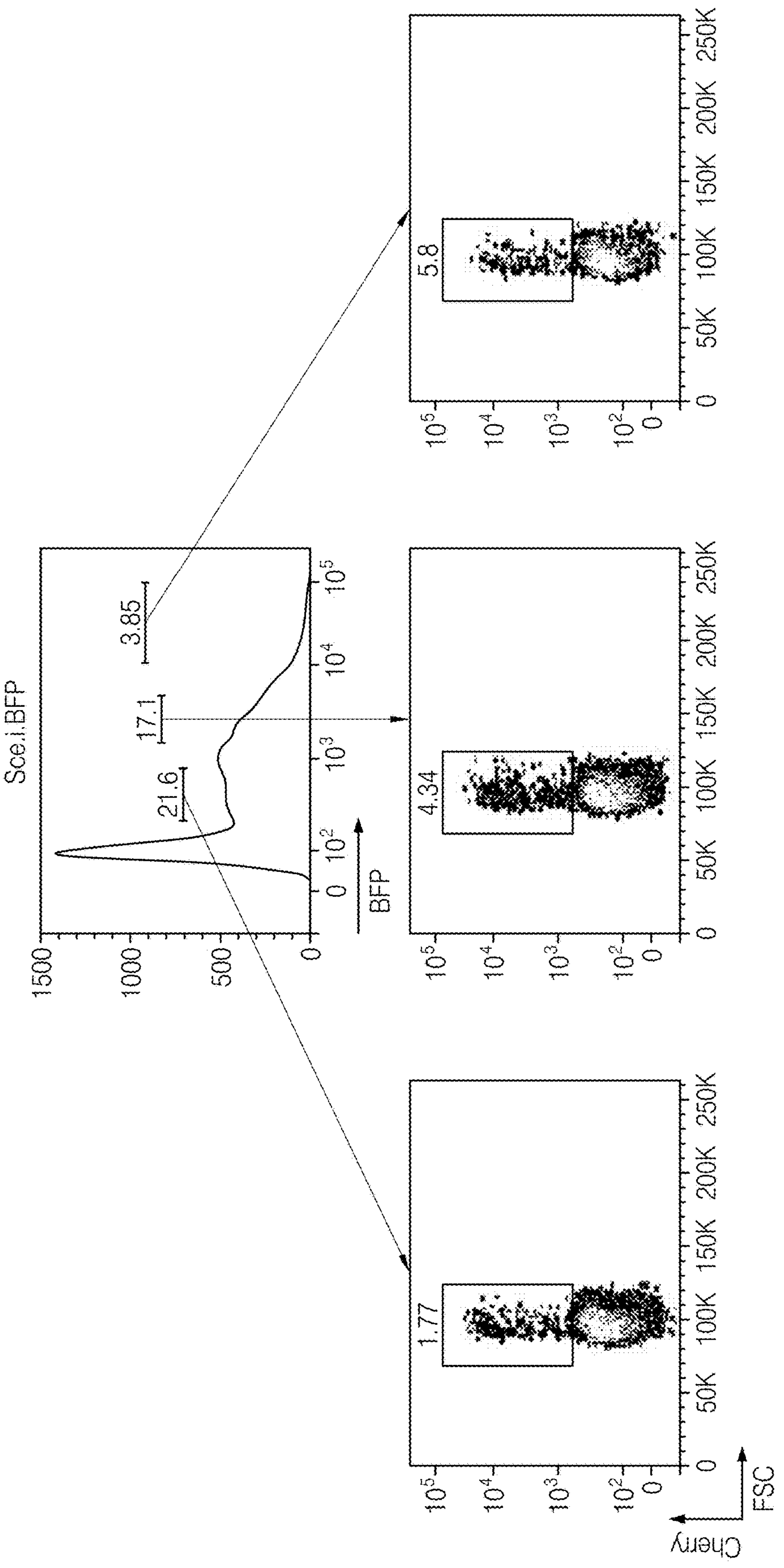
FIG. 4A shows gating analysis of HEK293 cells harboring Traffic Light Reporter transfected with I-SceI-IRES-BFP.
Figure 4B:
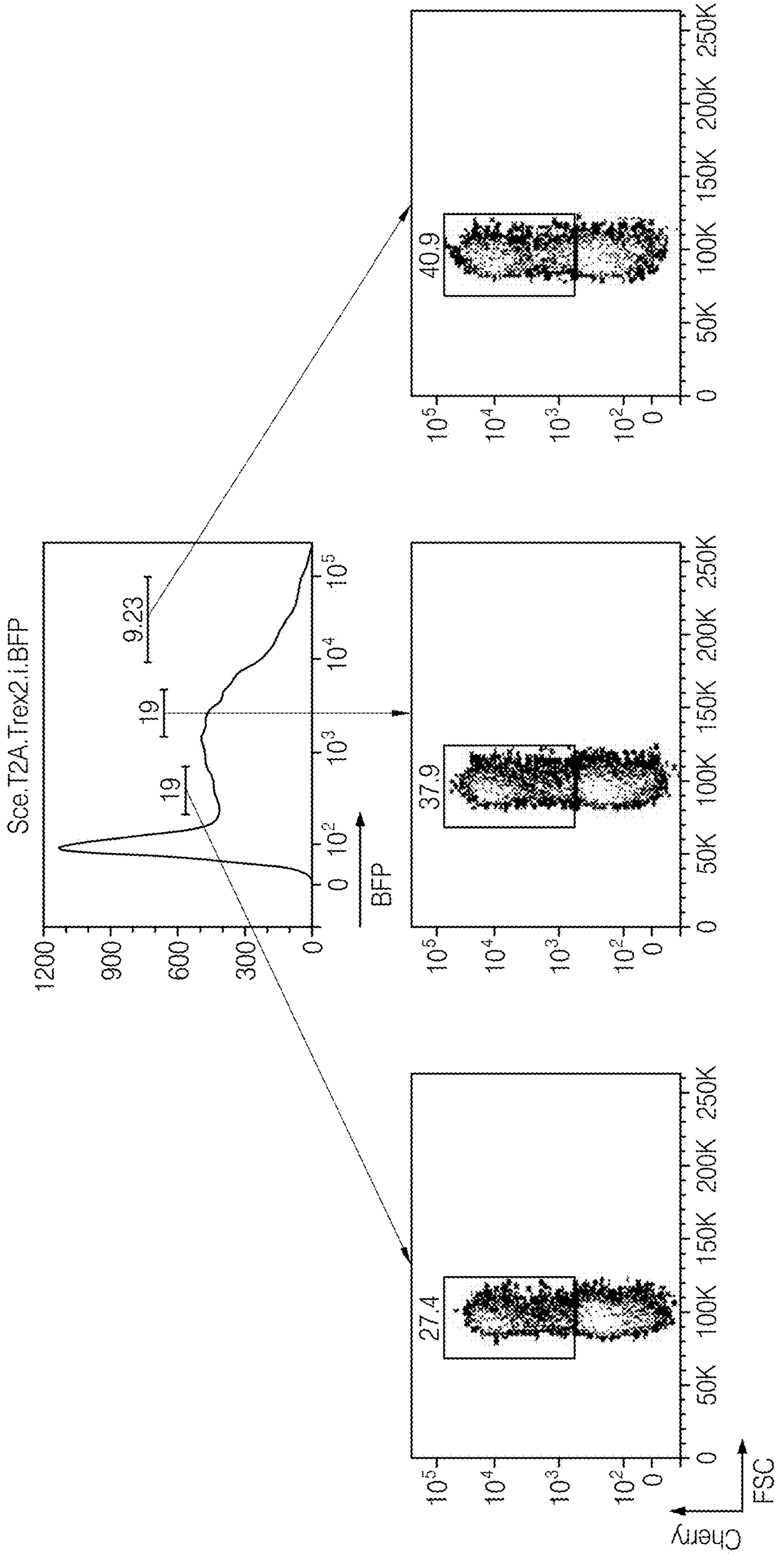
FIG. 4B shows a gating analysis of HEK293 cells harboring Traffic Light Reporter transfected with I-SceI-T2A-Trex2-IRES-BFP expression vectors.

To assess the total gene disruption rate, I-SceI and I-SceI-T2A-Trex2 transfected cells were sorted based on varying BFP expression levels. HEK 293 cells containing a genomically-integrated cassette corresponding to the targeted disruption reporter illustrated in FIG. 1A (TLR) were transduced with expression constructs comprising I-SceI-IRES-BFP (blue fluorescent protein) or I-SceI-T2A-Trex2-IRES-BFP. Expression of I-SceI-IRES-BFP and I-SceI-T2A-Trex2-IRES-BFP was measured in the transduced cells by a gating analysis of flow cytometry plots of BFP activity. Cells with low, low-medium, medium and high levels of BFP expression (corresponding to different levels of I-SceI endonuclease or I-SceI endonuclease/Trex2 exonuclease expression) were then assayed for induced mutagenic NHEJ events as visualized by mCherry+ expression. The data demonstrated that low levels of I-SceI alone resulted in lower mutation levels, while expression of I-SceI in combination with Trex2 result in high modification rates even at low levels of expression from the I-SceI-T2A-Trex2-IRES-BFP construct. See FIGS. 4A and 4B.

After the I-SceI and I-SceI-T2A-Trex2 transfected cells were sorted based on varying BFP expression levels, the area flanking the I-SceI target was amplified from each of the populations by PCR. 100 ng of each PCR product was digested in vitro with recombinant I-SceI (New England Biolabs) for 6 hours at 37° C. DNA was separated using a 1% agarose gel stained with ethidium bromide to look for a resistant band, indicative of a mutagenic event at the locus that destroyed the I-SceI target site. See FIG. 5A. Percent disruption was calculated by quantifying band intensity using Image J software, and dividing the intensity of the undigested band by the total. At low endonuclease expression levels, a 25-fold increase in total gene disruption between I-SceI and I-SceI coupled to Trex2 (2.2 to 50.2% respectively) was observed, and nearly 100% of targets were disrupted in the medium and high expression gates of I-SceI T2A Trex2 (90.3, and 97.1% respectively) See FIG. 5B.

These experiments indicate that while I-SceI exhibits a dose dependent increase in gene disruption, I-SceI coupled to Trex2 quickly becomes saturated. Sequence analysis of the I-SceI target site in high expressing cells confirmed that 100% of cells were modified in the I-SceI-T2A-Trex2 treated cells. See FIGS. 6A and 6B. Comparison of the mutation spectra between I-SceI alone and I-SceI.T2A.Trex2 showed a trend towards small deletion events in the exonuclease treated cells. See FIGS. 6A, 6B and 7. In a kinetic analysis, while all constructs exhibited similar expression patterns, Trex2 expression coincided with the appearance of disruption events at earlier time-points. See FIGS. 8A and 8B. In sum, coupling of endonucleases to Trex2 expression in a single open reading frame resulted in up to 25-fold enhancement in the efficiency of targeted gene disruption in cells from multiple species and in primary cell types, and is able to drive targeted knockout rates to near completion within 72 hrs.

Example 2

Trex2 Exonuclease Increases the Mutation Rate of a Variety of Homing Endonucleases The applicability of Trex2-enhanced disruption to multiple different nuclease scaffolds was evaluated. Targeted disruption reporter cassettes (mutNHEJ reporter cassettes) with target cleavage sites for I-Ltr, I-Gpi, I-Gze, I-MpeMI, I-PanMI, I-Cre, I-OnuI, I-HjeMI, and I-AniI (See Table 1) were generated by placing the endonuclease target site of interest placed in front of the mCherry fluorescent protein ORF in the +3 reading frame. HEK293T Reporter cell lines containing genomically-integrated I-Ltr, I-Gpi, I-Gze, I-MpeMI, I-PanMI, I-Cre, I-OnuI, I-HjeMI, and I-AniI TLR reporter cassettes were then generated. Each cell line was transfected with an expression construct for its respective enzyme with or without co-transfection of an expression construct encoding Trex2, and disruption rates were measured.

The effect of Trex2 co-expression with each of I-Ltr, I-Gpi, I-Gze, I-MpeMI, I-PanMI, I-Cre, I-OnuI, I-HjeMI, and I-AniI homing endonucleases was analyzed by flow cytometry. For each of the different Homing Endonucleases tested, disruption rates increased when coupled to Trex2, demonstrating that the Trex2 exonuclease can facilitate gene disruption from breaks generated by a variety of different homing endonucleases, which leave different 3' 4 bp overhangs and possess varying enzyme kinetics. See FIG. 10. This data demonstrates that Trex2 expression increases the mutagenesis rates associated with targeted DNA cleavage by a variety of homing endonucleases. Further, co-expression of Trex2 with I-Gze increased mCherry+ expression significantly over the background levels observed with I-Gze expression alone. See FIG. 10.

Homing Endonucleases in the panel having very low activity were rescued by coupling to Trex2. See FIG. 10. This suggests that Homing Endonucleases that appear inactive may be generating breaks at an undetectable rate, and that addition of Trex2 reveals these breaks by catalyzing end processing prior to break ligation. This is consistent with the observation that Trex2 can increase disruption rates of a higher activity enzyme, such as I-SceI, even at very low expression levels.

To test the ability of Trex2 to reveal breaks caused by Homing Endonucleases having very low activity, the effect of coupling Trex2 on the gene disruption rate of the I-AniI Homing Endonucleases was analyzed by flow cytometry. WT I-AniI exhibits very little activity in cells and expression of WT I-AniI alone does not exhibit targeted disruption activity. See FIGS. 12A and 12B. Coupling of Trex2 to WT I-AniI increases its gene disruption capacity to that of the highly active I-AniI variant, I-AniI Y2. See FIGS. 12A and 12B. I-AniI Y2 was subjected to several rounds of directed evolution to improve its activity. Coupling of Trex2 to an inactive form of I-AniI, I-AniI E148D, shows no increase in reporter expression. This data demonstrates that Trex2 expression increases the mutagenesis rates associated with targeted DNA cleavage by sub-active homing endonucleases.

Together, these results show that Trex2 can increase disruption rates for a variety of homing endonucleases and rescue low-activity endonucleases, effectively lowering the engineering bar for enzymes designed to produce gene disruption at novel target sites.

Example 3

Co-Expression of Trex2 Exonuclease Affects the Mutation Rate Associated with FokI Zinc Finger Nuclease Mediated Breaks A reporter cell line was generated that harbors a 5' ACC ATC TTC ttcaag GAC GAC GGC 3' (SEQ ID NO. 147) target site for a corresponding zinc finger nuclease containing a FokI nuclease domain. Expression vectors encoding the zinc finger nuclease were transduced into reporter cell lines harboring the TLR-FokI reporter cassette with and without Trex2. Co-expression of Trex2 with the zinc finger nuclease results in an increased mutation rate. See FIG. 11B.

Example 4

The Chimeric I-SceI-G4s-Trex2 Endo/Exo-Nuclease Fusion Protein Improves the Rate of Targeted Disruption Expression vectors comprising HA-I-SceI-BFP, (HA-I-SceI)-T2A-Trex2-BFP or (HA-I-SceI)-G4S-Trex2-BFP were constructed as described in Example 1. The I-SceI gene used to construct the expression vectors further encoded an N-terminal HA epitope tag. The (HA-I-SceI)-T2A-(HA-Trex2-BFP) expression vector expresses HA-I-SceI and Trex2 in a 1 to 1 ratio from a single promoter, but the T2A linker sequence allows for two separate proteins to be produced from a single translation. The (HA-I-SceI)-G4S-(HA-Trex2)-BFP expression vector produces an endo/exo-nuclease fusion protein where HA-I-SceI and Trex2 proteins are coupled together by a G4S linker peptide. The HA-I-SceI-BFP, (HA-I-SceI)-T2A-Trex2-BFP and (HA-I-SceI)-G4S-Trex2-BFP expression vectors were transduced into HEK293 cells containing a genomically-integrated cassette corresponding to the targeted disruption reporter illustrated in FIG. 1A.

Figure 3A:
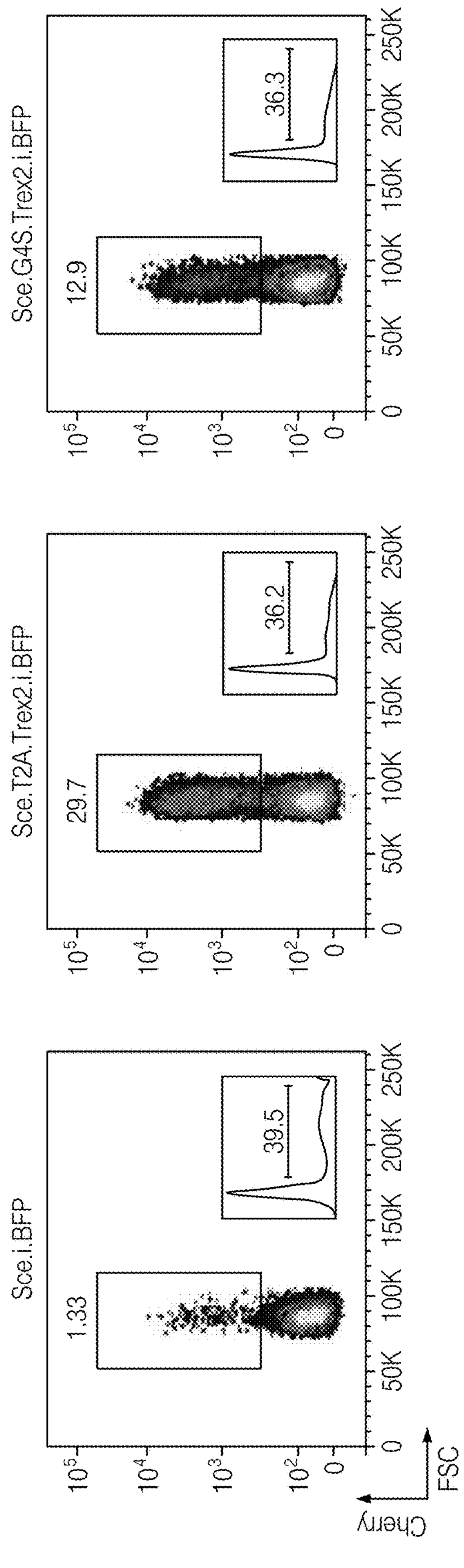
FIG. 3A shows representative flow plots of HEK293 cells harboring Traffic light Reporter transfected with expression vectors encoding I-SceI-IRES-BFP, I-SceI-T2A-Trex2-BFP, or I-SceI-G4S-Trex2-IRES BFP.

Following transduction of the cell line with the expression vectors, the cells were analyzed for mCherry+ expression by flow cytometry. The plot shown in FIG. 3A demonstrated that I-SceI-G4S-Trex2 endo/exo fusion proteins are active and increase targeted disruption rates over provision of I-SceI alone. See FIG. 3A-C.

However, Sce-G4S-Trex2, despite stable fusion protein expression, was inferior at inducing gene disruption compared to Sce-T2A-Trex2, possibly due to steric hindrance. See FIG. 3A.

Figure 3C:
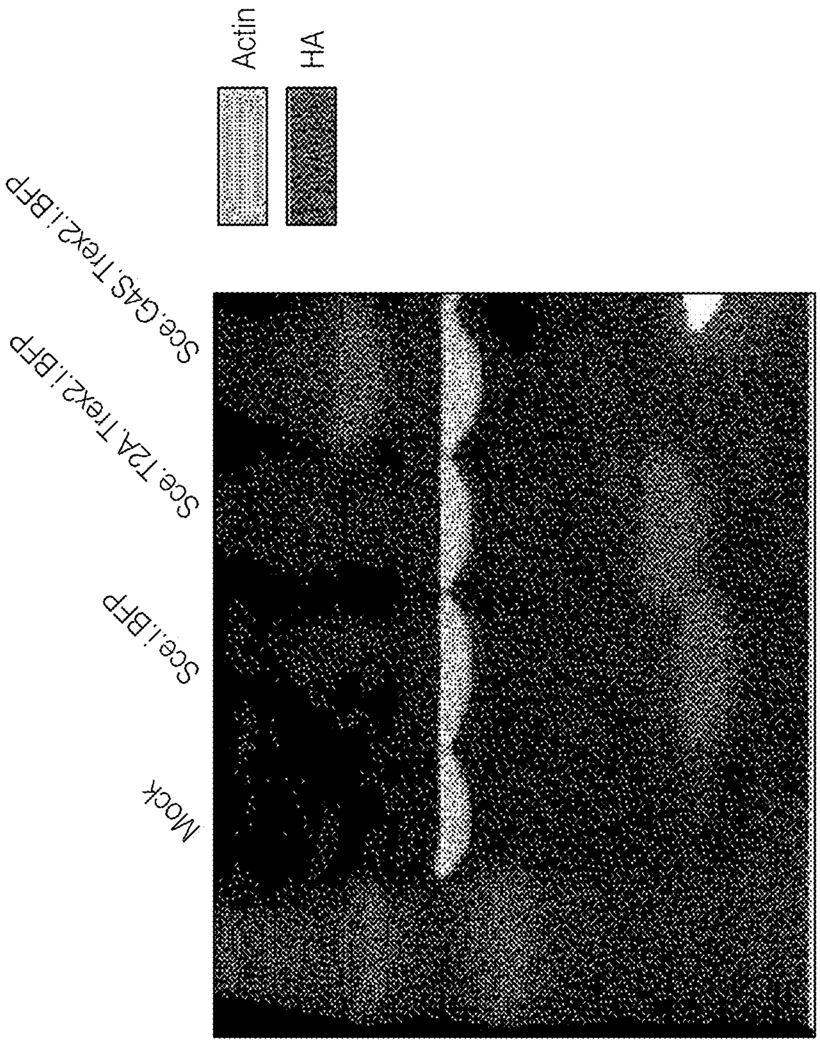
FIG. 3C is a licor western blot showing size and stability of the HA-tagged I-SceI in indicated HEK293T lysates.
Figure 3B:
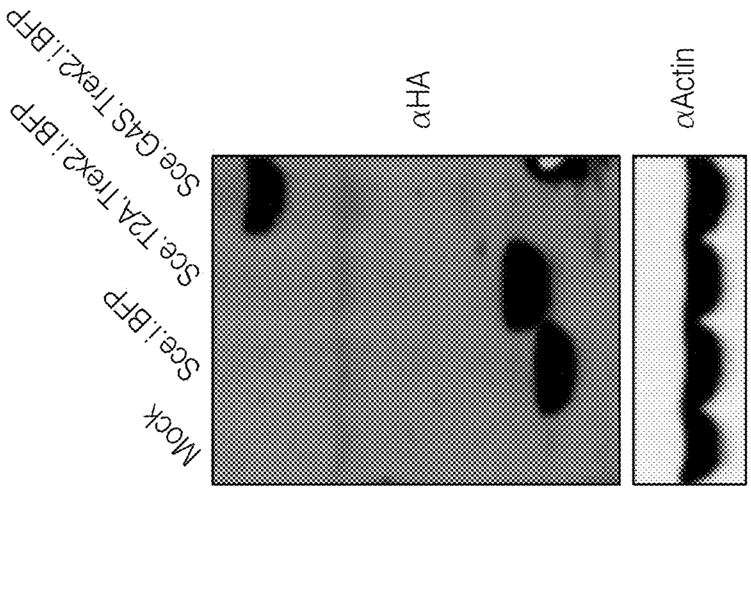
FIG. 3B shows an anti-HA western blot demonstrating equal expression of endonucleases, and stability of the (HA-)I-SceI, (HA-)I-SceI-T2A and (HA-)I-SceI-G4S-Trex2 proteins from FIG. 3A.

An anti-HA western blot was performed to assess the stability of the HA-I-SceI, HA-I-SceI-T2A and (HA-I-SceD-G4S-Trex2 proteins in the expressing cells. As shown in FIG. 3B and 3C, the chimeric (HA-I-SceD-G4S-Trex2 endo-exo fusion protein was expressed at the same levels as I-SceI alone, or I-SceI containing a residual T2A tag peptide.

Example 5

Co-Expression of I-SceI and Trex2 Exonuclease Increases the Rate of I-SceI-Induced Mutations in Primary Cells To determine if Trex2 would increase gene disruption rates in primary cells, primary murine embryonic fibroblasts (MEFs) were isolated from a mouse with an I-SceI site "knocked into" the Interleukin-2 receptor subunit gamma (IL2RG) locus ("Sce-SCID" mouse, unpublished data, G.C., D.J.R., A.M.S). MEFs were isolated from Sce-SCID embryos at 12-14 days gestation. Briefly, individual embryos were removed from the uterus and washed with PBS. The head and red tissue were removed from the embryo, and the remaining tissue was minced. The tissue was incubated with trypsin-EDTA for 10 minutes at 37° C., followed by centrifugation at 10,000×G for 5 minutes. The pellet was re-suspended in MEF media and plated at 37° C. MEF cells were cultured in glutamine-free Dulbecco's modified Eagle's medium supplemented with 2 mM L-glutamine, 10% Fetal Bovine Serum (FBS) and 1% penicillin/streptomycin.

$1.0\times10^5$ Sce-SCID MEF cells were seeded in a 24-well plate 24 hours prior to transduction with I-SceI or I-SceI.T2A.Trex2 expressing recombinant lentiviral vectors (LV). 0.5 μg DNA was used for each expression vector, and transfected using Fugene6 or XtremeGene9 (Roche) according to the manufacture's protocol. Cells were passaged 24 hours later and analyzed 72 hours post transduction. Total gene disruption at the I-SceI target site was assayed using the digestion assay described in Example 1. A 6-fold increase in disruption at the common gamma chain locus was observed with I-SceI coupled to Trex2 (I-SceI=15.8, I-SceI.T2A.Trex2=88.7). See FIGS. 9A and 9B. Additionally, since IL2RG is only expressed in a subset of differentiated hematopoietic cells, these experiments demonstrate Trex2 can facilitate high frequency disruption at unexpressed loci.

Example 6

Effect of Exonuclease Over-Expression on Repair of Endogenous DNA Damage

To determine if exonuclease over-expression alters the cells ability to repair other types of endogenous DNA damage, Trex2 expressing cells are treated with model DNA damage inducing agents. 1.0×106 Sce-SCID MEFs were seeded in a 10 cm dish 24 hours before transduction. 500 μL of 10×LV (pCVL.SFFV.sceD44A.IRES.BFP or T2A.TREX2.IRES.BFP) was added to the culture with 4 μg/mL polybrene. 24 hours post-transduction, cells were passaged to 15 cm plates. 72 hours post-transduction, 1.0×105 Sce-SCID MEFs were seeded in a 12-well plate with 1 mL media and treated as indicated with DNA damage inducing agents: Mitomycin C (Sigma Aldrich, St. Louis), Camptothecin (Sigma Aldrich, St. Louis), or ionizing radiation. 48 hours after exposure, cells were incubated in 0.5 m/mL PI as above and analyzed by flow cytometry. For CD34+ cells, 72 hours post-transduction with Trex2 expressing LV, $2.0\times10^5$ CD34+ HSCs were seeded in a 96-well plate in 200 μL of media, DNA damaging agents were added to the media, and plates analyzed as above. Over-expression of Trex2 had no adverse effect on cell cycle or sensitivity to model DNA damaging agents, suggesting cells maintain high fidelity DNA repair at lesions occurring independently of those created by the endonuclease. See FIGS. 13, 14, 15A, 15B, 15C, 16A and 16B.

Example 7

Co-Expression of I-SceI and End-Processing Enzymes Increases the Rate of I-SceI-Induced Mutations To determine if the results of coupling homing endonucleases with Trex2 could be extended to other DNA modifying enzymes, a library of 13 candidate enzymes possessing an array of biochemical end-processing activities derived from mammalian, bacterial or viral species was generated. See Table 2. The library of DNA end-processing enzymes was cloned into the pExodus vector with genes synthesized by Genscript (Piscataway, N.J.) as cDNA codon-optimized for human expression. See SEQ ID NOs. 110-145.

The library of DNA end-processing enzymes was screened by co-expressing each enzyme with either the homing endonuclease, I-SceI, or the Zinc Finger Nuclease, VF2468, in the respective HEK293T TLR cells. See FIGS. 17$A_1$, 17$A_2$, 17B, 18A, 19A and-19B. Five of DNA end-processing enzymes (Artemis, Tdt, Apollo, Rad2, and Exo1) robustly increased the gene disruption efficiency of I-SceI. See FIGS. 17 $A_1$, 17$A_2$ and 17B. Additionally, the gene disruption activity of these five enzymes was analyzed at three levels of I-SceI expression (quantified by the mean fluorescence intensity, MFI, of the BFP fluorophore). Coexpression of these enzymes with I-SceI increased I-SceI's mutagenic efficiency, even at low levels of endonuclease expression. See FIGS. 18A and 18B. In contrast, although several of the DNA end-processing enzymes possess 5' exonuclease activity, a significant effect of any enzyme on increasing the gene disruption efficiency of the VF2468 ZFN was not observed. See FIG. 19A.

In addition, the library of DNA end-processing enzymes was screened by co-expressing each enzyme with TALEN. See FIG. 19B.

TABLE 2

Library of DNA End-Processing Enzymes.

| Enzyme | Gene name | Activity | Species of origin | NLS added | Reference |
|---|---|---|---|---|---|
| Apollo | SNM1B | 5-3' exonuclease | Human | No | Lenain, C. et al., The Apollo 5' exonuclease functions together with TRF2 to protect telomeresfrom DNA repair. *Curr. Biol.* 16, 1303-1310 (2006). |
| Artemis | Artemis | 5-3' exonuclease | Human | No | Kurosawa, A., and Adachi, N. Functions and regulation of Artemis: a goddess in the maintenance ofgenome integrity. *J Radiat. Res.* (*Tokyo*) 51, 503-509 (2010). |
| Dna2 | DNA2 | 5-3' exonuclease, helicase | Human | No | Nimonkar, A. V., et al. BLM-DNA2-RPA-MRN and EXO1-BLM-RPA-MRN constitute two DNA end resection machineries for human DNA break repair. *Genes Dev* 25, 350-362 (2011). |
| Exo1 | EXO1 | 5-3' exonuclease | Human | No | Nimonkar, A. V. et al. BLM-DNA2-RPA-MRN and EXO1-BLM-RPA-MRN constitute two DNA end resection machineries for human DNA break repair. *Genes Dev* 25, 350-362 (2011). Orans, J., et al. Structures of human exonuclease 1 DNA complexes suggest a unified mechanism for nuclease family. *Cell* 145, 212-223 (2011). |

TABLE 2-continued

Library of DNA End-Processing Enzymes.

| Enzyme | Gene name | Activity | Species of origin | NLS added | Reference |
| --- | --- | --- | --- | --- | --- |
| Fen1 | FEN1 | 5' flap endonuclease | Human | No | Jagannathan, I., Pepenella, S. Hayes, J. J. Activity of FEN1 endonuclease on nucleosome substrates is dependent upon DNA sequence but not flap orientation. *J. Biol. Chem.* 286, 17521-17529 (2011). Tsutakawa, S. E., et al., Human flap endonuclease structures, DNA double-base flipping, and a unified understanding of the FEN1 superfamily. *Cell* 145, 198-211 (2011). |
| Mre11 | MRE11 | 5-3' and 3-5' exonuclease | Human | No | Garcia, V., Phelps, S. E., Gray, S., and Neale, M. J. Bidirectional resection of DNA double-strand breaks by Mre11 and Exo1. *Nature* 479, 241-244 (2011). |
| Rad2 | n/a (catalytic domain of Exo1) | 5-3' exonuclease (Exo1 catalytic domain) | Human | No | Lee, B. I., and Wilson, D. M., 3rd The RAD2 domain of human exonuclease 1 exhibits 5' to 3' exonuclease and flap structure-specific endonuclease activities. *J Bio.l Chem.* 274, 37763-37769 (1999). |
| TdT (terminal deoxynucleotidyl transferase) | TdT | Single-stranded Template independent DNA polymerase | Human | No | Mahajan, K. N., et al., Association of terminal deoxynucleotidyl transferase with Ku. *Proc. Natl. Acad. Sci. USA* 96, 13926-13931 (1999). |
| RecE | RecE | 5-3' exonuclease | E. coli | Yes | Zhang, J., Xing, X., Herr, A. B., and Bell, C. E. Crystal structure of *E. coli* RecE protein reveals a toroidal tetramer for processing double-stranded DNA breaks. *Structure* 17, 690-702 (2009). |
| Lambda exonuclease | λ exonuclease | 5-3' exonuclease | Bacteriophage λ | Yes | Zhang, J., McCabe, K. A., and Bell, C. E. Crystal structures of lambda exonuclease in complex withDNA suggest an electrostatic ratchet mechanism for processivity. *Proc. Natl. Acad. Sci. USA* 108, 11872-11877 (2011). |

TABLE 2-continued

Library of DNA End-Processing Enzymes.

| Enzyme | Gene name | Activity | Species of origin | NLS added | Reference |
|---|---|---|---|---|---|
| Sox (T24I mutation) | SOX | 5-3' alkaline exonuclease | Kaposi's sarcoma associated herpes virus | Yes | Glaunsinger, B., Chavez, L., and Ganem, D., The exonuclease and host shutoff functions of the SOX protein of Kaposi's sarcoma-associated herpesvirus are genetically separable. *J Virol.* 79, 7396-7401 (2005). Dahlroth, S. L., et al., Crystal structure of the shutoff and exonuclease protein from the oncogenic Kaposi's sarcoma-associated herpes virus. *FEBS J* 276, 6636-6645 (2009). |
| Vaccinia DNA polymerase | E9L | 3-5' exonuclease | Vaccinia poxvirus | Yes | Gammon, D. B., and Evans, D. H., The 3'-to-5' exonuclease activity of vaccinia virus DNA polymerase is essential and plays a role in promoting virus genetic recombination. *J. Virol.* 83, 4236-4250 (2009). |
| UL-12 | UL12 | 5-3' alkaline exonuclease | Herpes simplex virus (HSV)-1 | Yes | Reuven, N. B., et al. The herpes simplex virus type 1 alkaline nuclease and single-stranded DNA binding protein mediate strand exchange in vitro. *J. Virol.* 77, 7425-7433 (2003). Balasubramanian, N., et al. Physical interaction between the herpes simplex virus type 1 exonuclease, UL12, and the DNA double-strand break-sensing MRN complex. *J. Virol.* 84, 12504-12514 (2010). |

Example 8

Exonuclease Screen

An expression library containing both 3' and 5' specific exonucleases is screened by expressing the exonucleases in cells containing a targeted disruption reporter harboring a homing endonuclease target site, for example an I-SceI target site. The exonucleases are co-expressed in the reporter cells with a homing endonuclease, for example I-Sce-I, which generates 3' overhangs upon cleaving its target site. Exonucleases which increase the rate of disruption, as visualized by mCherry+ expression, of the homing endonuclease target site over expression of the homing endonuclease alone are then identified.

An expression library containing both 3' and 5' specific exonucleases is additionally screened by expressing the exonucleases in cells containing a targeted disruption reporter harboring a zinc finger endonuclease target site. The exonucleases are co-expressed in the reporter cells with a zinc finger endonuclease, which generates 5' overhangs upon cleaving its target site with FokI. Exonucleases which increase the rate of disruption, as visualized by mCherry+ expression, of the zinc finger endonuclease target site over expression of the zinc finger endonuclease alone are identified.

Example 9

Trex-Multiplex

Increasing disruption rates for individual nucleases by coupling endonuclease activity with exonuclease activity, enables multiple simultaneous changes to a genome (multiplexing).

Three homing endonuclease are designed to knock out three different genes (x, y, and z). In the absence of exonuclease co-expression, the efficiency of producing a disruptive mutation, knockout, for each gene individually is 10%, which means that the chance of successfully producing all three disruptive mutations in a single cell with a single round of endonuclease expression is 0.1%. An exonuclease, for example Trex2, is co-expressed with the three homing endonucleases to increase the rate of mutagenesis induced by the homing endonucleases. A 5-fold increase in the mutagenesis rate, to 50% for each individual gene, improves the chance of disrupting all three in a single cell, in a single round to 12.5%, a 125-fold difference.

Example 10

Reduction of Chromosomal Abnormalities During Endonuclease Mediated Targeted Disruption Endonucleases, such as homing endonucleases, zinc finger nucleases, and TAL effector nucleases, induce indiscriminate chromosomal abnormalities, such as translocations. To test the ability of co-expression of an exonuclease that facilitates disruption of an endonuclease target site to decrease the incidence of indiscriminate chromosomal abnormalities, an endonuclease, or a series of endonucleases are expressed in the presence and absence of Trex2. Karyotyping analysis or GCH array analysis is performed to determine if the incidence of genomic abnormalities induced by the endonucleases is reduced.

Example 11

Imparting Site-Specificity to Exonucleases

An exonuclease of interest, for example Trex2, is directly fused or coupled through a linker peptide to an endonuclease or to a DNA binding domain which specifically binds to a target site adjacent to the site where exonuclease activity is desired.

Example 12

Method of Treating, Preventing, or Inhibiting HIV Infection in a Human Patient

Hematopoetic stem cells are isolated from bone marrow obtained from a human subject. The isolated stem cells are contacted with an effective amount of a zinc finger nuclease (ZFN) having target sites in the human CCR-5 gene and contemporaneously contacted with a 5' exonuclease. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results received and the judgment of the attending physician. The protocol is preferably continued for at least about 1 or 2 weeks, preferably at least about 1 or 2 months, and may be continued on a chronic basis.

Example 13

Method of Treating, Preventing, or Inhibiting HIV Infection in a Human Patient

Hematopoetic stem cells are isolated from bone marrow obtained from a human subject. The isolated stem cells are contacted with an effective amount of a homing endonuclease engineered to cleave a target site in the human CCR-5 gene and contemporaneously contacted with Trex2 exonuclease. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results of the treatment and the judgment of the attending physician. The protocol is preferably continued for at least about 1 or 2 weeks, preferably at least about 1 or 2 months, and may be continued on a chronic basis.

Example 14

Method of Treating, Preventing, or Inhibiting HIV Infection in a Human Patient

Hematopoetic stem cells are isolated from bone marrow obtained from a human subject. The isolated stem cells are contacted with an effective amount of a fusion protein comprising an endonuclease domain linked to an exonuclease domain wherein the endonuclease domain comprises a homing endonuclease engineered to cleave a target site in the human CCR-5 gene or fragment thereof and wherein the exonuclease domain comprises Trex2 exonuclease or a fragment thereof. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results of the treatment and the judgment of the attending physician. The protocol is preferably continued for at least about 1 or 2 weeks, preferably at least about 1 or 2 months, and may be continued on a chronic basis.

Example 15

End-Modifying Enzyme Screen

An expression library containing end-modifying enzymes is screened by expressing the end-modifying enzymes in cells containing a targeted disruption reporter harboring a homing endonuclease target site, for example an I-SceI target site. The end-modifying enzymes are co-expressed in the reporter cells with a homing endonuclease, for example I-Sce-I, which generates 3' overhangs upon cleaving its target site. End-modifying enzymes which increase the rate of disruption, as visualized by mCherry+ expression, of the homing endonuclease target site over expression of the homing endonuclease alone are then identified.

An expression library containing end-modifying enzymes is additionally screened by expressing the exonucleases in cells containing a targeted disruption reporter harboring a zinc finger endonuclease target site. The end-modifying enzymes are co-expressed in the reporter cells with a zinc finger endonuclease, which generates 5' overhangs upon cleaving its target site with FokI. End-modifying enzymes which increase the rate of disruption, as visualized by mCherry+ expression, of the zinc finger endonuclease target site over expression of the zinc finger endonuclease alone are identified.

Example 16

Method of Treating, Preventing, or Inhibiting Cancer in a Human Patient

A patient having cancer is identified. The isolated an effective amount of an endonuclease targeting a site within the regulatory or coding sequence of an anti-apoptotic gene is administered in combination with an end processing enzyme. The patient is monitored for increased apoptosis and or decreased malignant cell proliferation. In some embodiments, tumor growth is monitored. The protocol may be administered on a periodic or chronic basis.

What is claimed is:

1. A method of increasing mutagenesis at a double-strand DNA (dsDNA) break at a selected dsDNA target site in a eukaryotic cell comprising:

a) selecting a dsDNA target site for mutagenesis;

b) introducing into the eukaryotic cell a TAL effector nuclease (TALEN) comprising a FokI nuclease domain, wherein the TALEN binds and cleaves the selected dsDNA target site; and Trex2 or a biologically active fragment thereof, wherein the Trex2, or biologically active fragment thereof, exhibits 3' to 5' exonuclease activity at the cleaved dsDNA target site, resulting in increased mutagenesis at the selected dsDNA target site as compared to mutagenesis that occurs in the absence of a Trex2, or biologically active fragment thereof.

2. The method of claim 1, wherein the dsDNA target site is within a gene.

3. The method of claim 1, wherein the dsDNA target site is within a non-coding sequence of a gene.

4. The method of claim 3, wherein the non-coding sequence is a regulatory sequence.

5. The method of claim 4, wherein the regulatory sequence is a promoter, enhancer, or splice site.

6. The method of claim 1, wherein the dsDNA target site is within a coding sequence of a gene.

7. The method of claim 2, wherein the gene is CCR-5.

8. The method of claim 2, wherein the gene is Stat3.

9. The method of claim 1, wherein the eukaryotic cell is a yeast cell.

10. The method of claim 1, wherein the eukaryotic cell is an algae cell.

11. The method of claim 1, wherein the eukaryotic cell is a plant cell.

12. The method of claim 1, wherein the eukaryotic cell is a mammalian cell, optionally a human cell.

13. The method of claim 1, wherein the mutagenesis is an insertion at the selected dsDNA target site.

14. The method of claim 1, wherein the mutagenesis is a deletion at the selected dsDNA target site.

15. The method of claim 1, wherein the TALEN and Trex2 or a biologically active fragment thereof are encoded by a single polynucleotide.

16. The method of claim 1, wherein the TALEN is coupled to Trex2 or a biologically active fragment thereof by a linker domain.

17. The method of claim 16, wherein the linker domain is a chemical linker.

18. The method of claim 16, wherein the linker domain is a peptide linker comprising 4 to 30 amino acids.

19. The method of claim 18, wherein the linker domain is a G4S linker.

20. The method of claim 18, wherein the linker domain is a T2A linker.

21. The method of claim 1, wherein the TALEN is coupled to Trex2 or a biologically active fragment thereof by an IRES sequence.

* * * * *

UNITED STATES PATENT AND TRADEMARK OFFICE

CERTIFICATE OF CORRECTION

PATENT NO. : 10,745,688 B2
APPLICATION NO. : 15/215428
DATED : August 18, 2020
INVENTOR(S) : Andrew M. Scharenberg et al.

It is certified that error appears in the above-identified patent and that said Letters Patent is hereby corrected as shown below:

In the Specification

Column 1, Lines 31-36:
"This invention was made with government support under Grant No. T32 GM07270 awarded by the U.S. National Institute of General Medical Sciences and Grant Nos. RL1CA133832, UL1DE019582, R01-HL075453, PL1HL092557, RL1-HL092553, RL1-HL92554, and U19AI96111 awarded by the National Institutes of Health."

Should read:
-- This invention was made with government Support under Grant Nos. CA133832, DE019582, HL075453, HL092557, HL092553, HL92554, and AI96111 awarded by the National Institutes of Health. --

Signed and Sealed this
Twenty-second Day of December, 2020

Andrei Iancu
*Director of the United States Patent and Trademark Office*